United States Patent
Leblond et al.

(10) Patent No.: US 8,927,589 B2
(45) Date of Patent: Jan. 6, 2015

(54) 3-ARYL-3-HYDROXY-2-AMINO-PROPIONIC ACID AMIDES, 3-HETEROARYL-3-HYDROXY-2-AMINOPROPIONIC ACID AMIDES AND RELATED COMPOUNDS HAVING ANALGESIC AND/OR IMMUNO STIMULANT ACTIVITY

(71) Applicant: Allergan, Inc., Irvine, CA (US)

(72) Inventors: Bertrand Leblond, Paris (FR); Eric Beausoleil, Paris (FR); Thierry Taverne, St. Martin Boulogne sur Mer (FR); John E. Donello, Dana Point, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/834,336

(22) Filed: Mar. 15, 2013

(65) Prior Publication Data

US 2013/0202653 A1    Aug. 8, 2013

Related U.S. Application Data

(63) Continuation of application No. 13/612,260, filed on Sep. 12, 2012, now Pat. No. 8,431,599, which is a continuation of application No. 11/814,598, filed as application No. PCT/US2006/002570 on Jan. 25, 2006, now Pat. No. 8,288,556.

(60) Provisional application No. 60/647,271, filed on Jan. 26, 2005.

(51) Int. Cl.
| | | |
|---|---|---|
| A61K 31/40 | (2006.01) |
| A61K 31/535 | (2006.01) |
| C07D 409/06 | (2006.01) |
| C07D 413/06 | (2006.01) |
| C07D 265/30 | (2006.01) |
| A61K 31/4025 | (2006.01) |
| A61K 31/5375 | (2006.01) |
| C07D 213/64 | (2006.01) |
| C07D 295/12 | (2006.01) |
| C07D 319/18 | (2006.01) |
| A61K 31/4409 | (2006.01) |
| A61K 31/4439 | (2006.01) |
| A61K 31/4545 | (2006.01) |
| A61K 31/4709 | (2006.01) |
| A61K 31/496 | (2006.01) |
| A61K 31/5377 | (2006.01) |
| A61K 31/541 | (2006.01) |

(52) U.S. Cl.
CPC .............. *C07D 265/30* (2013.01); *A61K 31/40* (2013.01); *A61K 31/4025* (2013.01); *A61K 31/5375* (2013.01); *C07D 213/64* (2013.01); *C07D 295/12* (2013.01); *C07D 319/18* (2013.01); *A61K 31/4409* (2013.01); *A61K 31/4439* (2013.01); *A61K 31/4545* (2013.01); *A61K 31/4709* (2013.01); *A61K 31/496* (2013.01); *A61K 31/5377* (2013.01); *A61K 31/541* (2013.01)

USPC ........ 514/422; 514/231.5; 548/525; 548/527; 544/146

(58) Field of Classification Search
None
See application file for complete search history.

(56) References Cited

U.S. PATENT DOCUMENTS

| | | |
|---|---|---|
| 2,884,426 A | 4/1959 | Kottler et al. |
| 2,918,466 A | 12/1959 | Kreysa |
| 3,065,265 A | 11/1962 | Gutmann et al. |
| 5,585,388 A | 12/1996 | Cosford |
| 5,767,121 A | 6/1998 | Takatani |
| 5,916,911 A | 6/1999 | Shayman et al. |
| 5,945,442 A | 8/1999 | Shayman et al. |
| 5,952,370 A | 9/1999 | Shayman et al. |
| 5,976,781 A | 11/1999 | Haldar |
| 6,030,995 A | 2/2000 | Shayman et al. |
| 6,051,598 A | 4/2000 | Shayman et al. |
| 6,407,064 B2 | 6/2002 | Masuda et al. |

(Continued)

FOREIGN PATENT DOCUMENTS

| | | |
|---|---|---|
| EP | 0185814 | 2/1986 |
| EP | 0720852 | 7/1996 |

(Continued)

OTHER PUBLICATIONS

Abe, Akira et al, Improved Inhibitors of Glucosylceramide Synthase, J. Biochem., 1992, 191-196, 111.

(Continued)

*Primary Examiner* — Nyeemah A Grazier
(74) *Attorney, Agent, or Firm* — Jonathan Y. Bass

(57) ABSTRACT

Compounds of Formulas 1 and 2

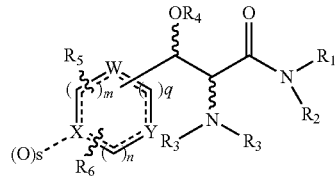

Formula 1

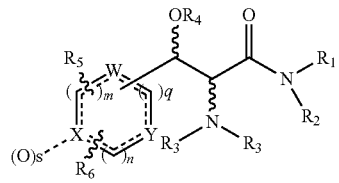

Formula 1 where the variables have the meaning disclosed in the specification, have analgesic and in some cases immunostimulant activity.

10 Claims, No Drawings

(56) References Cited

U.S. PATENT DOCUMENTS

| | | | |
|---|---|---|---|
| 6,617,340 | B1 | 9/2003 | Villhauer |
| 6,645,995 | B2 | 11/2003 | Kanstrup |
| 6,696,486 | B1 | 2/2004 | Bahl |
| 6,835,831 | B2 | 12/2004 | Hirth |
| 6,855,830 | B2 | 2/2005 | Hirth et al. |
| 7,041,831 | B2 | 5/2006 | Hirth |
| 7,125,863 | B2 | 10/2006 | Evans |
| 7,189,755 | B2 | 3/2007 | Sharma |
| 7,276,576 | B1 | 10/2007 | Lenzen |
| 7,309,714 | B2 | 12/2007 | Duffy |
| 8,153,666 | B2 | 4/2012 | Leblond |
| 8,173,683 | B2 | 5/2012 | Donello |
| 8,288,556 | B2 | 10/2012 | Leblond |
| 2002/0103384 | A1 | 8/2002 | Kanstrup |
| 2002/0198240 | A1 | 12/2002 | Shayman |
| 2003/0050299 | A1 | 3/2003 | Hirth et al. |
| 2003/0153768 | A1 | 8/2003 | Hirth |
| 2006/0111336 | A1 | 5/2006 | Duffy |
| 2007/0049619 | A1 | 3/2007 | Akahoshi |
| 2007/0093492 | A1 | 4/2007 | Jiaang |
| 2008/0200719 | A1 | 8/2008 | Kurosu et al. |
| 2009/0318449 | A1 | 12/2009 | Old et al. |
| 2010/0093793 | A1 | 4/2010 | Donello et al. |
| 2010/0105687 | A1 | 4/2010 | Donello et al. |
| 2010/0197730 | A1 | 8/2010 | Donello |
| 2011/0065747 | A1 | 3/2011 | Donello |
| 2011/0065748 | A1 | 3/2011 | Donello |
| 2011/0212995 | A1 | 9/2011 | Gil |

FOREIGN PATENT DOCUMENTS

| | | |
|---|---|---|
| EP | 0765865 | 4/1997 |
| EP | 0782992 | 7/1997 |
| FR | 2732894 | 10/1996 |
| JP | 02-250845 | 10/1990 |
| JP | 05-050499 | 3/1993 |
| JP | 09-216858 | 8/1997 |
| JP | 10-345671 | 12/1998 |
| RU | 1063026 | 7/1990 |
| WO | 95-05177 | 2/1995 |
| WO | 95-16786 | 6/1995 |
| WO | 98-33501 | 8/1998 |
| WO | 98-42657 | 10/1998 |
| WO | 01-04108 | 1/2001 |
| WO | 01-38227 | 5/2001 |
| WO | 01-38228 | 5/2001 |
| WO | 01-47874 | 7/2001 |
| WO | 02-12185 | 2/2002 |
| WO | 02-062777 | 8/2002 |
| WO | 03-008399 | 1/2003 |
| WO | 03-045928 | 6/2003 |
| WO | 2004-004773 | 1/2004 |
| WO | 2004-062601 | 7/2004 |
| WO | 2005-063275 | 7/2005 |
| WO | 2006-015830 | 2/2006 |
| WO | 2006-048140 | 5/2006 |
| WO | 2006-081273 | 8/2006 |

OTHER PUBLICATIONS

Abe, Akira et al, Structural and Stereochemical Studies of Potent Inhibitors of Glucosylceramide Synthase and Tumor Cell Growth, Journal of Lipid Research, 1995, 611-621, 36.

Beilstein Registry No. 2838658 (1979).

Bixler, Robert et al, Synthesis of β-(4-Pyridyl)-DL-Alanine and of β-(4-Pyridyl-I-oxide)-DL-, D-, and L-Alanine, Journal of Organic Chemistry, Apr. 1958, 575-584, 23, California Institute of Technology.

Burford, Hugh et al, Pharmacological Studies on Some New Acrylic Acid Amide Derivatives, Journal of Pharmaceutical Sciences, Dec. 1965, 1750-1754, 54(12).

CAS Registry No. 100861-23-2, 117886-10-9, 13789-60-1, 877037-01-9 (1957).

CAS Registry No. 13789-59-8, 13789-60-1 (1966).

CAS Registry No. 16444-08-9 (1967).

CAS Registry No. 17481-52-6 (1959).

CAS Registry No. 19196-74-8 (1968).

CAS Registry No. 4505-07-1 (1965).

CAS Registry No. 850755-27-0 (2005).

CAS Registry No. 861596-49-8 (1907).

CAS Registry No. 861596-51-2 (1907).

CAS Registry No. 90437-39-1 (1963).

CAS Registry No. 960291-08-1 (2007).

CAS Registry No. 98995-10-9 (1958).

CAS Registry No. 99169-72-9 (1957).

Cativiela, Carlos et al, On the Synthesis of Unsaturated 4(5H)-Imidazolones.2.Semi-Empirical SCF-MO (MNDO) Study on Geometric Factors Influencing the Reaction Course, Meterocycles, 1985, 2685-2692, 23(10).

Dixon, W. J., Efficient Analysis of Experimental Observations, Ann. Rev. Pharmacol Toxicol, 1980, 441-462, 20, Annual Reviews Inc.

Gregory, H. et al., Polypeptides. Part VII. Variations of the Phenylalanyl Position in the C-Terminal Tetrapeptide Amide Sequence of the Gastrins, Journal of the Chemical Society, 1968, 531-540.

Husain, Arifa et al, syn-Selective Additions to Garner Aldehyde: Synthesis of a Potent Glucosylceramide Synathase Inhibitor, Tetrahedron Letters, 2002, 8621-8623, 43.

Inokuchi et al, Amino Alcohol esters as ceramide analogs and pharmaceuticals containing them for treatment of nerve diseases, 1998, 1 pg.

Inokuchi, Jin-Ichi et al, A Synthetic Ceramide Analog (L-PDMP) Up-regulates Neuronal Function, Annals New York Academy of Sciences, 1998, 219-224, 1.

Inokuchi, Jin-Ichi et al, Antitumor Activity Via Inhibition of Glycosphingolipid Biosynthesis, Cancer Letters, 1987, 23-30, 38.

Inokuchi, Jin-Ichi et al, Preparation of the active isomer of 1-phenyl-2-decanoylamino-3-morpholino-1-propanol, inhibitor of murine glucocerebrosideb synthetase, J. Lipid Res., 1987, 565-571, 28.

Jimbo, Masayuki et al, Development of a New Inhibitor of Glucosylceramide Synthase, J. Biochem., 2000, 485-491, 124.

Kastron et al., Latvijas PSR Zinatnu Akademijas Vestis, Kimijas Serija, 1965, 474-477, 4.

Kim, Sun Ho et al., An experimental model for peripheral neuropathy produced by segmental spinal nerve ligation in the rat, Pain, 1992, 355-363, 50.

Kurosawa, Motohiro et al, 14C-Labeling of a Novel Atypical β-Adrenoceptor Agonist, SM-11044, Journal of Labelled Compounds and Radiopharmaceuticals, 1996, 285-297, 38 (3).

Lee, Lihusueh et al., Improved Inhibitors of Glucosylceramide Synthase, The Journal of Biological Chemistry, 1999, 14662-14669, vol. 274, No. 21, The American Sopciety for Biochemistry & Molecular Biology, Inc.

Mitchell, Scott et al, Glycosyltransferase Inhibitors: Synthesis of D-threo-PDMP, L-threo-PDMP, and Other Brain Glucosylceramide Synthase Inhibitors From D- or L-Serine, J. Org. Chem., 1998, 8837-8842, 63.

Miura, Tsuyoshi et al, Synthesis and Evaluation of morpholino- and Pyrrolidinosphingolipids as Inhibitors of Glucosylceramide Synthase, Bioorganic & Medicinal Chemistry, 1998, 1481-1489, 6.

Mizutani, Akihiro et al, Effects of Glucosylceramide Synthase Inhibitor and Ganglioside GQ1b on Synchronous Oscillations of Intracellular Ca2+ in Cultured Cortical Neurons, Biochemical and Biophyiscal Research Communications, 1996, 494-498, 222.

Nishida, Atsushi et al, Practical Synthesis of Threo-(1S, 2S)- and Erythro-(1R, 2S)-1-Phenyl-2-Palmitoylamino-3-morpholino-1-propanol (PPMP) From L-Serine, Synlett, Apr. 1998, 389-390.

Radin, Norman et al, Use of an Inhibitor of Glucosylceramide Synthesis, D-1-Phenyl-2-decanoylamino-3-morpholino-1-propanol, Neuroprotocols: A Companion to Methods in Neurosciences, 1993, 145-155, 3.

Shin, Seong-Ho et al, Tetrahedron Asymmetry, Tetrahedron: Asymmetry, 2000, 3293-3301, 11.

(56) References Cited

OTHER PUBLICATIONS

Slavish, Jacob et al, New PDMP Analogues Inhibit Process Outgrowth in an Insect Cell Line, Bioorganic & Medicinal Chemistry, 2004, 1487-1490, 14.

Soloshonok, Vadim et al, Gold(I)-Catalyzed Asymmetric Aldol Reactions of Isocyanoacetic Acid Derivatives with Fluoroaryl Aldehydes, Tetrahedron, 1996, 245-254, 52(1).

Suzuki, Shigeo et al, Stereochemical Studies of α-amino Alcohols. XI. N. Far.O Acetyl Migration in β-Phenylserine Amides, HCAPLUS, 1969, 1 Page.

Tabanella, Stefania et al., Preparation of Enantiomerically Pure Pyridyl Amino Acids from Serine, Organic & Biomolecular Chemistry, 2003, 4254-4261, 1 (23).

Tucker, Thomas et al., A Series of Potent HIV-1 Protease Inhibitors Containing a Hydroxyethyl Secondary Amine Transitiion State Isostere: Synthesis; Enzyme Inhibition, and Antiviral Activity, Journal of Medicinal Chemistry, 1992, 2525-2533, 35 (14).

U.S. Appl. No. 60/647,271, filed Jan. 26, 2005.

Venturella, Vincent et al, Synthesis of Several Derivatives of Phenyl(2-hdroxy-3-yrazyl)carbinol, Journal of Pharmaceutical Sciences, Feb. 1963, 142-146, 52(2).

Vlasenko et al, Study of the Anesthetic Properties of Beta Amino Alcohols, Biologicheskii Zhurnal Armenii, 1975, 18-20, 28(11).

Vunnam, Ranga Rao et al, Analogs of Ceramide That Inhibit Glucocerebroside Synthetase in Mouse Brain, Chemistry and Physics of Lipids, 1980, 265-278, 26.

Wen, Shi-Jun et al, Total Synthesis of Cyclomarin C, Organic Letters, 2004, 2721-2724, 6(16).

Zavala, Flora et al, Isolation and Characterization of the Common Intermediate in Dichotomous Reaction Catalyzed by Tryptophan Side Chain Oxidase, The Journal of Biological Chemistry, 1983, 334-351, 258(1).

3-ARYL-3-HYDROXY-2-AMINO-PROPIONIC ACID AMIDES, 3-HETEROARYL-3-HYDROXY-2-AMINOPROPIONIC ACID AMIDES AND RELATED COMPOUNDS HAVING ANALGESIC AND/OR IMMUNO STIMULANT ACTIVITY

CLAIM OF PRIORITY

This application is a continuation of U.S. application Ser. No. 13/612,260, filed Sep. 12, 2012, which is a continuation of U.S. application Ser. No. 11/814,598, filed Apr. 2, 2008, now issued U.S. Pat. No. 8,288,556, issued Oct. 16, 2012 which is a national stage application under 35 U.S.C. §371 of PCT application PCT/US2006/002570, filed on Jan. 25, 2006, which claims the benefit of U.S. provisional application Ser. No. 60/647,271, filed on Jan. 26, 2005, all of which are incorporated herein by reference in their entirety.

BACKGROUND OF THE INVENTION

1. Field of the Invention

The present invention relates to derivatives of 3-aryl-3-hydroxy-2-amino-propionic acid amides, 3-heteroaryl-3-hydroxy-2-amino-propionic acid amides and to related compounds having analgesic and in some cases immuno stimulant activity.

The present invention also relates to pharmaceutical compositions containing these compounds as active ingredient for alleviating or eliminating pain in mammals and/or stimulating the immune system in mammals and to methods of using said pharmaceutical compositions as analgesics and or immuno stimulants.

2. Background Art

Several compounds falling within one or more of the general definitions as "derivatives of 3-aryl-3-hydroxy-2-amino-propionic acid amides, of 3-heteroaryl-3-hydroxy-2-amino-propionic acid amides, of 1-aryl-1-hydroxy-2,3-diamino-propyl amines, 1-heteroaryl-1-hydroxy-2,3-diamino-propyl amines" are known in the patent and scientific literature.

For example, United States Patent Application Publications US 2003/0153768; US 2003/0050299 disclose several examples of the above-mentioned known compounds. The N-acyl compounds of these references are said to be useful as N-acylsphingosine glucosyltransferase inhibitors, the amide and the reduced compounds are described as intermediates in their preparations. Illustrative specific examples of compounds of these references are shown below:

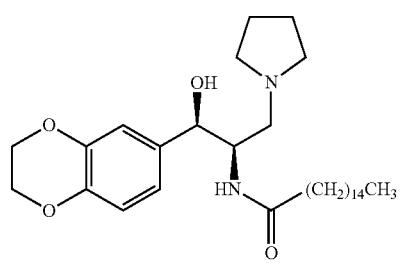

-continued

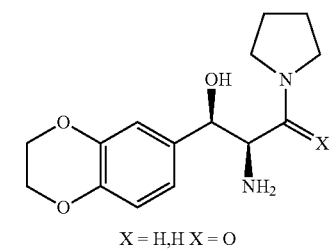

X = H,H X = O

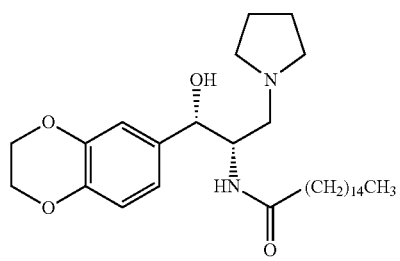

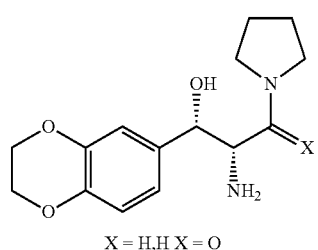

X = H,H X = O

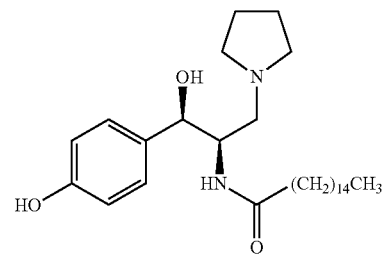

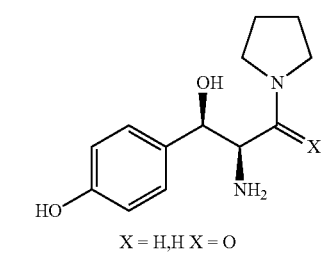

X = H,H X = O

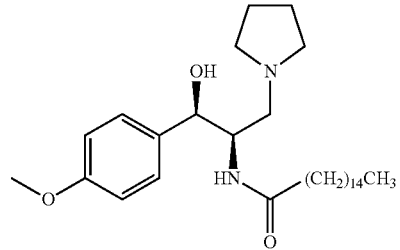

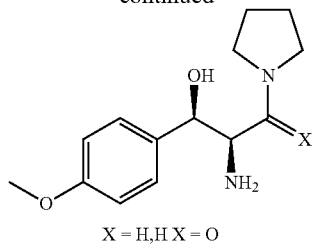

X = H,H    X = O

The publication Shin et al. *Tetrahedron Asymmetry*, 2000, 11, 3293-3301 discloses the following compounds:

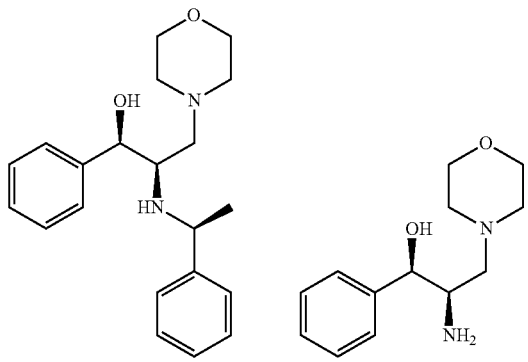

(1R,2R)-2-((S)-1-phenylethylamino)-3-morpholino-1-phenylpropan-1-ol     (1R,2R)-2-amino-3-morpholino-1-phenylpropan-1-ol

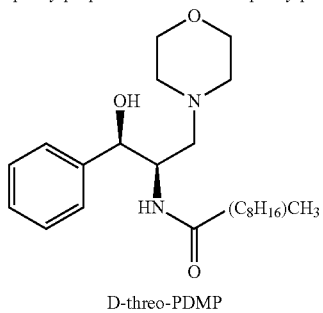

D-threo-PDMP

L-threo-PDMP and some other known compounds used in the methods of this invention are commercially available, in pure enantiomeric and racemic forms, as applicable, from Matreya, LLC Pleasant Gap, Pa.

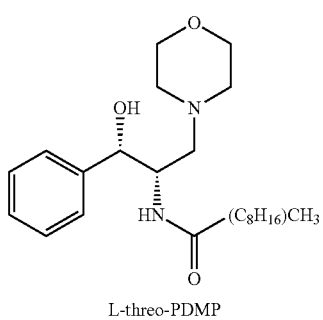

L-threo-PDMP

U.S. Pat. Nos. 5,945,442; 5,952,370; 6,030,995 and 6,051,598, which are all related to each other as being based on same or related disclosures, describe compounds which are structurally similar to the known compounds shown above. The compounds of these U.S. patent references are said to be inhibitors of the enzyme glucosylceramide (GlcCer) synthethase.

A publication in Journal of Labelled Compounds & Radiopharmaceuticals (1996), 38(3), 285-97 discloses the compound of the formula

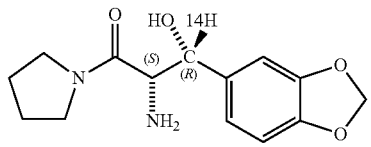

Published PCT application WO 01/38228 discloses

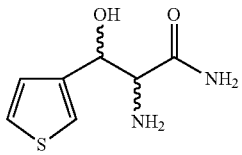 [SMILES: NC(=O)C(N)C(O)c1ccsc1]

in connection with a chromatographic method.

Kastron et al. in Latvijas PSR Zinatnu Akademijas Vestis, Kimijas Serija (1965) (4), 474-7 disclose the following compound.

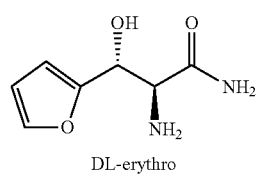 [SMILES: NC(=O)[C@@H](N)[C@@H](O)c1ccco1]

DL-erythro

Significantly, according to the best knowledge of the present inventors, none of the compounds of the prior art which are structurally similar to the novel compounds of the present invention are known in the prior art as analgesics or immunostimulants.

SUMMARY OF THE INVENTION

The present invention is directed to compounds of Formula 1

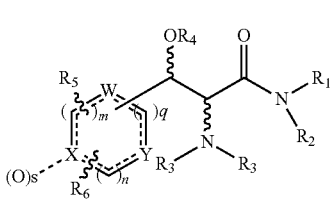

Formula 1 where $R_1$ is H or alkyl of 1 to 6 carbons,
$R_2$ is H, alkyl of 1 to 6 carbons or the $R_1$ and $R_2$ groups together with the nitrogen form a saturated or unsaturated 4, 5, 6 or 7 membered ring that optionally includes one or two heteroatoms independently selected from N, O and S, said 4, 5, 6 or 7 membered ring optionally being substituted with one or two COOH, $CH_2OH$, OH, $B(OH)_2$, cyano or halogen groups or with one or two alkyl groups having 1 to 6 carbons, or one or two carbons of said rings being attached to an oxygen to form keto groups and said 4, 5, 6 or 7 membered ring optionally being condensed with an aromatic or non-aromatic 5 or 6 membered ring that optionally includes 1 or heteroatoms selected from N, O and S;

$R_3$ is independently selected from H, alkyl of 1 to 20 carbons, cycloalkyl of 3 to 6 carbons, aryl or heteroaryl, aryl-alkyl, aryl-(hydroxy)alkyl, heteroaryl-alkyl or hetero-(hydroxy)alkyl where the alkyl moiety has 1 to 4 carbons, said aryl or heteroaryl groups being optionally substituted with 1 to 3 groups independently selected from the group consisting of halogen, alkyl of 1 to 6 carbons, alkoxy of 1 to 6 carbons and thioxy of 1 to 6 carbons, or $R_3$ is $CO-R_7$, $SO_2R_7$ or $CO-O-R_7$ where $R_7$ is H, alkyl of 1 to 1 to 20 carbons, alkyl of 1 to 20 carbons substituted with and $NH_2$ group or with an $NH-CO$alkyl group where the alkyl group has one to 6 carbons, aryl or heteroaryl, aryl-alkyl or heteroaryl-alkyl where the alkyl moiety has 1 to 4 carbons, said aryl or heteroaryl groups being optionally substituted with 1 to 3 groups independently selected from the group consisting of halogen, alkyl of 1 to 6 carbons, alkoxy of 1 to 6 carbons and thioxy of 1 to 6 carbons;

$R_4$ is H, alkyl of 1 to 6 carbons or $CO-R_8$ where $R_8$ is alkyl of 1 to 6 carbons; the wavy lines represent bonds connected to carbons having R or S configuration;

the dashed lines represent a bond or absence of a bond with the proviso that the ring containing the dashed lines is aromatic;

m, n and q are integers independently selected from 0, 1, 2 or 3 with the proviso that the sum of m, n and q is 2 or 3;

s is zero (0) or when X is N then s is zero (0) or 1;

W, X and Y independently represent a CH, $CR_5$, $CR_6$ or a heteroatom selected independently of N, O and S, and $R_5$ and $R_6$ are independently selected from H, halogen, alkyl of 1 to 6 carbons, halogen substituted alkyl of 1 to 6 carbons, alkoxy of 1 to 6 carbons and thioxy of 1 to 6 carbons, phenyl, or $R_5$ and $R_6$ together with the atoms to which they are attached jointly form a carbocyclic or a heterocyclic ring, the carbocyclic ring having 5 or 6 atoms in the ring, the heterocyclic ring having 5 or 6 atoms in the ring and 1 to 3 heteroatoms independently selected from N, O and S;

said carbocyclic or heterocyclic ring jointly formed by $R_5$ and $R_6$ being optionally substituted with 1 to 6 $R_9$ groups where $R_9$ is independently selected from halogen, alkyl of 1 to 6 carbons, alkoxy of 1 to 6 carbons and thioxy of 1 to 6 carbons or a pharmaceutically acceptable salt of said compound with the proviso that Formula 1 does not cover compounds where $R_4$ is H, $R_1$ and $R_2$ jointly with the nitrogen form a pyrrolidino or morpholino ring, the sum of m, n and q is 3, and none of W, X and Y represent a heteroatom with the further proviso that the formula does not cover the compounds of the formula below:

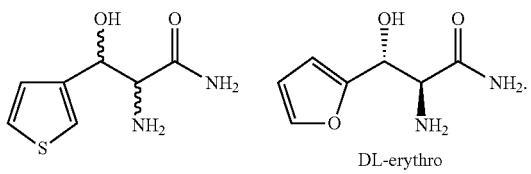

DL-erythro

The present invention is also directed to the compounds of Formula 2

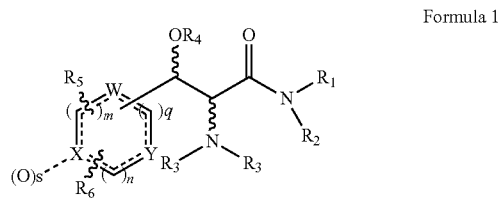

Formula 1 where $R_1$ is H or alkyl of 1 to 6 carbons, $R_2$ is H, alkyl of 1 to 6 carbons or the $R_1$ and $R_2$ groups together with the nitrogen form a saturated or unsaturated 4, 5, 6 or 7 membered ring that optionally includes one or two heteroatoms independently selected from N, O and S, said 4, 5, 6 or 7 membered ring optionally being substituted with one or two COOH, $CH_2OH$, OH, $B(OH)_2$, cyano or halogen groups or with one or two alkyl groups having 1 to 6 carbons, or one or two carbons of said rings being attached to an oxygen to form keto groups and said 4, 5, 6 or 7 membered ring optionally being condensed with an aromatic or non-aromatic 5 or 6 membered ring that optionally includes 1 or heteroatoms selected from N, O and S;

$R_3$ is independently selected from H, alkyl of 1 to 20 carbons, cycloalkyl of 3 to 6 carbons, aryl or heteroaryl, aryl-alkyl, aryl-(hydroxy)alkyl, heteroaryl-alkyl or hetero-(hydroxy)alkyl where the alkyl moiety has 1 to 4 carbons, said aryl or heteroaryl groups being optionally substituted with 1 to 3 groups independently selected from the group consisting of halogen, alkyl of 1 to 6 carbons, alkoxy of 1 to 6 carbons and thioxy of 1 to 6 carbons, or $R_3$ is $CO-R_7$, $SO_2R_7$ or $CO-O-R_7$ where $R_7$ is H, alkyl of 1 to 1 to 20 carbons, alkyl of 1 to 20 carbons substituted with an $NH_2$, $NHCOR_7$ or $NHCOOR_7$ group, aryl or heteroaryl, aryl-alkyl or heteroaryl-alkyl where the alkyl moiety has 1 to 4 carbons, said aryl or heteroaryl groups being optionally substituted with 1 to 3 groups independently selected from the group consisting of halogen, alkyl of 1 to 6 carbons, alkoxy of 1 to 6 carbons and thioxy of 1 to 6 carbons;

the wavy lines represent bonds connected to carbons having R or S configuration;

the dashed lines represent a bond or absence of a bond with the proviso that the ring containing the dashed lines is aromatic;

$R_9$ and $R_{10}$ are independently H, alkyl of 1 to 6 carbons or $OR_{11}$, or $R_9$ and $R_{10}$ jointly represent $NOR_{11}$ with the proviso that when the dashed lines between carbons 2 and 3 of the propionic acid moiety represents a bond then $R_{10}$ does not exist and $R_9$ is not $OR_{11}$ with the further proviso that when $R_9$ is $OR_{11}$ then $R_{10}$ is not hydrogen;

$R_{11}$ is H, alkyl of 1 to 6 carbons or $CO-R_{12}$ where $R_{12}$ is alkyl of 1 to 6 carbons;

m, n and q are integers independently selected from 0, 1, 2 or 3 with the proviso that the sum of m, n and q is 2 or 3;

s is zero (0) or when X is N then s is zero (0) or 1;

W, X and Y independently represent a CH, $CR_5$, $CR_6$ or a heteroatom selected independently of N, O and S, and $R_5$ and $R_6$ are independently selected from H, halogen, alkyl of 1 to 6 carbons, halogen substituted alkyl of 1 to 6 carbons, alkoxy of 1 to 6 carbons and thioxy of 1 to 6 carbons, phenyl, or $R_5$ and $R_6$ together with the atoms to which they are attached jointly form a carbocyclic or a heterocyclic ring, the carbocyclic ring having 5 or 6 atoms in the ring, the heterocyclic ring having 5 or 6 atoms in the ring and 1 to 3 heteroatoms independently selected from N, O and S;
said carbocyclic or heterocyclic ring jointly formed by $R_5$ and $R_6$ being optionally substituted with 1 to 6 $R_9$ groups where $R_9$ is independently selected from halogen, alkyl of 1 to 6 carbons, alkoxy of 1 to 6 carbons and thioxy of 1 to 6 carbons or a pharmaceutically acceptable salt of said compound.

The present invention is also directed to pharmaceutical compositions containing the above-noted novel compound to be used as analgesics and/or immunostimulants in mammals, and to methods of using said pharmaceutical compositions as analgesics or immunostimulants.

DETAILED DESCRIPTION OF THE INVENTION

A general description of the compounds of the invention is provided in the Summary Section of the present application for patent. Most compounds of the invention contain one or more asymmetric centers, such that the compounds may exist in enantiomeric as well as in diastereomeric forms. In fact, most of the compounds of the present invention have two asymmetric carbons adjacent to one another and therefore can exist in erythro or threo form, with each of these two forms having dextrorotatory (D) or levorotary (L) enantiomers. Although the threo form is generally preferred in accordance with the present invention for analgesic activity, unless it is specifically noted otherwise, the scope of the present invention includes all enantiomers, diastereomers and diastereomeric or racemic mixtures. In light of the foregoing, it should be clearly understood that the designation "DL" or "(+/−)" or "(±)" in this application includes the pure dextrorotatory enantiomer, the pure levorotatory enantiomer and all racemic mixtures, including mixtures where the two enantiomers are present in equal or in unequal proportions. Moreover, for simplicity sake in many of the structural formulas, such as in the example below, only one of the enantiomers is actually shown but when the designation "DL" or "(+/−)" or "(±)" appears it also includes the enantiomeric form (mirror image) of the structure actually shown in the formula.

For Example:

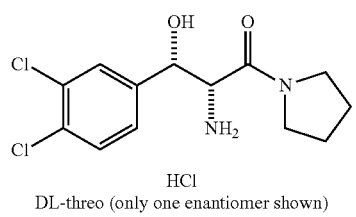 [SMILES: N[C@@H](C(=O)N1CCCC1)[C@@H](O)c1ccc(Cl)c(Cl)c1]

HCl
DL-threo (only one enantiomer shown)

Thus, in the example above, only one enantiomer is shown, but because the designation "DL" (or "(+/−)" or "(±)") appears below the formula, its optical isomer

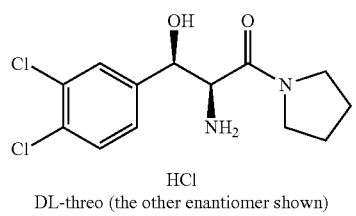 [SMILES: N[C@H](C(=O)N1CCCC1)[C@H](O)c1ccc(Cl)c(Cl)c1]

HCl
DL-threo (the other enantiomer shown)

and all racemic mixtures of the two optical isomers are also included.

In the case of some compounds of the present invention one enantiomer of the threo, and in some cases of the erythro, enantiomers is significantly more active as an analgesic than the other enantiomer of the same pair. For this reason the isolated enantiomer which is significantly more active than the other is considered a novel and inventive composition even if the racemic mixture or the other opposite enantiomer of the same compound have already been described in the prior art.

Some of the novel compounds of the present invention contain three or more asymmetric centers. An example is the following compound Compound 214

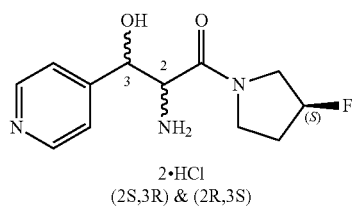

2·HCl
(2S,3R) & (2R,3S)

named Compound 214 in the description. The formula shown in the description for Compound 214 indicates two compounds of the threo isomer, but the two compounds indicated are not mirror images of each other, they are diastereomers. Another isomer pair is shown and described as Compound 215.

Compound 215

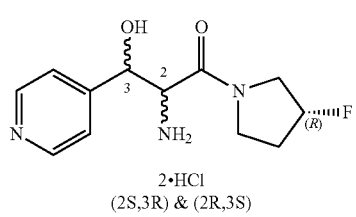

2·HCl
(2S,3R) & (2R,3S)

Keeping the foregoing examples in mind the reader one of ordinary skill in the art should readily understand the scope of each described example, although in a broad sense all isomers, enantiomers and racemic mixtures are within the scope of the invention.

The term "alkyl" in the general description and definition of the compounds includes straight chain as well as branch-chained alkyl groups.

Generally speaking the compounds of the invention may form salts with pharmaceutically acceptable acids or bases, and such pharmaceutically acceptable salts of the compounds of Formula 1 and of Formula 2 are also within the scope of the invention.

Referring now to the novel compounds of Formula 1, in a class of preferred compounds of the invention none of the W, X and Y groups is a heteroatom. Within this class, compounds are preferred where the sum of m, n and q is 3 and the aromatic group is unsubstituted or substituted with one or more halogen, alkyl of 1 to 6 carbons, or halogen substituted alkyl of 1 to 6 carbons. Compounds within this class are also preferred where the $R_5$ and $R_6$ groups form a carbocyclic ring, or a heterocyclic ring.

In another class of preferred compounds in accordance with Formula 1 one of the variables W, X and Y represents a heteroatom, preferably nitrogen and the sum of m, n and q is 3.

In still another class of preferred compounds in accordance with Formula 1 one or two of the variables W, X and Y represent a heteroatom, selected from N, O or S and the sum of m, n and q is 2.

Referring still to the compounds of Formula 1, compounds are preferred where $R_4$ is H or an acyl group, more preferably H.

With reference to the variables $R_3$, compounds in accordance with Formula 1 are preferred where both $R_3$ groups are H and where one $R_3$ group is H and the other is benzyl, monohalogeno, dihalogeno, methyl or methoxy substituted benzyl, cyclohexyl, an alkyl of 1 to 7 carbons, $COR_7$, $COOR_7$ where $R_7$ is alkyl of 1 to 15 carbons, benzyloxy, phenyl, methoxyphenyl, monohalogen or dihalogeno substituted phenyl, a 2-hydroxy-1-phenylethyl group or an alkyl group of 1 to 20 carbons itself substituted with an $NH_2$, $NHCOR_7$, or $NHCOOR_7$ group.

Referring now to the variables $R_1$ and $R_2$ in the compounds of Formula 1, compounds are preferred in accordance with the invention where $R_1$ and $R_2$ jointly form a pyrrolidine, a 3-fluoro or a 3,3-difluoro or an 3-hydroxy substituted pyrrolidine, a morpholine, a thiomorpholine, a piperazine, an alkyl substituted piperazine where the alkyl group has 1 to 6 carbons, an azetidine, a tetrahydrothiazole, an indoline, or a 2H-pyrrol ring or $R_1$ and $R_2$ are two alkyl groups of 1 to 3 carbons.

Referring now to the novel compounds of Formula 2, with respect to the variables W, X, Y, m, n, q, $R_1$, $R_2$, $R_5$, $R_6$, $R_3$ compounds are generally preferred in which these variables have the same preferences as in compounds of Formula 1.

With respect to $R_9$ and $R_{10}$, compounds are generally preferred where $R_9$ and $R_{10}$ are both hydrogen, where one of these two variables is hydroxy and the other is alkyl of 1 to 6 carbons, where the $R_9$ and $R_{10}$ groups jointly form an $NOR_{11}$ group, and where $R_9$ is hydrogen, the dashed line between carbons 2 and 3 represent a double bond and $R_{10}$ does not exist. With respect to $R_{11}$ compounds of Formula 2 are preferred where $R_{11}$ is H, or $COR_{12}$ where $R_{12}$ is alkyl of 1 to 3 carbons.

Presently still more preferred are Compounds of Formula 2 where $R_1$ and $R_2$ jointly with the nitrogen form a five-membered ring, where both $R_3$ groups are hydrogen and where one of the $R_3$ groups is hydrogen and the other is formyl.

The presently most preferred novel compounds of the invention are disclosed with their structural formulas in the ensuing Tables and or description, showing activity of exemplary compounds relevant to their ability to act as analgesics and/or immunostimulants.

Biological Activity, Modes of Administration

The novel compounds of the invention have analgesic and/or immunostimulant activity in mammals. Some of the compounds described in the introductory section which per se are known in the art, have been discovered by the present inventors to also have analgesic effect in mammals. To the best of the knowledge of the present inventors the analgesic or immunostimulant biological activity of the known compounds was not known before the present discovery.

An art-accepted model or assay for measuring an analgesic effect of a compound in chronic pain (in particular peripheral neuropathy) is the model known as Kim and Chung 1992, Pain 150, pp 355-363 (Chung model). This model involves the surgical ligation of the L5 (and optionally the L6) spinal nerves on one side in experimental animals. Rats recovering from the surgery gain weight and display a level of general activity similar to that of normal rats. However, these rats develop abnormalities of the foot, wherein the hindpaw is moderately everted and the toes are held together. More importantly, the hindpaw on the side affected by the surgery appears to become sensitive to low-threshold mechanical stimuli and will perceive pain instead of the faint sensation of touch. This sensitivity to normally non-painful touch, called "tactile allodynia", develops within the first week after surgery and lasts for at least two months. The allodynia response includes lifting the affected hindpaw to escape from the stimulus, licking the paw and holding it in the air for many seconds. None of these responses is normally seen in the control group.

To produce the tactile allodynia, rats are anesthetized before surgery. The surgical site is shaved and prepared either with betadine or Novacaine. Incision is made from the thoracic vertebra X111 down toward the sacrum. Muscle tissue is separated from the spinal vertebra (left side) at the L4-S2 levels. The L6 vertebra is located and the transverse process is carefully removed with a small rongeur to expose the L4-L6 spinal nerves. The L5 and L6 spinal nerves are isolated and tightly ligated with 6-0 silk thread. The same procedure is done on the right side as a control, except no ligation of the spinal nerves is performed.

After a complete hemostasis is confirmed, the wounds are sutured. A small amount of antibiotic ointment is applied to the incised area, and the rat is transferred to the recovery plastic cage under a regulated heat-temperature lamp.

On the day of the experiment, at least seven days after the surgery, typically six rats per test group are administered the test drugs by intraperitoneal (i.p.) injection or oral gavage (p.o.). For i.p. administration, the compounds are formulated in $H_2O$ and given in a volume of 1 ml/kg body weight by injecting into the intraperitoneal cavity. For p.o. administration, the compounds are formulated in $H_2O$ and given in a volume of 1 ml/kg body weight using an 18-gauge, 3 inch gavage needle that is slowly inserted through the esophagus into the stomach.

Tactile allodynia is assessed via von Frey hairs, which are a series of fine hairs with incremental differences in stiffness. Rats are placed in a plastic cage with a wire mesh bottom and allowed to acclimate for approximately 30 minutes. To establish the pre-drug baseline, the von Frey hairs are applied perpendicularly through the mesh to the mid-plantar region of the rats' hindpaw with sufficient force to cause slight buckling and held for 6-8 seconds. The applied force has been calculated to range from 0.41 to 15.1 grams. If the paw is sharply withdrawn, it is considered a positive response. A normal animal will not respond to stimuli in this range, but a surgically ligated paw will be withdrawn in response to a 1-2 gram hair. The 50% paw withdrawal threshold is determined using the method of Dixon, W. J., *Ann. Rev. Pharmacol. Toxicol.* 20:441-462 (1980) hereby incorporated by reference. Tactile allodynia is measured prior to and 15, 30, and 60 minutes after drug administration. The post-drug threshold is compared to the pre-drug threshold and the percent reversal of tactile sensitivity is calculated based on a normal threshold of 15.1 grams.

Table 1 below indicates the degree of pain reversal obtained in the Chung model with exemplary compounds of the invention. The intraperitonial (i.p.) and/or intravenous (iv) administration of the compounds was in doses ranging from 1 µg/kg to 300 µg/kg or 3 mg/kg PO and the peak percentage of reversal of allodynia was measured at 15, 30 or 60 minutes after administration, as is indicated in the table. Data are expressed as the highest % allodynia reversal (out of 3 time points: 15 min, 30 min, or 60 min. post-drug) with a minimum of a 20% allodynia reversal in the rat Chung model. Comparisons between groups (drug treated vs. saline treated) were made using a two-tailed, 2-sample, unpaired t-test. Compounds that are not shown which were not statistically analgesic following an IP dose of 300 ug/kg, but may still be analgesic. Compounds that do not exhibit significant analgesia at 100 mg/kg are not considered to be analgesic.

TABLE 1

| 22 | [3-pyridyl threo β-hydroxy α-amino pyrrolidine amide, 2·HCl, DL-threo] | 100% 60 min | 3000 μg/kg PO |
| --- | --- | --- | --- |
| 22 | [4-pyridyl threo β-hydroxy α-amino pyrrolidine amide, 2·HCl, DL-threo] | 100% 60 min | 100 μg/kg IP |
| 20 | [3-pyridyl threo β-hydroxy α-amino pyrrolidine amide, 2·HCl, DL-threo] | 92% 60 min | 30 μg/kg IP |
| 35 | [4-pyridyl threo β-hydroxy α-amino piperidine amide, 2·HCl, DL-threo] | 92% 60 min | 300 μg/kg IP |
| 23 | [3-thienyl threo β-hydroxy α-amino pyrrolidine amide, HCl, DL-threo] | 100% 60 min | 30 μg/kg PO |
| 24 | [2-thienyl threo β-hydroxy α-amino pyrrolidine amide, HCl, DL-threo] | 60% 60 min | 300 μg/kg IP |

TABLE 1-continued

| # | Structure | Yield/Time | Dose |
|---|---|---|---|
| 58 | 3-(pyridin-4-yl)-, Cbz-protected amino, pyrrolidine amide; HCl; DL-threo | 75% 60 min | 300 µg/kg IP |
| 59 | 3-(pyridin-4-yl)-, N-nonanoyl amino, pyrrolidine amide; HCl; DL-threo | 92% 60 min | 300 µg/kg IP |
| 27 | 3-(furan-3-yl)-, amino, pyrrolidine amide; HCl; DL-threo | 42% 30 min | 300 µg/kg IP |
| 29 | 3-(naphthalen-1-yl)-, amino, pyrrolidine amide; HCl; DL-threo | 47% 60 min | 300 µg/kg IP |
| 61 | 3-(pyridin-4-yl)-, N-methylamino, pyrrolidine amide; 2 HCl; DL-threo | 64% 60 min | 300 µg/kg IP |
| 34 | 3-(2-chloropyridin-4-yl)-, amino, 2,5-dihydropyrrole amide; 2·HCl; DL-threo | 62% 60 min | 300 µg/kg IP |

TABLE 1-continued
| Compound # | Chemical Formula | Peak % Pain reversal: time post dose | Dose µg/kg, Mode of administ. |
|---|---|---|---|
| 30 | 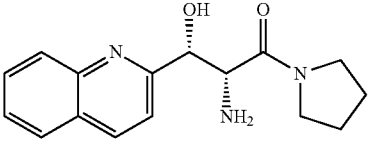<br>2 ·HCl<br>DL-threo | 53%<br>60 min | 300 µg/kg<br>IP |
| 64 | 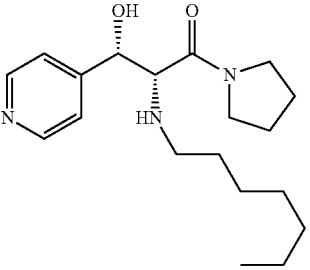<br>2 ·HCl<br>DL-threo | 100%<br>30 min | 300 µg/kg<br>IP |
| 55 | 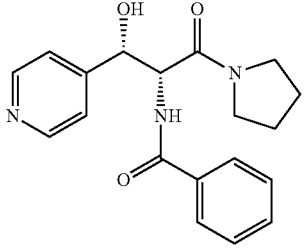<br>HCl<br>DL-threo | 58%<br>60 min | 300 µg/kg<br>IP |
| 56 | 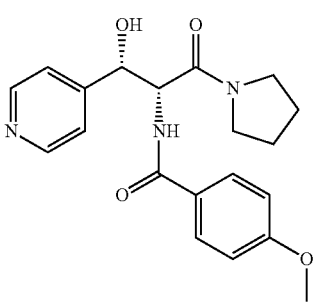<br>HCl<br>DL-threo | 67%<br>60 min | 300 µg/kg<br>IP |

TABLE 1-continued

| # | Structure | Yield / Time | Dose / Route |
|---|---|---|---|
| 67 | (pyridin-4-yl)-CH(OH)-CH(NH-CH2-C6H4-4-OMe)-C(O)-N(pyrrolidine); 2·HCl; DL-threo | 78% 60 min | 300 µg/kg IP |
| 68 | (pyridin-4-yl)-CH(OH)-CH(NH-CH2-C6H3-3,4-Cl2)-C(O)-N(pyrrolidine); 2·HCl; DL-threo | 94% 60 min | 300 µg/kg PO |
| 69 | (pyridin-4-yl)-CH(OH)-CH(NH-cyclohexyl)-C(O)-N(pyrrolidine); 2·HCl; DL-threo | 63% 30 min | 300 µg/kg IP |
| 41 | (2-chloropyridin-4-yl)-CH(OH)-CH(NH2)-C(O)-N(pyrrolidine); 2·HCl; DL-threo | 70% 60 min | 300 µg/kg IP |
| 49 | (2-oxo-1,2-dihydropyridin-3-yl)-CH(OH)-CH(NH2)-C(O)-N(pyrrolidine); HCl; DL-threo | 85% 60 min | 100 µg/kg IP |

TABLE 1-continued

| # | Structure | Yield/Time | Dose |
|---|---|---|---|
| 43 | 3-Cl-pyridin-4-yl-CH(OH)-CH(NH₂)-C(O)-N(pyrrolidine); 2·HCl; DL-threo | 96% 60 min | 300 µg/kg IP |
| 26 | benzothiophen-3-yl-CH(OH)-CH(NH₂)-C(O)-N(pyrrolidine); HCl; DL-threo | 92% 60 min | 300 µg/kg IP |
| 57 | pyridin-4-yl-CH(OH)-CH(NH-C(O)-3,4-diCl-phenyl)-C(O)-N(pyrrolidine); HCl; DL-threo | 51% 30 min | 300 µg/kg IP |
| 28 | naphthalen-2-yl-CH(OH)-CH(NH₂)-C(O)-N(pyrrolidine); HCl; (+/−) | 92% 60 min | 300 µg/kg IP |
| Compound 216 | pyridin-4-yl-CH(OH)-CH(NH-CHO)-C(O)-N(pyrrolidine); HCl; (±)-threo | 100% 60 min | 300 µg/kg IP |
| Compound 234 | pyridin-3-yl-(S)CH(OH)-(R)CH(NH-(R)CH(Ph)-CH₂OH)-C(O)-N(pyrrolidine); 2 HCl | 59% 60 min | 300 µg/kg IP |

TABLE 1-continued
| Compound 230 | 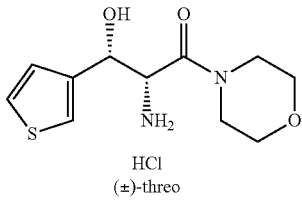 [SMILES: N[C@@H](C(=O)N1CCOCC1)[C@@H](O)c1ccsc1]<br>HCl<br>(±)-threo | 52%<br>30 min | 300 µg/kg<br>IP |
| --- | --- | --- | --- |
| Compound 236 | 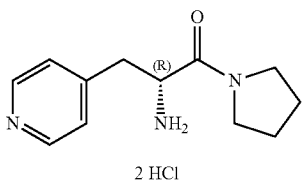<br>2 HCl | 32%<br>60 min | 300 µg/kg<br>IP |
| Compound 218 | 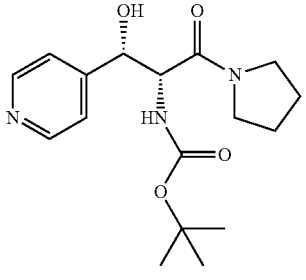<br>HCl<br>(±)-threo | 32%<br>60 min | 300 µg/kg<br>IP |
| Compound 239 | 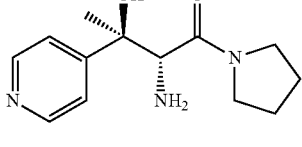<br>2 · HCl<br>(±)-erythro | 75%<br>30 min | 300 µg/kg<br>IP |
| Compound 238 | 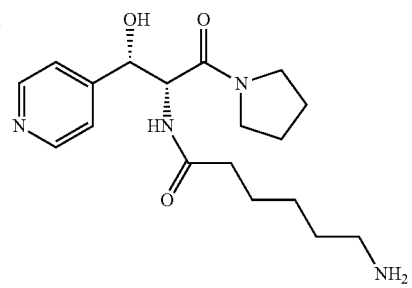<br>(±)-threo | 61%<br>60 min | 300 µg/kg<br>IP |
| Compound 205 | 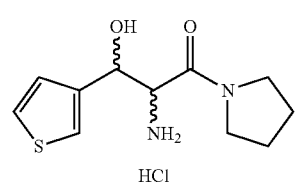<br>HCl<br>(±)-threo | 62%<br>30 min | 300 µg/kg<br>IP |

| | | | |
|---|---|---|---|
| Compound 206 | 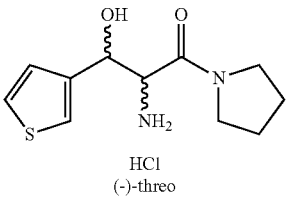 [SMILES: NC(C(=O)N1CCCC1)C(O)c1ccsc1]<br>HCl<br>(−)-threo | 67%<br>30 min | 300 μg/kg<br>IP |
| Compound 240 | 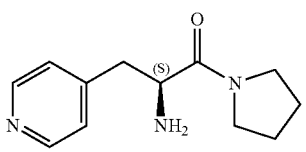<br>2 HCl | 70%<br>60 min | 30 μg/kg<br>IP |
| Compound 232 | 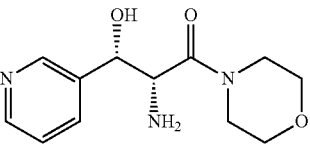<br>2·HCl<br>(±)-threo | 80%<br>60 min | 300 μg/kg<br>IP |
| Compound 220 | 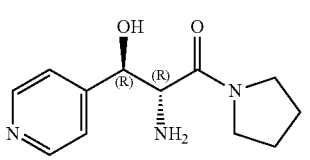<br>2·HCl<br>(−)-erythro | 32%<br>30 min | 300 μg/kg<br>IP |
| Compound 210 | 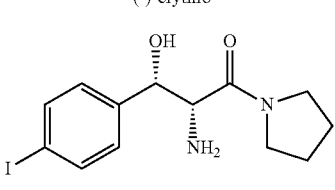<br>HCl<br>(±)-threo | 78%<br>60 min | 300 μg/kg<br>IP |
| Compound 221 | 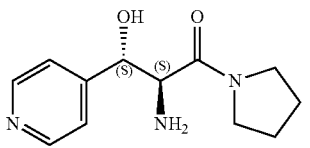<br>2·HCl<br>(+)-erythro | 87%<br>60 min | 300 μg/kg<br>IP |
| Compound 227 | 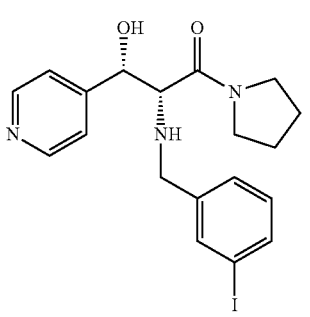<br>2·HCl<br>(±)-threo | 95%<br>30 min | 300 μg/kg<br>IP |

TABLE 1-continued

| Compound 226 | (structure: 4-pyridyl-CH(OH)-CH(NH-CH2-2-iodophenyl)-C(O)-pyrrolidine); 2·HCl (±)-threo | 95% 60 min | 300 μg/kg IP |
| --- | --- | --- | --- |
| Compound 207 | (structure: 3-pyridyl-CH(OH)-CH(NH2)-C(O)-pyrrolidine); 2·HCl (−)-threo | 96% 60 min | 300 μg/kg IP |
| Compound 213 | (structure: 4-pyridyl-CH(OH)-CH(NH2)-C(O)-3,3-difluoropyrrolidine); 2·HCl (±)-threo | 85% 30 min | 300 μg/kg IP |
| Compound 214 | (structure: 4-pyridyl-CH(OH)-3-CH(NH2)-2-C(O)-(S)-3-fluoropyrrolidine); 2·HCl (2S,3R) & (2R,3S) | 86% 60 min | 30 μg/kg IP |
| Compound 228 | (structure: 4-pyridyl-(R)CH(OH)-(S)CH(HN-CH2-3-iodophenyl)-C(O)-pyrrolidine); 2 HCl | 36% 60 min | 300 μg/kg IP |
| Compound 229 | (structure: 4-pyridyl-(S)CH(OH)-(R)CH(HN-CH2-3-iodophenyl)-C(O)-pyrrolidine); 2 HCl | 53% 60 min | 300 μg/kg IP |

TABLE 1-continued

| Compound | Structure | % | Dose |
|---|---|---|---|
| Compound 224 | 3-pyridyl-C(=NOH)-CH(NH₂)-C(=O)-N(pyrrolidine); 2·HCl (±) | 51% 60 min | 300 μg/kg IP |
| Compound 215 | 4-pyridyl-CH(OH)-CH(NH₂)-C(=O)-N(3-(R)-fluoropyrrolidine); 2·HCl (2S,3R) & (2R,3S) | 73% 60 min | 300 μg/kg IP |
| Compound 219 | 4-pyridyl-CH(OH)-CH(NH₂)-C(=O)-N(pyrrolidine); 2·HCl (±)-erythro | 82% 60 min | 30 μg/kg IP |
| Compound 203 | 4-pyridyl-(S)CH(OH)-(R)CH(NH₂)-C(=O)-N(pyrrolidine); 2 HCl (−)-threo | 87% 60 min | 300 μg/kg IP |
| Compound 204 | 4-pyridyl-(R)CH(OH)-(S)CH(NH₂)-C(=O)-N(pyrrolidine); 2 HCl (+)-threo | 50% 60 min | 300 μg/kg IP |
| Compound 40 | 4-pyridyl-CH(OH)-CH(NH₂)-C(=O)-N(Me)(Et); 2·HCl DL-threo | 47% 60 min | 300 μg/kg IP |
| Compound 247 | 4-pyridyl-(S)CH(OH)-(R)CH(NH₂)-C(=O)-N(3-(R)-hydroxypyrrolidine); 2·HCl + 4-pyridyl-(R)CH(OH)-(S)CH(NH₂)-C(=O)-N(3-(R)-hydroxypyrrolidine); 2·HCl | 42% 60 min | 300 μg/kg IP |

TABLE 1-continued

| Compound | Structure | | |
|---|---|---|---|
| Compound 254 | [structure: 1-methylimidazol-2-yl-CH(OH)-CH(NH₂)-C(O)-pyrrolidine, 2·HCl, DL-threo] | 62% 60 min | 300 µg/kg IP |
| Compound 248 | [structure: pyridin-4-yl-CH(OH)-CH(NH₂)-C(O)-N-(3S)-fluoropyrrolidine, 2·HCl, (−)-threo] | 59% 60 min | 30 µg/kg IP |
| Compound 255 | [structure: pyridin-3-yl-(S)CH(OH)-(R)CH(NH₂)-C(O)-N-(3S)-fluoropyrrolidine, 2·HCl + (R),(S) diastereomer, 2·HCl] | 60% 60 min | 300 µg/kg IP |
| Compound 256 | [structure: thien-3-yl-(S)CH(OH)-(R)CH(NH₂)-C(O)-N-(3S)-fluoropyrrolidine, 2·HCl + (R),(S) diastereomer, 2·HCl] | 62% 60 min | 300 µg/kg IP |

An art accepted method for measuring immuno stimulation comprises systemic administration of compounds to assay for the ability to stimulate the immune system, possibly due to nonspecific upregulation of the hemolymphoreticular system. This upregulation could result in increased numbers of lymphocytes of both T- and B-cell lineage. Although applicant does not wish to be bound by the biological theory of the immunostimulation, actual immunostimulatory efficacy of the compounds can be demonstrated in vivo by assaying splenic size in response to administration of the test compound to laboratory test species rats. Animals dosed at 200 mg/kg of Compound 22 of this invention exhibited a twenty-five percent increase in spleen size which demonstrates immunostimulatory potential of the compound. Generally speaking any compound that exhibits splenic enlargement following dosing of 200 mg/kg or less may be considered an immunostimulant.

Modes of Administration:

The compounds of the invention may be administered at pharmaceutically effective dosages. Such dosages are normally the minimum dose necessary to achieve the desired therapeutic effect; in the treatment of chromic pain, this amount would be roughly that necessary to reduce the discomfort caused by the pain to tolerable levels. For human adults such doses generally will be in the range 0.1-5000 mg/day; more preferably in the range 1 to 3000 mg/day, still more preferably in the range of 10 mg to 1000 mg/day. However, the actual amount of the compound to be administered in any given case will be determined by a physician taking into account the relevant circumstances, such as the severity of the pain, the age and weight of the patient, the patient's general physical condition, the cause of the pain, and the route of administration.

The compounds are useful in the treatment of pain in a mammal; particularly a human being. Preferably, the patient will be given the compound orally in any acceptable form, such as a tablet, liquid, capsule, powder and the like. However, other routes may be desirable or necessary, particularly if the patient suffers from nausea. Such other routes may include, without exception, transdermal, intraperitonial, parenteral, subcutaneous, intranasal, intrathecal, intramuscular, intravenous and intrarectal modes of delivery. Another aspect of the invention is drawn to therapeutic compositions comprising the novel compounds of the invention and pharmaceutically acceptable salts of these compounds and a pharmaceutically acceptable excipient. Such an excipient may be a carrier or a diluent; this is usually mixed with the active compound, or permitted to dilute or enclose the active compound. If a diluent, the carrier may be solid, semi-solid, or liquid material that acts as an excipient or vehicle for the active compound. The formulations may also include wetting agents, emulsifying agents, preserving agents, sweetening agents, and/or flavoring agents. If used as in an ophthalmic or infusion format, the formulation will usually contain one or more salt to influence the osmotic pressure of the formulation.

In another aspect, the invention is directed to methods for the treatment of pain, particularly chronic pain, through the administration of one or more of the novel or otherwise known compounds of the invention, or of pharmaceutically acceptable salts thereof to a mammal in need thereof. As indicated above, the compound will usually be formulated in a form consistent with the desired mode of delivery.

Compounds of the invention which are immunostimulants are administered subject to the same basic principles as the compounds having analgesic activity, in doses which are best determined on a case-by-case and/or species-by-species and, in case of humans, at times on a patient-by-patient basis. Generally speaking the effective dose will be in the range of 10 µg/kg to 200 mg/kg.

In this regard it is noted that the compounds of the threo configuration are more likely to have the analgesic activity, compounds of the erythro configuration are more likely to have immunostimulant activity, and among the erythro compounds those with an S configuration at carbon 2 of the propionic acid moiety are likely to have stronger immuno stimulant activity.

Synthetic Methods for Obtaining the Compounds of the Invention, Experimental

The compound of the invention can be synthesized by utilizing the synthetic methods described in the experimental below, or such modifications of the below described experimental methods which will become readily apparent to those skilled in the art in light of the present disclosure.
General $^1$H NMR spectra were recorded at ambient temperature with an Avance 300 (Bruker) spectrometer. The compounds were analyzed by reverse phase high performance liquid chromatography (HPLC) using a Waters Autopurification System equipped with a Waters 2525 Pump, a Waters 2696 photodiode array detector, and a XTerra column (Part. No. 186000482, 5 µm, C18, 4.5×50 mm)

The HPLC method used was a gradient of 5% solvent B to 100% in 7 min. Solvent A was H$_2$O with 0.05% TFA and solvent B was CH$_3$CN with 0.05% TFA (Method A).

Melting points were measured with a Büchi B-545 melting point apparatus and were uncorrected. To isolate reaction products the solvent were removed by evaporation using a vacuum rotatory evaporator, the water bath temperature not exceeding 40° C.

Absolute configuration of compounds of the invention, where applicable, can generally speaking be determined in accordance with methods known in the state of the art, such as X-ray christallography. Compounds 203 and 204 are mentioned as examples for which the absolute configurations were determined by X-ray christallography analysis of the corresponding (1S)-camphanylamide D-(10) camphorsulfonic acid salt. As a result Compound 204 was assigned (2S, 3R). Its enantiomer, Compound 203 was assigned by default the (2R,3S) absolute configuration.

General Synthetic Routes

The compound of the invention can be synthesized by utilizing the synthetic methods described in a general sense immediately below and in more detail in the experimental section of the present application, or by such modifications of the below described experimental methods which will become readily apparent to those skilled in the art in light of the present disclosure.

A general synthetic route to the novel compounds of the invention which are amides of substituted (+/−)-threo-3-hydroxy-2-aminopropionic acid of the Generalized Structure 1 is described below.

General Structure 1

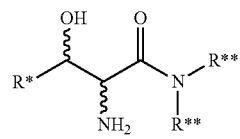

In General Structure 1, for the sake of simplicity of description R* substantially corresponds to the 5, 6, or 7 membered ring structure on the left side of Formula 1 (as the formula is depicted in the Summary and in the instant claims) and R** substantially corresponds to the R$_1$ groups in Formula General Reaction Scheme 1

1.

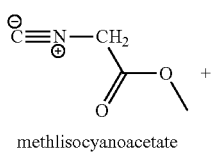

methylisocyanoacetate

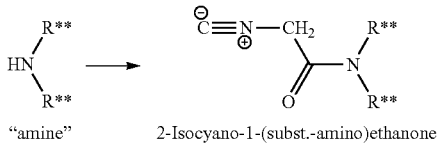

"amine"     2-Isocyano-1-(subst.-amino)ethanone

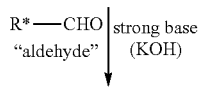

R*—CHO | strong base
"aldehyde" | (KOH)

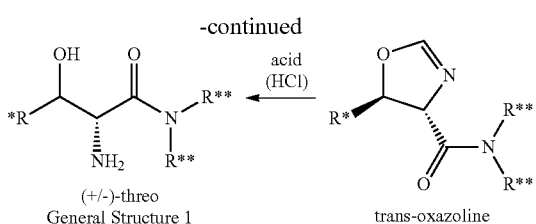

Thus, in accordance with General Scheme 1, methyl isocyanoacetate (or ethyl isocyanoacetate available commercially) is reacted with an "amine" which includes the R** groups to provide the 2-isocyanoacetic acid amide derivative shown in the general scheme. Typical examples for the amines used in the reaction are pyrrolidine, piperidine, azetidine, morpholine, 2,5-dihydro-1H-pyrrole, dialkylamines such as diethylamine, 3-fluoro-, 3,3-difluoro or 3-hydroxy substituted pyrrolidines. Specific examples of these "amines"

abound in the experimental description. The 2-isocyanoacetic acid amide derivative is then reacted in the presence of base (such as KOH) with an "aldehyde" which includes the R* group to provide a trans "oxazoline" with high diastereoselectivity (trans:cis ratios generally >97:3) as shown in the general reaction scheme 1. The trans oxazoline is then treated with a strong acid, such as HCl, to open the ring and to provide the threo-3-substituted-3-hydroxy-2-amino-propionic acid amides (with threo:erythro ratios generally >97:3) of the invention as shown in General Scheme 1.

Compounds of Formula 1 where the amino group of formula NH(R**)$_2$ is a weaker nucleophile, such as indoline, thiomorpholine and the like, can be made as illustrated in Reaction Scheme 2 for the synthesis of (±)-threo-2-amino-3-hydroxy-1-(indolin-1-yl)-3-(pyridin-4-yl)propan-1-one dihydrochloride Compound 243 and (±)-threo-2-amino-3-hydroxy-1-(thiazolidin-3-yl)-3-(pyridin-4-yl)propan-1-one dihydrochloride Compound 242.

Reaction Scheme 2

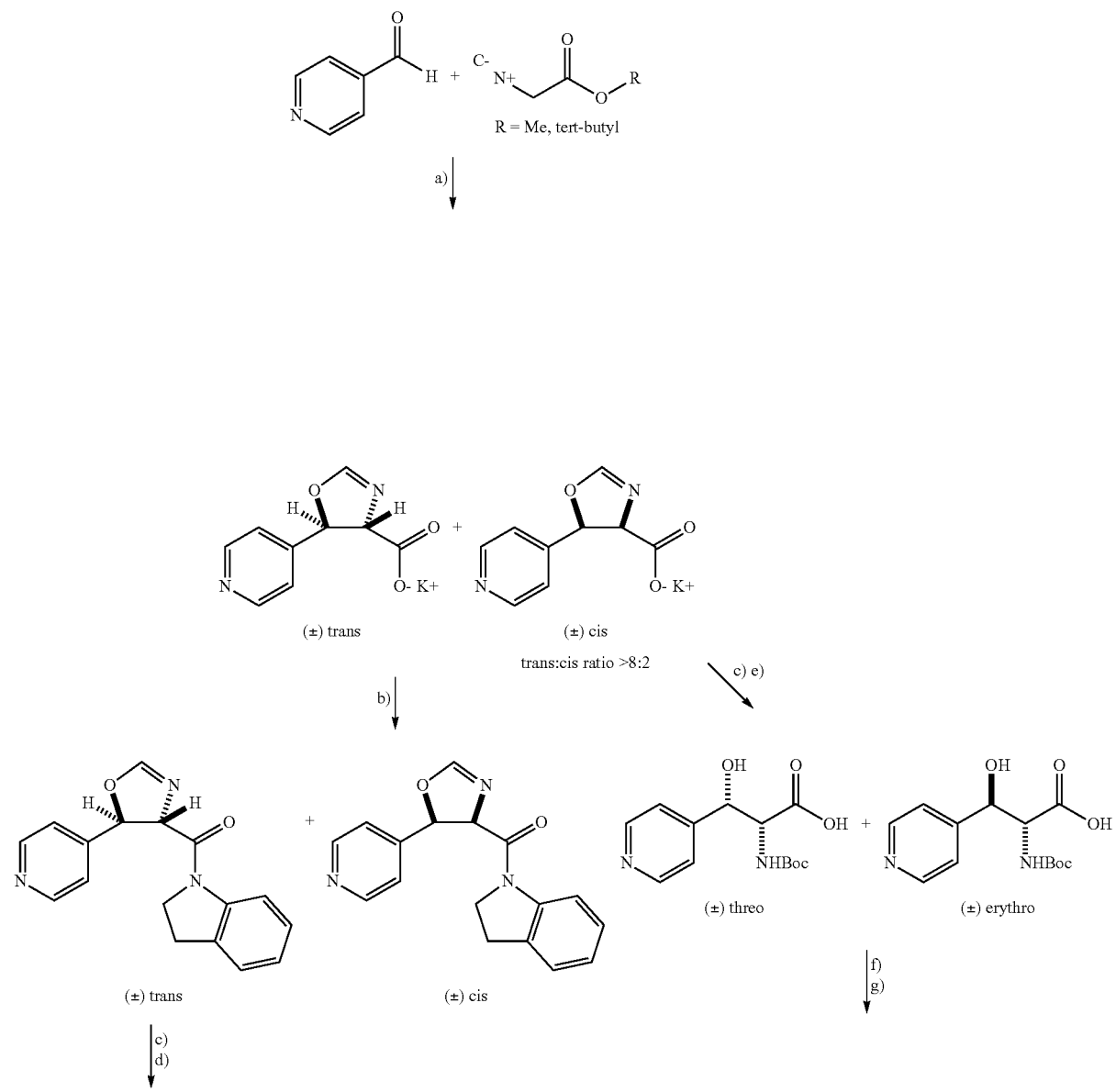

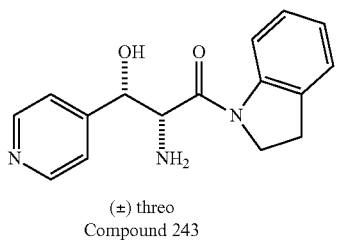

(±) threo
Compound 243

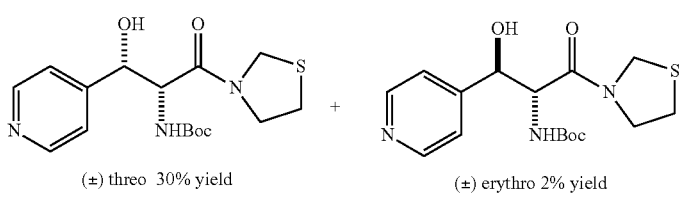

(±) threo 30% yield     (±) erythro 2% yield

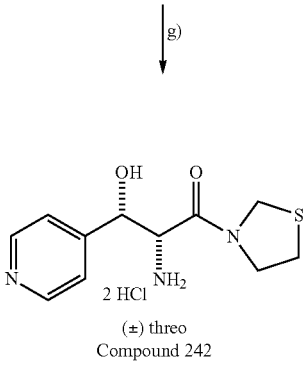

(±) threo
Compound 242 a) KOH, MeOH; b) Indoline, EDCl, TEA, HOBT, CH$_2$Cl$_2$. c) HCl (1M) in MeOH d) i. Silica Gel Chromatography. ii HCl (0.1M) in i-PrOH e) BOC$_2$O, NaOH, Dioxane. f) Thiazolidine, EDCl, TEA, HOBT, CH$_2$Cl$_2$; g) Silica Gel Chromatography g) HCl (1M) in MeOH.

In Reaction Scheme 2 EDCl stands for 1-(3-dimethylaminopropyl)-ethylcarbodiimide hydrochloride; HOBT stands for 1-hydroxybenzotriazole; BOC$_2$O stands for di-t-butyldicarbonate and TEA stands for triethylamine.

As it will be readily understood by those skilled in the art, for a more general synthetic route, such as the one shown in Reaction Scheme 2, the 4-pyridyl group can be substituted with an R* group (as defined in connection with Scheme 1) and the indoline can be substituted with other weak nucleophilic amines of the formula NH(R)$_2$ (R defined as in connection with Reaction Scheme 1) to provide other compounds of Formula 1 analogous to compounds 242 and 243.

Isomerically pure and/or enantiomerically pure compounds and further derivatives of the 3-substituted-3-hydroxy-2-amino-propionic acid amides are obtained by separation techniques and reactions which, per se, are well known to the synthetic chemist. The experimental section of the present invention abounds in examples of such separation techniques and reactions. Some of the typical separation techniques and reactions are generally described below.

Separation of threo and erythro isomers, when both are formed in the reactions leading to the compounds of the invention, can typically be separated by chromatographic methods. The more abundantly formed threo isomers can also be converted into the erythro isomers by oxidizing to the ketone level the hydroxyl group in the 3 position of the propanoic acid moiety and subsequently reducing the resulting ketone to the hydroxyl level. (See, for example, the preparation of Compound 219).

Separation of enantiomeric mixtures can be performed on Chiralpack columns which are well known in the art. (See, for example, the preparation of Compound 204).

The amino function in the 2-position of the propanoic acid moiety is, generally speaking, more reactive towards acylation and carbamoylation than the hydroxyl group in the 3 position. Therefore, acylated derivatives of the 2-amino function can be prepared by using acyl chlorides such as acetyl chloride and hexanoyl chloride. (See, Method G and the preparation of Compound 51). Carbamate derivatives of the 2-amino function can be obtained by using chloroformates, such as benzylchloroformate. (See, for example, the preparation of Compound 58). The tertiary butyl carbamoyl function can also serve as a removable protecting group of the 2-amino function. (see for example the preparation of Compounds 219 and 224). When the 2-amino function of the compounds of the invention is already acylated or bears a carbamoyl group, then the 3-hydroxy group of the propanoic acid moiety can be subjected to acylation by reagents such as acetic anhydride. (See for example the preparation of Compound 217).

Alkylation of the 2-amino function is readily performed by condensing the compound bearing the 2-NH$_2$ group with an aldehyde to obtain a Schiff base intermediate which can be reduced, without isolation, to provide the N-alkyl, arylalkyl or heteroaryl-alkyl compound. The procedure described for preparing Compound 234 can be generalized to make compounds of the invention where the 2-amino function bears an aryl(hydroxy)alkyl or heteroaryl(hydroxy)alkyl group.

Several compounds of the invention of Formula 2 can be obtained by derivatization of compounds of Formula 1, or by such modification of the synthetic routes leading to compounds of Formula 1 which will become readily apparent to those skilled in the art in light of the present disclosure. For example, compounds of Formula 2 where R$_9$ is OH or OR$_{11}$ and R$_{10}$ is alkyl can be made by using a "ketone" bearing the R$_{10}$ group, instead of the "aldehyde" in General Reaction Scheme 1.

Compounds of Formula 2 where the R$_9$ and R$_{10}$ groups jointly form an oxime (NOH) group can be obtained by oxidizing the 3-hydroxyl group of the propanoic acid moiety to the ketone stage and reacting the resulting ketone with hydroxylamine.

Another general synthetic route for making several compounds of Formula 2 is illustrated in Synthetic Scheme 3 adapted for synthesizing (R)-2-amino-3-(pyridin-4-yl)-1-(pyrrolidin-1-yl)propan-1-one dihydrochloride, Compound 236 of the present invention.

Synthetic Scheme 3

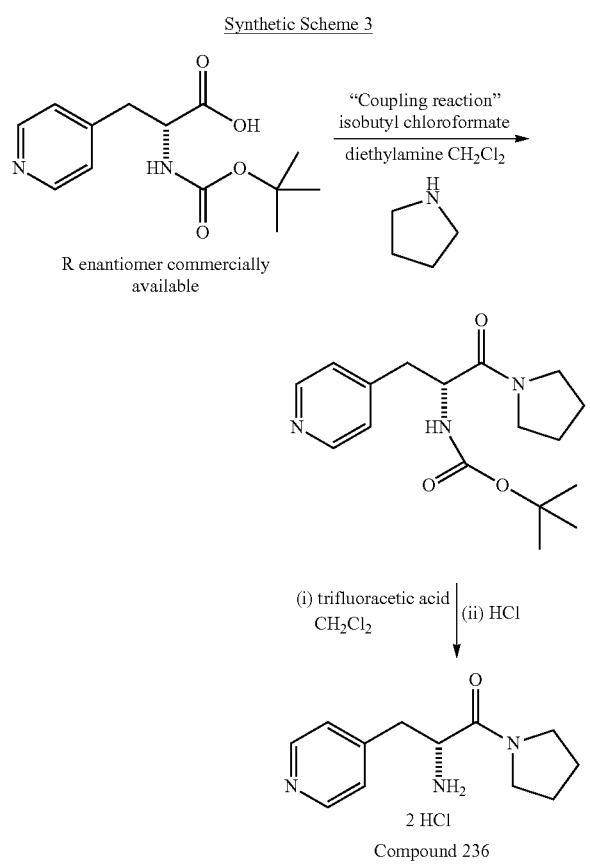

As it will be readily understood by those skilled in the art, for a more general synthetic route, such as the one shown in Reaction Synthetic Scheme 3, the 4-pyridyl group can be substituted with an R* group (as defined in connection with Scheme 1) and the pyrrolidine can be substituted with amines of the formula NH(R)$_2$ (R defined as in connection with Reaction Scheme 1) to provide other compounds of Formula 2 analogous to compound 236 or to its enantiomer (S)-2-amino-3-(pyridin-4-yl)-1-(pyrrolidin-1-yl)propan-1-one dihydrochloride Compound 240.

Detailed Description of the Synthesis of Preferred Compounds

Experimental

Preparation of Compound 12

2-Isocyano-1-(pyrrolidin-1-yl)ethanone BLE 04098

To stirred and cooled (0° C.) methyl isocyanoacetate (96% technical grade, 5.0 g, 47.8 mmol) was slowly added in 0.75 h pyrrolidine (6.5 mL, 78 mmol). The mixture was stirred for 1.5 h with continued cooling and then concentrated. The resulting oil was co-evaporated twice from CH$_2$Cl$_2$:hexane to remove residual pyrrolidine. 2-Isocyano-1-(pyrrolidin-1-yl)ethanone BLE 04098 was obtained as a yellow solid (6.85 g, 98% yield) and used in the next step without purification.

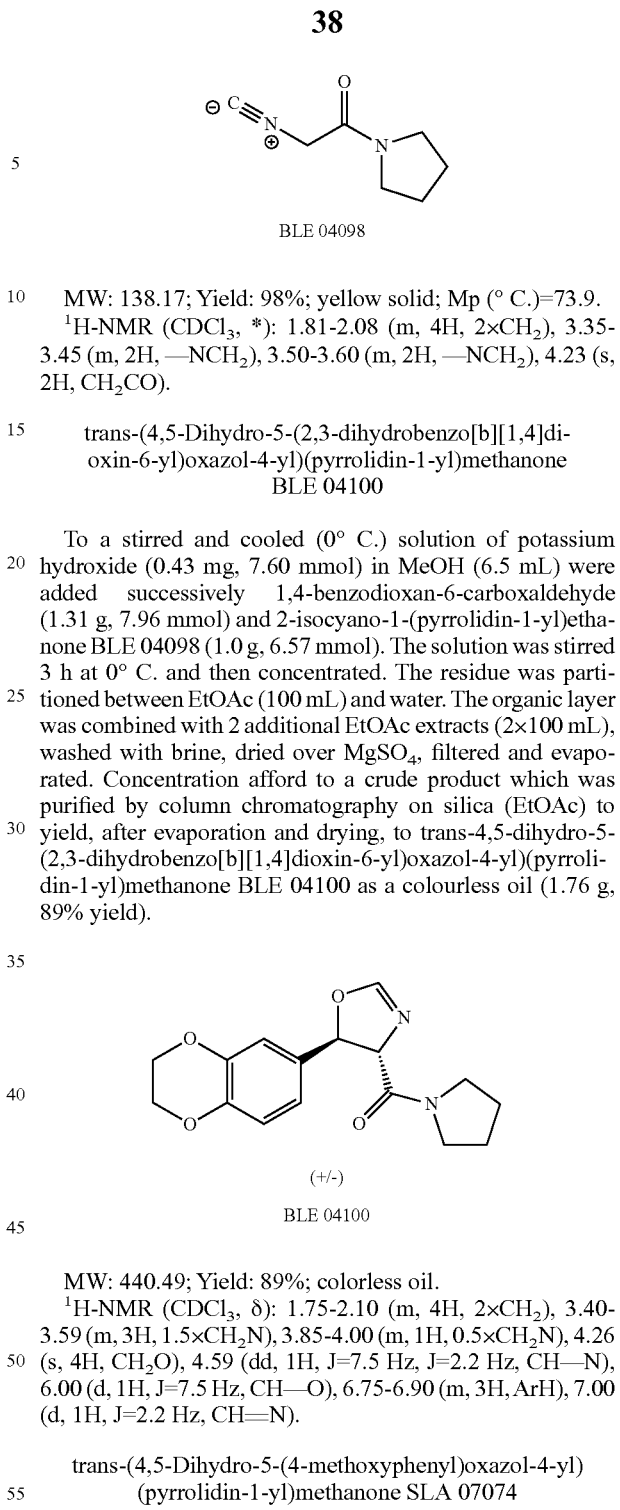

BLE 04098

MW: 138.17; Yield: 98%; yellow solid; Mp (° C.)=73.9.
$^1$H-NMR (CDCl$_3$, *): 1.81-2.08 (m, 4H, 2×CH$_2$), 3.35-3.45 (m, 2H, —NCH$_2$), 3.50-3.60 (m, 2H, —NCH$_2$), 4.23 (s, 2H, CH$_2$CO).

trans-(4,5-Dihydro-5-(2,3-dihydrobenzo[b][1,4]dioxin-6-yl)oxazol-4-yl)(pyrrolidin-1-yl)methanone BLE 04100

To a stirred and cooled (0° C.) solution of potassium hydroxide (0.43 mg, 7.60 mmol) in MeOH (6.5 mL) were added successively 1,4-benzodioxan-6-carboxaldehyde (1.31 g, 7.96 mmol) and 2-isocyano-1-(pyrrolidin-1-yl)ethanone BLE 04098 (1.0 g, 6.57 mmol). The solution was stirred 3 h at 0° C. and then concentrated. The residue was partitioned between EtOAc (100 mL) and water. The organic layer was combined with 2 additional EtOAc extracts (2×100 mL), washed with brine, dried over MgSO$_4$, filtered and evaporated. Concentration afford to a crude product which was purified by column chromatography on silica (EtOAc) to yield, after evaporation and drying, to trans-4,5-dihydro-5-(2,3-dihydrobenzo[b][1,4]dioxin-6-yl)oxazol-4-yl)(pyrrolidin-1-yl)methanone BLE 04100 as a colourless oil (1.76 g, 89% yield).

BLE 04100

MW: 440.49; Yield: 89%; colorless oil.
$^1$H-NMR (CDCl$_3$, δ): 1.75-2.10 (m, 4H, 2×CH$_2$), 3.40-3.59 (m, 3H, 1.5×CH$_2$N), 3.85-4.00 (m, 1H, 0.5×CH$_2$N), 4.26 (s, 4H, CH$_2$O), 4.59 (dd, 1H, J=7.5 Hz, J=2.2 Hz, CH—N), 6.00 (d, 1H, J=7.5 Hz, CH—O), 6.75-6.90 (m, 3H, ArH), 7.00 (d, 1H, J=2.2 Hz, CH=N).

trans-(4,5-Dihydro-5-(4-methoxyphenyl)oxazol-4-yl) (pyrrolidin-1-yl)methanone SLA 07074

To a stirred and cooled (0° C.) solution of potassium hydroxide (0.37 g, 6.57 mmol) in methanol (30 mL) was added a mixture of 4-methoxybenzaldehyde (0.88 mL, 7.23 mmol) and 2-isocyano-1-(pyrrolidin-1-yl)ethanone BLE 04098 (1.0 g, 6.57 mmol). The solution was stirred 4 h with continued cooling and then concentrated. The residue was partitioned between ethyl acetate and water. The organic layer was combined with additional ethyl acetate extracts, washed with aqueous sodium chloride and dried over MgSO$_4$. Concentration afforded a crude product as a glassy solid. Flash chromatography over silica (ethyl acetate) yielded to trans- (4,5-dihydro-5-(4-methoxyphenyl)oxazol-4-yl)(pyrrolidin-1-yl)methanone SLA 07074 as a pale yellow solid (1.2 g, 90.5%).

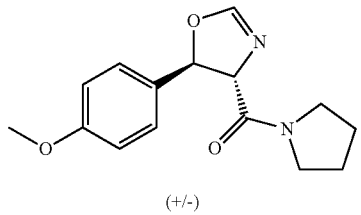

(+/-)
SLA 07074

MW: 274.32; Yield: 90.5%; pale yellow solid; Mp (° C.): 91.2.
$R_f$:0.30 (EtOAc).
$^1$H-NMR (CDCl$_3$, *): 1.75-2.08 (m, 4H, 2×CH$_2$), 3.40-3.58 (m, 3H, CH$_2$N), 3.52 (s, 3H, CH$_3$O), 3.88-3.98 (m, 1H, CH$_2$N), 4.59 (dd, 1H, J=7.6 Hz, J=2.2 Hz, CH—N), 6.06 (d, 1H, J=7.6 Hz, CH—O), 6.90 (d, 2H, J=8.7 Hz, ArH), 7.01 (d, 1H, J=2.2 Hz, CH=N), 7.25 (d, 2H, J=8.7 Hz, ArH).
MS-ESI m/z (% rel. Int.): 275.1 ([MH]$^+$, 10), 247.1 (100).
HPLC: Method A, detection UV 280 nm, SLA 07074 RT=5.2 min, peak area 92%.

DL-threo-2-Amino-3-hydroxy-3-(4-methoxyphenyl)-1-(pyrrolidin-1-yl)propan-1-one hydrochloride SLA 07078

To a stirred solution of trans-(4,5-dihydro-5-(4-methoxyphenyl)oxazol-4-yl)(pyrrolidin-1-yl)methanone SLA 07074 (1.61 g, 5.93 mmol) in methanol (13 mL) was added hydrochloric acid (1 mL). After heating at 50° C. for 3 h the mixture reaction was concentrated and the resulting yellow oil was co-evaporated twice with ethyl acetate before solidifying. Trituration (ethyl acetate) and drying afforded DL-threo-2-amino-3-hydroxy-3-(4-methoxyphenyl)-1-(pyrrolidin-1-yl)propan-1-one hydrochloride SLA 07078 as a white solid (1.64 g, 93%).

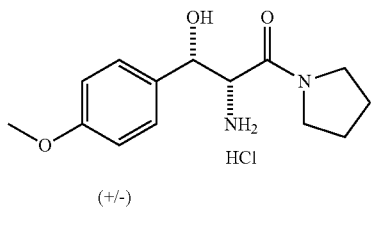

(+/-)
SLA 07078

MW: 300.78; Yield: 93%; white Solid; Mp (° C.): 177.0.
$^1$H-NMR (CD$_3$OD, *): 1.32-1.50 (m, 1H, 0.5×CH$_2$), 1.50-1.88 (m, 3H, 1.5×CH$_2$), 2.15-2.28 (m, 1H, CH$_2$N), 3.15-3.42 (m, 3H, 1.5×CH$_2$N), 3.79 (s, 3H, CH$_3$O), 4.06 (d, 1H, J=9.2 Hz, CH—N), 4.78 (d, 1H, J=9.2 Hz, CHO), 6.94 (d, 2H, J=8.5 Hz, ArH), 7.34 (d, 2H, J=8.5 Hz, ArH).
$^{13}$C-NMR (CD$_3$OD, *): 24.8, 26.6, 47.2, 47.6, 55.9, 59.6, 73.9, 115.0 (2×C), 128.9 (2×C), 132.5, 161.7, 166.4.

DL-threo-2-amino-3-(2,3-dihydrobenzo[b][1,4]dioxin-6-yl)-3-hydroxy-1-(pyrrolidin-1-yl)propan-1-one hydrochloride Compound 12

To a stirred solution of trans-4,5-dihydro-5-(2,3-dihydrobenzo[b][1,4]dioxin-6-yl)oxazol-4-yl)(pyrrolidin-1-yl) methanone BLE 04100 (1.74 g, 5.77 mmol) in methanol (15 mL) was added hydrochloric acid (1 mL). After heating at 50° C. for 3 h the mixture reaction was concentrated and the resulting yellow oil was co-evaporated twice with ethyl acetate before solidifying. Trituration (ethyl acetate) and drying afforded DL-threo-2-amino-3-(2,3-dihydrobenzo[b][1,4]dioxin-6-yl)-3-hydroxy-1-(pyrrolidin-1-yl)propan-1-one hydrochloride Compound 12 as a white solid (1.85 g, 95%).

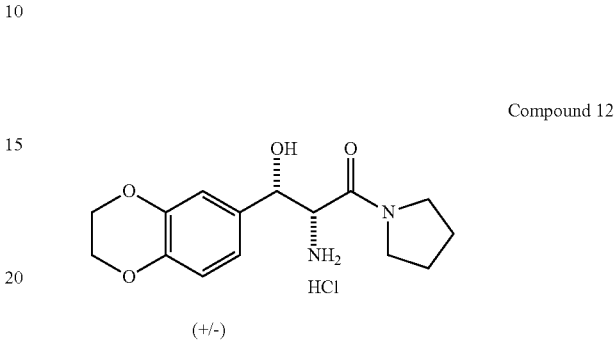

Compound 12

(+/-)

MW: 328.79; Yield: 95.0%; White Solid; Mp (° C.): 176.2.
$^1$H-NMR (CD$_3$OD, *): 1.42-1.58 (m, 1H, 0.5×CH$_2$), 1.58-1.70 (m, 1H, 0.5×CH$_2$), 1.70-1.88 (m, 2H, CH$_2$), 3.20-3.45 (m, 4H, 2×N—CH$_2$), 4.06 (d, 1H, J=9.1 Hz, CH—N), 4.25 (s, 2H, OCH$_2$), 4.75 (d, 1H, J=9.2 Hz, CH—O), 4.89 (s, 2H, OCH$_2$), 6.82-6.95 (m, 3H, ArH).
$^{13}$C-NMR (CD$_3$OD, *): 24.9, 26.7, 47.3, 47.6, 59.5, 65.7, 73.6, 116.4, 118.3, 120.3, 133.7, 145.1, 145.6, 166.4.

Preparation of Compound 18
Method B:

To a stirred and cooled (0° C.) solution of potassium hydroxide (380 mg, 5.80 mmol) in MeOH (5 mL) were added successively aldehyde (5.80 mmol) and 2-isocyano-1-(pyrrolidin-1-yl)ethanone BLE 04098 (0.8 g, 5.8 mmol). The solution was stirred 3 h at 0° C. and then concentrated. The residue was partitioned between CH$_2$Cl$_2$ (100 mL) and water. The organic layer was washed with brine, dried over MgSO$_4$, filtered and evaporated. Concentration afford to a crude product which was purified by column chromatography on silica (cyclohexane:EtOAc=70:30 to 0:100) to yield, after evaporation and drying, to an intermediate oxazoline. To a stirred solution of oxazoline in methanol (15 mL) was added hydrochloric acid (1 mL, 12 mmol). After heating at 60° C. for 2 h, the mixture reaction was then concentrated and the resulting yellow oil was coevaporated twice with MeOH before solidifying. Trituration in EtOAc:MeOH=10:1 followed by filtration gave title compound as a white solid.

DL-threo-2-Amino-3-(biphenyl-4-yl)-3-hydroxy-1-(pyrrolidin-1-yl)propan-1-one hydrochloride Compound 18

The compound was prepared according to method B with 4-phenylbenzaldehyde (1.05 g, 5.78 mmol). DL-threo-2-Amino-3-(biphenyl-4-yl)-3-hydroxy-1-(pyrrolidin-1-yl)propan-1-one hydrochloride Compound 18 was obtained as a pale brown solid (0.55 g, 28% yield).

Compound 18

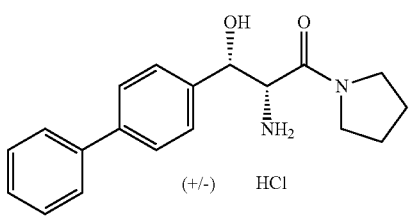

(+/−) HCl

MW: 346.85; Yield: 28%; Pale Brown Solid; Mp (° C.): 197.3.

$^1$H-NMR (CD$_3$OD, *): 1.25-1.42 (m, 1H, 0.5×CH$_2$), 1.50-1.60 (m, 1H, 0.5×CH$_2$), 1.60-1.80 (m, 1H, 0.5×CH$_2$), 2.20-2.30 (m, 2H, N—CH$_2$), 3.15-3.30 (m, 2H, N—CH$_2$), 3.30-3.45 (1H, m, N—CH$_2$), 4.13 (d, 1H, J=9.2 Hz, CH—N), 4.85-4.95 (m, 1H, CH—O), 7.32-7.38 (m, 1H, ArH), 7.46 (dd, 2H, J=7.1 Hz, J=7.8 Hz, ArH), 7.52 (d, 2H, J=8.3 Hz, ArH), 7.58-7.70 (m, 4H, ArH).

$^{13}$C-NMR (CD$_3$OD, *): 24.8, 26.5, 47.2, 47.6, 59.5, 78.7, 127.9, 128.1, 128.2, 128.8, 130.0, 139.7, 141.6, 143.3, 166.3.

MS-ESI m/z (% rel. Int.): 311.2 ([MH]$^+$, 60).

HPLC: Method A, detection UV 254 nm, Compound 18 RT=4.50 min, peak area 99.9%.

Preparation of 2-Isocyano Derivatives: SLA 07116B, SLA 07116C, SLA 07118, SLA 07130A, SLA 07178, and SLA 07184A.

2-Isocyano-1-(piperidin-1-yl)ethanone SLA 07116B

Prepared in accordance with Method B with methyl isocyanoacetate (2.46 g, 24.63 mmol) and piperidine (3.22 mL, 37.85 mmol). The reaction mixture was stirred 1 h at RT and then concentrated. The residue was dissolved in dichloromethane (50 mL) and the organic layer was washed with 10% aqueous citric acid (2×25 mL), dried over MgSO$_4$, filtered and evaporated. 2-Isocyano-1-(piperidin-1-yl)ethanone SLA 07116B was obtained as an orange solid (3.13 g, 83% yield).

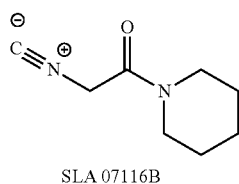

SLA 07116B

MW: 152.19; Yield: 83%; Orange Solid; Mp (° C.): 81.6.

$^1$H-NMR (CDCl$_3$, *): 1.56-1.74 (m, 6H, CH$_2$C), 3.33 (t, 2H, J=5.7 Hz, CH$_2$N), 3.58 (t, 2H, J=5.7 Hz, CH$_2$N), 4.29 (s, 2H, CH$_2$CO).

tert-Butyl 4-(2-isocyanoacetyl)piperazine-1-carboxylate SLA 07116C

Prepared in accordance with Method B with methyl isocyanoacetate (2.51 g, 25.29 mmol) and piperazine-1-carboxylic acid tert-butyl ester (6.28 g, 33.85 mmol. The reaction mixture was stirred 1 h at RT and then concentrated. The residue was dissolved in dichloromethane (50 mL) and the organic layer was washed with 10% aqueous citric acid (2×25 mL), dried over MgSO$_4$, filtered and evaporated. tert-Butyl 4-(2-isocyanoacetyl)piperazine-1-carboxylate SLA 07116C was obtained as a colorless oil (0.41 g, 6.5% yield).

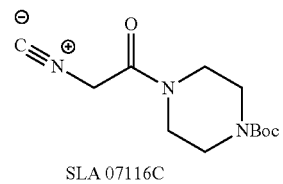 [SMILES: C#[N+]CC(=O)N1CCN(C(=O)OC(C)(C)C)CC1]

SLA 07116C

MW: 253.14; Yield: 6.5%; Colorless oil.

$^1$H-NMR (CDCl$_3$, *): 1.47 (s, 9H, tBu), 3.38 (t, 2H, J=5.3 Hz, CH$_2$N), 3.45-3.53 (m, 4H, CH$_2$N), 3.62 (t, 2H, J=5.5 Hz, CH$_2$N), 4.32 (s, 2H, CH$_2$CO).

2-Isocyano-1-morpholinoethanone SLA 07118

Prepared in accordance with Method B with methyl isocyanoacetate (2.51 g, 25.30 mmol) and morpholine (3.30 mL, 38.05 mmol). The reaction mixture was stirred 24 h at RT and then concentrated. The residue was dissolved in dichloromethane (50 mL) and the organic layer was washed with 10% aqueous citric acid (2×25 mL), dried over MgSO$_4$, filtered and evaporated. 2-Isocyano-1-morpholinoethanone SLA 07118 was obtained as a brown oil (2.28 g, 58% yield).

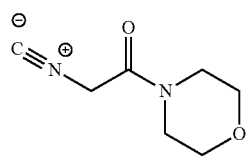

SLA 07118

MW: 154.17; Yield: 58%; Brown Oil.

R$_f$: 0.20 (EtOAc:cyclohexane=50:50).

$^1$H-NMR (CDCl$_3$, *): 3.42 (t, 2H, J=4.9 Hz, CH$_2$N), 3.65 (t, 2H, J=5.1 Hz, CH$_2$N), 3.73 (t, 4H, J=5.0 Hz, CH$_2$O), 4.31 (s, 2H, CH$_2$CO).

2-Isocyano-1-thiomorpholinoethanone SLA 07130A

Prepared in accordance with Method B with methyl isocyanoacetate (2.50 g, 25.28 mmol) and thiomorpholine (4.25 mL, 37.85 mmol). The reaction mixture was stirred 22 h at RT and then concentrated. The residue was dissolved in dichloromethane (50 mL) and the organic layer was washed with 10% aqueous citric acid (2×25 mL), dried over MgSO$_4$, filtered and evaporated. 2-Isocyano-1-thiomorpholinoethanone SLA 07130A was obtained as a yellow solid (3.05 g, 71% yield).

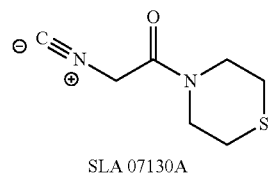

SLA 07130A

MW: 170.23; Yield: 71%; Yellow Solid; Mp (° C.): 144.4.

R$_f$: 0.35 (EtOAc:cyclohexane=50:50).

¹H-NMR (CDCl₃, *): 2.68 (m, 4H, 2×CH₂S), 3.67 (m, 2H, N—CH₂), 3.90 (m, 2H, N—CH₂), 4.31 (s, 2H, COCH₂).

2-Isocyano-1-(2H-pyrrol-1(5H)-yl)ethanone SLA 07178

Prepared in accordance with Method B with methyl isocyanoacetate (1.00 g, 10.10 mmol) and dihydro-1H-pyrrole (1.01 mL, 15.15 mmol). The reaction mixture was stirred 5 h at 50° C. and concentrated. The residue was dissolved in dichloromethane (50 mL) and the organic layer was washed with 10% aqueous citric acid (2×25 mL), dried over MgSO₄, filtered and evaporated. 2-Isocyano-1-(2H-pyrrol-1(5H)-yl) ethanone SLA 07178 was obtained (1.0 g, 73% yield) as a yellow solid.

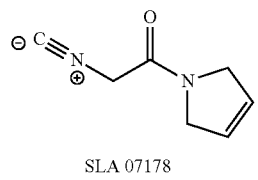

SLA 07178

MW: 136.15; Yield: 73%; Yellow Solid.
$R_f$:0.35 (EtOAc:cyclohexane=50:50).
¹H-NMR (CDCl₃, *): 4.23 (s, 4H, 2×CH₂N), 4.31 (s, 2H, CH₂N), 5.80-5.86 (m, 1H, CH═C), 5.90-5.95 (m, 1H, CH═C).

N,N-Diethyl-2-isocyanoacetamide SLA 07184A

Prepared in accordance with Method B with methyl isocyanoacetate (2.50 g, 25.29 mmol) and diethylamine (1.96 mL, 37.94 mmol). The reaction mixture was stirred 5 h at 50° C. and concentrated. The residue was dissolved in dichloromethane (50 mL) and the organic layer was washed with 10% aqueous citric acid (2×25 mL), dried over MgSO₄, filtered and evaporated. N,N-Diethyl-2-isocyanoacetamide SLA 07184A was obtained (1.213 g, 34% yield) as a brown oil.

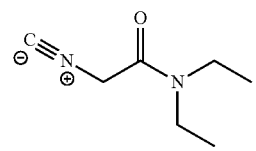

SLA 07184A

MW: 140.18; Yield: 34%; Brown Oil.
$R_f$:0.35 (EtOAc:cyclohexane=50:50).
¹H-NMR (CDCl₃, *): 1.15-1.26 (m, 6H, CH₃), 3.21-3.30 (m, 2H, CH₂N), 3.38-3.45 (m, 2H, CH₂N), 4.26 (s, 2H, CH₂CO).
Preparation of Oxazolines: BLE 04110B, SLA 07122A, SLA 07124A, SLA 07124B, SLA 07132, BLE 04110A, Compound 19, BLE 04124A, BLE 04124B, BLE 04124C, BLE 04124D, BLE 04130B, BLE 04130C, BLE 04130D, BLE 04136B, BLE 04136C, BAL 01016, BLE 04136D, BAL 01014, SLA 07194A, SLA 07174, BAL 01028A, BLA 01028B, SLA 07158 and SLA 07180.

trans-(4,5-Dihydro-5-(pyridin-3-yl)oxazol-4-yl)(pyrrolidin-1-yl)methanone BLE 04110B General Method D for Oxazolines Formation:
To a stirred and cooled (0° C.) solution of potassium hydroxide (0.55 g, 9.80 mmol) in methanol (10 mL) were added a mixture of 3-pyridine carboxaldehyde (1.03 mL, 10.84 mmol) and 2-isocyano-1-(pyrrolidin-1-yl)ethanone BLE 04098 (1.50 g, 10.86 mmol). The solution was stirred 3 h at 0° C. and then concentrated. The residue was partitioned between ethyl acetate (100 mL) and water. The organic layer was combined with two additional ethyl acetate extracts (2×100 mL), washed with aqueous sodium chloride and dried over MgSO₄, filtered and evaporated. Concentration afforded a crude product which was purified by column chromatography on silica (CH₂Cl₂:MeOH=98:2) to yield to trans-(4,5-dihydro-5-(pyridin-3-yl)oxazol-4-yl)(pyrrolidin-1-yl) methanone BLE 04110B (0.95 g, 39% yield) as a pale yellow pale solid.

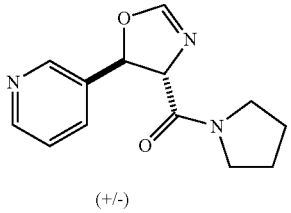

(+/-)
BLE 04110B

MW: 245.28; Yield: 39%; Yellow Pale Solid; Mp (° C.): 107.0.
¹H-NMR (CDCl₃, *): 1.78-2.10 (m, 4H, 2×CH₂), 3.40-3.61 (m, 3H, CH₂N), 3.90-4.04 (m, 1H, CH₂N), 4.59 (dd, 1H, J=7.7 Hz, J=2.2 Hz, CH—N), 6.21 (d, 1H, J=7.7 Hz, CH—O), 7.04 (d, 1H, J=2.2 Hz, O—CH═N), 7.33 (m, 1H, ArH), 7.64 (m, 1H, ArH), 8.59 (d, 2H, J=2.8 Hz, ArH).
¹³C-NMR (CDCl₃, *): 24.2, 26.0, 46.4, 46.6, 75.7, 79.3, 123.7, 133.5, 135.3, 147.6, 149.9, 155.2, 166.2.

trans-(4,5-Dihydro-5-(pyridin-4-yl)oxazol-4-yl)(piperidin-1-yl)methanone SLA 07122A SLA 07122A was prepared in accordance with method D using 2-isocyano-1-(piperidin-1-yl)ethanone (0.4 g, 26.3 mmol), potassium hydroxide (0.15 g, 26.7 mmol) in methanol (5 mL) and pyridine-4-carbaldehyde (0.37 mL, 40.9 mmol). The solution was stirred 20 h at 0° C. trans-(4,5-Dihydro-5-(pyridin-4-yl)oxazol-4-yl)(piperidin-1-yl)methanone SLA 07122A was obtained as a yellow solid (0.353 g, 52% yield).

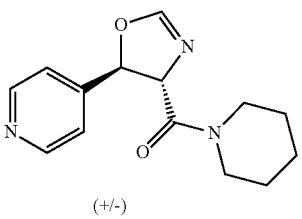

(+/-)
SLA 07122A

MW: 259.30; Yield: 52%; Yellow Solid; Mp (° C.): 111.7.
$R_f$:0.80 (MeOH:CH₂Cl₂=10:90).

¹H-NMR (CDCl₃, *): 1.55-1.78 (m, 6H, 3×CH₂), 3.45-3.60 (m, 2H, CH₂N), 3.70-3.85 (m, 2H, CH₂N), 4.60 (dd, 1H, J=7.8 Hz, J=2.3 Hz, CH—N), 6.27 (d, 1H, J=7.8 Hz, CH—O), 7.01 (d, 1H, J=2.3 Hz, CH=N), 7.23 (dd, 2H, J=4.5 Hz, J=1.6 Hz, ArH), 8.61 (dd, 2H, J=4.5 Hz, J=1.5 Hz, ArH).

trans-(4,5-Dihydro-5-(pyridin-4-yl)oxazol-4-yl)(morpholino)methanone SLA 07124A SLA 07118 was prepared in accordance with method D using 2-isocyano-1-morpholinoethanone (0.40 g, 25.95 mmol), potassium hydroxide (0.146 g, 26.0 mmol) in methanol (5 mL) and pyridine-4-carbaldehyde (0.36 mL, 40.4 mmol). The solution was stirred 22 h at 0° C. trans-(4,5-Dihydro-5-(pyridin-4-yl)oxazol-4-yl)(morpholino)methanone SLA 07124A was obtained as a yellow solid (0.168 g, 25% yield).

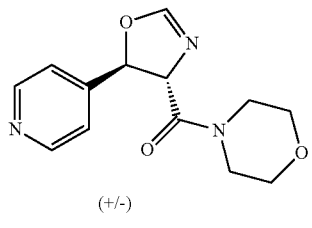

SLA 07124A

MW: 261.28; Yield: 25%; Yellow Solid; Mp (° C.): 90.5. R$_f$:0.30 (EtOAc:cyclohexane=20:80).
¹H-NMR (CDCl₃, *): 3.46-4.02 (m, 8H, 2×CH₂O, 2×CH₂N), 4.56 (dd, 1H, J=7.8 Hz, J=2.3 Hz, CH—N), 6.27 (d, 1H, J=7.9 Hz, CH—O), 7.02 (d, 1H, J=2.3 Hz, CH=N), 7.24 (dd, 2H, J=4.6 Hz, J=1.4 Hz, ArH), 8.63 (dd, 2H, J=4.5 Hz, J=1.6 Hz, ArH).

trans-(4,5-Dihydro-5-(pyridin-4-yl)oxazol-4-yl)(4-tert-butyloxycarbonyl-piperazin-1-yl)methanone SLA 07124B SLA 07124B was prepared in accordance with method D using tert-butyl 4-(2-isocyanoacetyl)piperazine-1-carboxylate SLA 07116C (0.41 g, 16.20 mmol), potassium hydroxide (0.91 g, 16.2 mmol) in methanol (5 mL) and pyridine-4-carbaldehyde (0.227 mL, 25.2 mmol). The solution was stirred 22 h at 0° C. trans-(4,5-Dihydro-5-(pyridin-4-yl)oxazol-4-yl)(4-tert-butyloxycarbonyl-piperazin-1-yl)methanone SLA 07124B was obtained as a pale yellow solid (0.335 g, 58% yield).

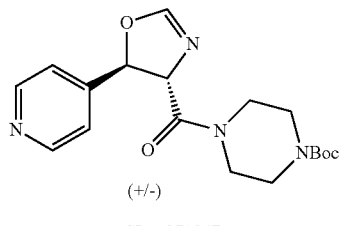

SLA 07124B

MW: 360.41; Yield: 58%; Pale Yellow Solid; Mp (° C.): 157.2° C.

¹H-NMR (CDCl₃, *): 1.47 (s, 9H, tBu), 3.25-4.02 (m, 8H, CH₂N), 4.58 (dd, 1H, J=7.8 Hz, J=2.3 Hz, CH—N), 6.27 (d, 1H, J=7.8 Hz, CH—O), 7.01 (d, 1H, J=2.3 Hz, CH=N), 7.24 (dd, 2H, J=4.6 Hz, J=1.4 Hz, ArH), 8.62 (dd, 2H, J=4.5 Hz, J=1.6 Hz, ArH).

trans-(4,5-Dihydro-5-(pyridin-4-yl)oxazol-4-yl)(thiomorpholino)methanone SLA 07132

SLA 07132 was prepared in accordance with method D using 2-Isocyano-1-thiomorpholinoethanone SLA 07130A (0.752 g, 4.41 mmol), potassium hydroxide (0.250 g, 4.45 mmol) in methanol (10 mL) and pyridine-4-carbaldehyde (0.436 mL, 4.85 mmol). The solution was stirred 24 h at 0° C. trans-(4,5-Dihydro-5-(pyridin-4-yl)oxazol-4-yl)(thiomorpholino)methanone SLA 07132 was obtained as a yellow foam (1.01 g, 83%).

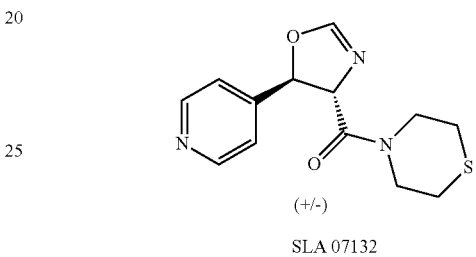

SLA 07132

MW: 277.35; Yield: 83%; Yellow Foam.
R$_f$:0.80 (MeOH:CH₂Cl₂=10:90).
¹H-NMR (CDCl₃, *): 2.53-2.92 (m, 4H, 2×CH₂), 3.58-3.70 (m, 1H, CH₂N), 3.78-3.88 (m, 1H, CH₂N), 4.15-4.30 (m, 2H, CH₂N), 4.56 (dd, J=7.8 Hz, J=2.3 Hz, 2H, CH—N), 6.27 (d, 1H, J=7.8 Hz, CH—O), 7.02 (d, 1H, J=2.3 Hz, N=CH—O), 7.22 (d, 2H, J=6.1 Hz, ArH), 8.61 (dd, 2H, J=6.1 Hz, ArH).
¹³C-NMR (CDCl₃, *): 27.3, 28.0, 45.4, 48.6, 74.9, 79.6, 120.0 (2×C), 148.5, 150.3 (2×C), 154.8, 166.2.

trans-(4,5-Dihydro-5-(pyridin-2-yl)oxazol-4-yl)(pyrrolidin-1-yl)methanone BLE 04110A BLE 04110A was prepared in accordance with method D using 2-pyridine carboxaldehyde (1.02 mL, 10.84 mmol). Trans-(4,5-dihydro-5-(pyridin-2-yl)oxazol-4-yl)(pyrrolidin-1-yl)methanone BLE 04110A was obtained as a yellow pale oil (0.45 g, 19% yield).

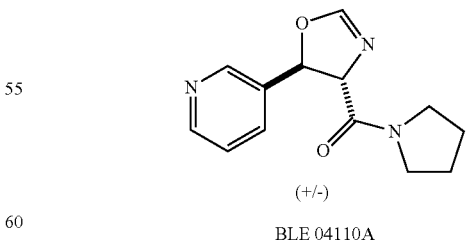

BLE 04110A

MW: 245.28; Yield: 19%; Yellow Pale Oil.
¹H-NMR (CDCl₃, *): 1.73-2.08 (m, 4H, 2×CH₂), 3.35-3.70 (m, 3H, CH₂N), 3.85-4.00 (m, 1H, CH₂N), 5.05 (dd, 1H, J=6.9 Hz, J=2.2 Hz, CH—N), 6.18 (d, 1H, J=6.9 Hz, CH—O), 7.02 (d, 1H, J=2.1 Hz, O—CH=N), 7.25 (m, 1H, ArH), 7.43 (d, 1H, J=7.8 Hz, ArH), 7.69 (dt, 1H, J=7.8 Hz, J=1.8 Hz ArH), 8.62 (m, 1H, ArH).

$^{13}$C-NMR (CDCl$_3$, *): 24.2, 25.9, 46.3, 46.5, 73.4, 81.3, 121.5, 123.2, 136.8, 149.8, 154.8, 158.0, 166.9.

trans-(4,5-Dihydro-5-(pyridin-4-yl)oxazol-4-yl)(pyrrolidin-1-yl)methanone Compound 19

SLA 07092 was prepared in accordance with method D using pyridine-4-carbaldehyde (1.88 mL, 19.76 mmol), KOH (1.01 g, 18.00 mmol) in methanol (18 mL) and 2-isocyano-1-(pyrrolidin-1-yl)ethanone BLE 04098 (2.73 g, 19.76 mmol). The residue was partitioned between ethyl acetate (200 mL) and water (150 mL). The organic layer was combined with additional ethyl acetate extracts (2×150 mL), washed with aqueous sodium chloride (2×150 mL) and dried over MgSO$_4$, filtered and evaporated. Trans-(4,5-dihydro-5-(pyridin-4-yl)oxazol-4-yl)(pyrrolidin-1-yl)methanone Compound 19 was obtained as a white solid (4.32 g, 98% yield).

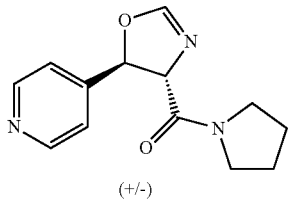

Compound 19

(+/−)

MW: 245.28; Yield: 98%; White Solid; Mp (° C.)=69.2. R$_f$:0.65 (MeOH:CH$_2$Cl$_2$=10:90).

$^1$H-NMR (CDCl$_3$, *): 1.78-2.06 (m, 4H, 2×CH$_2$), 3.44-3.60 (m, 3H, CH$_2$N), 3.90-4.01 (m, 1H, CH$_2$N), 4.52 (dd, 1H, J=7.9 Hz, J=2.2 Hz, CH—N), 6.19 (d, J=7.9 Hz, 1H, CH—O), 7.03 (d, 1H, J=2.2 Hz, N=CH—O), 7.24 (dd, 2H, J=4.5 Hz, J=1.5 Hz, ArH), 8.61 (dd, 2H, J=4.5 Hz, J=1.5 Hz, ArH).

trans-(4,5-Dihydro-5-(thiophen-3-yl)oxazol-4-yl)(pyrrolidin-1-yl)methanone BLE 04124A BLE 04124A was prepared in accordance with method D using thiophen-3-carboxaldehyde (0.475 mL, 5.42 mmol), KOH (0.276 mg, 4.92 mmol) in methanol (5 mL) and 2-isocyano-1-(pyrrolidin-1-yl)ethanone BLE 04098 (0.75 g, 5.43 mmol). After work-up the residue obtained was recrystallized from ethyl acetate to obtain after filtration trans-(4,5-dihydro-5-(thiophen-3-yl)oxazol-4-yl)(pyrrolidin-1-yl)methanone BLE 04110A as a yellow pale solid (0.498 g, 40% yield).

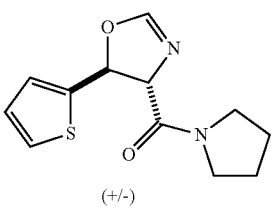

(+/−)

BLE 04124A

MW: 250.32; Yield: 40.5%; Yellow Pale Solid; Mp (° C.): 105.9.

$^1$H-NMR (CDCl$_3$, *): 1.78-2.10 (m, 4H, CH$_2$), 3.42-3.61 (m, 3H, CH$_2$N), 3.90-4.02 (m, 1H, CH$_2$N), 4.63 (dd, 1H, J=7.4 Hz, J=2.2 Hz, CH—N), 6.20 (d, 1H, J=7.4 Hz, CH—O), 6.98 (d, 1H, J=2.2 Hz, O—CH=N), 7.03 (dd, 1H, J=5.0 Hz, J=1.3 Hz, CH=C), 7.30 (dt, 1H, J=3.0 Hz, J=1.3 Hz, CH=C), 7.36 (dd, 1H, J=5.0 Hz, J=3.0 Hz, CH=C).

$^{13}$C-NMR (CDCl$_3$, *): 24.2, 26.0, 46.4, 46.6, 74.6, 77.9, 122.7, 125.1, 127.3, 140.4, 155.3, 166.7.

MS-ESI m/z (% rel. Int.): 251.0 ([MH]$^+$, 17), 223 (40), 179.9 (60), 151.9 (63), 123.9 (100).

HPLC: Method A, detection UV 254 nm, BLE 04124A, RT=4.4 min, peak area 98.0%.

trans-(4,5-Dihydro-5-(thiophen-2-yl)oxazol-4-yl)(pyrrolidin-1-yl)methanone BLE 04124B BLE 04124B was prepared in accordance with method D using thiophen-2-carboxaldehyde (0.507 mL, 5.42 mmol), KOH (0.276 mg, 4.92 mmol) in methanol (5 mL) and 2-isocyano-1-(pyrrolidin-1-yl)ethanone BLE 04098 (0.75 g, 5.43 mmol). After work-up the residue obtained was purified by column chromatography (EtOAc) to led after evaporation to trans-(4,5-dihydro-5-(thiophen-2-yl)oxazol-4-yl)(pyrrolidin-1-yl)methanone BLE 04124B as a yellow pale solid (0.713 g, 58% yield).

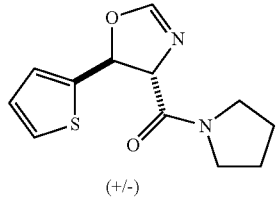

(+/−)

BLE 04124B

MW: 250.32; Yield: 58%; Yellow Pale Solid; Mp (° C.): 71.3.

$^1$H-NMR (CDCl$_3$, *): 1.78-2.10 (m, 4H, CH$_2$), 3.42-3.62 (m, 3H, CH$_2$N), 3.90-4.03 (m, 1H, CH$_2$N), 4.76 (dd, 1H, J=7.3 Hz, J=2.2 Hz, CH—N), 6.37 (d, 1H, J=7.3 Hz, CH—O), 6.96 (d, 1H, J=2.2 Hz, O—CH=N), 7.00 (dd, 1H, J=5.0 Hz, J=3.5 Hz, CH=C), 7.11 (d, 1H, J=3.1 Hz, CH=C), 7.33 (dd, 1H, J=5.0 Hz, J=0.7 Hz, CH=C).

$^{13}$C-NMR (CDCl$_3$, *): 24.2, 26.0, 46.4, 46.6, 75.5, 77.6, 126.3 (2×C), 127.1, 142.0, 154.9, 166.3.

MS-ESI m/z (% rel. Int.): 251.0 ([MH]$^+$, 15), 223 (100).

HPLC: Method A, detection UV 254 nm, BLE 04124B, RT=3.8 min, peak area>90%.

trans-(4,5-Dihydro-5-(thiazol-2-yl)oxazol-4-yl)(pyrrolidin-1-yl)methanone BLE 04124C BLE 04124C was prepared in accordance with method D using 2-thiazolecarboxaldehyde (0.476 mL, 5.42 mmol), KOH (0.276 mg, 4.92 mmol) in methanol (5 mL) and 2-isocyano-1-(pyrrolidin-1-yl)ethanone BLE 04098 (0.75 g, 5.43 mmol). After work-up the residue obtained was purified by column chromatography (EtOAc) to led after evaporation to trans-(4,5-dihydro-5-(thiazol-2-yl)oxazol-4-yl)(pyrrolidin-1-yl)methanone BLE 04124C as a colourless oil (0.564 g, 45.5% yield).

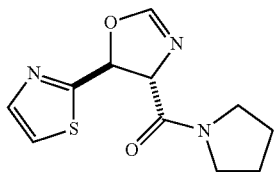

(+/-)

BLE 04124C

MW: 251.3; Yield: 45.5%; colourless Oil.
¹H-NMR (CDCl₃, *): 1.80-2.10 (m, 4H, CH₂), 3.47-3.70 (m, 3H, CH₂N), 3.91-4.02 (m, 1H, CH₂N), 5.18 (dd, 1H, J=6.4 Hz, J=2.2 Hz, CH—N), 6.40 (d, 1H, J=6.4 Hz, CH—O), 6.97 (d, 1H, J=2.2 Hz, O—CH=N), 7.38 (d, 1H, J=3.3 Hz, CH=C), 7.81 (d, 1H, J=3.3 Hz, CH=C).
¹³C-NMR (CDCl₃, *): 24.2, 26.0, 46.4, 46.5, 73.7, 78.2, 120.1, 143.3, 154.3, 166.1, 168.2.
MS-ESI m/z (% rel. Int.): 252.0 ([MH]⁺, 18), 225 (30), 198.9 (37), 153.9 (48), 143.0 (100).
HPLC: Method A, detection UV 254 nm, BLE 04124C, RT=3.5 min, peak area>90%.

trans-(5-(Benzo[b]thiophen-3-yl)-4,5-dihydrooxazol-4-yl)(pyrrolidin-1-yl)methanone BLE 04124D BLE 04124D was prepared in accordance with method D using thianaphtene-3-carboxaldehyde (0.88 g, 5.42 mmol), KOH (0.276 mg, 4.92 mmol) in methanol (5 mL) and 2-isocyano-1-(pyrrolidin-1-yl)ethanone BLE 04098 (0.75 g, 5.43 mmol). After work-up the residue obtained was purified by column chromatography (EtOAc) to led after evaporation to trans-(5-(benzo[b]thiophen-3-yl)-4,5-dihydrooxazol-4-yl)(pyrrolidin-1-yl)methanone BLE 04124D as a white solid (1.12 g, 75.5% yield).

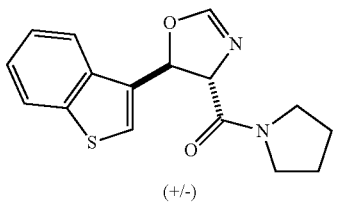

(+/-)

BLE 04124D

MW: 300.38; Yield: 75.5%; White Solid; Mp (° C.): 92.2.
¹H-NMR (CDCl₃, *): 1.75-2.08 (m, 4H, CH₂), 3.36-3.49 (m, 1H, CH₂N), 3.50-3.62 (m, 1H, CH₂N), 3.89-4.00 (m, 1H, CH₂N), 4.75 (dd, 1H, J=7.6 Hz, J=2.2 Hz, CH—N), 6.54 (d, 1H, J=7.6 Hz, CH—O), 7.08 (d, 1H, J=2.2 Hz, O—CH=N), 7.35 (m, 2H, ArH), 7.45 (s, 1H, C=CH—S), 7.67-7.75 (m, 1H, ArH), 7.84-7.92 (m, 1H, ArH).
¹³C-NMR (CDCl₃, *): 24.2, 26.0, 46.5, 46.6, 73.3, 77.7, 121.8, 123.1, 124.1, 124.6, 124.8, 134.0, 136.4, 141.0, 155.4, 166.6.
MS-ESI m/z (% rel. Int.): 301.0 ([MH]⁺, 30), 273.0 (100).
HPLC: Method A, detection UV 254 nm, BLE 04124D, RT=4.2 min, peak area 92.0%.

trans-(5-(Furan-3-yl)-4,5-dihydrooxazol-4-yl)(pyrrolidin-1-yl)methanone BLE 04130B BLE 04130B was prepared in accordance with method D using 3-furaldehyde (0.453 g, 5.42 mmol), KOH (0.276 mg, 4.92 mmol) in methanol (5 mL) and 2-isocyano-1-(pyrrolidin-1-yl)ethanone BLE 04098 (0.75 g, 5.43 mmol). After work-up the residue was washed with a minimum of ethyl acetate to led, after filtration and drying, to trans-(5-(furan-3-yl)-4,5-dihydrooxazol-4-yl)(pyrrolidin-1-yl)methanone BLE 04130B as a white solid (0.837 g, 72.5% yield).

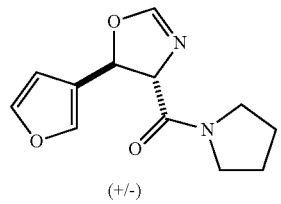

(+/-)

BLE 04130B

MW: 234.25; Yield: 72.5%; White Solid; Mp (° C.): 136.7.
¹H-NMR (CDCl₃, *): 1.80-2.10 (m, 4H, CH₂), 3.47-3.58 (m, 3H, CH₂N), 3.91-4.02 (m, 1H, CH₂N), 4.61 (dd, 1H, J=7.3 Hz, J=2.1 Hz, CH—N), 6.10 (d, 1H, J=7.3 Hz, CH—O), 6.36 (dd, 1H, J=1.6 Hz, J=0.6 Hz, CH=C), 6.95 (d, 1H, J=2.1 Hz, O—CH=N), 7.44 (t, 1H, J=1.6 Hz, OCH=C); 7.50 (d, 1H, J=0.6 Hz, OCH=C).
¹³C-NMR (CDCl₃, *): 24.2, 26.0, 46.4, 46.6, 70.0, 74.0, 108.1, 124.0, 140.4, 144.2, 155.3, 166.6.

trans-(4,5-Dihydro-5-(naphthalen-3-yl)oxazol-4-yl)(pyrrolidin-1-yl)methanone BLE 04130C BLE 04130C was prepared in accordance with method D using 2-naphtaldehyde (0.847 g, 5.42 mmol), KOH (0.276 mg, 4.92 mmol) in methanol (5 mL) and 2-isocyano-1-(pyrrolidin-1-yl)ethanone BLE 04098 (0.75 g, 5.43 mmol). After work-up the residue was washed with a minimum of ethyl acetate to led, after filtration and drying, to trans-(4,5-dihydro-5-(naphthalen-3-yl)oxazol-4-yl)(pyrrolidin-1-yl)methanone BLE 04130C as a white solid (0.791 g, 54.5% yield).

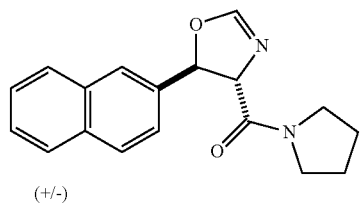

(+/-)

BLE 04130C

MW: 294.35; Yield: 54.5%; White Solid; Mp (° C.): 117.9.
¹H-NMR (CDCl₃, *): 1.78-2.07 (m, 4H, CH₂), 3.37-3.49 (m, 1H, CH₂N), 3.49-3.61 (m, 2H, CH₂N), 3.88-3.99 (m, 1H, CH₂N), 4.67 (dd, 1H, J=7.7 Hz, J=2.2 Hz, CH—N), 6.31 (d, 1H, J=7.7 Hz, CH—O), 7.10 (d, 1H, J=2.2 Hz, O—CH=N), 7.38 (dd, 1H, J=8.5 Hz, J=1.7 Hz, ArH); 7.45-7.54 (m, 2H, ArH), 7.79-7.90 (m, 4H, ArH).
¹³C-NMR (CDCl₃, *): 23.8, 25.7, 46.1, 46.2, 75.3, 81.4, 122.7, 124.9, 126.1, 126.2, 127.4, 127.7, 128.7, 132.8, 132.9, 136.5, 155.2, 166.4.
MS-ESI m/z (% rel. Int.): 295.1 ([MH]⁺, 40), 267.1 (100).
HPLC: Method A, detection UV 254 nm, BLE 04130C, RT=4.2 min, peak area 92.0%.

trans-(4,5-Dihydro-5-(naphthalen-4-yl)oxazol-4-yl)(pyrrolidin-1-yl)methanone BLE 04130D BLE 04130D was prepared in accordance with method D using 1-naphtaldehyde (0.736 mL, 5.42 mmol), KOH (0.276 mg, 4.92 mmol) in methanol (5 mL) and 2-isocyano-1-(pyrrolidin-1-yl)ethanone BLE 04098 (0.75 g, 5.43 mmol). After work-up the residue was purified by column chromatography on silica (EtOAc:cyclohexane=80:20 to 90:10) to led, after evaporation, to trans-(4,5-dihydro-5-(naphthalen-4-yl)oxazol-4-yl)(pyrrolidin-1-yl)methanone BLE 04130D as a colorless gum (0.850 g, 58.5% yield).

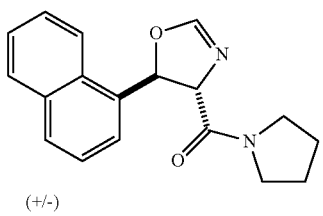

BLE 04130D

MW: 294.35; Yield: 58.5%; Colorless gum.

$^1$H-NMR (CDCl$_3$, *): 1.75-2.02 (m, 4H, CH$_2$), 3.25-3.37 (m, 1H, CH$_2$N), 3.52-3.67 (m, 2H, CH$_2$N), 3.82-3.93 (m, 1H, CH$_2$N), 4.62 (dd, 1H, J=7.0 Hz, J=2.0 Hz, CH—N), 6.89 (d, 1H, J=7.0 Hz, CH—O), 7.16 (d, 1H, J=2.0 Hz, O—CH═N), 7.44-7.58 (m, 4H, ArH), 7.80-7.90 (m, 3H, ArH).

$^{13}$C-NMR (CDCl$_3$, *): 24.2, 25.9, 46.5 (2×C), 75.3, 79.2, 122.5, 123.0, 125.4, 126.0, 126.8, 128.7, 129.0, 129.9, 133.9, 135.5, 155.5, 166.9.

MS-ESI m/z (% rel. Int.): 295.1 ([MH]$^+$, 50), 267.1 (100).

HPLC: Method A, detection UV 254 nm, BLE 04130D, RT=4.2 min, peak area 95.0%.

trans-(4,5-Dihydro-5-(quinolin-2-yl)oxazol-4-yl)(pyrrolidin-1-yl)methanone BLE 04136B BLE 04136B was prepared in accordance with method D using 2-quinoline carbaldehyde (0.852 g, 5.42 mmol), KOH (0.276 mg, 4.92 mmol) in methanol (5 mL) and 2-isocyano-1-(pyrrolidin-1-yl)ethanone BLE 04098 (0.75 g, 5.43 mmol). After work-up the residue was purified by column chromatography on silica (EtOAc) to led, after evaporation, to trans-(4,5-dihydro-5-(quinolin-2-yl)oxazol-4-yl)(pyrrolidin-1-yl)methanone BLE 04136B as a yellow pale solid (0.966 g, 60.3% yield).

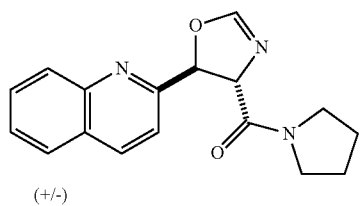

BLE 04136B

MW: 295.34; Yield: 60.3%; Yellow Pale Solid; Mp (° C.): 93.8.

$^1$H-NMR (CDCl$_3$, *): 1.85-2.10 (m, 4H, CH$_2$), 3.50-3.66 (m, 2H, CH$_2$N), 3.67-3.80 (m, 1H, CH$_2$N), 3.92-4.03 (m, 1H, CH$_2$N), 5.32 (dd, 1H, J=7.8 Hz, J=2.1 Hz, CH—N), 6.31 (d, 1H, J=7.8 Hz, CH—O), 7.06 (d, 1H, J=2.1 Hz, O—CH═N), 7.51-7.60 (m, 2H, ArH); 7.72 (t, 1H, J=8.4 Hz, ArH), 7.83 (t, 1H, J=8.1 Hz, ArH), 8.07 (d, 1H, J=8.4 Hz, ArH), 8.20 (d, 1H, J=8.4 Hz, ArH).

$^{13}$C-NMR (CDCl$_3$, *): 24.3, 26.2, 46.5, 46.7, 73.0, 82.1, 119.2, 126.9, 127.7, 127.8, 129.5, 129.9, 137.2, 147.7, 155.0, 158.2, 167.3.

trans-(4,5-Dihydro-5-(isoquinolin-4-yl)oxazol-4-yl)(pyrrolidin-1-yl)methanone BLE 04136C BLE 04136C was prepared in accordance with method D using 4-quinoline carbaldehyde (0.852 g, 5.42 mmol), KOH (0.276 mg, 4.92 mmol) in methanol (5 mL) and 2-isocyano-1-(pyrrolidin-1-yl)ethanone BLE 04098 (0.75 g, 5.43 mmol). After work-up the residue was washed with a minimum of EtOAc to led, after filtration and drying, to trans-(4,5-dihydro-5-(isoquinolin-4-yl)oxazol-4-yl)(pyrrolidin-1-yl)methanone BLE 04136C as a white solid (0.640 g, 40% yield).

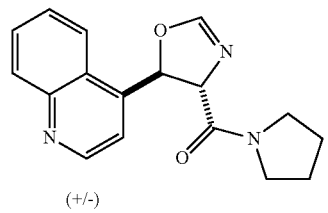

BLE 04136C

MW: 295.34; Yield: %; White Solid; Mp (° C.): 152.0.

$^1$H-NMR (CDCl$_3$, *): 1.85-2.08 (m, 4H, CH$_2$), 3.28-3.40 (m, 1H, CH$_2$N), 3.54-3.69 (m, 2H, CH$_2$N), 3.84-3.95 (m, 1H, CH$_2$N), 4.57 (dd, 1H, J=6.8 Hz, J=2.1 Hz, CH—N), 6.93 (d, 1H, J=6.8 Hz, CH—O), 7.15 (d, 1H, J=2.1 Hz, O—CH═N), 7.41 (d, 1H, J=4.5 Hz, ArH); 7.59 (m, 1H, ArH), 7.76 (m, 1H, ArH), 7.91 (d, 1H, J=8.3 Hz, ArH), 8.16 (d, 1H, J=8.3 Hz, ArH), 8.92 (d, 1H, J=4.5 Hz, ArH).

$^{13}$C-NMR (CDCl$_3$, *): 24.2, 25.9, 46.7 (2×C), 75.6, 77.8, 116.4, 123.1, 124.8, 127.5, 129.6, 130.5, 145.5, 148.4, 150.3, 155.0, 166.0.

trans-(4,5-Dihydro-5-(quinolin-3-yl)oxazol-4-yl)(pyrrolidin-1-yl)methanone BAL 01016

To a stirred and cooled (0° C.) solution of KOH (0.31 g, 5.43 mmol) in 5 mL MeOH were added successively quinoline-3-carboxaldehyde (0.85 g, 5.43 mmol) and 2-isocyano-1-pyrrolidin-1-yl-ethanone BLE 04134 (0.75 g, 5.43 mmol). The mixture was stirred at 0° C. until precipitation and concentrated. The mixture was partitioned between EtOAc (50 mL) and H$_2$O (25 mL). The aqueous layer was extracted twice with EtOAc (25 ml). The EtOAc fractions were combined, washed twice with brine (2×25 mL), dried over MgSO$_4$ and filtered. After evaporation and drying trans-(4,5-dihydro-5-(quinolin-3-yl)oxazol-4-yl)(pyrrolidin-1-yl)methanone BAL 01016 was obtained (0.96 g, 60% yield) as a white solid.

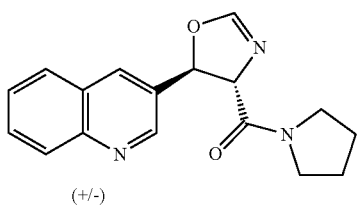

BAL 01016

MW: 295.34; Yield: 60%; White Solid; Mp (° C.): 144.4. Rf: 0.15 (EtOAc).

$^1$H NMR (CDCl$_3$, *): 1.75-2.10 (m, 4H, 2×CH$_2$), 3.40-3.62 (m, 3H, CH$_2$N), 3.90-4.05 (m, 1H, CH$_2$N), 4.70 (dd, 1H, J=7.8 Hz, J=2.2 Hz, CH—N), 6.40 (d, 1H, J=7.8 Hz, CH—O), 7.10 (d, 1H, J=2.2 Hz, OCH=N), 7.58 (dt, 1H, J=1.1 Hz, J=8.0 Hz, ArH)), 7.73 (dt, 1H, J=1.4 Hz, J=6.9 Hz, ArH), 7.83 (dd, 1H, J=1.2 Hz, J=8.2 Hz, ArH), 8.12 (m, 2H, ArH), 8.87 (d, 1H, J=2.2 Hz, ArH).

$^{13}$C-NMR (CDCl$_3$, *): 24.2, 26.0, 46.6, 46.6, 75.8, 79.7, 127.3, 127.5, 127.9, 129.4, 130.0, 132.3, 133.2, 148.1, 148.4, 155.3, 166.2.

MS-ESI m/z (% rel. Int.): 296.1 ([MH]$^+$, 5), 314.1 (100).

trans-(5-(Furan-2-yl)-4,5-dihydrooxazol-4-yl)(pyrrolidin-1-yl)methanone BLE 04136D BLE 04136C was prepared in accordance with method D using 2-furaldehyde (0.449 mL, 5.42 mmol), KOH (0.276 mg, 4.92 mmol) in methanol (5 mL) and 2-isocyano-1-(pyrrolidin-1-yl)ethanone BLE 04098 (0.75 g, 5.43 mmol). After work-up the residue was purified by column chromatography on silica (cyclohexane:EtOAc=100:0 to 0:100) to led, after evaporation, to trans-(5-(furan-2-yl)-4,5-dihydrooxazol-4-yl)(pyrrolidin-1-yl)methanone BLE 04136D as a yellow pale oil (0.742 g, 58.5% yield).

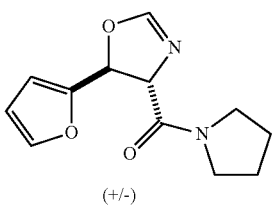

BLE 04136D

MW: 234.25; Yield: 58.5%; Yellow Pale Oil.

$^1$H-NMR (CDCl$_3$, *): 1.80-2.10 (m, 4H, CH$_2$), 3.47-3.60 (m, 3H, CH$_2$N), 3.94-4.06 (m, 1H, CH$_2$N), 4.94 (dd, 1H, J=7.4 Hz, J=2.2 Hz, CH—N), 6.14 (d, 1H, J=7.4 Hz, CH—O), 6.37 (dd, 1H, J=3.3 Hz, J=1.8 Hz, CH=C), 6.48 (d, 1H, J=3.3 Hz, CH=C), 6.93 (d, 1H, J=2.2 Hz, O—CH=N), 7.44 (d, 1H, J=1.8 Hz, OCH=C).

$^{13}$C-NMR (CDCl$_3$, *): 24.2, 26.0, 46.4, 46.5, 71.3, 74.5, 110.2, 110.5, 143.6, 150.4, 155.0, 166.3.

trans-(4,5-Dihydro-5-(2-methoxypyridin-3-yl)oxazol-4-yl)(pyrrolidin-1-yl)methanone BAL 01014

BAL 01014 was prepared in accordance with method D using 2-methoxy-3-pyridinecarboxaldehyde (0.64 ml, 5.43 mmol), KOH (0.305 mg, 5.43 mmol) in methanol (5 mL) and 2-isocyano-1-(pyrrolidin-1-yl)ethanone BLE 04098 (0.75 g, 5.43 mmol). After work-up trans-(4,5-dihydro-5-(2-methoxypyridin-3-yl)oxazol-4-yl)(pyrrolidin-1-yl)methanone BAL 01014 was obtained (0.74 mg, 50% yield) as a white solid.

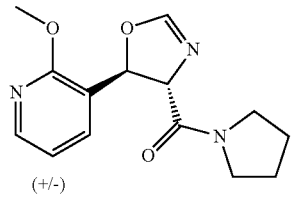

BAL 01014

MW: 275.30; Yield: 50%; White Solid; Mp (° C.): 110.1. Rf: 0.25 (EtOAc).

$^1$H NMR (CDCl$_3$, *): 1.82-2.10 (m, 4H, 2×CH$_2$), 3.40-3.62 (m, 3H, CH$_2$N), 3.80-3.90 (m, 3H, CH$_2$N), 3.93 (s, 3H, OMe), 4.61 (dd, 1H, J=7 Hz, J=2 Hz, CH—N), 6.14 (d, 1H, J=7 Hz, CH—O), 6.90 (dd, 1H, J=7.3 Hz, J=5 Hz, ArH), 7.02 (d, 1H, J=2 Hz, OCH=N), 7.60 (dd, 1H, J=7.3 Hz, J=1.7 Hz, ArH)), 8.13 (dd, 1H, J=5 Hz, J=1.8 Hz, ArH).

$^{13}$C-NMR (CDCl$_3$, *): 24.3, 26.1, 46.3, 46.6, 53.5, 73.5, 78.1, 116.8, 122.2, 135.2, 146.5, 155.3, 160.5 and 167.4.

MS-ESI m/z (% rel. Int.): 276.1 ([MH]$^+$, 42).

HPLC: Method A, detection UV 254 nm, BAL 01014 RT=3.63 min, peak area 97.2%.

trans-N,N-Diethyl-4,5-dihydro-5-(pyridin-4-yl)oxazole-4-carboxamide SLA 07194A

SLA 07194A was prepared in accordance with method D using pyridine-4-carbaldehyde (1.14 mL, 9.52 mmol), KOH (0.54 g, 9.60 mmol) in methanol (5 mL) and N,N-diethyl-2-isocyanoacetamide SLA 07184A (1.21 g, 8.65 mmol). After work-up and column chromatography on florisil (ethyl acetate) trans-N,N-diethyl-4,5-dihydro-5-(pyridin-4-yl)oxazole-4-carboxamide SLA 07194A was obtained as a brown oil (0.25 g, 12% yield).

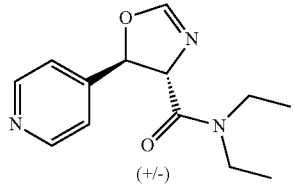

SLA 07194 A

MW: 247.29; Yield: 12%; Brown Oil.

R$_f$:0.15 (AcOEt=100).

$^1$H-NMR (CDCl$_3$, *): 1.16-1.34 (m, 6H, CH$_3$), 3.30-3.80 (m, 4H, CH$_2$N), 4.60 (dd, 1H, J=7.7 Hz, J=2.2 Hz, CH—N), 6.22 (d, 1H, J=7.7 Hz, CH—O), 7.06 (d, J=2.2 Hz, CH=N), 7.23 (d, 2H, J=5.8 Hz, ArH), 8.61 (d, 2H, J=6.0 Hz, ArH).

Preparation of 2-chloropyridine-4-carbaldehyde SLA 07156

Methyl 2-chloropyridine-4-carboxylate SLA 07150

2-Chloro-isonicotinic acid (5.10 g, 32.38 mmol) was dissolved in methanol (150 mL). Thionyl chloride (12 mL) was added. This suspension was stirred 5 h at 70° C. and concentrated in vacuo. The residue was dissolved in dichloromethane (250 mL) washed with a solution of 10% aqueous $K_2CO_3$ (2×150 mL) dried with $MgSO_4$, filtered and evaporated. Methyl 2-chloropyridine-4-carboxylate SLA 07150 was obtained as a yellow solid (5.06 g, 91%).

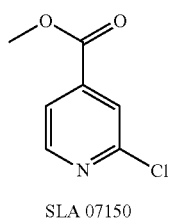

SLA 07150

MW: 171.58; Yield: 91%; Yellow Solid; Mp (° C.): 33.0.
$R_f$:0.80 (MeOH:$CH_2Cl_2$=10:90).
$^1$H-NMR ($CDCl_3$, *): 3.98 (s, 3H, $CH_3$), 7.78 (dd, 1H, J=5.1 Hz, J=1.3 Hz, ArH), 7.89 (d, 1H, J=0.6 Hz ArH), 8.55 (dd, 1H, J=5.1 Hz, J=0.6 Hz, ArH).

(2-Chloropyridin-4-yl)methanol SLA 07152

Methyl 2-chloropyridine-4-carboxylate (2.50 g, 14.60 mmol) was dissolved in anhydrous THF (50 mL) and this solution was cooled to −78° C. under $N_2$ atmosphere. Diisobutylaluminium hydride 1.0 M in hexanes (63.3 mL, 63.30 mmol) was added dropwise stabilizing the temperature between −50° C. and −70° C. The reaction mixture was stirred 1.5 h at −78° C. and allowed to stand at room temperature for 3 h. A solution of aqueous 10% $NH_4Cl$ was slowly added and the mixture was extracted with ethyl acetate (3×300 mL). The combined organic layers were washed with water (3×20 mL), brine (2×20 mL), dried over $MgSO_4$, filtered and evaporated. (2-Chloropyridin-4-yl)methanol SLA 07152 was obtained as a yellow oil (1.97 g, 94% yield).

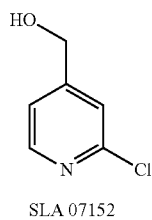

SLA 07152

MW: 143.71; Yield: 94%; Yellow Oil.
$R_f$:0.35 (EtOAc:cyclohexane=30:70).
$^1$H-NMR ($CDCl_3$, *): 2.95 (s broad, 1H, OH), 4.75 (s, 2H, $CH_2O$), 7.21 (dd, 1H, J=5.1 Hz, J=1.2 Hz, ArH), 7.37 (d, 1H, J=1.2 Hz ArH), 8.29 (d, 1H, J=5.1 Hz, ArH).
MS-ESI m/z (rel. int.): 144.0 ([MH]$^+$, 100).
HP LC: Method A, detection UV 254 nm, SLA 07152 RT=3.45 min, peak area 99.9%.

2-Chloropyridine-4-carbaldehyde SLA 07156

In a 250 mL tricol equipped with a low temperature thermometer and two equalizing dropping funnels was charged oxalyl dichloride (1.24 g, 9.81 mmol) in dichloromethane (15 mL) and this solution was stirred under $N_2$ at −78° C. The first equalizing dropping funnel was connected to a nitrogen flow line and was charged with a solution of (2-chloropyridin-4-yl)methanol SLA 07152 (0.94 g, 6.54 mmol) with dichloromethane (15 mL). The other was charged with a solution of dimethyl sulfoxide anhydrous (1.7 mL, 19.63 mmol) in dichloromethane (2 mL) and this solution was added dropwise (25 min) in order to stabilize the temperature between −60° C. and −70° C. At the end of the addition the reaction solution was warmed to −60° C. over a period of 20 min then the solution of (2-chloropyridin-4-yl)methanol SLA 07152 was added dropwise (50 min) keeping the temperature between −50° C. and −60° C. in the reactor then the mixture reaction was warmed to −45° C. over a period of 30 min. The dropping funnel was washed with dichloromethane (2×5 mL) and charged with a solution of triethylamine (480 µl, 6.51 mmol) in dichloromethane (4 mL) which was added (10 min) to the reaction mixture and finally the reaction flask was allowed to warm to 0° C. over 10 min. The reaction solution was transferred to a 500 mL separatory funnel charged with 130 mL of a 5% aqueous $NH_4Cl$ solution. The two phases were separated the aqueous phase was extracted with dichloromethane (3×50 mL) and the combined organic phases were washed with 1 M aqueous phosphate buffer (pH=7; 4×100 mL), then dried over $MgSO_4$, filtered and evaporated. 2-Chloropyridine-4-carbaldehyde SLA 07156 was obtained as an orange solid (0.740 g, 76% yield).

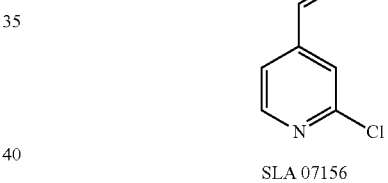

SLA 07156

MW: 141.57; Yield: 76%; Orange Solid.
$R_f$:0.35 (EtOAc:cyclohexane=30:70).
$^1$H-NMR ($CDCl_3$, *): 7.65 (dd, 1H, J=5.0 Hz, J=1.3 Hz, ArH), 7.75 (d, 1H, J=1.3 Hz, ArH) 8.66 (d, 1H, J=5.0 Hz, ArH), 10.05 (s, 1H, CHO).

trans-(5-(2-Chloropyridin-4-yl)-4,5-dihydrooxazol-4-yl)(pyrrolidin-1-yl)methanone SLA 07174

SLA 07174 was prepared in accordance with method D using 2-chloropyridine-4-carbaldehyde SLA 07156 (0.12 g, 1.05 mmol), KOH (0.06 g, 1.05 mmol) in methanol (10 mL) and 2-isocyano-1-(pyrrolidin-1-yl)ethanone BLE 04098 (0.146 g, 1.05 mmol). The solution was stirred 24 h with continued cooling. After work-up trans-(5-(2-chloropyridin-4-yl)-4,5-dihydrooxazol-4-yl)(pyrrolidin-1-yl)methanone SLA 07174 was obtained as a yellow solid (0.19 g, 66% yield).

(+/-)

SLA 07174

MW: 279.72; Yield: 66%; Yellow Solid; Mp (° C.): 116.3.
¹H-NMR (CDCl₃, *): 1.86-2.07 (m, 4H, CH₂), 3.45-3.62 (m, 3H, CH₂N), 3.93-4.01 (m, 1H, CH₂N), 4.50 (dd, J=8.0 Hz, J=2.3 Hz, 1H, CH—N), 6.19 (d, 1H, J=8.0 Hz, CH—O), 7.02 (d, 1H, J=2.3 Hz, CH=N), 7.17 (td, 1H, J=5.1 Hz J=0.9 Hz, J=0.4 Hz, ArH), 7.29 (d, 1H, J=0.7 Hz, ArH), 8.38 (d, 1H, J=5.1 Hz, ArH).
¹³C-NMR (CDCl₃, *): 22.5, 24.4, 44.9, 45.0, 74.3, 77.3, 117.2, 119.0, 148.6, 150.4, 150.6, 153.1, 164.0.

trans-(5-(3-Bromopyridin-4-yl)-4,5-dihydrooxazol-4-yl)(pyrrolidin-1-yl)methanone BAL 01028A BAL 01028A was prepared in accordance with method D using 3-bromo-4-pyridinecarboxaldehyde (1.010 g, 5.43 mmol), KOH (0.305 g, 5.43 mmol) in methanol (5 mL) and 2-isocyano-1-pyrrolidin-1-yl-ethanone BLE 04134 (0.75 g, 5.43 mmol). The mixture was stirred at 0° C. until precipitation and concentrated. The mixture was partitioned between EtOAc (50 ml) and H₂O (25 ml). The aqueous layer was extracted twice with EtOAc (25 mL). The EtOAc fractions were combined, washed twice with brine (2×25 mL), dried over MgSO₄ and filtered. After evaporation and trans-(5-(3-bromopyridin-4-yl)-4,5-dihydrooxazol-4-yl)(pyrrolidin-1-yl)methanone BAL 01028A was obtained (1.20 g, 68% yield) as a white solid.

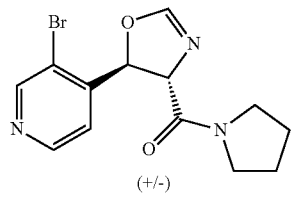

(+/-)

BAL 01028A

MW: 324.17; Yield: 68%; White Solid; Mp (° C.): 160.8.
Rf: 0.25 (EtOAc=100).
¹H NMR (CDCl₃, *): 1.82-2.08 (m, 4H, 2×CH₂), 3.45-3.65 (m, 3H, CH₂N), 3.80-3.92 (m, 1H, CH₂N), 4.60 (dd, 1H, J=2.1 Hz, J=6.1 Hz, CH—N), 6.30 (d, 1H, J=6.1 Hz, CH—O), 7.10 (d, 1H, J=2.1 Hz, OCH=N), 7.30 (d, 1H, J=5.0 Hz, ArH)), 8.55 (d, 1H, J=5.0 Hz, ArH), 8.72 (s, 1H, ArH).
¹³C-NMR (CDCl₃, *): 24.3, 26.0, 46.4, 46.6, 74.5, 79.6, 118.6, 121.1, 148.3, 148.8, 152.1, 155.1, 166.2.
MS-ESI m/z (% rel. Int.): 324.1/326.1 ([MH]⁺, 50/50), 239.0 (100).
HPLC: Method A, detection UV 254 nm, BAL 01028A RT=3.50 min, peak area 96.8%.

trans-(5-(3-Chloropyridin-4-yl)-4,5-dihydrooxazol-4-yl)(pyrrolidin-1-yl)methanone BAL 01028B BAL 01028B was prepared in accordance with method D using 2-isocyano-1-pyrrolidin-1-yl-ethanone BLE 04134 (0.75 g, 5.43 mmol), KOH (0.305 g, 5.43 mmol) in methanol (5 mL) and 3-chloro-isonicotinaldehyde (0.769 g, 5.43 mmol). The solution was stirred 3 h at 0° C. trans-(5-(3-Chloropyridin-4-yl)-4,5-dihydrooxazol-4-yl)(pyrrolidin-1-yl)methanone BAL 01028B (1.20 g, 65% yield) was obtained as a white solid.

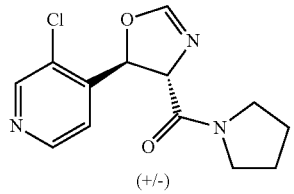

(+/-)

BAL 01028B

MW: 279.72; Yield: 65%; White Solid; Mp (° C.): 162.
Rf: 0.25 (EtOAc=100).
¹H NMR (CDCl₃, *): 1.82-2.08 (m, 4H, CH₂), 3.45-3.65 (m, 3H, CH₂N), 3.82-3.93 (m, 1H, CH₂N), 4.62 (dd, 1H, J=2.1 Hz, J=6.1 Hz, CH—N), 6.38 (d, 1H, J=6.1 Hz, CH—O), 7.08 (d, 1H, J=2.1 Hz, OCH=N), 7.33 (d, 1H, J=5.0 Hz, ArH), 8.52 (d, 1H, J=5.0 Hz, ArH), 8.59 (s, 1H, ArH).
¹³C-NMR (CD₃OD, *): 24.3, 26.0, 46.4, 46.6, 74.4, 77.9, 120.6, 128.8, 146.6, 148.3, 149.7, 155.0, 166.1.
MS-ESI m/z (% rel. Int.): 280.1/282.1 ([MH]⁺, 39/14).
HPLC: Method A, detection UV 254 nm, BAL 01028B RT=3.47 min, peak area 97.2%.

trans-(5-(2-Chloropyridin-4-yl)-4,5-dihydrooxazol-4-yl)(2H-pyrrol-1(5H)-yl)methanone SLA 07158

SLA 07158 was prepared in accordance with method D using 2-chloropyridine-4-carbaldehyde SLA 07156 (0.47 g, 3.31 mmol), KOH (0.184 g, 3.33 mmol) in methanol (10 mL) and 2-Isocyano-1-(2H-pyrrol-1 (5H)-yl)ethanone SLA 07178 (0.410 g, 3.01 mmol). The solution was stirred 2 h with continued cooling. After work-up and column chromatography on florisil (EtOAc), trans-(5-(2-chloropyridin-4-yl)-4,5-dihydrooxazol-4-yl)(2H-pyrrol-1(5H)-yl)methanone SLA 07158 was obtained as a yellow solid (0.597 g, 84%).

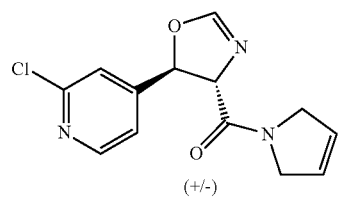

(+/-)

SLA 07158

MW: 277.71; Yield: 84%; Yellow Solid; Mp (° C.): 90.2.
R_f:0.10 (EtOAc).
¹H-NMR (CDCl₃, *): 4.26-4.37 (m, 3H, CH₂N), 4.48-4.52 (dd, 1H, J=2.3 Hz, J=8.0 Hz, CH—N), 4.75-4.85 (m, 1H, CH₂N), 5.80-5.95 (m, 2H, CH=CH), 6.20 (d, 1H, J=8 Hz, CH—O), 7.02 (d, J=2.3 Hz, CH=N), 7.17 (td, 1H, J=5.1 Hz, J=0.8 Hz, J=0.6 Hz, ArH), 7.30 (t, 1H, J=0.6 Hz, ArH), 8.38 (d, 1H, J=5.1 Hz, ArH).
¹³C-NMR (CDCl₃, *): 53.4, 53.9, 75.8, 78.9, 118.9, 120.7, 125.2, 125.4, 150.3, 151.9, 152.3, 154.

trans-(4,5-Dihydro-5-(pyridin-4-yl)oxazol-4-yl)(2H-pyrrol-1(5H)-yl)methanone SLA 07180

SLA 07158 was prepared in accordance with method D using pyridine-4-carbaldehyde (0.293 mL, 2.40 mmol), KOH (0.13 g, 2.32 mmol) in methanol (10 mL) and 2-isocyano-1-(2H-pyrrol-1(5H)-yl)ethanone SLA 07178 (0.301 g, 2.20 mmol). The solution was stirred 2 h with continued cooling. After work-up and column chromatography on florisil (EtOAc), trans-(4,5-dihydro-5-(pyridin-4-yl)oxazol-4-yl)(2H-pyrrol-1(5H)-yl)methanone SLA 07180 was obtained (0.284 g, 53% yield) as a yellow oil.

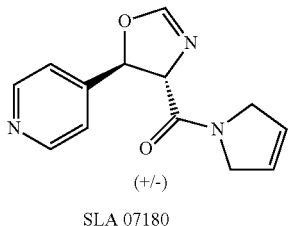 [SMILES: O=C([C@H]1N=CO[C@@H]1c1ccncc1)N1CC=CC1]

SLA 07180

MW: 243.26; Yield: 53%; Yellow Oil.

$R_f$: 0.15 (AcOEt).

$^1$H-NMR (CDCl$_3$, *): 4.28-4.33 (m, 3H, CH$_2$N), 4.52-4.56 (dd, 1H, J=7.8 Hz, J=2.2 Hz, CH—N), 4.73-4.82 (m, 1H, CH$_2$N), 5.80-5.93 (m, 2H, CH=CH), 6.18 (d, 1H, J=7.8 Hz, CH—O), 7.08 (d, J=2.2 Hz, CH=N), 7.27 (d, 2H, J=6.0 Hz, ArH), 8.59 (d, 2H, J=6.0 Hz, ArH).

$^{13}$C-NMR (CDCl$_3$, *): 53.6, 53.9, 75.8, 79.7, 120.2, 125.3, 125.6, 148.7, 150.5, 155.3, 166.1.

Preparation of Compound 20, Compound 21, Compound 22, Compound 23, Compound 24, Compound 25, Compound 26, Compound 27, Compound 28, Compound 29, Compound 30, Compound 31, Compound 32, Compound 34, Compound 35, Compound 36, Compound 37, Compound 38, Compound 39, Compound 40, Compound 41, Compound 42, Compound 43, Compound 44, Compound 45, Compound 46, Compound 48, Compound 49 and Compound 50.

General Method for Oxazolines Acidic Hydrolysis: Method E:

DL-threo-2-Amino-3-hydroxy-3-(pyridin-3-yl)-1-(pyrrolidin-1-yl)propan-1-one dihydrochloride Compound 20

To a solution of trans-(4,5-dihydro-5-(pyridin-3-yl)oxazol-4-yl)(pyrrolidin-1-yl)methanone BLE 04110B (0.932 g, 3.80 mmol) in methanol (10 mL) was added hydrochloric acid 37% (1.2 mL). After heating (50° C.) the mixture for 2.25 h the reaction mixture was concentrated and the crude product was coevaporated twice with ethyl acetate. After trituration with ethyl acetate, filtration and drying DL-threo-2-amino-3-hydroxy-3-(pyridin-3-yl)-1-(pyrrolidin-1-yl)propan-1-one dihydrochloride Compound 20 was obtained as a white solid (1.10 g, 94% yield).

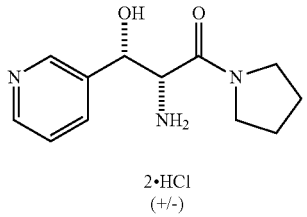

Compound 20

MW: 308.2; Yield: 94%; White Solid; Mp (° C.): 123.4.

$^1$H-NMR (CD$_3$OD, *): 1.65-2.00 (m, 4H, 2×CH$_2$), 2.82-3.11 (m, 1H, —CH$_2$N), 3.30-3.57 (m, 2H, CH$_2$N), 3.57-3.77 (m, 1H, CH$_2$N), 4.54 (d, 1H, J=5.3 Hz, CH—N), 5.38 (d, 1H, J=5.3 Hz, CH—O), 8.15 (dd, 1H, J=7.6 Hz, J=5.0 Hz, ArH), 8.68 (d, 1H, J=7.6 Hz, ArH), 8.89 (d, 1H, J=7.6 Hz, ArH), 8.96 (s, 1H, ArH).

$^{13}$C-NMR (CD$_3$OD, *): 24.9, 26.9, 47.7, 48.2, 58.1, 69.6, 128.7, 141.5, 141.6, 143.1, 146.5, 165.4.

DL-threo-2-Amino-3-hydroxy-3-(pyridin-2-yl)-1-(pyrrolidin-1-yl)propan-1-one dihydrochloride Compound 21

Compound 21 was prepared following method E with trans-(4,5-dihydro-5-(pyridin-2-yl)oxazol-4-yl)(pyrrolidin-1-yl)methanone BLE 04110 B (0.44 g, 1.79 mmol), hydrochloric acid 37% (1.0 mL) and methanol (10 mL). After 2.5 h at 50° C. and work-up DL-threo-2-amino-3-hydroxy-3-(pyridin-2-yl)-1-(pyrrolidin-1-yl)propan-1-one dihydrochloride Compound 21 was obtained as a yellow solid (0.44 g, 84% yield).

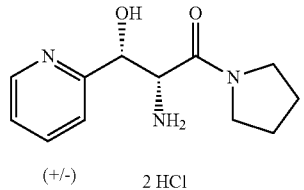

Compound 21

MW: 308.28; Yield: 84%; Yellow Solid.

$^1$H-NMR (CD$_3$OD, *): 1.75-2.01 (m, 4H, 2×CH$_2$), 3.10-3.22 (m, 1H, CH$_2$N), 3.39-3.60 (m, 2H, CH$_2$N), 3.63-3.75 (m, 1H, CH$_2$N), 4.71 (d, 1H, J=5.0 Hz, CH—N), 5.55 (d, 1H, J=5.0 Hz, CH—O), 8.05 (t, 1H, J=6.4 Hz, ArH), 8.13 (d, 1H, J=8.0 Hz, ArH), 8.61 (t, 1H, J=8.0 Hz, ArH), 8.84 (d, 1H, J=5.6 Hz, ArH).

DL-threo-2-Amino-3-hydroxy-3-(pyridin-4-yl)-1-(pyrrolidin-1-yl)propan-1-one dihydrochloride Compound 22

Compound 22 was prepared following method E with trans-(4,5-dihydro-5-(pyridin-4-yl)oxazol-4-yl)(pyrrolidin-1-yl)methanone Compound 19 (0.750 g, 3.07 mmol), hydrochloric acid 37% (1.0 mL) and methanol (10 mL). After 3.0 h at 50° C. and work-up DL-threo-2-amino-3-hydroxy-3-(pyridin-4-yl)-1-(pyrrolidin-1-yl)propan-1-one dihydrochloride Compound 22 was obtained as a white solid (0.935 g, 99% yield).

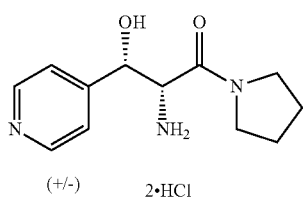

Compound 22

MW: 308.28; Yield: 99%; White Solid; Mp (° C.): 117.0.

$^1$H-NMR (CD$_3$OD, *): 1.75-2.03 (m, 4H, 2×CH$_2$), 2.93-3.08 (m, 1H, CHN), 3.32-3.75 (m, 3H, 2×CH$_2$), 4.54 (d, 1H, J=5.9 Hz, CHN), 5.40 (d, 1H, J=5.9. Hz, CH—O), 8.21 (d, 2H, J=5.8 Hz, ArH), 8.94 (d, 2H, J=5.8 Hz, ArH).

MS-ESI m/z (% rel. int.): 236.1 ([MH]$^+$, 17), 219 (25), 148 (100).

HPLC: Method A, detection UV 254 nm, Compound 22 RT=0.8 min, peak area 96.3%.

DL-threo-2-Amino-3-hydroxy-1-(pyrrolidin-1-yl)-3-(thiophen-3-yl)propan-1-one hydrochloride Compound 23

Compound 23 was prepared following method E with trans-(4,5-dihydro-5-(thiophen-3-yl)oxazol-4-yl)(pyrrolidin-1-yl)methanone BLE 04124A (0.486 g, 1.94 mmol), hydrochloric acid 37% (0.6 mL) and methanol (10 mL). After 3.5 h at 50° C. and work-up DL-threo-2-amino-3-hydroxy-1-(pyrrolidin-1-yl)-3-(thiophen-3-yl)propan-1-one hydrochloride Compound 23 was obtained as a white solid (0.480 g, 89.5% yield).

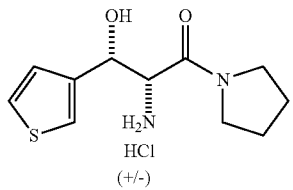

Compound 23

MW: 276.7; Yield: 89.5%; White Solid; Mp (° C.): 227.4.

$^1$H-NMR (CD$_3$OD, *): 1.47-1.88 (m, 4H, 2×CH$_2$), 2.31-2.46 (m, 1H, CH$_2$N), 3.18-3.46 (m, 3H, CH$_2$N), 4.16 (d, 1H, J=9.0 Hz, CH—N), 4.97 (d, 1H, J=9.0 Hz, CH—O), 7.14 (dd, 1H, J=4.9 Hz, J=1.1 Hz, ArH), 7.40-7.50 (m, 2H, ArH).

$^{13}$C-NMR (CD$_3$OD, *): 24.9, 26.7, 47.3, 47.6, 59.2, 70.6, 124.1, 127.1, 127.7, 142.3, 166.3.

DL-threo-2-Amino-3-hydroxy-1-(pyrrolidin-1-yl)-3-(thiophen-2-yl)propan-1-one hydrochloride Compound 24

Compound 24 was prepared following method E with trans-(4,5-dihydro-5-(thiophen-2-yl)oxazol-4-yl)(pyrrolidin-1-yl)methanone BLE 04124B (0.677 g, 2.70 mmol), hydrochloric acid 37% (0.6 mL) and methanol (10 mL). After 3.5 h at 50° C. and work-up DL-threo-2-amino-3-hydroxy-1-(pyrrolidin-1-yl)-3-(thiophen-2-yl)propan-1-one hydrochloride Compound 24 was obtained as a white solid (0.630 g, 84.5% yield).

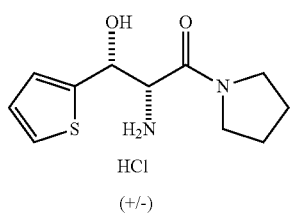

Compound 24

MW: 276.7; Yield: 84.5%; White Solid; Mp (° C.): 183.2.

$^1$H-NMR (CD$_3$OD, *): 1.49-1.90 (m, 4H, 2×CH$_2$), 2.36-2.48 (m, 1H, CH$_2$N), 3.20-3.48 (m, 3H, CH$_2$N), 4.18 (d, 1H, J=9.1 Hz, CH—N), 5.14 (d, 1H, J=9.1 Hz, CH—O), 7.00-7.08 (m, 2H, ArH), 7.45 (dd, 1H, J=4.9 Hz, J=1.6 Hz, ArH).

$^{13}$C-NMR (CD$_3$OD, *): 24.9, 26.8, 47.3, 47.7, 59.6, 70.5, 126.3, 127.0, 128.2, 144.5, 166.1.

DL-threo-2-amino-3-hydroxy-1-(pyrrolidin-1-yl)-3-(thiazol-2-yl)propan-1-one dihydrochloride Compound 25

Compound 25 was prepared following method E with trans-(4,5-dihydro-5-(thiazol-2-yl)oxazol-4-yl)(pyrrolidin-1-yl)methanone BLE 04124C (0.558 g, 2.22 mmol), hydrochloric acid 37% (0.6 mL) and methanol (10 mL). After 3.5 h at 50° C. and work-up DL-threo-2-amino-3-hydroxy-1-(pyrrolidin-1-yl)-3-(thiazol-2-yl)propan-1-one dihydrochloride Compound 25 was obtained as a pale yellow solid (0.532 g, 76.5% yield).

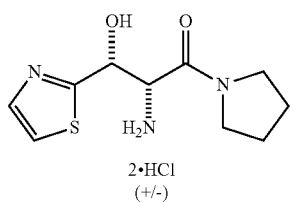

Compound 25

MW: 276.7; Yield: 76.5%; Pale Yellow Solid; Mp (° C.): 145.8.

$^1$H-NMR (CD$_3$OD, *): 1.75-2.00 (m, 4H, 2×CH$_2$), 3.05-3.17 (m, 1H, —CH$_2$N), 3.36-3.58 (m, 2H, CH$_2$N), 3.58-3.70 (m, 1H, CH$_2$N), 4.67 (d, 1H, J=5.4 Hz, CH—N), 5.49 (d, 1H, J=5.4 Hz, CH—O), 7.84 (d, 1H, J=3.4 Hz ArH), 7.99 (d, 1H, J=3.4 Hz, ArH).

$^{13}$C-NMR (CD$_3$OD, *): 24.9, 27.0, 47.7, 48.0, 57.5, 69.9, 123.6, 142.1, 165.3, 173.3.

DL-threo-2-Amino-3-(3a,7a-dihydrobenzo[b]thiophen-3-yl)-3-hydroxy-1-(pyrrolidin-1-yl)propan-1-one hydrochloride Compound 26

Compound 26 was prepared following method E with trans-(5-(benzo[b]thiophen-3-yl)-4,5-dihydrooxazol-4-yl)(pyrrolidin-1-yl)methanone BLE 04124D (1.050 g, 3.49 mmol), hydrochloric acid 37% (1.2 mL) and methanol (10 mL). After 3.5 h at 50° C. and work-up DL-threo-2-amino-3-(3a,7a-dihydrobenzo[b]thiophen-3-yl)-3-hydroxy-1-(pyrrolidin-1-yl)propan-1-one hydrochloride Compound 26 was obtained as a white solid (0.970 g, 85% yield).

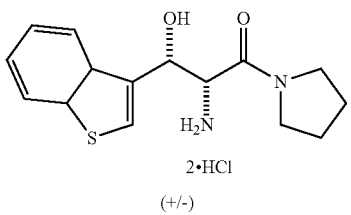

Compound 26

MW: 326.84; Yield: 85%; White Solid; Mp (° C.): 207.0.

$^1$H-NMR (CD$_3$OD, *): 0.92-1.09 (m, 2H, 2×CH$_2$), 1.42-1.60 (m, 2H, 2×CH$_2$), 1.83-1.98 (m, 1H, CH$_2$N), 2.76-2.91 (m, 1H, CH$_2$N), 3.06-3.25 (m, 2H, —CH$_2$N), 4.30 (d, 1H, J=9.5 Hz, CH—N), 5.29 (d, 1H, J=9.5 Hz, CH—O), 7.35-7.43 (m, 2H, ArH), 7.78-7.89 (m, 2H, ArH), 7.90-7.97 (m, 1H, ArH).

$^{13}$C-NMR (CD$_3$OD, *): 24.5, 26.4, 47.3, 47.4, 59.0, 69.5, 123.1, 124.0, 125.4, 126.1, 126.8, 136.6, 138.3, 141.9, 166.1.

DL-threo-2-Amino-3-(furan-3-yl)-3-hydroxy-1-(pyrrolidin-1-yl)propan-1-one hydrochloride Compound 27

Compound 27 was prepared following method E with trans-(5-(furan-3-yl)-4,5-dihydrooxazol-4-yl)(pyrrolidin-1-yl)methanone BLE 04130B (0.800 g, 3.41 mmol), hydrochloric acid 37% (0.6 mL) and methanol (10 mL). After 3.5 h at 50° C. and work-up DL-threo-2-amino-3-(furan-3-yl)-3-hydroxy-1-(pyrrolidin-1-yl)propan-1-one hydrochloride Compound 27 was obtained as a white solid (0.738 g, 83% yield).

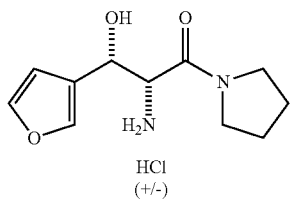

Compound 27

MW: 260.72; Yield: 83%; White Solid; Mp (° C.): 218.0.

$^1$H-NMR (CD$_3$OD, *): 1.62-1.95 (m, 4H, 2×CH$_2$), 2.82-2.95 (m, 1H, CH$_2$N), 3.22-3.38 (m, 1H, CH$_2$N), 3.39-3.55 (m, 2H, CH$_2$N), 4.19 (d, 1H, J=8.4 Hz, CH—N), 4.90 (d, 1H, J=8.4 Hz, CH—O), 6.49 (m, 1H, ArH), 7.52-7.57 (m, 2H, ArH).

$^{13}$C-NMR (CD$_3$OD, *): 24.9, 26.7, 47.4, 48.0, 58.7, 67.2, 109.8, 125.9, 142.0, 145.2, 166.3.

DL-threo-2-Amino-3-hydroxy-3-(naphthalen-2-yl)-1-(pyrrolidin-1-yl)propan-1-one hydrochloride Compound 28

Compound 28 was prepared following method E with trans-(4,5-dihydro-5-(naphthalen-3-yl)oxazol-4-yl)(pyrrolidin-1-yl)methanone BLE 04130C (0.745 g, 2.53 mmol), hydrochloric acid 37% (0.6 mL) and methanol (10 mL). After 3.5 h at 50° C. and work-up DL-threo-2-amino-3-hydroxy-3-(naphthalen-2-yl)-1-(pyrrolidin-1-yl)propan-1-one hydrochloride Compound 28 was obtained as a white solid (0.706 g, 87% yield).

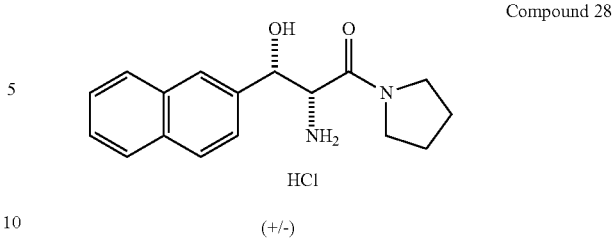

Compound 28

MW: 320.81; Yield: 87%; White Solid; Mp (° C.): 173.8.

$^1$H-NMR (CD$_3$OD, *): 0.93-1.10 (m, 1H, CH$_2$), 1.20-1.37 (m, 1H, CH$_2$), 1.44-1.71 (m, 2H, CH$_2$), 1.99-2.10 (m, 1H, CH$_2$N), 3.11-3.26 (m, 2H, CH$_2$N), 3.31-3.41 (m, 1H, CH$_2$N), 4.23 (d, 1H, J=9.1 Hz, CH—N), 5.06 (d, 1H, J=9.1 Hz, CH—O), 7.50-7.63 (m, 3H, ArH), 7.87-7.97 (m, 4H, ArH).

$^{13}$C-NMR (CD$_3$OD, *): 24.6, 26.3, 47.2, 47.5, 59.4, 74.3, 125.1, 126.9, 127.7, 127.8, 128.8, 129.0, 129.4, 134.5, 135.0, 138.0, 166.4.

DL-threo-2-Amino-3-hydroxy-3-(naphthalen-1-yl)-1-(pyrrolidin-1-yl)propan-1-one hydrochloride Compound 29

Compound 29 was prepared following method E with trans-(4,5-dihydro-5-(naphthalen-4-yl)oxazol-4-yl)(pyrrolidin-1-yl)methanone BLE 04130D (0.794 g, 2.69 mmol), hydrochloric acid 37% (0.6 mL) and methanol (10 mL). After 3.5 h at 50° C. and work-up DL-threo-2-amino-3-hydroxy-3-(naphthalen-1-yl)-1-(pyrrolidin-1-yl)propan-1-one hydrochloride Compound 29 was obtained as a white solid (0.768 g, 89% yield).

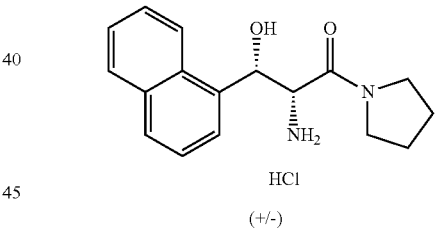

Compound 29

MW: 320.81; Yield: 89%; White Solid; Mp (° C.): 177.8.

$^1$H-NMR (CD$_3$OD, *): 0.71-0.91 (m, 2H, CH$_2$), 1.29-1.51 (m, 3H, CH$_2$), 2.54-2.67 (m, 1H, CH$_2$N), 2.88-3.02 (m, 1H, CH$_2$N), 3.02-3.16 (m, 1H, CH$_2$N), 4.27 (d, 1H, J=9.8 Hz, CH—N), 5.67 (d, 1H, J=9.8 Hz, CH—O), 7.50-7.61 (m, 3H, ArH), 7.90-7.98 (m, 3H, ArH), 8.08-8.14 (m, 1H, ArH).

$^{13}$C-NMR (CD$_3$OD, *): 24.4, 26.2, 47.1, 47.3, 59.5, 70.3, 124.0, 126.5 (2×C), 127.2, 127.4, 129.9, 130.4, 132.1, 135.0, 137.1, 166.1.

DL-threo-2-Amino-3-hydroxy-1-(pyrrolidin-1-yl)-3-(quinolin-2-yl)propan-1-one dihydrochloride Compound 30

Compound 30 was prepared following method E with trans-(4,5-dihydro-5-(quinolin-2-yl)oxazol-4-yl)(pyrrolidin-1-yl)methanone BLE 04136B (0.923 g, 3.13 mmol), hydrochloric acid 37% (0.6 mL) and methanol (15 mL). After 3.5 h at 50° C. and work-up DL-threo-2-amino-3-hydroxy-1-(pyrrolidin-1-yl)-3-(quinolin-2-yl)propan-1-one dihydrochloride Compound 30 was obtained as a yellow solid (1.098 g, 98% yield).

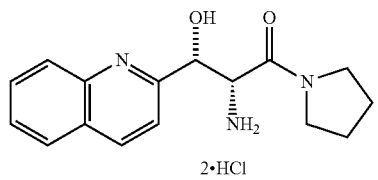

Compound 30

MW: 358.26; Yield: 98%; Yellow Solid; Mp (° C.): 131.5.

$^1$H-NMR (CD$_3$OD, *): 1.69-2.07 (m, 4H, CH$_2$), 3.16-3.34 (m, 3H, CH$_2$), 3.37-3.60 (m, 2H, CH$_2$N), 3.77-3.88 (m, 1H, CH$_2$—N), 5.85 (d, 1H, J=4.9 Hz, CH—O), 8.03 (t, 1H, J=7.6 Hz, ArH), 8.17-8.30 (m, 2H, ArH), 8.40 (d, 1H, J=8.3 Hz, ArH), 8.56 (d, 1H, J=8.6 Hz, ArH), 9.25 (d, 1H, J=8.6 Hz, ArH), not seen under H$_2$O (d, 1H, CH—NH$_2$).

$^{13}$C-NMR (CD$_3$OD, *): 24.9, 27.0, 47.9, 48.2, 57.3, 70.3, 121.5, 122.5, 130.4, 130.5, 131.5, 136.5, 140.2, 148.5, 157.8, 164.8.

DL-threo-2-Amino-3-hydroxy-3-(isoquinolin-4-yl)-1-(pyrrolidin-1-yl)propan-1-one dihydrochloride Compound 31

Compound 31 was prepared following method E with trans-(4,5-dihydro-5-(isoquinolin-4-yl)oxazol-4-yl)(pyrrolidin-1-yl)methanone BLE 04136C (0.597 g, 2.02 mmol), hydrochloric acid 37% (0.4 mL) and methanol (10 mL). After 3.5 h at 50° C. and work-up DL-threo-2-amino-3-hydroxy-3-(isoquinolin-4-yl)-1-(pyrrolidin-1-yl)propan-1-one dihydrochloride Compound 31 was obtained as a off white solid (0.716 g, 99% yield).

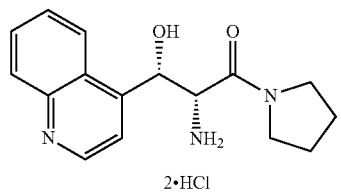

Compound 31

MW: 358.27; Yield: 99%; Off White Solid; Mp (° C.): 158.5.

$^1$H-NMR (CD$_3$OD, *): 1.04-1.32 (m, 2H, CH$_2$), 1.51-1.72 (m, 2H, CH$_2$), 2.05-2.20 (m, 1H, CH$_2$N), 2.68-2.80 (m, 1H, CH$_2$N), 3.20-2.47 (m, 1H, CH$_2$N), 4.57 (d, 1H, J=8.5 Hz, CH—NH$_2$), 5.99 (d, 1H, J=8.5 Hz, CH—OH), 8.09 (t, 1H, J=8.6 Hz, ArH), 8.27 (t, 1H, J=8.6 Hz, ArH), 8.38 (d, 1H, J=8.6 Hz, ArH), 8.45 (d, 1H, J=8.6 Hz, ArH), 8.55 (d, 1H, J=5.6 Hz, ArH), 9.35 (d, 1H, J=5.6 Hz, ArH).

$^{13}$C-NMR (CD$_3$OD, *): 24.6, 26.5, 47.5, 48.0, 58.2, 69.1, 122.3, 122.6, 125.9, 127.7, 131.7, 136.7, 138.9, 146.1, 159.4, 165.2.

N-(DL-threo-1-hydroxy-3-oxo-3-(pyrrolidin-1-yl)-1-(quinolin-3-yl)propan-2-yl)formamide hydrochloride Compound 32

Compound 32 was prepared following method E with trans-(4,5-dihydro-5-(quinolin-3-yl)oxazol-4-yl)(pyrrolidin-1-yl)methanone BAL 01016 (0.905 g, 3.41 mmol), hydrochloric acid 37% (0.6 mL) and methanol (10 mL). After 2 h at RT and work-up N-(DL-threo-1-hydroxy-3-oxo-3-(pyrrolidin-1-yl)-1-(quinolin-3-yl)propan-2-yl)formamide hydrochloride Compound 32 was obtained as a white solid (240 mg, 20.0% yield).

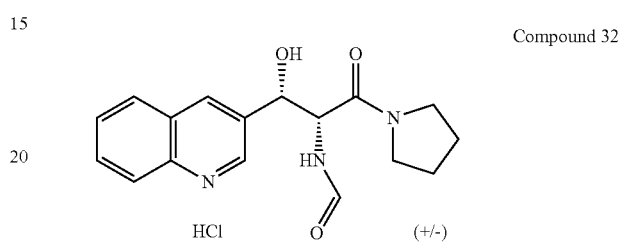

Compound 32

MW: 349.81; Yield: 20.0%; White Solid; Mp (° C.): 203.2.

$^1$H NMR (CD$_3$OD, *): 1.78-2.09 (m, 4H, CH$_2$), 3.35-3.58 (m, 2H, CH$_2$N), 3.58-3.80 (m, 2H, CH$_2$N), 5.28 (d, 1H, J=4 Hz, CH—N), 5.51 (d, 1H, J=4 Hz, CH—O), 8.00 (t, 2H, J=7.1 Hz, ArH)), 8.18 (t, 1H, J=6.9 Hz, ArH), 8.26 (d, 1H, J=8.6 Hz, ArH), 8.36 (d, 1H, J=8.3 Hz, ArH), 9.18 (s, 1H, CHO), 9.26 (s, 1H, ArH).

$^{13}$C-NMR (CD$_3$OD, *): 25.1, 27.0, 47.5, 48.3, 55.5, 71.2, 121.4, 129.9, 130.6, 131.5, 136.2, 137.3, 138.5, 145.3, 145.8, 163.4, 168.7.

MS-ESI m/z (% rel. Int.): 314 ([MH]$^+$, 50), 158.1 (100).

HPLC: Method A, detection UV 254 nm, Compound 32 RT=3.36 min, peak area 99.9%.

DL-threo-2-Amino-3-hydroxy-1-(pyrrolidin-1-yl)-3-(quinolin-3-yl)propan-1-one dihydrochloride Compound 33

Compound 33 was prepared following method E with trans-(4,5-dihydro-5-(quinolin-3-yl)oxazol-4-yl)(pyrrolidin-1-yl)methanone BAL 01016 (0.91 g, 3.41 mmol), hydrochloric acid 37% (0.6 mL) and methanol (10 mL). After 3 h at 50° C. and work-up DL-threo-2-amino-3-hydroxy-1-(pyrrolidin-1-yl)-3-(quinolin-3-yl)propan-1-one dihydrochloride Compound 33 (678 mg, 55% yield) was obtained as a white solid.

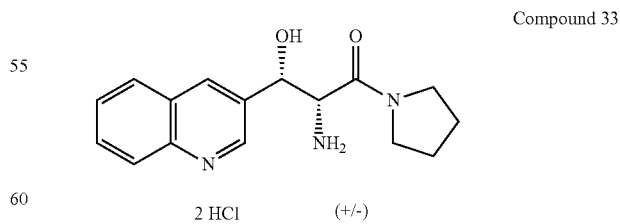

Compound 33

MW: 358.26; Yield: 55%; White Solid; Mp (° C.): 190.9.

$^1$H NMR (CD$_3$OD, *): 1.57-1.80 (m, 2H, CH$_2$), 1.80-1.99 (m, 2H, CH$_2$), 3.01-3.20 (m, 1H, CH$_2$N), 3.35-3.61 (m, 2H, CH$_2$N), 3.61-3.82 (m, 1H, CH$_2$N), 4.70 (d, 1H, J=5.0 Hz, CH—N), 5.58 (d, 1H, J=5.0 Hz, CH—O), 7.96-8.11 (m, 1H,

ArH), 8.18-8.29 (m, 1H, ArH), 8.29-8.38 (m, 1H, ArH), 8.38-8.49 (m, 1H, ArH), 9.28 (s, 1H, ArH), 9.34 (s, 1H, ArH).
$^{13}$C-NMR (CD$_3$OD, *): 24.9, 26.9, 47.8, 48.3, 58.2, 69.8, 121.8, 130.0, 130.8, 131.9, 135.4, 136.9, 139.3, 145.1, 146.2, 165.6.
MS-ESI m/z (% rel. Int.): 286.2 ([MH]$^+$, 100).
HPLC: Method A, detection UV 254 nm, Compound 33 RT=3.15 min, peak area 97.0%.

DL-threo-2-Amino-3-(2-chloropyridin-4-yl)-3-hydroxy-1-(2H-pyrrol-1 (5H)-yl)propan-1-one dihydrochloride Compound 34.

Compound 34 was prepared following method E with trans-(5-(2-chloropyridin-4-yl)-4,5-dihydrooxazol-4-yl)(2H-pyrrol-1(5H)-yl)methanone SLA 07158 (0.597 g, 2.02 mmol), hydrochloric acid 37% (1.0 mL) and methanol (10 mL). After 2 h at room temperature and work-up DL-threo-2-amino-3-(2-chloropyridin-4-yl)-3-hydroxy-1-(2H-pyrrol-1(5H)-yl)propan-1-one dihydrochloride Compound 34 (0.656 mg, 91% yield) was obtained as a pale yellow solid.

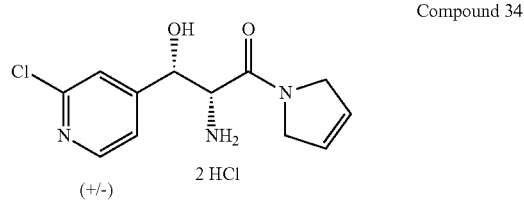 [SMILES: N[C@@H](C(=O)N1CC=CC1)[C@@H](O)c1ccnc(Cl)c1 ; "2 HCl"]

Compound 34

MW: 340.63; Yield: 91%; Pale Yellow Solid; Mp (° C.): 196.2.
$^1$H-NMR (CD$_3$OD, *): 3.45-3.50 (m, 1H, CH$_2$N), 4.04-4.15 (m, 1H, CH$_2$N), 4.22-4.36 (m, 3H, CH$_2$N & C$\underline{H}$NH$_2$), 5.05 (d, 1H, J=7.1 Hz, —CHO), 5.71 (d, 1H, J=4.3 Hz, CH=CH), 5.84 (d, 1H, J=4.3 Hz, CH=CH), 7.47 (d, 1H, J=5.0 Hz, ArH), 7.57 (s, 1H, ArH), 8.39 (d, 1H, J=5.0 Hz, ArH).
$^{13}$C-NMR (CD$_3$OD, *): 54.3, 54.5, 58.2, 71.7, 122.0, 123.5, 125.7, 126.3, 151.0, 152.8, 154.0, 165.8.

DL-threo-2-Amino-3-hydroxy-3-(pyridin-4-yl)-1-(piperidin-1-yl)propan-1-one dihydrochloride Compound 35

Compound 35 was prepared following method E with trans-(4,5-dihydro-5-(pyridin-4-yl)oxazol-4-yl)(piperidin-1-yl)methanone SLA 07122A (0.33 g, 1.27 mmol), hydrochloric acid 37% (1.0 mL) and methanol (10 mL). After 3 h at 50° C. and work-up DL-threo-2-amino-3-hydroxy-3-(pyridin-4-yl)-1-(piperidin-1-yl)propan-1-one dihydrochloride Compound 35 was obtained as a yellow solid (0.375 g, 91% yield).

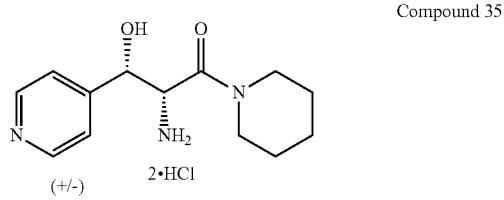 [SMILES: N[C@@H](C(=O)N1CCCCC1)[C@@H](O)c1ccncc1 ; "2·HCl"]

Compound 35

MW: 322.31; Yield: 91%; Yellow Solid; Mp (° C.): 145.
$^1$H-NMR (CD$_3$OD, *): 1.05-1.17 (m, 1H, CH$_2$) 1.28-1.65 (m, 5H, CH$_2$), 2.75-3.00 (m, 1H, CH$_2$N), 3.10-3.22 (m, 1H, CH$_2$N), 3.23-3.38 (m, 1H, CH$_2$N), 3.53-3.65 (m, 1H, CH$_2$N), 4.68 (d, 1H, J=5.8 Hz, C$\underline{H}$NH$_2$), 5.14 (d, 1H, J=5.8 Hz, CHO), 8.06 (d, 2H, J=6.0 Hz, ArH), 8.79 (d, 2H, J=6.5 Hz, ArH).

DL-threo-2-Amino-3-hydroxy-3-(pyridin-4-yl)-1-(morpholin-1-yl)propan-1-one dihydrochloride Compound 36

Compound 36 was prepared following method E with trans-(4,5-dihydro-5-(pyridin-4-yl)oxazol-4-yl)(morpholino)methanone SLA 07124A (0.146 g, 0.56 mmol), hydrochloric acid 37% (1.0 mL) and methanol (10 mL). After 3 h at 50° C. and work-up DL-threo-2-amino-3-hydroxy-3-(pyridin-4-yl)-1-(morpholin-1-yl)propan-1-one dihydrochloride Compound 36 was obtained as a pale yellow solid (0.143 g, 89% yield).

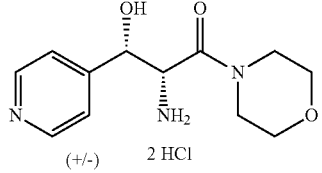

Compound 36

MW: 287.78; Yield: 89%; Pale Yellow Solid; Mp (° C.): 115.9.
$^1$H-NMR (CD$_3$OD, *): 3.32-3.82 (m, 8H, 4×CH$_2$), 5.41 (d, 1H, J=5.0 Hz, CHO—), 8.28 (d, 2H, J=5.9 Hz, ArH), 8.97 (d, 2H, J=5.8 Hz, ArH), C$\underline{H}$NH$_2$ not seen.

DL-threo-2-Amino-3-hydroxy-3-(pyridin-4-yl)-1-(piperazin-1-yl)propan-1-one trihydrochloride Compound 37

Compound 37 was prepared following method E with trans-(4,5-dihydro-5-(pyridin-4-yl)oxazol-4-yl)(4-tert-butyloxycarbonyl-piperazin-1-yl)methanone SLA 07124B (0.31 g, 0.86 mmol), hydrochloric acid 37% (1.0 mL) and methanol (10 mL). After 3 h at 50° C. and work-up DL-threo-2-amino-3-hydroxy-3-(pyridin-4-yl)-1-(piperazin-1-yl)propan-1-one trihydrochloride Compound 37 was obtained as a yellow solid (0.303 g, 71%).

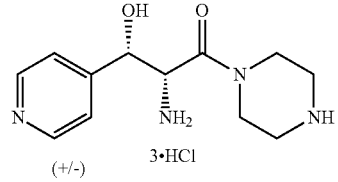

Compound 37

MW: 359.8; Yield: 71%; Yellow Solid; Mp (° C.): 201.4.
R$_f$: 0.20 (CH$_2$Cl$_2$:MeOH=90:10), free base.
$^1$H-NMR (CD$_3$OD, *): 3.31-3.48 (m, 4H, 2×CH$_2$), 3.63-3.90 (m, 2H, CH$_2$N), 4.00-4.35 (m, 2H, CH$_2$N), 5.15 (d, 1H, J=4.5 Hz, C$\underline{H}$NH$_2$), 5.58 (d, 1H, J=4.5 Hz, CHO), 8.38 (d, 2H, J=6.4 Hz, ArH), 9.04 (d, 2H, J=6.5 Hz, ArH).

DL-threo-2-amino-3-hydroxy-3-(pyridin-4-yl)-1-thiomorpholinopropan-1-one dihydrochloride Compound 38

Compound 38 was prepared following method E with trans-(4,5-dihydro-5-(pyridin-4-yl)oxazol-4-yl)(thiomorpholino)methanone SLA 07132 (0.926 g, 3.36 mmol), hydrochloric acid 37% (1.1 mL) and methanol (10 mL). After 3 h at 50° C. and work-up DL-threo-2-amino-3-hydroxy-3-(pyridin-4-yl)-1-thiomorpholinopropan-1-one dihydrochloride Compound 38 was obtained as a pale yellow solid (1.1 g, 99% yield).

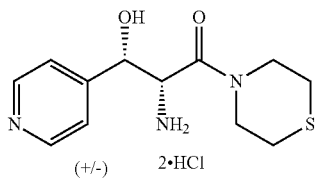

Compound 38

MW: 340.35; Yield: 99%; Pale Yellow Solid; Mp (° C.): 200.6.
$^1$H-NMR (CD$_3$OD, *): 2.42-2.52 (m, 1H, CH$_2$), 2.53-2.70 (m, 1H, CH$_2$), 2.70-2.90 (m, 2H, CH$_2$), 3.45-3.71 (m, 2H, CH$_2$N), 3.87-4.00 (m, 1H, CH$_2$N), 4.18-4.28 (m, 1H, CH$_2$N), 5.44 (d, 1H, J=5.1 Hz, CHO), 8.34 (d, 2H, J=5.9 Hz, ArH), 9.03 (d, 2H, J=5.6 Hz, ArH), —CHNH$_2$ not seen (under H$_2$O).
$^{13}$C-NMR (CD$_3$OD, *): 27.9, 28.7, 46.6, 50.0, 56.0, 71.3, 126.9 (2×C), 143.2 (2×C), 161.3, 165.7.

DL-threo-2-Amino-3-hydroxy-3-(pyridin-4-yl)-1-(2H-pyrrol-1(5H)-yl)propan-1-one dihydrochloride Compound 39

Compound 39 was prepared following method E with trans-(4,5-dihydro-5-(pyridin-4-yl)oxazol-4-yl)(2H-pyrrol-1(5H)-yl)methanone SLA 07180 (0.276 g, 1.14 mmol), hydrochloric acid 37% (1.0 mL) and methanol (10 mL). After 2.5 h at RT and work-up DL-threo-2-amino-3-hydroxy-3-(pyridin-4-yl)-1-(2H-pyrrol-1(5H)-yl)propan-1-one dihydrochloride Compound 39 was obtained (343 mg, 99% yield) as a white solid.

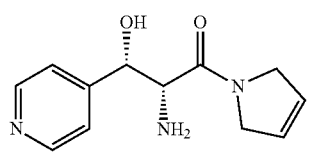

Compound 39

MW: 306.27; Yield: 99%; White Solid; Mp (° C.): 186.3.
$^1$H-NMR (CD$_3$OD, *): 3.91-4.02 (m, 1H, CH—NH$_2$), 4.09-4.21 (m, 1H, CH$_2$), 4.27-4.41 (m, 1H, CH$_2$), 4.44-4.59 (m, 1H, CH$_2$), 4.55 (d, 1H, J=5.7 Hz, CH$_2$N), 5.46 (d, 1H, J=5.7 Hz, CHO), 5.80-5.90 (m, 2H, CH=CH), 8.24 (d, 1H, J=6.3 Hz, ArH), 8.93 (d, 1H, J=5.7 Hz, ArH).
$^{13}$C-NMR (CD$_3$OD, *): 54.6, 54.7, 57.6, 71.0, 125.9, 126.4, 126.8 (2×C), 143.1 (2×C), 161.6, 165.5.
MS-ESI m/z (% rel. Int.): 234.1 ([MH]$^+$, 5), 137.1 (100).

DL-threo-2-Amino-N,N-diethyl-3-hydroxy-3-(pyridin-4-yl)propanamide dihydrochloride Compound 40

Compound 40 was prepared following method E with trans-N,N-diethyl-4,5-dihydro-5-(pyridin-4-yl)oxazole-4-carboxamide diethylamide SLA 07194A (254 mg, 1.03 mmol), hydrochloric acid 37% (1.0 mL) and methanol (10 mL) After 2 h at RT and work-up DL-threo-2-amino-N,N-diethyl-3-hydroxy-3-(pyridin-4-yl)propanamide dihydrochloride Compound 40 was obtained (212 mg, 67% yield) as a pale yellow solid.

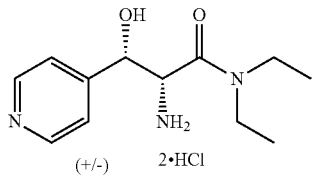

Compound 40

MW: 310.30; Yield: 67%; Pale Yellow Solid; Mp (° C.): 159.6° C.
R$_f$:0.10 (CH$_2$Cl$_2$:MeOH=90:10), free base.
$^1$H-NMR (CD$_3$OD, *): 1.01-1.12 (m, 6H, 2×CH$_3$), 3.01-3.31 (m, 3H, CH$_2$), 3.40-3.52 (m, 1H, CH$_2$), 4.64 (d, 1H, J=6.8 Hz, CHN), 5.31 (d, 1H, J=6.8 Hz, CHO), 8.22 (d, 1H, J=6.4 Hz, ArH), 8.94 (d, 1H, J=6.4 Hz, ArH).
$^{13}$C-NMR (CD$_3$OD, *): 12.9, 14.4, 42.1, 43.4, 55.9, 72.1, 126.9 (2×C), 143.3 (2×C), 161.5, 166.1.
MS-ESI m/z (% rel. Int.): 238.1 ([MH]$^+$, 5), 137.1 (100).

DL-threo-2-Amino-3-(2-chloropyridin-4-yl)-3-hydroxy-1-(pyrrolidin-1-yl)propan-1-one dihydrochloride Compound 41

Compound 41 was prepared following method E with trans-(5-(2-chloropyridin-4-yl)-4,5-dihydrooxazol-4-yl)(pyrrolidin-1-yl)methanone SLA 07174 (0.179 g, 0.64 mmol), hydrochloric acid 37% (1.0 mL) and methanol (7 mL). After 2 h at RT and work-up DL-threo-2-amino-3-(2-chloropyridin-4-yl)-3-hydroxy-1-(pyrrolidin-1-yl)propan-1-one dihydrochloride Compound 41 was obtained (212 mg, 67 (142 mg, 65% yield) as a pale yellow solid.

Compound 41

MW: 342.65; Yield: 65%; Pale Yellow Solid; Mp (° C.): 184.3.
R$_f$:0.15 (CH$_2$Cl$_2$:MeOH=90:10), free base.
$^1$H-NMR (CD$_3$OD, *): 1.50-1.90 (m, 4H, 2×CH$_2$), 2.50-2.61 (m, 1H, CH$_2$N), 3.25-3.38 (m, 1H, CH$_2$N), 3.40-3.53 (m, 2H, CH$_2$N), 4.26 (d, 1H, J=7.7 Hz, CHN), 4.99 (d, 1H, J=7.7 Hz, CHO), 7.45 (d, 1H, J=4.5 Hz, ArH), 7.53 (s, 1H, ArH), 8.41 (d, 1H, J=4.9 Hz, ArH).
$^{13}$C-NMR (CD$_3$OD, *): 24.9, 26.7, 47.5, 48.0, 58.4, 71.9, 122.0, 123.5, 151.1, 152.7, 154.0, 165.7.
MS-ESI m/z (% rel. Int.): 270.1/272.1 ([MH]$^+$, 40/13), 171.0/172.0 (100/32).

DL-threo-2-Amino-3-(3-bromopyridin-4-yl)-3-hydroxy-1-(pyrrolidin-1-yl)propan-1-one dihydrochloride Compound 42

Compound 42 was prepared following method E with trans-(5-(3-bromopyridin-4-yl)-4,5-dihydrooxazol-4-yl)

(pyrrolidin-1-yl)methanone BAL 01028A (1.141 g, 3.52 mmol), hydrochloric acid 37% (0.6 mL) and methanol (15 mL). After 3 h at 50° C. and work-up DL-threo-2-amino-3-(3-bromopyridin-4-yl)-3-hydroxy-1-(pyrrolidin-1-yl)propan-1-one dihydrochloride Compound 42 was obtained as a white solid (667 mg, 49% yield).

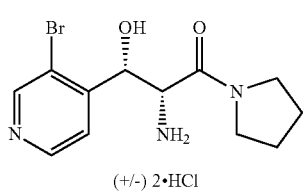

Compound 42

(+/-) 2·HCl

MW: 387.10; Yield: 49.0%; White Solid; Mp (° C.): 216.3.
$^1$H NMR (CD$_3$OD, *): 1.73-1.99 (m, 4H, 2×CH$_2$), 3.01-3.05 (m, 1H, CH$_2$N), 3.44-3.51 (m, 2H, CH$_2$N), 3.60-3.73 (m, 1H, CH$_2$N), 4.60 (d, 1H, J=5.5 Hz, CH—N), 5.54 (d, 1H, J=5.5 Hz, CH—O), 8.26 (d, 1H, J=5.7 Hz, ArH)), 8.86 (d, 1H, J=5.7 Hz, ArH), 9.10 (s, 1H, ArH).
$^{13}$C-NMR (CD$_3$OD, *): 24.8, 27.1, 56.4, 70.1, 122.7, 127.6, 145.1, 148.4, 156.8, 165.0, 2×C not seen.
MS-ESI m/z (% rel. Int.): 314.1/316.1 ([MH]$^+$, 35/35), 215.0/217 (50/50).
HPLC: Method A, detection UV 254 nm, Compound 42 RT=3.08 min, peak area 92.8%.

DL-threo-2-Amino-3-(3-chloropyridin-4-yl)-3-hydroxy-1-(pyrrolidin-1-yl)propan-1-one dihydrochloride Compound 43

Compound 43 was prepared following method E with trans-(5-(3-chloropyridin-4-yl)-4,5-dihydrooxazol-4-yl)(pyrrolidin-1-yl)methanone BAL 01028B (0.925 g, 3.31 mmol), hydrochloric acid 37% (0.6 mL) and methanol (15 mL). After 2 h at 50° C. and work-up DL-threo-2-amino-3-(3-chloropyridin-4-yl)-3-hydroxy-1-(pyrrolidin-1-yl)propan-1-one dihydrochloride Compound 43 was obtained as a white solid (599 mg, 53% yield).

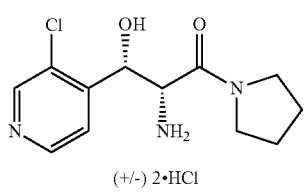

Compound 43

(+/-) 2·HCl

MW: 342.65; Yield: 53%; White Solid; Mp (° C.): 214.0.
$^1$H NMR (CD$_3$OD, *): 1.75-2.02 (m, 4H, 2×CH$_2$), 3.13-3.25 (m, 1H, CH$_2$N), 3.39-3.62 (m, 2H, CH$_2$N), 3.65-3.80 (m, 1H, CH$_2$N), 4.66 (d, 1H, J=4.5 Hz, CH—N), 5.66 (d, 1H, J=4.6 Hz, CH—O), 8.40 (d, 1H, J=5.8 Hz, ArH), 8.93 (d, 1H, J=5.8 Hz, ArH), 9.13 (s, 1H, ArH).
$^{13}$C-NMR (CD$_3$OD, *): 23.3, 25.6, 46.6, 46.8, 54.6, 66.5, 126.5, 132.4, 141.7, 142.9, 155.6, 163.4.
MS-ESI m/z (% rel. Int.): 270/272 ([MH]$^+$, 33/11), 171/173 (100/32).
HPLC: Method A, detection UV 254 nm, Compound 43 RT=2.80 min, peak area 97.2%.
DL-threo-3-Hydroxy-1-oxo-3-(1-oxy-pyridin-4-yl)-1-(pyrrolidin-1-yl)propan-2-ylcarbamate BAL 01060.

To a solution of DL-threo-3-hydroxy-1-oxo-3-(pyridin-4-yl)-1-(pyrrolidin-1-yl)propan-2-ylcarbamate (300 mg, 0.81 mmol, free base obtained from Compound 58 by K$_2$CO$_3$, CH$_2$Cl$_2$ treatment) in dichloromethane (40 mL) was added MCPBA (350 mg, 2.03 mmol). The resulting mixture was stirred overnight at room temperature. The mixture was concentrated and the crude product was purified by column chromatography (EtOAc:MeOH=70:30). DL-threo-3-Hydroxy-1-oxo-3-(1-oxy-pyridin-4-yl)-1-(pyrrolidin-1-yl)propan-2-ylcarbamate BAL 01060 was obtained as a white solid (292 mg, 94% yield).

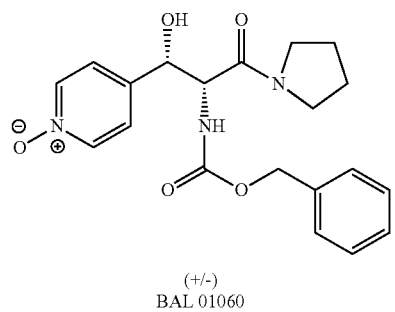 [SMILES: O=C(N[C@@H](C(=O)N1CCCC1)[C@@H](O)c1cc[n+]([O-])cc1)OCc1ccccc1]

(+/-)
BAL 01060

MW: 385.41; Yield: 94%; White Solid.
$^1$H NMR CDCl$_3$, *): 1.71-2.00 (m, 4H, 2×CH$_2$), 3.35-3.53 (m, 3H, CH$_2$N), 3.54-3.68 (m, 1H, CH$_2$N), 4.65 (dd, 1H, J=9.6 Hz, J=2.0 Hz, CH—N), 4.90-5.12 (m, 3H, CH$_2$O & OH), 5.20 (d, 1H, J=1.9 Hz, CH—O), 5.83 (d, 1H, J=9.6 Hz, NH), 7.20-7.40 (m, 7H, ArH), 8.08 (d, 2H, J=7.1 Hz, ArH).

DL-threo-2-Amino-3-hydroxy-3-(1-oxy-pyridin-4-yl)-1-pyrrolidin-1-yl-propan-1-one hydrochloride Compound 44

[2-Hydroxy-2-(1-oxy-pyridin-4-yl)-1-(pyrrolidine-1-carbonyl)-ethyl]-carbamic acid benzyl ester BAL 01060 (0.26 g, 0.67 mmol) was dissolved in a 6 N hydrochloric acid solution (10 mL). The solution was stirred for 0.75 h at 100° C. The residue was concentrated, dissolved in MeOH:EtOAc=50:50 and heated at reflux. After cooling, the mixture was evaporated, triturated in MeOH and filtered to obtain DL-threo-2-amino-3-hydroxy-3-(1-oxy-pyridin-4-yl)-1-pyrrolidin-1-yl-propan-1-one hydrochloride Compound 44 (65 mg, 33% yield) as a white solid.

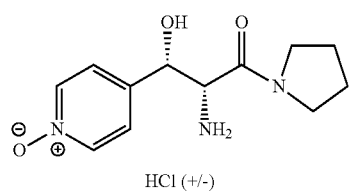

Compound 44

HCl (+/-)

MW: 287.74; Yield: 33%; White Solid; Mp (° C.): 178.5.
$^1$H NMR (D$_2$O, *): 1.55-1.93 (m, 4H, 2×CH$_2$), 2.65-3.80 (m, 1H, CH$_2$N), 3.22-3.56 (m, 3H, CH$_2$N), 4.43 (d, 1H, J=7.6 Hz, CH—N), 5.19 (d, 1H, J=7.6 Hz, CH—O), 7.69 (d, 2H, J=6.1 Hz, ArH), 8.39 (d, 2H, J=6.9 Hz, ArH).

$^{13}$C-NMR (D$_2$O, *): 24.1, 25.8, 47.3, 48.0, 57.4, 70.5, 125.7 (2×C), 139.9 (2×C), 143.7, 165.1.

MS-ESI m/z (% rel. Int.): 252.1 ([MH]$^+$, 18), 120.0 (100).

HPLC: Method A, detection UV 254 nm, Compound 44 RT=0.8 min, peak area 99.9%.

DL-threo-2-(Dimethylamino)-3-hydroxy-3-(pyridin-4-yl)-1-(pyrrolidin-1-yl)propan-1-one dihydrochloride Compound 45

DL-threo-2-Amino-3-hydroxy-3-(pyridin-4-yl)-1-(pyrrolidin-1-yl)propan-1-one dihydrochloride Compound 22 (0.50 g, 1.62 mmol) and para formaldehyde (0.245 g, 8.11 mmol) were stirred in methanol (25 mL) for 10 min. Sodium cyanoborohydride (0.612 g, 9.73 mmol) was added. The solution was stirred 19 h at 50° C. and then concentrated. The residue was partitioned between dichloromethane and water. The aqueous layer was basified with 1N sodium hydroxyde (pH=10). The organic layer was combined with additional dichloromethane extracts, washed with aqueous sodium chloride and dried with MgSO$_4$. The crude product was purified by column chromatography on silica (CH$_2$Cl$_2$:MeOH=95:05). DL-threo-2-(dimethylamino)-3-hydroxy-3-(pyridin-4-yl)-1-(pyrrolidin-1-yl)propan-1-one SLA 07140 was obtained (187 mg, 44%) as a yellow oil. To a stirred solution of DL-threo-2-(dimethylamino)-3-hydroxy-3-(pyridin-4-yl)-1-(pyrrolidin-1-yl)propan-1-one SLA 07140 (0.142 g, 0.54 mmol) in ethyl acetate (5 mL) was added dropwise via syringe 4 mL of a solution of HCl in Et$_2$O (0.3 M). The reaction mixture was stirred at 0° C. for 0.5 h. The precipitate was filtered, washed with Et$_2$O and dried. DL-threo-2-(Dimethylamino)-3-hydroxy-3-(pyridin-4-yl)-1-(pyrrolidin-1-yl)propan-1-one dihydrochloride Compound 45 was obtained (0.077 g, 43% yield) as a white solid.

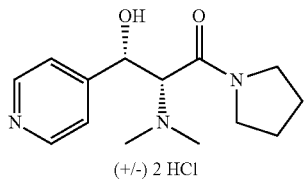

Compound 45

(+/-) 2 HCl

MW: 336.34; Yield: 43%; White Solid; Mp (° C.): 201.0.

$^1$H-NMR (CD$_3$OD, *): 1.48-1.64 (m, 2H, CH$_2$), 1.65-1.83 (m, 2H, CH$_2$), 2.60-2.72 (m, 1H, CH$_2$N), 3.15-3.33 (m, 1H, CH$_2$), 3.30-3.52 (m, 2H, CH$_2$), 4.60 (d, 1H, J=8.4 Hz, CHNH$_2$), 5.41 (d, 1H, J=8.4 Hz, CHO), 8.10 (d, 2H, J=6.6 Hz, ArH), 8.84 (d, 2H, J=6.7 Hz, ArH).

DL-threo-2-Amino-1-(pyridin-4-yl)-3-(pyrrolidin-1-yl)propan-1-ol Compound 46

To a stirred suspension of DL-threo-2-amino-3-hydroxy-3-(pyridin-4-yl)-1-(pyrrolidin-1-yl)propan-1-one dihydrochloride Compound 22 (0.86 g, 2.80 mmol) in tetrahydrofuran (108 mL) under nitrogen atmosphere was slowly added, in two portions, lithium aluminium hydride (0.64 g, 16.82 mmol) at 0° C. The mixture reaction was stirred at RT for 20 h and quenched by a slow, dropwise addition of 2 N aqueous sodium hydroxyde (8.4 mL, 6 eq). The yellow precipitate was filtered. The organic layer was washed by water (80 mL) and the organic layer was removed and combined with additional ethyl acetate extracts (4×200 mL) and dried over MgSO$_4$, filtered and evaporated. The crude product was purified by column chromatography on silica (CH$_2$Cl$_2$:MeOH:NH$_3$=94:05:01). After evaporation and drying DL-threo-2-amino-1-(pyridin-4-yl)-3-(pyrrolidin-1-yl)propan-1-ol Compound 46 was obtained (0.075 g, 12% yield) as a pale yellow solid.

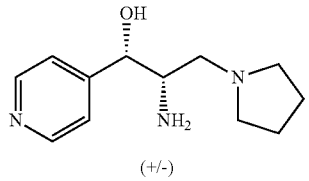

Compound 46

(+/-)

MW: 221.30; Yield: 12%; Pale Yellow Solid.

R$_f$:0.35 (CH$_2$Cl$_2$:MeOH:NH$_3$=90:08:02).

$^1$H-NMR (CD$_3$OD, *): 1.60-1.80 (m, 4H, 2×CH$_2$), 2.30-2.80 (m, 6H, 3×CH$_2$N), 3.14-3.19 (m, 1H, CHNH$_2$), 4.68 (d, 1H, J=3.0 Hz, CHO), 7.30 (d, 2H, J=6.0 Hz, ArH), 8.55 (d, 2H, J=6.0 Hz, ArH).

$^{13}$C-NMR (CD$_3$OD, *): 23.5 (2×C), 54.1, 54.7 (2×C), 60.1, 74.5, 121.4 (2×C), 149.5 (2×C), 152.1.

MS-ESI m/z (rel. int.): 222.1 ([MH]$^+$, 100), 205.0 (80), 189.0 (45), 151.0 (70), 134.0 (42), 121.9 (100), 107.9 (40).

DL-threo-2-Amino-3-hydroxy-3-(2-methoxypyridin-3-yl)-1-(pyrrolidin-1-yl)propan-1-one dihydrochloride Compound 48.

Trans-(4,5-Dihydro-5-(2-methoxypyridin-3-yl)oxazol-4-yl)(pyrrolidin-1-yl)methanone BAL 01014 (0.465 g, 1.69 mmol) was dissolved in methanol (6 mL). The solution of hydrochloric acid (37%, 0.3 mL) was added via a syringe at RT. The mixture was stirred for 3 h at RT. The residue was concentrated, dissolved in the minimum of MeOH, precipitated with EtOAc and filtered to obtain a white solid DL-threo-2-amino-3-hydroxy-3-(2-methoxypyridin-3-yl)-1-(pyrrolidin-1-yl)propan-1-one dihydrochloride Compound 48 (103 mg, 18.0% yield).

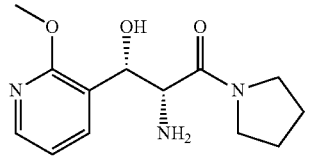

Compound 48

(+/-) 2·HCl

MW: 338.23; Yield: 18.0%; White Solid; Mp (° C.): 171.5.

$^1$H NMR (CD$_3$OD, *): 1.85-2.10 (m, 4H, CH$_2$), 3.30-3.82 (m, 4H, CH$_2$N), 4.26 (s, 3H, OCH$_3$), 4.60 (d, 1H, J=3.7 Hz, CH—N), 5.45 (d, 1H, J=3.7 Hz, CH—O), 7.39 (dd, 1H, J=5.6 Hz, J=7.3, ArH), 8.32 (dd, 1H, J=5.6 Hz, J=7.3 Hz, ArH).

$^{13}$C-NMR (CD$_3$OD, *): 24.9, 27.1, 47.8, 47.9, 56.4, 56.7, 66.0, 119.2, 125.6, 141.5, 143.9, 160.6, 166.1.

MS-ESI m/z (% rel. Int.): 266.2 ([MH]$^+$, 30), 248.2.0 (100).

HPLC: Method A, detection UV 254 nm, Compound 48 RT=3.31 min, peak area 97.9%.

3-(DL-threo-2-Amino-1-hydroxy-3-oxo-3-pyrrolidin-1-yl-propyl)-1H-pyridin-2-one hydrochloride Compound 49

Trans-(4,5-Dihydro-5-(2-methoxypyridin-3-yl)oxazol-4-yl)(pyrrolidin-1-yl)methanone BAL 01014 (0.684 g, 2.487 mmol) was dissolved in methanol (10 mL). A solution of hydrochloric acid (37%, 0.6 mL) was added via syringe at RT. The mixture was stirred for 22 h at reflux. The residue was concentrated, triturated with EtOAc and filtered to obtain a yellow pale solid 3-(DL-threo-2-amino-1-hydroxy-3-oxo-3-pyrrolidin-1-yl-propyl)-1H-pyridin-2-one hydrochloride Compound 49 (136 mg, 19.0% yield).

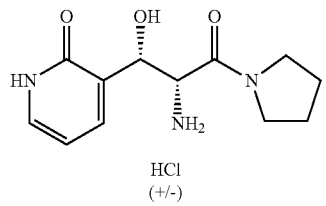

Compound 49

MW: 287.74; Yield: 19.0%; Yellow Pale Solid; Mp (° C.): 180.
$^{1}$H NMR (CD$_{3}$OD, *): 1.82-2.09 (m, 4H, 2×CH$_{2}$), 3.35-3.80 (m, 4H, 2×CH$_{2}$N), 4.63 (s, 1H, CH—N), 5.17 (s, 1H, CH—O), 6.56 (t, 1H, ArH)), 7.5 (d, 1H, J=6.1 Hz, ArH), 7.86 (d, 1H, J=6.5 Hz, ArH).
$^{13}$C-NMR (CD$_{3}$OD, *): 24.2, 26.0, 46.6, 46.6, 75.8, 79.7, 127.3, 127.5, 127.9, 129.4, 130.0, 132.3, 133.2, 148.1, 148.4, 155.3, 166.2.
MS-ESI m/z (% rel. Int.): 252.1 ([MH]$^{+}$, 18), 163.0 (100).
HPLC: Method A, detection UV 254 nm, Compound 49 RT=1.13 min, peak area 84.0%.
Preparation of Compound 51, Compound 52, Compound 53, Compound 54 Compound 55, Compound 56 and Compound 57.
General Procedures.
Method F:
To a suspension of DL-threo-2-amino-3-hydroxy-3-(pyridin-4-yl)-1-(pyrrolidin-1-yl)propan-1-one dihydrochloride Compound 22 (0.150 g, 0.44 mmol) in CH$_{2}$Cl$_{2}$ (4 mL) was added TEA (0.185 mL, 1.32 mmol) and the reaction mixture was stirred for 10 min and cooled in an ice bath with continuous stirring. The acyl chloride (0.484 mmol) was dissolved in CH$_{2}$Cl$_{2}$ (1 mL) and added dropwise to the reaction mixture. The reaction mixture was allowed to reach room temperature, stirred for 16 h and partitioned with H$_{2}$O (3×4 mL), washed with brine (3×4 mL), NaOH (0.5 M, 3×4 mL) and the organic layer was evaporated, adsorbed on silica gel (0.3 g) with EtOAc. The desired product was isolated by column chromatography using a gradient 0 to 8% [v/v] MeOH in EtOAc. The solid obtained was dissolved in ethanol (1 mL) and a solution of HCl (0.8 M, 1 mL) in EtOH was added. Evaporation of the volatiles led to the corresponding hydrochloride salt.

N-(DL-threo-1-Hydroxy-3-oxo-1-(pyridin-4-yl)-3-(pyrrolidin-1-yl)propan-2-yl)hexanamide hydrochloride Compound 51

The compound was prepared according to method F with hexanoyl chloride (59 mg, 0.484 mmol) and DL-threo-2-amino-3-hydroxy-3-(pyridin-4-yl)-1-(pyrrolidin-1-yl)propan-1-one dihydrochloride Compound 22. N-(DL-threo-1-Hydroxy-3-oxo-1-(pyridin-4-yl)-3-(pyrrolidin-1-yl)propan-2-yl)hexanamide hydrochloride Compound 51 was obtained as an off white solid. (56 mg, 34% yield).

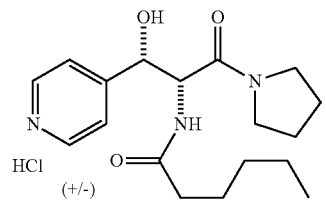

Compound 51

MW: 369.89; Yield: 34%; Off White Solid; Mp (° C.): 182.0.
$^{1}$H-NMR (CD$_{3}$OD, *): 0.84 (t, 3H, J=6.7, CH$_{3}$), 1.10-1.32 (m, 4H, CH$_{2}$), 1.35-1.50 (m, 2H, CH$_{2}$), 1.80-2.00 (m, 4H, CH$_{2}$), 2.05-2.30 (m, 2H, CH$_{2}$), 3.35-3.45 (m, 2H, CH$_{2}$), 3.50-3.65 (m, 2H, CH$_{2}$), 5.09 (d, 1H, J=3.7 Hz, N—CH), 5.38 (d, 1H, J=3.7 Hz, O—CH), 8.14 (d, 2H, J=6.3 Hz, ArH), 8.80 (d, 2H, J=6.3 Hz, ArH).
MS-ESI m/z (% rel. int.): 334.2 ([MH]$^{+}$, 10).
HPLC: Method A, detection UV 214 nm, Compound 51 RT=3.90 min, peak area 99.0%.

N-(DL-threo-1-Hydroxy-3-oxo-1-(pyridin-4-yl)-3-(pyrrolidin-1-yl)propan-2-yl)heptanamide hydrochloride Compound 52

The compound was prepared according to method F with heptanoyl chloride (72 mg, 0.484 mmol) and DL-threo-2-amino-3-hydroxy-3-(pyridin-4-yl)-1-(pyrrolidin-1-yl)propan-1-one dihydrochloride Compound 22. N-(DL-threo-1-Hydroxy-3-oxo-1-(pyridin-4-yl)-3-(pyrrolidin-1-yl)propan-2-yl)heptanamide hydrochloride Compound 52 was obtained as an off white solid. (192 mg, 66% yield).

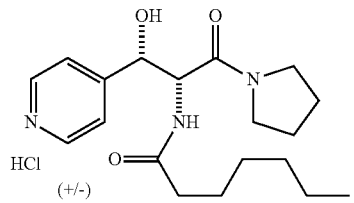

Compound 52

MW: 383.91; Yield: 66%; Off White Solid; Mp (° C.): 187.1.
$^{1}$H-NMR (CD$_{3}$OD, *): 0.88 (t, 3H, J=3.7 Hz, CH$_{3}$), 1.15-1.37 (m, 6H, CH$_{2}$), 1.37 (m, 2H, CH$_{2}$), 1.85-2.02 (m, 4H, CH$_{2}$), 1.18-2.27 (m, 2H, CH$_{2}$), 3.37-3.50 (m, 2H, N—CH$_{2}$), 3.55-3.70 (m, 2H, NCH$_{2}$), 5.14 (d, 1H, N—CH), 5.42 (d, 1H, O—CH), 8.19 (d, 2H, J=6.3 Hz, ArH), 8.83 (d, 2H, J=6.3 Hz, ArH).
$^{13}$C-NMR (CD$_{3}$OD, *): 14.4, 23.6, 25.0, 26.7, 27.0, 29.9, 32.6, 36.4, 47.5-56.7, 72.6, 126.6, 142.0, 164.5, 169.2, 175.9.
MS-ESI m/z (% rel. Int.): 348.2 ([MH]$^{+}$, 10).
HPLC: Method A, detection UV 254 nm, Compound 52 RT=4.10 min, peak area 99.0%.

N-(DL-threo-1-Hydroxy-3-oxo-1-(pyridin-4-yl)-3-(pyrrolidin-1-yl)propan-2-yl)octanamide hydrochloride Compound 53

The compound was prepared according to method F with octanoyl chloride (78 mg, 0.484 mmol) and DL-threo-2-amino-3-hydroxy-3-(pyridin-4-yl)-1-(pyrrolidin-1-yl)propan-1-one dihydrochloride Compound 22. N-(DL-threo-1-Hydroxy-3-oxo-1-(pyridin-4-yl)-3-(pyrrolidin-1-yl)propan-2-yl)octanamide hydrochloride Compound 53 was obtained as an off white solid. (131 mg, 75% yield).

Compound 53

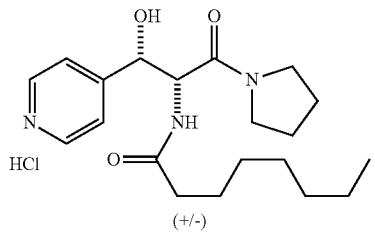

(+/-)

MW: 397.94; Yield: 75%; Off White Solid; Mp (° C.): 185.9.

$^1$H-NMR (CD$_3$OD, *): 0.91 (t, 3H, J=6.4 Hz, CH$_3$), 1.12-1.37 (m, 8H, CH$_2$), 1.40-1.52 (m, 2H, CH$_2$), 1.81 (m, 4H, CH$_2$), 2.12-2.25 (m, 2H, CH$_2$), 3.40-3.52 (m, 2H, N—CH$_2$), 3.55-3.65 (m, 2H, N—CH$_2$), 5.14 (d, 1H, J=3.7 Hz, N—CH), 5.43 (d, 1H, J=3.7 Hz, OCH), 8.19 (d, 2H, J=6.3 Hz, ArH), 8.84 (d, 2H, J=6.3 Hz, ArH).

$^{13}$C-NMR (CD$_3$OD, *): 14.4, 23.7, 24.9, 25.0, 25.5, 26.8, 27.0, 30.1, 30.2, 32.8, 34.3, 36.5, 47.5, 56.8, 71.6, 72.6, 126.7, 126.9, 142.1, 143.7, 164.5, 169.2, 176.0.

MS-ESI m/z (% rel. Int.): 362.2 ([MH]$^+$, 10).

HPLC: Method A, detection UV 254 nm, Compound 53 RT=4.37 min, peak area 99.9%.

N-(DL-threo-1-Hydroxy-3-oxo-1-(pyridin-4-yl)-3-(pyrrolidin-1-yl)propan-2-yl)palmitamide hydrochloride Compound 54

The compound was prepared according to method F with palmitoyl chloride (133 mg, 0.484 mmol) and DL-threo-2-amino-3-hydroxy-3-(pyridin-4-yl)-1-(pyrrolidin-1-yl)propan-1-one dihydrochloride Compound 22. N-(DL-threo-1-Hydroxy-3-oxo-1-(pyridin-4-yl)-3-(pyrrolidin-1-yl)propan-2-yl)palmitamide hydrochloride Compound 54 was obtained as an off white solid. (105 mg, 47% yield).

Compound 54

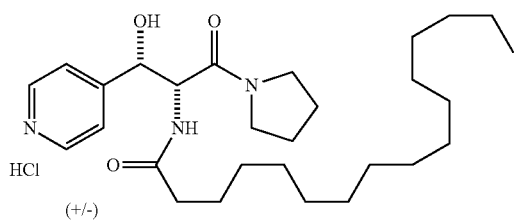

(+/-)

MW: 510.15; Yield: 47%; White Solid; Mp (° C.): 185.9.

$^1$H-NMR (CD$_3$OD, *): 0.92 (t, 3H, CH$_3$), 1.18-1.42 (m, 24H, CH$_2$), 1.42-1.58 (m, 2H, CH$_2$), 1.85 (m, 4H, CH$_2$), 2.15 (m, 2H, CH$_2$), 3.41-3.50 (m, 2H, CH$_2$), 3.50-3.68 (m, 2H, CH$_2$), 5.14 (d, 1H, J=3.5 Hz, N—CH), 5.42 (d, 1H, J=3.5 Hz, O—CH), 8.18 (d, 2H, J=6.0 Hz, ArH), 8.82 (d, 2H, J=5.7 Hz, ArH).

$^{13}$C-NMR (CD$_3$OD, *): 14.4, 23.7, 25.0, 26.8, 27.0, 30.3, 30.4, 30.5, 30.6, 30.7, 30.8, 33.1, 36.4, 47.5, 56.8, 72.6, 126.6, 142.1, 164.5, 169.2, 175.9.

MS-ESI m/z (% rel. Int.): 474.2 ([MH]$^+$, 40).

HPLC: Method A, detection UV 254 nm, Compound 54 RT=6.36 min, peak area 97.0%.

N-(DL-threo-1-Hydroxy-3-oxo-1-(pyridin-4-yl)-3-(pyrrolidin-1-yl)propan-2-yl)benzamide hydrochloride Compound 55

The compound was prepared according to method F with benzoyl chloride (141 mg, 0.484 mmol) and DL-threo-2-amino-3-hydroxy-3-(pyridin-4-yl)-1-(pyrrolidin-1-yl)propan-1-one dihydrochloride Compound 22. N-(DL-threo-1-Hydroxy-3-oxo-1-(pyridin-4-yl)-3-(pyrrolidin-1-yl)propan-2-yl)benzamide hydrochloride Compound 55 was obtained as an off white solid. (67 mg, 34% yield).

Compound 55

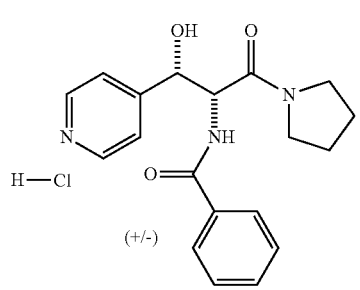

(+/-)

MW: 375.85; Yield: 34%; Off White Solid; Mp (° C.): 212.

$^1$H-NMR (CD$_3$OD, *): 1.69-1.91 (m, 4H, CH$_2$), 3.25-3.40 (m, 2H, N—CH$_2$), 3.40-3.58 (m, 2H, N—CH$_2$), 5.22 (d, 1H, J=3.7 Hz, N—CH), 5.43 (d, 1H, J=3.5 Hz, O—CH), 7.32 (t, 2H, J=7.8 Hz, ArH), 7.40 (t, 1H, J=6.9 Hz, ArH), 7.63 (d, 2H, J=7.1 Hz, ArH), 8.08 (d, 2H, J=6.6 Hz, ArH), 8.66 (d, 2H, J=6.1 Hz, ArH).

$^{13}$C-NMR (CD$_3$OD, *): 25.0, 27.1, 47.6, 57.6, 72.7, 126.6, 128.4, 129.7, 133.3, 134.4, 142.1, 164.5, 169.0, 169.7.

MS-ESI m/z (% rel. Int.): 340.2 ([MH]$^+$, 5).

HPLC: Method A, detection UV 254 nm, Compound 55 RT=3.66 min, peak area 99.0%.

N-(DL-threo-1-Hydroxy-3-oxo-1-(pyridin-4-yl)-3-(pyrrolidin-1-yl)propan-2-yl)-4-methoxy-benzamide hydrochloride Compound 56

The compound was prepared according to method F with 4-methoxybenzoyl chloride (82 mg, 0.484 mmol) and DL-threo-2-amino-3-hydroxy-3-(pyridin-4-yl)-1-(pyrrolidin-1-yl)propan-1-one dihydrochloride Compound 22. N-(DL-threo-1-Hydroxy-3-oxo-1-(pyridin-4-yl)-3-(pyrrolidin-1-yl)propan-2-yl)-4-methoxy-benzamide hydrochloride Compound 56 was obtained as an off white solid. (105 mg, 58% yield).

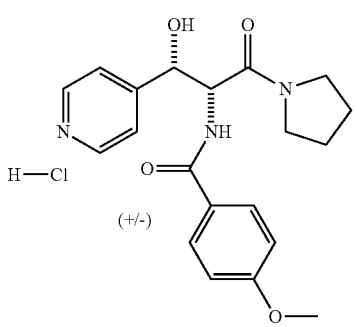

Compound 56

MW: 405.87; Yield: 58%; Off White Solid; Mp(° C.): 205.3 (dec).

$^1$H-NMR (CD$_3$OD, *): 1.82-2.08 (m, 4H, CH$_2$), 3.45-3.55 (m, 2H, CH$_2$—N), 3.60-3.70 (m, 2H, NCH$_2$), 3.86 (s, 3H, O—CH$_3$), 5.35 (d, 1H, J=3.7 Hz, N—CH), 5.56 (d, 1H, J=3.6 Hz, O—CH), 6.99 (dd, 2H, J=6.9 Hz, J=1.9 Hz), 7.76 (dd, 2H, J=6.9 Hz, J=1.9 Hz, ArH), 8.21 (d, 2H, J=6.6 Hz, ArH), 8.79 (d, 2H, J=6.6 Hz, ArH).

$^{13}$C-NMR (CD$_3$OD, *): 25.0, 27.1, 47.6, 56.0, 57.5, 72.7, 114.9, 115.2, 126.3, 126.6, 130.4, 133.7, 142.1, 164.4, 164.5, 169.1.

MS-ESI m/z (% rel. Int.): 370.2 ([MH]$^+$, 10).

HPLC: Method A, detection UV 254 nm, Compound 56 RT=3.76 min, peak area 99%.

3,4-Dichloro-N-(DL-threo-1-Hydroxy-3-oxo-1-(pyridin-4-yl)-3-(pyrrolidin-1-yl)propan-2-yl)benzamide Compound 57

The compound was prepared according to method F with 3,4-dichlorobenzoyl chloride (101 mg, 0.484 mmol) and DL-threo-2-amino-3-hydroxy-3-(pyridin-4-yl)-1-(pyrrolidin-1-yl)propan-1-one dihydrochloride Compound 22. 3,4-Dichloro-N-(DL-threo-1-hydroxy-3-oxo-1-(pyridin-4-yl)-3-(pyrrolidin-1-yl)propan-2-yl)benzamide Compound 57 was obtained as an off white solid. (92 mg, 55% yield).

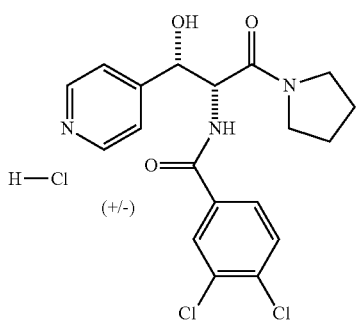

Compound 57

MW: 444.74; Yield: 55%; Off White Solid; Mp (° C.): 319.5 (dec).

$^1$H-NMR (CD$_3$OD, *): 1.82-2.05 (m, 4H, CH$_2$), 3.40-3.70 (m, 4H, N—CH$_2$), 5.33 (d, 1H, J=3.9 Hz, N—CH), 5.55 (d, 1H, J=4.0 Hz, O—CH), 7.61-7.75 (m, 2H, ArH), 7.96 (d, 1H, J=1.5 Hz, ArH), 8.22 (d, 2H, J=6.4 Hz, ArH), 8.81 (d, 2H, J=6.0 Hz, ArH).

$^{13}$C-NMR (CD$_3$OD, *): 25.0, 27.0, 57.8, 72.6, 126.6, 128.3, 130.7, 131.9, 133.8, 134.7, 137.2, 142.2, 164.3, 167.2, 168.8.

MS-ESI m/z (% rel. Int.): 408.0, ([MH]$^+$, 10)

HPLC: Method A, detection UV 254 nm, Compound 57 RT=4.28 min, peak area 99.9%.

Preparation of Compound 58, Compound 59, Compound 60, Compound 61, Compound 62, Compound 63, Compound 64, Compound 65, Compound 66 Compound 67, Compound 68, Compound 69.

General Procedures.

Method G (in CH$_2$Cl$_2$):

To a stirred solution of DL-threo-2-amino-3-hydroxy-3-(pyridin-4-yl)-1-(pyrrolidin-1-yl)propan-1-one dihydrochloride Compound 22 (0.15 g, 0.49 mmol) in 10 mL of CH$_2$Cl$_2$ at +4° C. were added triethylamine (200 µl, 1.45 mmol) and very slowly acid chloride in 3 mL of CH$_2$Cl$_2$. The mixture was stirred overnight at RT under nitrogen and then partitioned between CH$_2$Cl$_2$ and 1 N aqueous sodium carbonate. The organic layer was evaporated and the obtained residue purified by column chromatography on silica (EtOAc:MeOH=95:5). The hydrochloride salt was obtained in MeOH at 0° C. with 0.3 M HCl in diethylether to give after evaporation of solvents and drying the acylated compound.

Method H (in MeOH):

To a stirred solution of DL-threo-2-amino-3-hydroxy-3-(pyridin-4-yl)-1-(pyrrolidin-1-yl)propan-1-one dihydrochloride Compound 22 (0.20 g, 0.65 mmol) in 3 mL of MeOH were added triethylamine (180 µl, 1.30 mmol) and aldehyde (or ketone). The mixture was stirred overnight at RT under nitrogen and then was added AcOH (200 µL, 3.2 mmol) and NaBH$_3$CN. After 5 h at 20° C., MeOH was evaporated and the residue was partitioned between CH$_2$Cl$_2$ and 1 N aqueous sodium carbonate. The organic layer was evaporated and the obtained residue was purified by column chromatography on silica (EtOAc:MeOH or CH$_2$Cl$_2$:MeOH). The hydrochloride salt was obtained in MeOH at 0° C. with 0.3 M HCl in diethylether to give after evaporation of solvents and drying the alkylated compound.

Benzyl DL-threo-3-hydroxy-1-oxo-3-(pyridin-4-yl)-1-(pyrrolidin-1-yl)propan-2-ylcarbamate hydrochloride Compound 58

The compound was prepared according to method G with benzyl chloroformate (91 mg, 0.53 mmol). After work-up benzyl DL-threo-3-hydroxy-1-oxo-3-(pyridin-4-yl)-1-(pyrrolidin-1-yl)propan-2-ylcarbamate hydrochloride Compound 58 was obtained as a white solid (90 mg, 46% yield).

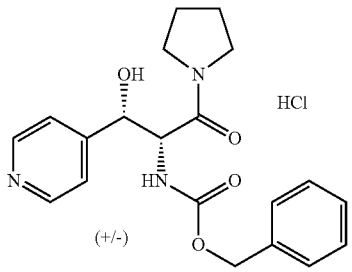

Compound 58

MW: 405.9; Yield: 46.0%; White Solid; Mp (° C.): 185.3. R$_f$: 0.38 (MeOH:EtOAc=10:90) free base.

¹H-NMR (CD₃OD, *): 1.87-2.03 (m, 4H, 2×CH₂), 3.40-3.48 (m, 2H, CH₂N), 3.56-3.62 (m, 2H, CH₂N), 4.85-5.04 (m, 3H, CH₂O, CHO), 5.39 (d, 1H, J=2.8 Hz, NH), 7.26-7.36 (m, 5H, ArH), 8.12 (d, 2H, J=6.0 Hz, ArH), 8.69 (d, 2H, J=6.0 Hz, ArH).

¹³C-NMR (CD₃OD, *): 25.0, 27.0, 47.5, 48.0, 58.8, 67.9, 72.7, 126.6 (2×C), 129.1, 129.2, 129.5, 138.1, 141.9 (2×C), 158.1, 164.4, 169.2.

MS-ESI m/z (% rel. Int.): 370.1 ([MH]⁺, 15), 219.0 (100).

HPLC: Method A, detection UV 254 nm, Compound 58 RT=4.10 min, peak area 99.8%.

N-(DL-threo-3-hydroxy-1-oxo-3-(pyridin-4-yl)-1-(pyrrolidin-1-yl)propan-2-yl)decanamide hydrochloride Compound 59

The compound was prepared according to method G with decanoyl chloride (111 μL, 0.53 mmol). After work-up N-(DL-threo-3-hydroxy-1-oxo-3-(pyridin-4-yl)-1-(pyrrolidin-1-yl)propan-2-yl)decanamide hydrochloride Compound 59 was obtained as a white solid (115 mg, 55% yield).

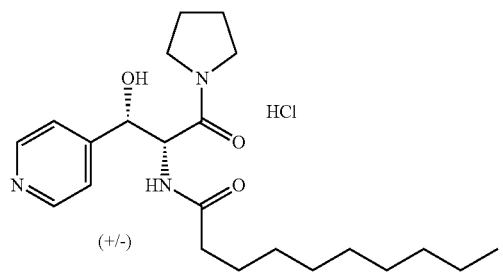

Compound 59

MW: 425.99; Yield: 55%; White Solid; Mp (° C.): 184.8. R_f:0.22 (MeOH:EtOAc=5:95) free base.

¹H-NMR (CD₃OD, *): 0.90 (t, 3H, J=7.0 Hz, CH₃), 1.26-1.34 (m, 12H, 6×CH₂), 1.42-1.50 (m, 2H, CH₂), 1.86-1.98 (m, 4H, 2×CH₂), 2.13-2.20 (m, 2H, CH₂CO), 3.41-3.46 (m, 2H, CH₂N), 3.52-3.61 (m, 2H, CH₂N), 5.12 (d, 1H, J=3.8 Hz, CH), 5.40 (d, 1H, J=3.7 Hz, CH), 8.16 (d, 2H, J=6.5 Hz, ArH), 8.97 (d, 2H, J=6.7 Hz, ArH).

¹³C-NMR (CD₃OD, *): 14.4, 23.7, 25.0, 26.8, 27.0, 30.3, 30.4, 30.6, 33.0, 36.5, 47.5, 56.8, 72.6, 126.6 (2×C), 142.1 (2×C), 164.4, 169.2, 175.9.

MS-ESI m/z (% rel. Int.): 390.1 ([MH]⁺, 20), 219.1 (100).

HPLC: Method A, detection UV 254 nm, Compound 59 RT=4.9 min, peak area 99.5%.

DL-threo-2-(Benzylamino)-3-hydroxy-3-(pyridin-4-yl)-1-(pyrrolidin-1-yl)propan-1-one dihydrochloride Compound 60

The compound was prepared according to method H with benzaldehyde (78 mg, 0.72 mmol). After column chromatography (EtOAc:MeOH=95:5) and HCl treatment DL-threo-2-(benzylamino)-3-hydroxy-3-(pyridin-4-yl)-1-(pyrrolidin-1-yl)propan-1-one dihydrochloride Compound 60 was obtained as a white solid (114 mg, 46% yield).

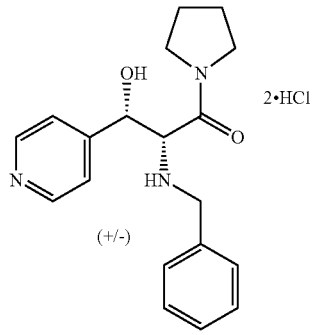

Compound 60

MW: 398.33; Yield: 46%; White Solid; Mp (° C.): 131.5. R_f:0.60 (MeOH:EtOAc=10:90) free base.

¹H-NMR (CD₃OD, *): 1.35-1.72 (m, 4H, 2×CH₂), 2.10-2.18 (m, 1H, CH₂N), 2.78-2.86 (m, 1H, CH₂N), 3.18-3.24 (m, 2H, CH₂N), 4.22 (d, 1H, J=8.5 Hz, CH), 4.26-4.36 (m, 2H, CH₂N), 5.18 (d, 1H, J=8.5 Hz, CH), 7.43-7.51 (m, 5H, BzH), 7.86 (d, 2H, J=6.6 Hz, ArH), 8.69 (d, 2H, J=6.6 Hz, ArH).

¹³C-NMR (CD₃OD, *): 24.7, 26.3, 47.3, 47.9, 51.4, 63.9, 72.4, 126.2, 130.3, 131.0, 131.4, 131.5, 148.9, 156.1, 163.9.

MS-ESI m/z (% rel. Int.): 326.1 ([MH]⁺, 100), 227.0 (80).

HPLC: Method A, detection UV 254 nm, Compound 60 RT=4.30 min, peak area 98.2%.

DL-threo-3-Hydroxy-2-(methylamino)-3-(pyridin-4-yl)-1-(pyrrolidin-1-yl)propan-1-one dihydrochloride Compound 61

The compound was prepared according to method H with paraformaldehyde (21 mg, 0.65 mmol). After column chromatography (EtOAc:MeOH=7:3) and HCl treatment DL-threo-3-hydroxy-2-(methylamino)-3-(pyridin-4-yl)-1-(pyrrolidin-1-yl)propan-1-one dihydrochloride Compound 61 was obtained as a pale yellow solid (28 mg, 13% yield).

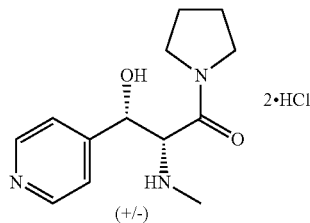

Compound 61

MW: 322.23; Yield: 13%; Pale Yellow Solid. R_f:0.20 (MeOH:EtOAc=30:70) free base.

¹H-NMR (CD₃OD, *): 1.60-1.80 (m, 4H, 2×CH₂), 2.61 (s, 1H, CH₃), 2.68-2.76 (m, 1H, CH₂N), 3.24-3.57 (m, 3H, CH₂N), 4.53 (d, 1H, J=6.8 Hz, CH), 5.26 (d, 1H, J=7.0 Hz, CH), 8.11 (d, 2H, J=5.8 Hz, ArH), 8.85 (d, 2H, J=5.6 Hz, ArH).

¹³C-NMR (CD₃OD, *): 24.8, 26.7, 32.8, 47.7, 48.3, 65.4, 71.7, 126.7 (2×C), 143.4 (2×C), 161.1, 163.9.

MS-ESI m/z (% rel. Int.): 251.1 ([MH]⁺, 10), 151.0 (100).

HPLC: Method A, detection UV 254 nm, Compound 61 RT=0.70 min, peak area 97.5%.

DL-threo-3-Hydroxy-2-(pentylamino)-3-(pyridin-4-yl)-1-(pyrrolidin-1-yl)propan-1-one dihydrochloride Compound 62

The compound was prepared according to method H with valeraldehyde (60 mg, 0.68 mmol). After column chromatography (EtOAc:MeOH=95:5) and HCl treatment DL-threo-3-hydroxy-2-(pentylamino)-3-(pyridin-4-yl)-1-(pyrrolidin-1-yl)propan-1-one dihydrochloride Compound 62 was obtained as a white solid (107 mg, 44% yield).

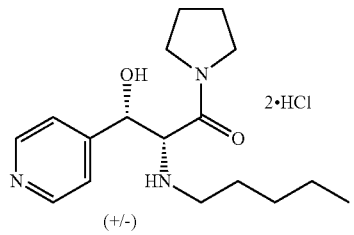

Compound 62

MW: 378.34; Yield: 44%; White Solid; Mp (° C.): 86.6. $R_f$:0.30 (MeOH:EtOAc=20:80) free base.

$^1$H-NMR (CD$_3$OD, *): 0.95 (t, 3H, J=6.4 Hz, CH$_3$), 1.32-1.40 (m, 6H, 3×CH$_2$), 1.70-1.87 (m, 4H, 2×CH$_2$), 2.70-2.75 (m, 1H, CH$_2$N), 2.90-3.00 (m, 1H, CH$_2$N), 3.10-3.39 (m, 3H, CH$_2$N), 3.46-3.60 (m, 1H, CH$_2$N), 4.61 (d, 1H, J=7.5 Hz, CH), 5.39 (d, 1H, J=7.5 Hz, CH), 8.22 (d, 2H, J=6.2 Hz, ArH), 8.97 (d, 2H, J=6.2 Hz, ArH).

$^{13}$C-NMR (CD$_3$OD, *): 9.3, 14.1, 23.2, 24.8, 26.7, 26.8, 29.7, 47.6, 47.9, 64.5, 72.1, 126.8 (2×C), 143.3 (2×C), 161.1, 164.1.

MS-ESI m/z (% rel. Int.): 306.3 ([MH]$^+$, 15), 207.1 (100).

HPLC: Method A, detection UV 254 nm, Compound 62 RT=3.60 min, peak area 98.5%.

DL-threo-3-Hydroxy-2-(hexylamino)-3-(pyridin-4-yl)-1-(pyrrolidin-1-yl)propan-1-one dihydrochloride Compound 63

The compound was prepared according to method H with hexanal (71 mg, 0.68 mmol). After column chromatography (EtOAc:MeOH=95:5) and HCl treatment DL-threo-3-hydroxy-2-(hexylamino)-3-(pyridin-4-yl)-1-(pyrrolidin-1-yl)propan-1-one dihydrochloride Compound 63 was obtained as a beige solid (112 mg, 45% yield).

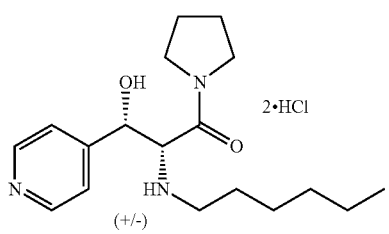

Compound 63

MW: 392.36; Yield: 45%; Beige Solid; Mp (° C.): 108.2. $R_f$:0.35 (MeOH:EtOAc=20:80) free base.

$^1$H-NMR (CD$_3$OD, *): 0.94 (t, 3H, J=7.2 Hz, CH$_3$), 1.30-1.42 (m, 6H, 3×CH$_2$), 1.66-1.90 (m, 6H, 3×CH$_2$), 2.68-2.74 (m, 1H, CH$_2$N), 2.90-2.99 (m, 1H, CH$_2$N), 3.09-3.16 (m, 1H, CH$_2$N), 3.32-3.39 (m, 1H, CH$_2$N), 3.47-3.60 (m, 2H, CH$_2$N), 4.60 (d, 1H, J=7.7 Hz, CH), 5.38 (d, 1H, J=7.7 Hz, CH), 8.24 (s, 2H, ArH), 8.97 (s, 2H, ArH).

$^{13}$C-NMR (CD$_3$OD, *): 14.3, 23.4, 24.8, 26.7, 27.1, 27.2, 32.4, 47.6, 64.4, 72.1, 126.9 (2×C), 143.2 (2×C), 161.3, 164.1.

MS-ESI m/z (% rel. Int.): 320.1 ([MH]$^+$, 30), 221.1 (100).

HPLC: Method A, detection UV 254 nm, Compound 63 RT=3.80 min, peak area 97.8%.

DL-threo-3-Hydroxy-2-(heptylamino)-3-(pyridin-4-yl)-1-(pyrrolidin-1-yl)propan-1-one dihydrochloride Compound 64

The compound was prepared according to method H with heptaldehyde (82 mg, 0.68 mmol). After column chromatography with EtOAc:MeOH=95:5 and HCl treatment DL-threo-3-hydroxy-2-(heptylamino)-3-(pyridin-4-yl)-1-(pyrrolidin-1-yl)propan-1-one dihydrochloride Compound 64 was obtained as a white solid (121 mg, 47% yield).

Compound 64

MW: 406.39; Yield: 47%; White Solid; Mp (° C.): 242.4. $R_f$:0.40 (MeOH:EtOAc=20:80) free base.

$^1$H-NMR (CD$_3$OD, *): 0.92 (t, 3H, J=7.0 Hz, CH$_3$), 1.32-1.40 (m, 8H, 4×CH$_2$), 1.65-1.90 (m, 6H, 3×CH$_2$), 2.71-2.76 (m, 1H, CH$_2$N), 2.90-2.99 (m, 1H, CH$_2$N), 3.09-3.38 (m, 1H, CH$_2$N), 3.47-3.62 (m, 2H, CH$_2$N), 4.61 (d, 1H, J=7.5 Hz, CH), 5.39 (d, 1H, J=7.5 Hz, CH), 8.24 (d, 2H, J=6.0 Hz, ArH), 8.97 (d, 2H, J=5.9 Hz, ArH).

$^{13}$C-NMR (CD$_3$OD, *): 14.4, 23.6, 24.8, 26.7, 27.1, 27.5, 29.9, 32.7, 47.7, 64.4, 72.1, 126.9 (2×C), 143.2 (2×C), 161.4, 164.1.

MS-ESI m/z (% rel. Int.): 334.1 ([MH]$^+$, 45), 235.1 (100).

HPLC: Method A, detection UV 254 nm, Compound 64 RT=4.00 min, peak area 97.5%.

DL-threo-2-(4-Methylbenzylamino)-3-hydroxy-3-(pyridin-4-yl)-1-(pyrrolidin-1-yl)propan-1-one Compound 65

The compound was prepared according to method H with 4-methylbenzaldehyde (86 mg, 0.70 mmol). After column chromatography (EtOAc:MeOH=95:5) and HCl treatment DL-threo-2-(4-methylbenzylamino)-3-hydroxy-3-(pyridin-4-yl)-1-(pyrrolidin-1-yl)propan-1-one Compound 65 was obtained as a white solid (137 mg, 51% yield).

Compound 65

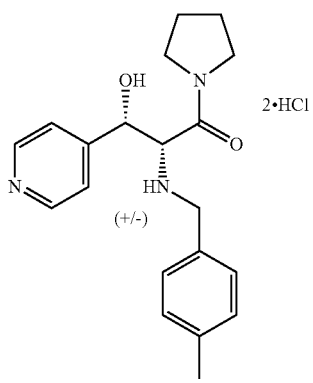

MW: 412.35; Yield: 51%; White Solid; Mp (° C.): 87.5. $R_f$:0.20 (MeOH:EtOAc=5:95) free base.

$^1$H-NMR (CD$_3$OD, *): 1.49-2.12 (m, 4H, 2×CH$_2$), 2.30-2.40 (m, 1H, CH$_2$N), 2.35. (s, 3H, CH$_3$), 2.75-2.95 (m, 1H, CH$_2$N), 3.18-3.25 (m, 2H, CH$_2$N), 4.12-4.32 (m, 3H, CH$_2$N, CH), 5.30 (d, 1H, J=7.9 Hz, CH), 7.24-7.39 (m, 4H, BzH), 8.11 (d, 2H, J=6.7 Hz, ArH), 8.89 (d, 2H, J=6.6 Hz, ArH).

$^{13}$C-NMR (CD$_3$OD, *): 21.2, 24.7, 26.3, 26.4, 47.4, 47.9, 51.2, 63.4, 72.4, 126.1, 126.6 (2×C), 128.2, 130.9, 131.4, 131.5, 141.4, 143.5 (2×C), 148.9, 156.1; 160.5, 163.8.

MS-ESI m/z (% rel. Int.): 340.1 ([MH]$^+$, 10), 104.9 (100).

HPLC: Method A, detection UV 254 nm, Compound 65 RT=3.70 min, peak area 97.3%.

DL-threo-2-(4-Chlorobenzylamino)-3-hydroxy-3-(pyridin-4-yl)-1-(pyrrolidin-1-yl)propan-1-one Compound 66

The compound was prepared according to method H with 4-chlorobenzaldehyde (98 mg, 0.70 mmol). After column chromatography (EtOAc:MeOH=95:5) and HCl treatment DL-threo-2-(4-chlorobenzylamino)-3-hydroxy-3-(pyridin-4-yl)-1-(pyrrolidin-1-yl)propan-1-one Compound 66 was obtained as a white solid (126 mg, 45% yield).

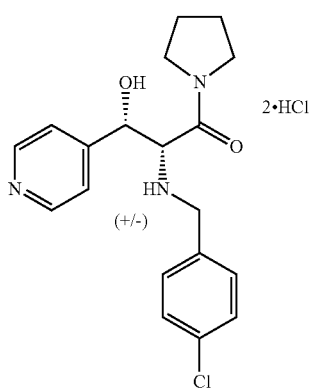

Compound 66

MW: 432.77; Yield: 45%; White Solid; Mp (° C.): 122.7. $R_f$:0.20 (MeOH:EtOAc=5:95) free base.

$^1$H-NMR (CD$_3$OD, *): 1.54-1.75 (m, 4H, 2×CH$_2$), 2.41-2.49 (m, 1H, CH$_2$N), 3.08-3.15 (m, 1H, CH$_2$N), 3.19-3.27 (m, 2H, CH$_2$N), 4.25-4.47 (m, 3H, CH$_2$N, CH), 5.34 (d, 1H, J=7.9 Hz, CH), 7.46-7.55 (m, 4H, BzH), 8.15 (d, 2H, J=6.0 Hz, ArH), 8.92 (d, 2H, J=5.7 Hz, ArH).

$^{13}$C-NMR (CD$_3$OD, *): 24.7, 26.5, 47.5, 47.8, 50.8, 63.8, 72.3, 126.7 (2×C), 130.3, 133.4, 137.1, 143.5 (2×C), 149.0, 160.6, 163.8.

MS-ESI m/z (% rel. Int.): 360.1/362.1 ([MH]$^+$, 20), 124.9 (100).

HPLC: Method A, detection UV 254 nm, Compound 66 RT=3.70 min, peak area 97.0%.

DL-threo-2-(4-Methoxybenzylamino)-3-hydroxy-3-(pyridin-4-yl)-1-(pyrrolidin-1-yl)propan-1-one one Compound 67

The compound was prepared according to method H with 4-methoxybenzaldehyde (95 mg, 0.70 mmol). After column chromatography (EtOAc:MeOH=95:5) and HCl treatment DL-threo-2-(4-methoxybenzylamino)-3-hydroxy-3-(pyridin-4-yl)-1-(pyrrolidin-1-yl)propan-1-one one Compound 67 was obtained as a white solid (123 mg, 44% yield).

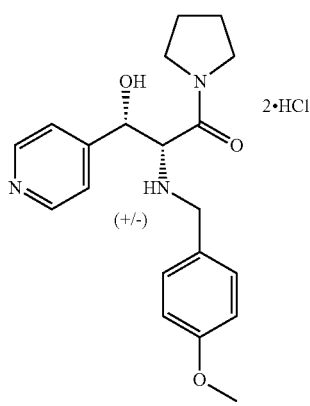

Compound 67

MW: 428.35; Yield: 44%; White Solid; Mp (° C.): 193.2. $R_f$:0.20 (MeOH:EtOAc=5:95) free base.

$^1$H-NMR (CD$_3$OD, *): 1.51-1.72 (m, 4H, 2×CH$_2$), 2.38-2.41 (m, 1H, CH$_2$N), 2.94-3.01 (m, 1H, CH$_2$N), 3.18-3.28 (m, 2H, CH$_2$N), 3.81 (s, 3H, CH$_3$O), 4.18-4.34 (m, 3H, CH$_2$N, CH), 5.31 (d, 1H, J=7.3 Hz, CH), 6.97 (d, 2H, J=8.5 Hz, ArH), 7.42 (d, 2H, J=8.5 Hz, ArH), 8.13 (d, 2H, J=6.5 Hz, ArH), 8.91 (d, 2H, J=6.3 Hz, ArH).

$^{13}$C-NMR (CD$_3$OD, *): 24.7, 26.5, 47.5, 47.9, 51.1, 55.9, 63.2, 72.3, 115.5, 122.9, 126.8 (2×C), 133.1, 143.3 (2×C), 160.9, 162.4, 163.8.

MS-ESI m/z (% rel. Int.): 356.1 ([MH]$^+$, 10), 120.9 (100).

HPLC: Method A, detection UV 254 nm, Compound 67 RT=3.50 min, peak area 98.6%.

DL-threo-2-(3,4-Dichlorobenzylamino)-3-hydroxy-3-(pyridin-4-yl)-1-(pyrrolidin-1-yl)propan-1-one dihydrochloride Compound 68

The compound was prepared according to method H with 3,4-dichlorobenzaldehyde (122 mg, 0.70 mmol). After column chromatography (EtOAc:MeOH=95:5) and HCl treatment DL-threo-2-(3,4-dichlorobenzylamino)-3-hydroxy-3-(pyridin-4-yl)-1-(pyrrolidin-1-yl)propan-1-one dihydrochloride Compound 68 was obtained as a white solid (153 mg, 50% yield).

Compound 68

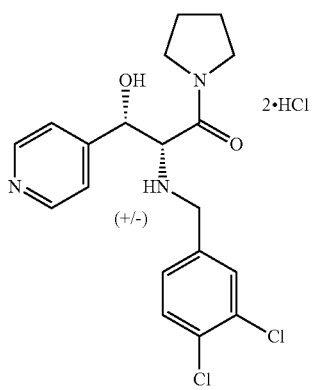

MW: 467.22; Yield: 50%; White Solid; Mp (° C.): 190.3. $R_f$:0.20 (MeOH:EtOAc=5:95) free base.

$^1$H-NMR (CD$_3$OD, *): 1.58-1.76 (m, 4H, 2×CH$_2$), 2.48-2.55 (m, 1H, CH$_2$N), 2.85-3.00 (m, 1H, CH$_2$N), 3.18-3.26 (m, 2H, CH$_2$N), 4.23-4.41 (m, 2H, CH$_2$N), 4.54 (d, 1H, J=7.7 Hz, CH), 5.34 (d, 1H, J=7.2 Hz, CH), 7.48 (d, 1H, J=8.3 Hz, ArH), 7.63 (dd, 1H, J=8.2 Hz, J=1.4 Hz, ArH), 7.75 (s, 1H, ArH), 8.16 (d, 2H, J=5.4 Hz, ArH), 8.92 (d, 2H, J=5.3 Hz, ArH).

$^{13}$C-NMR (CD$_3$OD, *): 23.2, 25.0, 46.0, 46.4, 48.9, 62.5, 70.7, 125.3, 130.2, 130.6, 130.7, 132.3, 133.6, 141.9, 159.2, 162.3.

MS-ESI m/z (% rel. Int.): 394.1/396.1 ([MH]$^+$, 40), 110.0 (100).

HPLC: Method A, detection UV 254 nm, Compound 68 RT=3.90 min, peak area 99.0%.

DL-threo-2-(4-Methoxybenzylamino)-3-hydroxy-3-(pyridin-4-yl)-1-(pyrrolidin-1-yl)propan-1-one Compound 69

The compound was prepared according to method H with cyclohexanone (75 µL, 0.70 mmol). After column chromatography (EtOAc:MeOH=95:5) and HCl treatment DL-threo-2-(4-methoxybenzylamino)-3-hydroxy-3-(pyridin-4-yl)-1-(pyrrolidin-1-yl)propan-1-one Compound 69 as a white solid (154 mg, 61% yield).

Compound 69

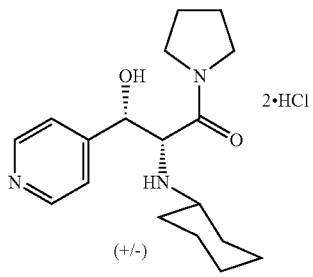

MW: 390.35; Yield: 61%; White Solid; Mp (° C.): 144.1. $R_f$:0.25 (MeOH:EtOAc=5:95) free base.

$^1$H-NMR (CD$_3$OD, *): 1.16-2.15 (m, 15H, 7×CH$_2$, CH), 2.65-2.72 (m, 1H, CH$_2$N), 3.07-3.15 (m, 1H, CH$_2$N), 3.43-3.65 (m, 2H, CH$_2$N), 4.61 (d, 1H, J=7.8 Hz, CH—N), 5.35 (d, 1H, J=7.8 Hz, CH—O), 8.21 (d, 2H, J=6.3 Hz, ArH), 8.95 (d, 2H, J=6.1 Hz, ArH).

$^{13}$C-NMR (CD$_3$OD, *): 23.2, 24.0, 24.2, 24.4, 25.2, 28.2, 29.3, 46.1, 57.4, 60.5, 71.0, 125.4 (2×C), 141.8 (2×C), 159.5, 162.6.

MS-ESI m/z (% rel. Int.): 318.2 ([MH]$^+$, 40; 219.1, 100).

HPLC: Method A, detection UV 254 nm, Compound 69 RT=3.40 min, peak area 99.7%.

Preparation of (±)-threo-2-amino-3-(furan-2-yl)-3-hydroxy-1-(pyrrolidin-1-yl)propan-1-one hydrochloride Compound 201 trans-5-(Furan-2-yl)-4,5-dihydrooxazol-4-yl)(pyrrolidin-1-yl)methanone BLE 04136D.

BLE 04136D was prepared in accordance with method D using 2-furaldehyde (0.449 mL, 5.42 mmol), KOH (0.276 mg, 4.92 mmol) in methanol (5 mL) and 2-isocyano-1-(pyrrolidin-1-yl)ethanone BLE 04098 (0.75 g, 5.42 mmol). After work-up the residue was purified by column chromatography (SiO$_2$, cyclohexane:EtOAc=100:0 to 0:100) to led, after evaporation, to trans-5-(furan-2-yl)-4,5-dihydrooxazol-4-yl)(pyrrolidin-1-yl)methanone BLE 04138D (0.742 g, 58.5% yield) as a pale yellow oil.

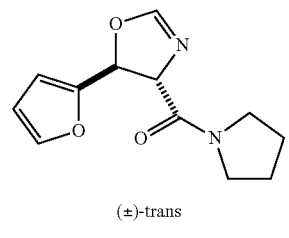

BLE 04136D

MW: 234.25; Yield: 58.5%; Pale Yellow Oil.

$^1$H-NMR (CDCl$_3$,*): 1.80-2.10 (m, 4H, CH$_2$), 3.47-3.60 (m, 3H, CH$_2$N), 3.93-4.03 (m, 1H, CH$_2$N), 4.94 (dd, 1H, J=7.4 Hz, J=2.2 Hz, CH—N), 6.14 (d, 1H, J=7.4 Hz, CH—O), 6.37 (dd, 1H, J=3.3 Hz, J=1.8 Hz, CH═C), 6.47 (d, 1H, J=3.3 Hz, CH═C), 6.92 (d, 1H, J=2.2 Hz, O—CH═N), 7.44 (t, 1H, J=1.6 Hz, OCH═C).

(±)-threo-2-Amino-3-(furan-2-yl)-3-hydroxy-1-(pyrrolidin-1-yl)propan-1-one hydrochloride Compound 201

Compound 201 was prepared following method E with trans-(5-(furan-2-yl)-4,5-dihydrooxazol-4-yl)(pyrrolidin-1-yl)methanone BLE 04136D (0.30 g, 1.28 mmol), hydrochloric acid 37% (0.3 mL) and methanol (10 mL). After overnight at RT and work-up (±)-threo-2-amino-3-(furan-2-yl)-3-hydroxy-1-(pyrrolidin-1-yl)propan-1-one hydrochloride (0.22 g, 66% yield) was obtained as a pale brown solid.

Compound 201

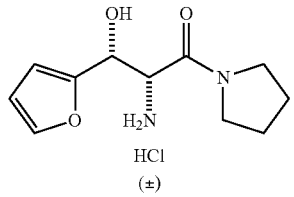

MW: 260.72; Yield: 66%; Pale Brown Solid; Mp (° C.): 159.8

$^{1}$H-NMR (CD$_{3}$OD,*): 1.62-1.95 (m, 4H, 2×CH$_{2}$), 2.72-2.85 (m, 1H, CH$_{2}$N), 3.22-3.35 (m, 1H, CH$_{2}$N), 3.38-3.55 (m, 2H, CH$_{2}$N), 4.35 (d, 1H, J=8.5 Hz, CH—N), 4.91 (d, 1H, J=8.5 Hz, CH—O), 6.45 (m, 2H, ArH), 7.52-7.57 (m, 1H, ArH).

$^{13}$C-NMR (CD$_{3}$OD,*): 24.9, 26.9, 47.4, 47.6, 57.4, 67.8, 109.9, 111.9, 144.4, 153.0, 166.0.

MS-ESI m/z (% rel. Int.): 225.1 ([MH]$^{+}$, 18), 207.1 (100).

HPLC: Method A, detection UV 254 nm, Compound 201 RT=2.87 min, peak area 92.0%.

Preparation of (−)-(2R,3S)-2-amino-3-hydroxy-3-(pyridin-4-yl)-1-(pyrrolidin-1-yl)propan-1-one dihydrochloride Compound 203 and (+)-(2S,3R)-2-amino-3-hydroxy-3-(pyridin-4-yl)-1-(pyrrolidin-1-yl)propan-1-one dihydrochloride Compound 204

Extraction of the Free Base of Compound 22:

(±)-threo-2-Amino-3-hydroxy-3-(pyridin-4-yl)-1-(pyrrolidin-1-yl)propan-1-one dihydrochloride Compound 22 (350 mg, 1.14 mmol) was dissolved in 20 mL of a K$_{2}$CO$_{3}$ (10%) solution and the aqueous mixture was then saturated with NaCl. The aqueous phase was extracted by a mixture CH$_{2}$Cl$_{2}$:2-PrOH=9:1 (6×15 mL). The organic phase was dried over MgSO$_{4}$ and evaporated to afford 226 mg (85% yield) of the free base of Compound 22.

Analytical Chiral Separation:

20 μL of a 1 mg/mL solution of Compound 22 were injected on Chiralpak AD: flow-rate=1 mL/min, temperature=25° C., mobile phase: hexane:ethanol=1:1, detection by UV at 220 nm and by polarimeter, Rt (−)=8.20 min, Rt (+)=10.61 min, k (−)=1.72, k (+)=2.51, α=1.47 and resolution Rs=3.08.

Semi-Preparative Chiral Separation:

A solution of 100 mg/mL was prepared and 10 μL of this solution were injected every 4.5 min on Chiralpak AD, flow-rate=1 mL/min, mobile phase hexane:ethanol=4:6, detection by UV at 254 nm 135 successive injections were done. The two main fractions were identified by UV and collected in two different flasks. The solvent was removed in vacuo at 30° C. The resulting solid was dissolved in 50 mL of CH$_{2}$Cl$_{2}$ and then filtered on a 0.45 μm millipore membrane. After evaporation of CH$_{2}$Cl$_{2}$, the solid was dissolved in 50 mL of methanol and then filtered. The salts were regenerated according to the procedure reported above.

Regeneration of the Salt:

After the chiral separation, about 63 mg of each enantiomer of the free base were dissolved in 100 mL of ethanol and 6.7 mL of HCl (0.2 N, 5 eq) were added. The solvent was evaporated, then 50 mL of ethanol were added and then removed in vacuo and the products were dried over P$_{2}$O$_{5}$ under vacuum overnight. The enantiomeric purity of the products was checked by analytical injection of the regenerated salts:

(−)-(2R,3S)-2-Amino-3-hydroxy-3-(pyridin-4-yl)-1-(pyrrolidin-1-yl)propan-1-one dihydrochloride Compound 203

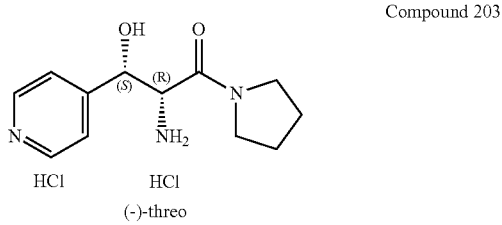

Compound 203

(−)-threo

MW: 308.20; 83 mg obtained; Yield: 23.5%; White Solid; Mp (° C.): 183.5 Enantiomeric excess=99.3%

$\alpha^{25}_{D}$=−22.7 (MeOH, c=0.51).

(+)-(2S,3R)-2-Amino-3-hydroxy-3-(pyridin-4-yl)-1-(pyrrolidin-1-yl)propan-1-one dihydrochloride Compound 204

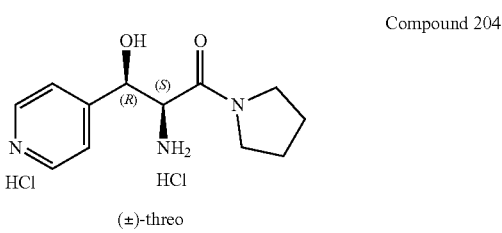

Compound 204

(±)-threo

MW: 308.20; 82 mg obtained; Yield: 23.5%; White Solid; Mp (° C.): 176.9

Enantiomeric excess=98.5%

$\alpha^{25}_{D}$=+23.1 (MeOH, c=1).

Preparation of (+)-threo-2-amino-3-hydroxy-1-(pyrrolidin-1-yl)-3-(thiophen-3-yl)propan-1-one hydrochloride Compound 205 and (−)-threo-2-amino-3-hydroxy-1-(pyrrolidin-1-yl)-3-(thiophen-3-yl) propan-1-one hydrochloride Compound 206

Extraction of the Free Base:

(±)-threo-2-amino-3-hydroxy-1-(pyrrolidin-1-yl)-3-(thiophen-3-yl)propan-1-one hydrochloride Compound 23 (243 mg, 0.88 mmol) was dissolved in 10 mL of a Na$_{2}$CO$_{3}$ (10%) solution and the aqueous mixture was then saturated with NaCl. The aqueous phase was extracted by 5×15 mL of a mixture CH$_{2}$Cl$_{2}$:2-PrOH=9:1. The organic phase was dried over MgSO$_{4}$ and evaporated to afford 190 mg (90%) of the free base of Compound 23.

Analytical Chiral Separation:

20 μL of a 1 mg/mL solution of Compound 23 were injected on an analytical Chiralpak AD: flow-rate=1 mL/min, temperature=25° C., mobile phase: ethanol, detection by UV at 220 nm and by polarimeter, Rt (+)=4.98 min, Rt (−)=6.23 min, k (+)=0.55, k (−)=0.93, α=1.17 and resolution Rs=3.34.

Regeneration of the Salt:

After the chiral separation, about 70 mg of each enantiomer of the free base were dissolved in 100 mL of ethanol and 3.6 mL of HCl (0.2 N, 2.5 eq) were added. The solvent was evaporated then 50 mL of ethanol were added and then removed in vacuo. The product was dissolved in 2 mL of methanol and 3 mL of ethyl acetate were added. The solvents were removed to give a white solid and then, the solids were dried over $P_2O_5$ under vacuum overnight.

Semi-Preparative Chiral Separation:

A 175 mg/mL solution of the free base was prepared and 6 μL of this solution were injected every 3 min on an analytical Chiralpak AD, flow-rate=1 mL/min, mobile phase ethanol, detection by UV at 254 nm. 150 successive injections were done. The two main fractions were identified by UV and collected in two different flasks. The solvent was removed in vacuo at 30° C. The resulting solid was dissolved in 50 mL of $CH_2Cl_2$ and then filtered on a 0.45 μm millipore membrane. After evaporation of $CH_2Cl_2$, the solid was dissolved in 50 mL of methanol and then filtered. The salt was regenerated according to the procedure reported above.

The enantiomeric purity of the products was checked by analytical injection of the regenerated salts:

(+)-threo-2-Amino-3-hydroxy-1-(pyrrolidin-1-yl)-3-(thiophen-3-yl)propan-1-one hydrochloride Compound 205

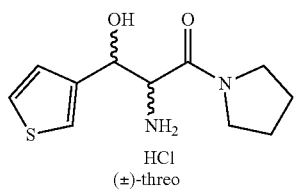

Compound 205

MW: 276.78; 83 mg obtained; Yield: 34%; White Solid; Mp (° C.): too hygroscopic.

Enantiomeric excess=99.5%

$\alpha^{25}_D$=+ 20.4 (MeOH, c=0.5).

(−)-threo-2-Amino-3-hydroxy-1-(pyrrolidin-1-yl)-3-(thiophen-3-yl)propan-1-one hydrochloride Compound 206

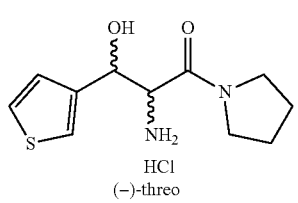

Compound 206

MW: 276.78; 77 mg obtained; Yield: 32%; White Solid; Mp (° C.): too hygroscopic.

Enantiomeric excess=99.0%

$\alpha^{25}_D$=−20.0 (MeOH, c=0.52).

Preparation of (−)-threo-2-amino-3-hydroxy-3-(pyridin-3-yl)-1-(pyrrolidin-1-yl)propan-1-one dihydrochloride Compound 207 and (+)-threo-2-amino-3-hydroxy-3-(pyridin-3-yl)-1-(pyrrolidin-1-yl)propan-1-one dihydrochloride Compound 208

Semi-preparative separation was performed on Chiralpak AD (250×10 mm):

The semi-preparative chiral separation needed three steps:

First step A: A 80 mg/mL solution of (±)-threo-2-amino-3-hydroxy-3-(pyridin-3-yl)-1-(pyrrolidin-1-yl)propan-1-one Compound 20 free base (220 mg) racemate was prepared and 200 μL of this solution were injected every 8 min on Chiralpak AD, flow-rate=4 mL/min, mobile phase: ethanol, detection by UV at 290 nm. Two main fractions were collected after 13 successive injections:

1A containing about 61 mg of (−) enantiomer Compound 207 free base with ee>97%.

2A containing about 135 mg of mixture+/−enantiomers in a 74/26 ratio.

Second step B: A 30 mg/mL solution of fraction 2A was prepared and 100 μL of this solution were injected every 6 min on Chiralpak AD, flow-rate=4 mL/min, mobile phase: ethanol, detection by UV at 290 nm. Two main fractions were collected after 45 successive injections:

1B containing about 27 mg of (−) enantiomer Compound 207 free base with ee>97%.

2B containing about 105 mg of mixture (+)/(−) in a 93/7 ratio.

Third step C: A 15 mg/mL solution of fraction 2B was prepared and 250 μL of this solution were injected every 6 min on Chiralpak AD, flow-rate=4 mL/min, mobile phase: ethanol, detection by UV at 254 nm. Two main fractions were collected after 28 successive injections:

1C containing about 7 mg of (−) enantiomer Compound 207 free base with ee>97%.

2C containing about 89 mg of (+) enantiomer with ee>97%.

Fractions 1A, 1B and 1C of (−) enantiomer Compound 207 free base were mixed together. Fraction 2C of (+) enantiomer Compound 208 free base was taken alone. For the both enantiomers, the solvent was removed in vacuo at 30° C. The resulting solid was dissolved in 50 mL of $CH_2Cl_2$ and then filtered on a 0.45 μm millipore membrane. After evaporation of $CH_2Cl_2$, the solid was dissolved in 50 mL of methanol and then filtered. The salt was regenerated according to the procedure reported below. The intermediate fraction collected contains 25 mg of a mixture of the both enantiomers in 50/50 (+)/(−) ratio and some impurities.

Regeneration of the Salt (Dihydrochloride):

After the chiral separation, about 90-95 mg of each enantiomers of the free base were dissolved in 100 mL of ethanol and 10 mL of HCl (0.2 N, 5 eq) were added. The solvent was evaporated and 50 mL of ethanol were added and then removed in vacuo. The product was dissolved in 1 mL of methanol and 5 mL of ethyl acetate were added to precipitate the salt. The solvents were removed to give a white solid and then, the solids were dried over $P_2O_5$ under vacuum overnight.

The enantiomeric purity of the products was checked by analytical HPLC injection of the regenerated dihydrochloride salts:

(−)-threo-2-Amino-3-hydroxy-3-(pyridin-3-yl)-1-(pyrrolidin-1-yl)propan-1-one dihydrochloride Compound 207

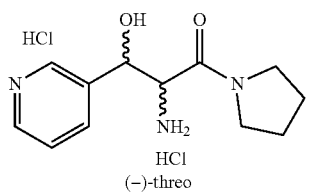

Compound 207
(−)-threo

MW: 308.20; 124 mg obtained; Yield: 43%; White Solid; Mp (° C.): 120.4

Enantiomeric excess=97.8% measured by HPLC at 220 nm (Chiralpak AD)
RT=6.24 min, eluent ethanol, flow 1 mL/min.
$\alpha^{25}_D$=−15.9 (MeOH, c=1).

(+)-threo-2-Amino-3-hydroxy-3-(pyridin-3-yl)-1-(pyrrolidin-1-yl)propan-1-one dihydrochloride Compound 208

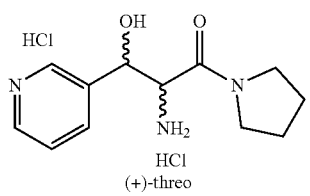

Compound 208
(+)-threo

MW: 308.20; 117 mg obtained; Yield: 40.5%; White Solid; Mp (° C.): 120.1

Enantiomeric excess=98.0% measured by HPLC at 220 nm (Chiralpak AD)
RT=7.39 min, eluent ethanol, flow 1 mL/min.
$\alpha^{25}_D$=+ 15.8 (MeOH, c=1).

Preparation of (±)-threo-2-amino-3-hydroxy-3-(2-iodophenyl)-1-(pyrrolidin-1-yl)propan-1-one hydrochloride Compound 209 trans-(4,5-Dihydro-5-(2-iodophenyl)oxazol-4-yl)(pyrrolidin-1-yl)methanone VIB 01090A VIB 01090A was prepared in accordance with method D using 2-isocyano-1-(pyrrolidin-1-yl)ethanone SLA 09100 (327.9 mg, 2.155 mmol), potassium hydroxide (121 mg, 2.155 mmol) in methanol (2.2 mL) and 2-iodo-benzaldehyde (500 mg, 2.155 mmol). The solution was stirred for 3 h at 0° C. After work-up the crude product was purified by column chromatography (florisil, EtOAc:MeOH=9:1) to obtain after evaporation trans-(4,5-dihydro-5-(2-iodophenyl)oxazol-4-yl)(pyrrolidin-1-yl)methanone VIB 01090A as a yellow oil (364 mg, 44% yield).

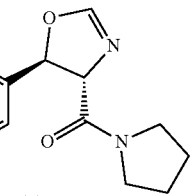

(±) - trans
VIB 01090A

MW: 384.22; Yield: 44%; Yellow Oil.
$R_f$:0.51 (EtOAc:MeOH=9:1).
$^1$H-NMR (CDCl$_3$, δ): 1.85-2.07 (m, 4H, 2×CH$_2$), 3.50-3.62 (m, 3H, CH$_2$), 3.78-3.90 (m, 1H, CH$_2$), 4.57 (dd, 1H, J=5.6 Hz, J=1.9 Hz, CH—N), 6.19 (d, 1H, J=5.6 Hz, CH—O), 7.05 (dt, 1H, J=7.7 Hz, J=1.6 Hz, ArH), 7.15 (d, 1H, J=1.9 Hz, HC=N), 7.27 (dd, 1H, J=7.9 Hz, J=1.6 Hz, ArH), 7.39 (t, 1H, J=7.3 Hz, ArH), 7.87 (d, 1H, J=7.8 Hz, ArH).
$^{13}$C-NMR (CDCl$_3$, δ): 24.3, 26.0, 46.3, 46.6, 74.8, 84.4, 95.0, 126.5, 128.4, 129.9, 139.8, 142.2, 155.7, 167.1.

(±)-threo-2-Amino-3-hydroxy-3-(2-iodophenyl)-1-(pyrrolidin-1-yl)propan-1-one hydrochloride Compound 209

Compound 209 was prepared following method E with trans-(4,5-dihydro-5-(2-iodophenyl)oxazol-4-yl)(pyrrolidin-1-yl)methanone VIB 01090A (0.345 g, 0.89 mmol), HCl 37% (0.22 mL) and methanol (4 mL). After heating at 50° C. for 3 h and work-up, a triturated with EtOAc followed by filtration and drying afforded to (±)-threo-2-amino-3-hydroxy-3-(2-iodophenyl)-1-(pyrrolidin-1-yl)propan-1-one hydrochloride Compound 209 as a white solid (287 mg, 74% yield).

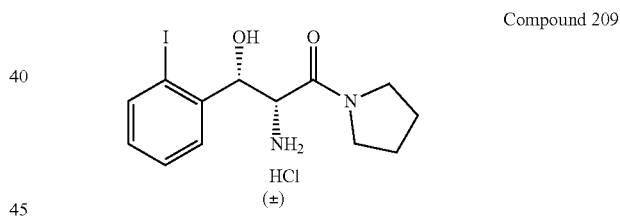

Compound 209
(±)

MW: 396.65; Yield: 74%; White Solid; Mp (° C.): 164.0
$^1$H-NMR (CD$_3$OD, δ): 1.47-1.90 (m, 4H, 2×CH$_2$), 1.95-2.10 (m, 1H, CH$_2$), 3.25-3.55 (m, 3H, CH$_2$), 4.23 (d, 1H, J=9.0 Hz, CH⁻N), 5.20 (d, 1H, J=9.0 Hz, CH—O), 7.11 (t, 1H, J=7.4 Hz, ArH), 7.50 (t, 1H, J=7.5 Hz, ArH), 7.78 (d, 2H, J=7.9 Hz, ArH), 7.88 (d, 2H, J=7.7 Hz, ArH).
$^{13}$C-NMR (CD$_3$OD, δ): 24.8, 26.8, 47.8, 48.1, 58.6, 75.8, 98.3, 130.1, 130.8, 131.8, 141.1, 143.8, 165.6.
MS-ESI m/z (% rel. Int.): 360.9 ([MH]$^+$, 100), 342.9 (40).
HPLC: Method A, detection UV 254 nm, Compound 209 RT=3.88 min, peak area 97.8%.

Preparation of (±)-threo-2-amino-3-hydroxy-3-hydroxy-3-(4-iodophenyl)-1-(pyrrolidin-1-yl)propan-1-one dihydrochloride Compound 210 trans-(4,5-Dihydro-5-(4-iodophenyl)oxazol-4-yl)(pyrrolidin-1-yl)methanone VIB 01090B VIB 01090B was prepared in accordance with method D using 2-isocyano-1-(pyrrolidin-1-yl)ethanone SLA 09100

(327.9 mg, 2.155 mmol), potassium hydroxide (121 mg, 2.155 mmol) in methanol (2.2 mL) and 4-iodobenzaldehyde (500 mg, 2.155 mmol). The solution was stirred for 3 h at 0° C. After work-up, the crude product was washed in a minimum amount of MeOH and filtered to obtain after drying trans-(4,5-dihydro-5-(4-iodophenyl)oxazol-4-yl)(pyrrolidin-1-yl)methanone VIB 01090B as a white solid (0.377 g, 52% yield).

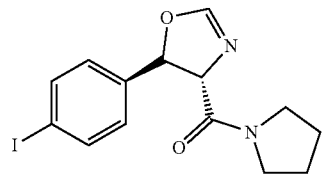

(±)-trans

VIB 01090B

MW: 384.22; Yield: 52%; White Solid; Mp (° C.): 115.1

$^1$H-NMR (CDCl$_3$, δ): 1.75-2.10 (m, 4H, 2×CH$_2$), 3.35-3.60 (m, 3H, CH$_2$), 3.88-4.02 (m, 1H, CH$_2$), 4.53 (dd, 1H, J=7.7 Hz, J=1.9 Hz, CH—N), 6.09 (d, 1H, J=7.7 Hz, CH—O), 6.92-7.11 (m, 3H, 2×ArH & CH=N), 7.69-7.70 (dd, 2H, J=8.4 Hz, J=1.7 Hz, ArH).

$^{13}$C-NMR (CDCl$_3$, δ): 24.1, 26.0, 46.2, 46.4, 75.7, 80.8, 94.0, 127.6 (2×C), 137.9 (2×C), 139.4, 155.2, 166.4.

(±)-threo-2-Amino-3-hydroxy-3-hydroxy-3-(4-iodophenyl)-1-(pyrrolidin-1-yl)propan-1-one dihydrochloride Compound 210

Compound 210 was prepared following method E with trans-(4,5-dihydro-5-(4-iodophenyl)oxazol-4-yl)(pyrrolidin-1-yl)methanone VIB 01090B (0.345 g, 0.89 mmol), hydrochloric acid 37% (0.24 mL) and methanol (4.4 mL). After heating at 50° C. for 3 h and work-up, a trituration with EtOAc followed by filtration and drying afforded to (±)-threo-2-amino-3-hydroxy-3-(4-iodophenyl)-1-(pyrrolidin-1-yl)propan-1-one hydrochloride Compound 210 as a white solid (247.5 mg, 64% yield).

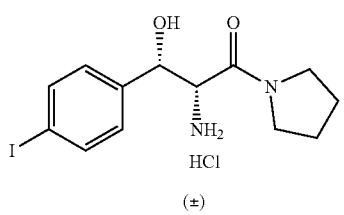

Compound 210

(±)

MW: 396.65; Yield: 64%; White Solid; Mp (° C.): 184.4

$^1$H-NMR (CD$_3$OD, δ): 1.35-1.9 (m, 4H, 2×CH$_2$), 2.20-2.33 (m, 1H, CH$_2$), 3.18-3.40 (m, 3H, CH$_2$), 4.11 (d, 1H, J=8.9 Hz, CH–N), 4.82 (d, 1H, J=8.9 Hz, CH—O), 7.22 (d, 2H, J=8.2 Hz, ArH), 7.76 (d, 2H, J=8.2 Hz, ArH).

$^{13}$C-NMR (CD$_3$OD, δ): 24.8, 26.6, 47.3, 47.7, 59.2, 73.6, 95.1, 129.8 (2×C), 138.9 (2×C), 140.6, 166.1.

MS-ESI m/z (% rel. Int.): 360.9 ([MH]$^+$, 100), 342.9 (85).

HPLC: Method A, detection UV 254 nm, Compound 210 RT=4.08 min, peak area 96.8%.

Preparation of (±)-threo-2-amino-3-hydroxy-3-(3-iodophenyl)-1-(pyrrolidin-1-yl)propan-1-one hydrochloride Compound 211 trans-(4,5-dihydro-5-(3-iodophenyl)oxazol-4-yl) (pyrrolidin-1-yl)methanone SLA 09104

To a stirred and cooled (0° C.) solution of KOH (0.144 g, 2.57 mmol) in methanol (10 mL) was added 3-iodobenzaldehyde (0.500 mg, 2.15 mmol) and 1-isocyano-3-(pyrrolidin-1-yl)propan-2-one (0.295 g, 2.13 mmol). The solution was stirred 24 h with continued cooling and then concentrated. Water (50 mL) was added and the solution was extracted with EtOAc (3×50 mL). The organic layer was washed with brine (50 mL), dried over MgSO$_4$, filtered and evaporated. trans-(4,5-Dihydro-5-(3-iodophenyl)oxazol-4-yl)(pyrrolidin-1-yl) methanone SLA 09104 was obtained (0.63 g, 80% yield) as a pale yellow solid.

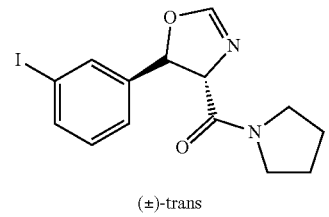

(±)-trans

SLA 09104

MW: 370.19; Yield: 80%; Pale Yellow Solid.

$^1$H-NMR (CDCl$_3$, δ): 1.80-2.08 (m, 4H, 2×CH$_2$), 3.42-3.58 (m, 3H, 1.5×CH$_2$), 3.90-3.96 (m, 1H, 0.5×CH$_2$), 4.56 (dd, 1H, J=7.7 Hz, J=2.2 Hz, CH—N), 6.10 (d, 1H, J=7.7 Hz, CH—O), 7.01 (d, 1H, J=2.2 Hz, CH=N), 7.11 (t, 1H, J=6.8 Hz, ArH), 7.29 (m, 1H, ArH), 7.66 (m, 2H, ArH).

$^{13}$C-NMR (CDCl$_3$, δ): 24.2, 26.0, 46.5, 46.6, 75.8, 80.4, 94.7, 125.0, 130.6, 134.6, 137.5, 142.0, 155.2, 166.3.

(±)-threo-2-Amino-3-hydroxy-3-(3-iodophenyl)-1-(pyrrolidin-1-yl)propan-1-one hydrochloride Compound 211 trans-(4,5-Dihydro-5-(3-iodophenyl)oxazol-4-yl)(pyrrolidin-1-yl)methanone SLA 09104 (0.620 g, 1.67 mmol) was dissolved in methanol (5 mL). The solution was stirred at room temperature and a solution of HCl (37%, 1 mL) was added via syringe and the mixture was stirred at 50° C. for 6 h. The mixture was concentrated and triturated with EtOAc. After filtration and drying (±)-threo-2-amino-3-hydroxy-3-(3-iodophenyl)-1-(pyrrolidin-1-yl)propan-1-one hydrochloride Compound 211 was obtained (586 mg, 88% yield) as a white solid.

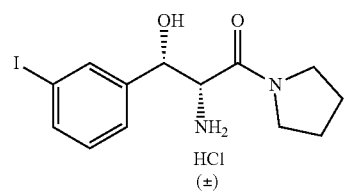

Compound 211

(±)

MW: 396.65; Yield: 88%; White Solid; Mp (° C.): 183.7

$^{1}$H-NMR (CD$_3$OD, δ): 1.35-1.50 (m, 1H, 0.5×CH$_2$), 1.58-1.82 (m, 3H, 1.5×CH$_2$), 2.08-2.18 (m, 1H, 0.5×CH$_2$), 3.21-3.45 (m, 4H, 2×CH$_2$), 4.09 (d, 1H, J=9.1 Hz, CH—N), 4.80 (d, 1H, J=9.2 Hz, CH—O), 7.19 (t, 1H, J=7.1 Hz, ArH), 7.49 (d, 1H, J=7.6 Hz, ArH), 7.74 (m, 2H, ArH).

MS-ESI m/z (% rel. Int.): 360.9 ([MH]$^+$, 100), 342.9 (40).

HPLC: Method A, detection UV 254 nm, Compound 211 RT=4.07 min, peak area 93.4%.

Preparation of (±)-threo-2-amino-3-hydroxy-1-(4-methylpiperazin-1-yl)-3-(pyridin-4-yl)propan-1-one trihydrochloride Compound 212

2-Isocyano-1-(4-methyl-piperazin-1-yl)-ethanone VIB 01128

Prepared in accordance with Method B with methyl isocyanoacetate (1.0 g, 10.09 mmol) and N-methylpiperazine (1.37 mL, 15.14 mmol). The reaction mixture was stirred overnight at RT and then concentrated. The residue was dissolved in dichloromethane (50 mL) and evaporated. The residue was coevaporated three times with a mixture of CH$_2$Cl$_2$:cyclohexane=50:50 (3×10 mL). After drying 2-isocyano-1-(4-methyl-piperazin-1-yl)-ethanone VIB 01128 was obtained as yellow solid (1.67 g, 99% yield).

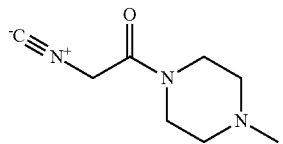

VIB 01128

MW: 167.21; Yield: 99%; Yellow Solid; Mp (° C.)=106.0

$^{1}$H NMR (CDCl$_3$, δ): 2.32 (m, 3H, Me) 2.38-2.50 (m, 4H, 2×CH$_2$), 3.42 (t, 2H, J=4.7 Hz, CH$_2$), 3.66 (t, 2H, J=4.7 Hz, CH$_2$), 4.30 (s, 2H, CH$_2$).

$^{13}$C-NMR (CDCl$_3$, δ): 42.4, 44.4, 45.5, 46.0, 54.3, 54.5, 160.8, 161.2.

trans-(4,5-Dihydro-5-(pyridin-4-yl)oxazol-4-yl)(4-methylpiperazin-1-yl)methanone VIB 01130

To a stirred and cooled (0° C.) solution of KOH (0.335 g, 5.98 mmol) in 7 mL MeOH were added successively pyridine-4-carbaldehyde (0.705 g, 6.58 mmol) and 2-isocyano-1-(4-methyl-piperazin-1-yl)-ethanone VIB 01128 (1.00 g, 6.58 mmol). The mixture was stirred at 0° C. until precipitation and concentrated. The mixture was partitioned between EtOAc (20 mL) and H$_2$O (10 mL). The aqueous layer was extracted twice with EtOAc (60 mL). The EtOAc fractions were combined, washed twice with brine (2×10 mL), dried over MgSO$_4$ and filtered. After evaporation and drying trans-(4,5-dihydro-5-(pyridin-4-yl)oxazol-4-yl)(4-methylpiperazin-1-yl)methanone VIB 01130 was obtained (1.282 g, 78% yield) as a yellow oil.

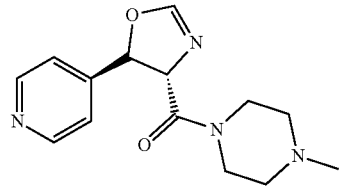

(±)-trans

VIB 01130

MW: 274.32; Yield: 78%; Yellow Oil.

$^{1}$H NMR (CDCl$_3$, δ): 2.32 (m, 3H, Me) 2.35-2.58 (m, 4H, 2×CH$_2$), 3.50-3.70 (m, 2H, CH$_2$—N), 3.80-4.00 (m, 2H, CH$_2$—N), 4.59 (dd, 1H, J=7.8 Hz, J=2.2 Hz, CH—N), 6.27 (d, 1H, J=7.8 Hz, O—CH), 7.02 (d, 1H, J=2.2 Hz, OCH=N), 7.23 (d, 2H, J=4.7 Hz, ArH), 8.62 (dd, 2H, J=4.5 Hz, J=1.6 Hz, ArH).

$^{13}$C-NMR (CDCl$_3$, δ): 42.6, 45.7, 46.0, 54.6, 55.1, 74.7, 79.6, 120.0 (2×C), 148.6, 150.3 (2×C), 154.8, 166.0.

MS-ESI m/z (% rel. Int.): 275.2 ([MH]$^+$, 40), 190.1 (35), 147.0 (40), 127.0 (100).

HPLC: Method A, detection UV 254 nm, VIB 01130 RT=0.70 min, peak area 99.9%.

(±)-threo-2-Amino-3-hydroxy-1-(4-methylpiperazin-1-yl)-3-(pyridin-4-yl)propan-1-one trihydrochloride Compound 212

To a solution of trans-(4,5-dihydro-5-(pyridin-4-yl)oxazol-4-yl)(4-methylpiperazin-1-yl)methanone VIB 01130 (1.235 g, 4.50 mmol) in MeOH (15 mL) was added HCl 37% (1.6 mL). After heating (50° C.) the mixture for 3.5 h a white solid precipitated and the reaction mixture was concentrated and the crude product was coevaporated twice with ethyl acetate. After trituration with ethyl acetate, filtration and drying, (±)-threo-2-amino-3-hydroxy-1-(4-methylpiperazin-1-yl)-3-(pyridin-4-yl)propan-1-one trihydrochloride Compound 212 (1.62 g, 96% yield) was obtained as a white solid.

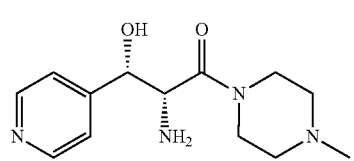

Compound 212

3 HCl
(±)

MW: 373.71; Yield: 96%; White Solid; Mp (° C.): 203.1

$^{1}$H-NMR (CD$_3$OD, δ): 2.95 (s, 3H, Me), 3.10-3.40 (m, 4H, 2×CH$_2$), 3.48-3.80 (m, 2H, CH$_2$), 4.19-4.49 (m, 1H, 0.5×CH$_2$), 4.51-4.79 (m, 1H, 0.5×CH$_2$), 5.06 (d, 1H, J=4.3 Hz, CH—NH$_2$), 5.35-5.63 (m, 1H, CH—O), 8.30 (s broad, 2H, ArH), 8.95 (d, 2H, J=6.7 Hz, ArH).

MS-ESI m/z (% rel. Int.): 265.1 ([MH]$^+$, 5), 248.1 (20), 156.1 (20), 148.0 (100).

HPLC: Method A, detection UV 254 nm, Compound 212 RT=0.68 min, peak area 99.9%.

Preparation of (±)-threo-2-amino-1-(3,3-difluoropyrrolidin-1-yl)-3-hydroxy-3-(pyridin-4-yl)propan-1-one dihydrochloride Compound 213

1-(3,3-Difluoropyrrolidin-1-yl)-2-isocyanoethanone VIB 01158

To stirred and cooled (0° C.) methyl isocyanoacetate (96% technical grade, 345 mg, 3.48 mmol) was slowly added 3,3-difluoropyrrolidine hydrochloride (500 mg, 3.48 mmol), triethylamine (487 µL, 3.48 mmol) and MeOH (1 mL). The mixture was stirred for 15 h at RT and then concentrated.

The resulting oil was coevaporated twice from EtOAc. 1-(3,3-Difluoropyrrolidin-1-yl)-2-isocyanoethanone VIB 01158 was obtained as a yellow oil (305 mg, 60% yield) and used in the next step without purification.

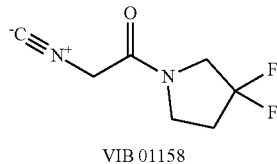

VIB 01158

MW: 174.17; Yield: 60%; Yellow Oil.

$^1$H NMR (CDCl$_3$, δ): 2.30-2.62 (m, 2H, CH$_2$) 3.65-3.90 (m, 4H, CH$_2$), 4.25 (d, 2H, J=17.5 Hz, CH$_2$).

trans-(3,3-Difluoropyrrolidin-1-yl)(4,5-dihydro-5-(pyridin-4-yl)oxazol-4-yl)methanone VIB 01160

To a stirred and cooled (0° C.) solution of KOH (0.098 g, 1.75 mmol) in MeOH (2 mL) were added successively pyridine-4-carbaldehyde (0.206 g 1.92 mmol) and 1-(3,3-difluoropyrrolidin-1-yl)-2-isocyanoethanone VIB 01158 (0.305 g, 1.75 mmol). The mixture was stirred at 0° C. for 3 h. After evaporation of MeOH, the mixture was partitioned between EtOAc (50 mL) and H$_2$O (40 mL). The aqueous layer was extracted with EtOAc (4×50 mL). The fractions were combined, washed twice with brine (2×20 mL), dried over MgSO$_4$ and filtered. After evaporation and drying trans-(3,3-difluoropyrrolidin-1-yl)(4,5-dihydro-5-(pyridin-4-yl)oxazol-4-yl)methanone VIB 01160 (0.33 g, 67% yield) was obtained as a yellow oil.

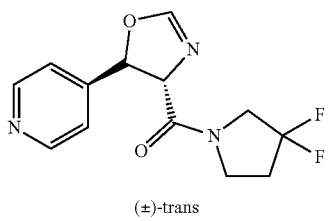

(±)-trans

VIB 01160

MW: 281.26; Yield: 67%; Yellow Oil.

$^1$H NMR (CDCl$_3$, δ): 2.30-2.60 (m, 2H, CH$_2$) 3.67-3.99 (m, 3H, 1.5×CH$_2$), 4.22-4.59 (m, 2H, CH—N & 0.5×CH$_2$), 6.17 (d, 1H, J=7.8 Hz, CH—O), 7.04 (dd, 1H, J=3.2 Hz, J=2.5 Hz, HC=N), 7.20-7.38 (m, 2H, ArH), 8.55-8.70 (m, 2H, ArH).

(±)-threo-2-Amino-1-(3,3-difluoropyrrolidin-1-yl)-3-hydroxy-3-(pyridin-4-yl)propan-1-one dihydrochloride Compound 213

To a solution of trans-(3,3-difluoropyrrolidin-1-yl)(4,5-dihydro-5-(pyridin-4-yl)oxazol-4-yl)methanone VIB 01160 (0.305 g, 1.08 mmol) in methanol (4 mL) was added hydrochloric acid 37% (395 µL). After heating (50° C.) the mixture for 3.5 h the reaction mixture was concentrated and the crude product was coevaporated twice with EtOAc. After trituration with EtOAc, filtration and drying, (±)-threo-2-amino-1-(3,3-difluoropyrrolidin-1-yl)-3-hydroxy-3-(pyridin-4-yl)propan-1-one dihydrochloride Compound 213 (269 mg, 44% yield) was obtained as a beige solid.

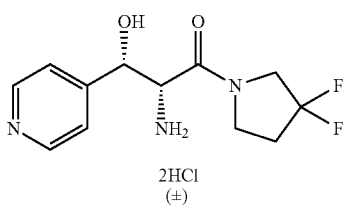

Compound 213

2HCl
(±)

MW: 344.19; Yield: 44%; Beige Solid; Mp (° C.): 182.2

$^1$H-NMR (CD$_3$OD, δ): 2.25-2.62 (m, 2H, CH$_2$), 3.30-4.20 (m, 4H, CH$_2$), 4.55 (d, 1H, J=5.5 Hz, 0.35×CH$^-$N), 4.66 (d, 1H, J=5.5 Hz, 0.65×CH$^-$N), 5.42 (m, 1H, CH—O), 8.23 (d, 2H, J=4.8 Hz, ArH), 8.94 (d, 2H, J=5.9 Hz, ArH).

MS-ESI m/z (% rel. Int.): 272.2 ([MH]$^+$, 15), 254.1 (15), 178.1 (20), 148.1 (100), 137.1 (95).

HPLC: gradient of solvent B:solvent A=5:95 to 100% solvent B in 7 min Solvent A was H$_2$O with 0.1% Et$_3$N and solvent B was CH$_3$CN with 0.1% Et$_3$N; detection UV 254 nm, Compound 213 RT=4.70 min, peak area 98.1%.

Preparation of (2S,3R)- & (2R,3S)-2-amino-1-((S)-3-fluoropyrrolidin-1-yl)-3-hydroxy-3-(pyridin-4-yl)propan-1-one dihydrochlorides Compounds 214

1-((S)-3-Fluoropyrrolidin-1-yl)-2-isocyanoethanone VIB 01166

To stirred and cooled (0° C.) methyl isocyanoacetate (96% technical grade, 1.18 g, 11.9 mmol) was slowly added (S)-(+)-3-fluoropyrrolidine hydrochloride (97%, 1.5 g, 11.9 mmol), triethylamine (1.67 mL, 11.9 mmol) and MeOH (3 mL). The mixture was stirred for 15 h at RT and concentrated. The mixture was stirred for 15 h at RT and concentrated. Water was added (50 mL) and the mixture was extracted with EtOAc (3×50 mL), dried over MgSO$_4$, filtered and evaporated to obtained crude 1-1(5)-3-fluoropyrrolidin-1-yl)-2-isocyanoethanone VIB 01166 (1.47 g, 79% yield) as a brown oil which was used in the next step without purification.

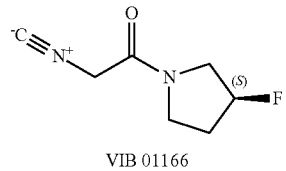

VIB 01166

MW: 156.152; Yield: 79%; Brown Oil.
$^1$H NMR (CDCl$_3$, δ): 1.85-2.50 (m, 2H, CH$_2$), 3.40-4.35 (m, 6H, 3×CH$_2$), 5.17-5.47 (m, 1H, CHF).
MS-ESI m/z (% rel. Int.): 171.1 ([MH$^+$+Na], 100), 157.1 ([MH]$^+$, 82), 130.1 (95).

trans-((S)-3-Fluoropyrrolidin-1-yl)((4S,5R)- & 4R,5S)-4,5-dihydro-5-(pyridin-4-yl)oxazol-4-yl) methanones VIB 01168

To a stirred and cooled (0° C.) solution of KOH (0.526 g, 9.39 mmol) in MeOH (10 mL) were added successively pyridine-4-carbaldehyde (1.10 g, 10.33 mmol) and 1-((S)-3-fluoropyrrolidin-1-yl)-2-isocyanoethanone VIB 01166 (1.47 g, 9.39 mmol). The mixture was stirred at 0° C. to RT for 24 h. After evaporation of MeOH, the mixture was partitioned between EtOAc (40 mL) and H$_2$O (20 mL). The aqueous layer was extracted with EtOAc (6×40 mL). The EtOAc fractions were combined, washed twice with brine (2×10 mL), dried over MgSO$_4$, filtered and evaporated. The crude product was purified by column chromatography (florisil, EtOAc:MeOH=9:1). After evaporation and drying trans-((S)-3-fluoropyrrolidin-1-yl)((4S,5R)- & 4R,5S)-4,5-dihydro-5-(pyridin-4-yl)oxazol-4-yl)methanones VIB 01168 (590 mg, diastereoisomeric mixture in ratio 1:1, 24% yield) were obtained as a yellow oil.

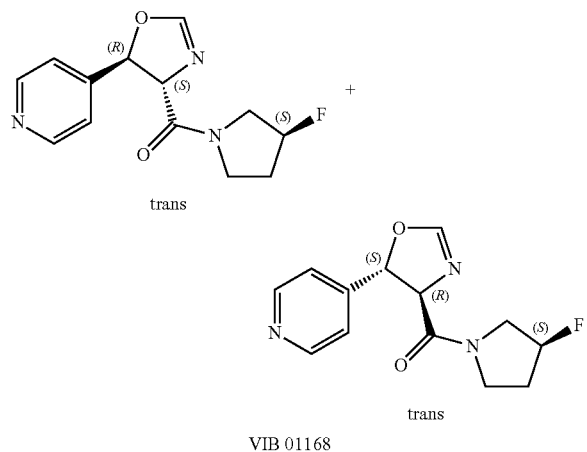

VIB 01168

MW: 263.27; Yield: 24%; Yellow Oil.
$^1$H NMR (CDCl$_3$, δ): 1.89-2.46 (m, 2H, CH$_2$) 3.5-4.45 (m, 4H, CH$_2$), 4.46-4.60 (m, 1H, CH—N), 5.16-5.45 (m, 1H, CH—F), 6.12-6.25 (m, 1H, CH—O), 6.95-7.18 (m, 1H, CH=N), 7.20-7.40 (m, 2H, ArH), 8.50-8.70 (m, 2H, ArH).

(2S,3R)- & (2R,3S)-2-Amino-1-((S)-3-fluoropyrrolidin-1-yl)-3-hydroxy-3-(pyridin-4-yl)propan-1-one dihydrochlorides Compounds 214

To a solution of ((S)-3-fluoropyrrolidin-1-yl)((4S,5R)- & 4R,5S)-4,5-dihydro-5-(pyridin-4-yl)oxazol-4-yl)methanones VIB 01168 (0.590 g, 2.24 mmol) in methanol (8 mL) was added hydrochloric acid 37% (686 μL). After heating (50° C.) the mixture for 3.5 h the reaction mixture was concentrated and the crude product was coevaporated twice with EtOAc. After trituration with EtOAc, filtration and drying (2S,3R)- & (2R,3S)-2-amino-1-((S)-3-fluoropyrrolidin-1-yl)-3-hydroxy-3-(pyridin-4-yl)propan-1-one dihydrochlorides Compounds 214 (474 mg, diastereoisomeric mixture in ratio 1:1, 68% yield) were obtained as a pale yellow solid.

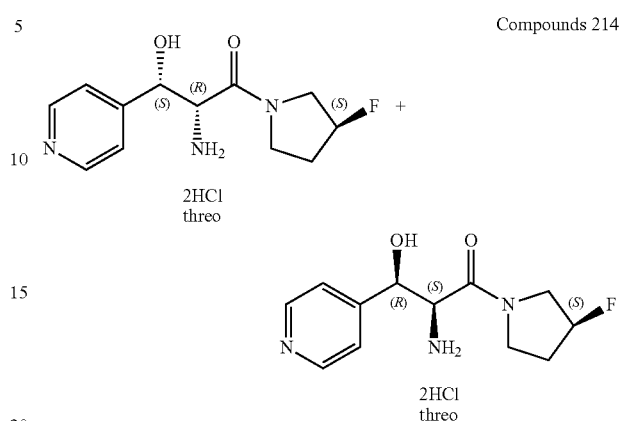

Compounds 214

MW: 326.2; Yield: 68%; Pale Yellow Solid; Mp (° C.): 173.1.
$^1$H-NMR (CD$_3$OD, δ): 1.82-2.38 (m, 2H, CH$_2$), 2.80-4.15 (m, 4H, 2×CH$_2$), 4.35-4.68 (m, 1H, CH$^-$N), 5.00-5.50 (m, 2H, CH—O & CH—F), 8.11-8.32 (m, 2H, ArH), 8.82-9.00 (m, 2H, ArH).
MS-ESI m/z (% rel. Int.): 254.2 ([MH]$^+$, 15), 237.1 (20), 148.1 (100), 137.1 (70).
HPLC: gradient of solvent B:solvent A=5:95 to 100% solvent B in 7 min.
Solvent A was H$_2$O with 0.1% Et$_3$N and solvent B was CH$_3$CN with 0.1%
Et$_3$N; detection UV 254 nm, Compounds 214 RT=4.35 min, peak area 99.0%.

Preparation of (2S,3R)- & (2R,3S)-2-amino-1-((R)-3-fluoropyrrolidin-1-yl)-3-hydroxy-3-(pyridin-4-yl) propan-1-one dihydrochlorides Compounds 215

1-((R)-3-Fluoropyrrolidin-1-yl)-2-isocyanoethanone BLE 04170

To stirred and cooled (0° C.) methyl isocyanoacetate (96% technical grade, 0.79 g, 7.96 mmol) was slowly added (R)-(−)-3-fluoropyrrolidine hydrochloride (1.0 g, 7.96 mmol), triethylamine (1.11 mL, 7.96 mmol) and MeOH (2.5 mL). The mixture was stirred for 15 h at RT and concentrated. Water was added (50 mL) and the mixture was extracted with EtOAc (3×50 mL), dried over MgSO$_4$, filtered and evaporated to obtained crude 1-((R)-3-fluoropyrrolidin-1-yl)-2-isocyanoethanone BLE 04170 as a brown oil (0.96 g, 77% yield) which was used in the next step without further purification.

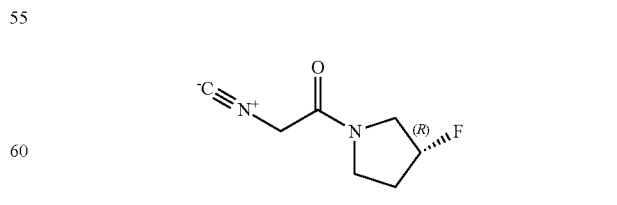

BLE 04170

MW: 156.152; Yield: 77%; Brown Oil.
$^1$H NMR (CDCl$_3$, δ): 1.85-2.50 (m, 2H, CH$_2$), 3.40-4.35 (m, 6H, 3×CH$_2$), 5.17-5.47 (m, 1H, CHF).

trans-((R)-3-Fluoropyrrolidin-1-yl)((4S,5R)- & 4R,5S)-4,5-dihydro-5-(pyridin-4-yl)oxazol-4-yl) methanones BLE 04172

To a stirred and cooled (0° C.) solution of KOH (0.34 g, 6.06 mmol) in MeOH (4.5 mL) were added successively pyridine-4-carbaldehyde (0.71 g, 6.66 mmol) and a solution of BLE 04170 (0.95 g, 6.06 mmol) in MeOH (2.5 mL) The mixture was stirred at 0° C. to RT for 15 h. After evaporation of MeOH, the mixture was partitioned between EtOAc (40 mL) and H$_2$O (20 mL). The aqueous layer was extracted with EtOAc (3×40 mL). The EtOAc fractions were combined, washed with brine (50 mL), dried over MgSO$_4$, filtered and evaporated. The crude product was purified by column chromatography (florisil, EtOAc:MeOH=9:1). After evaporation and drying trans-((R)-3-fluoropyrrolidin-1-yl)((4S,5R)- & 4R,5S)-4,5-dihydro-5-(pyridin-4-yl)oxazol-4-yl)methanones BLE 04172 (653 mg, diastereoisomeric mixture in ratio 1:1, 41% yield) were obtained as a colorless oil.

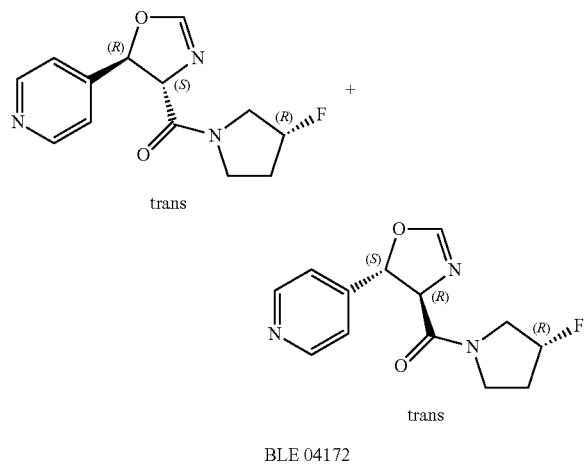

BLE 04172

MW: 263.27; Yield: 41%; Colorless Oil.

$^1$H NMR (CDCl$_3$, δ): 1.89-2.46 (m, 2H, CH$_2$) 3.5-4.45 (m, 4H, 2×CH$_2$), 4.46-4.60 (m, 1H, CH—N), 5.16-5.45 (m, 1H, CH—F), 6.12-6.25 (m, 1H, CH—O), 6.95-7.18 (m, 1H, CH=N), 7.20-7.40 (m, 2H, ArH), 8.50-8.70 (m, 2H, ArH).

(2S,3R)- & (2R,3S)-2-Amino-1-((R)-3-fluoropyrrolidin-1-yl)-3-hydroxy-3-(pyridin-4-yl)propan-1-one dihydrochlorides Compounds 215

To a solution of trans-((R)-3-fluoropyrrolidin-1-yl)((4S, 5R)- & 4R,5S)-4,5-dihydro-5-(pyridin-4-yl)oxazol-4-yl) methanones BLE 04172 (0.65 g, 2.47 mmol) in methanol (8 mL) was added hydrochloric acid 37% (757 µL). After heating (50° C.) the mixture for 3.5 h the reaction mixture was concentrated and the crude product was coevaporated twice with EtOAc. After trituration with EtOAc, filtration and drying (2S,3R)- & (2R,3S)-2-amino-1-((R)-3-fluoropyrrolidin-1-yl)-3-hydroxy-3-(pyridin-4-yl)propan-1-one dihydrochlorides Compounds 215 (544 mg, diastereoisomeric mixture in ratio 1:1, 68% yield) were obtained as a pale yellow solid.

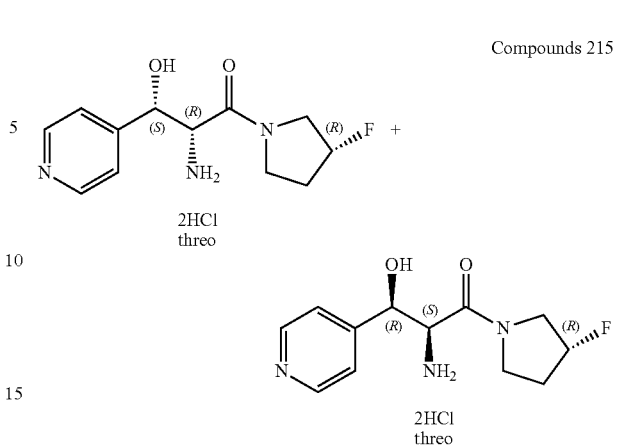

Compounds 215

MW: 326.2; Yield: 68%; Pale Yellow Solid; Mp (° C.): 134.5

$^1$H-NMR (CD$_3$OD, δ): 1.82-2.38 (m, 2H, CH$_2$), 2.80-4.15 (m, 4H, CH$_2$), 4.35-4.68 (m, 1H, CH$^-$N), 5.00-5.50 (m, 2H, CH—O & CHF), 8.11-8.32 (m, 2H, ArH), 8.82-9.00 (m, 2H, ArH).

Preparation of N-((±)-threo-1-hydroxy-3-oxo-1-(pyridin-4-yl)-3-(pyrrolidin-1-yl)propan-2-yl)formamide hydrochloride Compound 216 trans-(4,5-Dihydro-5-(pyridin-4-yl)oxazol-4-yl)(pyrrolidin-1-yl)methanone Compound 19 (0.200 g, 0.81 mmol) was dissolved in methanol (5 mL). Dowex 50WX8-200 (0.5 mL, washed beforehand by a 0.5 M solution of HCl then water) was added at RT. The mixture was stirred for 1 h at 50° C. and after cooling was filtered off MeOH was evaporated and the residue was dried to give 150 mg of a pasty product (150 mg, 61.0% yield). The free base form was dissolved in a minimum of a mixture of EtOAc:MeOH=95:5 and a 0.4 M solution of HCl in ether (1.3 mL, 0.52 mmol) was added at +4° C. After evaporation of solvents, the product was precipitated with diethyl ether, filtered and dried to obtain N-((±)-threo-1-hydroxy-3-oxo-1-(pyridin-4-yl)-3-(pyrrolidin-1-yl)propan-2-yl)formamide hydrochloride Compound 216 as a beige solid (100 mg, 41.0% yield).

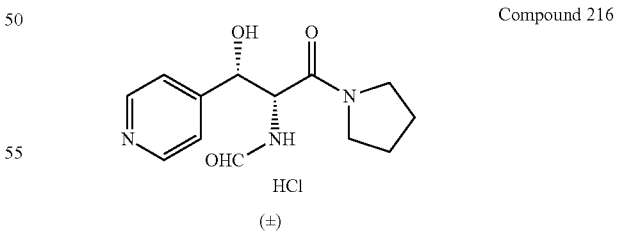

Compound 216

MW: 299.75; Yield: 41.0%; Beige Solid; Mp (° C.): 203.1 R$_f$:0.35 (CH$_2$Cl$_2$:MeOH=90:10) free base.

$^1$H-NMR (CD$_3$OD, *): 1.87-2.00 (m, 4H, 2×CH$_2$), 3.41-3.46 (m, 2H, CH$_2$—N), 3.62-3.66 (m, 2H, CH$_2$—N), 5.18 (d, 1H, J=3.6 Hz, CH—N), 5.40 (d, 1H, J=3.8 Hz, CH—O), 7.99 (s, 1H, CH=O), 8.16 (d, 2H, J=5.8 Hz, ArH), 8.81 (d, 2H, J=5.5 Hz, ArH).

$^{13}$C-NMR (CD$_3$OD, *): 25.0, 27.0, 47.5, 48.3, 55.6, 72.4, 126.6 (2×C), 142.1 (2×C), 163.4, 164.1, 168.5.

MS-ESI m/z (% rel. Int.): 264.1 ([MH]$^+$, 10), 148.0 (100).

HPLC: Method A, detection UV 254 nm, Compound 216 RT=1.30 min, peak area 98.0%.

Preparation of N-((±)-threo-2-acetoxy-2-pyridin-4-yl-1-(pyrrolidine-1-carbonyl)-ethyl)-formamide hydrochloride Compound 217

N-((±)-threo-1-hydroxy-3-oxo-1-(pyridin-4-yl)-3-(pyrrolidin-1-yl)propan-2-yl)formamide hydrochloride Compound 216 (0.220 g, 0.80 mmol) was dissolved in CH$_2$Cl$_2$ (10 mL) with triethylamine (280 µL, 2 mmol) at 0° C. Then acetic anhydride (160 µL, 1.6 mmol) was added slowly and the mixture was stirred for 72 h at RT. The solvent was evaporated and the residue was dried under vacuum. After column chromatography (SiO$_2$, EtOAc:MeOH=90:10) to give a pasty product (100 mg, 41% yield). The product obtained was dissolved in MeOH (10 mL) and a solution of HCl (0.4 M, 1 mL) in Et$_2$O was added at 0° C. Evaporation of the volatiles led to acetic acid N-((±)-threo-2-acetoxy-2-pyridin-4-yl-1-(pyrrolidine-1-carbonyl)-ethyl)-formamide hydrochloride Compound 217 was obtained as a white solid (110 mg, 40% yield).

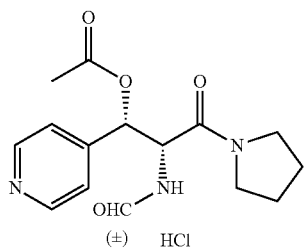

Compound 217

MW: 341.79; Yield: 40.0%; White Solid; Mp (° C.): 173.9.

R$_f$:0.25 (EtOAc:MeOH=90:10, free base).

$^1$H-NMR (CD$_3$OD,*): 1.80-2.00 (m, 4H, 2×CH$_2$), 2.19 (s, 3H, CH$_3$) 3.29-3.64 (m, 4H, 2×CH$_2$—N), 5.34 (s, 1H, N—CH), 6.44 (s, 1H, O—CH), 8.01 (s, 1H, CHO), 8.16 (s, 2H, ArH), 8.85 (s, 2H, ArH).

$^{13}$C-NMR (CD$_3$OD, *): 20.5, 25.0, 27.0, 47.6, 47.7, 53.9, 73.4, 126.7 (2×C), 142.8 (2×C), 144.3, 163.3, 166.9, 170.9.

MS-ESI m/z (% rel. Int.): 306.1 ([MH]$^+$, 10), 261.1 (100).

HPLC: Method A, detection UV 254 nm, Compound 217 RT=0.90 min, peak area 97.0%.

Preparation of tert-butyl(±)-threo-1-hydroxy-3-oxo-1-(pyridin-4-yl)-3-(pyrrolidin-1-yl)propan-2-ylcarbamate hydrochloride Compound 218

(±)-threo-2-Amino-3-hydroxy-3-(pyridin-4-yl)-1-(pyrrolidin-1-yl)propan-1-one dihydrochloride Compound 22 (2.90 g, 9.3 mmol) was dissolved in CH$_2$Cl$_2$ (250 mL) with Et$_3$N (4.3 mL, 30.7 mmol) at 0° C. Di-tert-butyl dicarbonate (2.45 g, 11.2 mmol) in CH$_2$Cl$_2$ (50 mL) was added slowly and the mixture was stirred for 15 h at RT. Brine (50 mL) was added and the product was extracted with CH$_2$Cl$_2$. After drying over MgSO$_4$ and filtration, CH$_2$Cl$_2$ was evaporated and the residue was dried in vacuum. After column chromatography (SiO$_2$, EtOAc:MeOH=90:10), tert-butyl(±)-threo-1-hydroxy-3-oxo-1-(pyridin-4-yl)-3-(pyrrolidin-1-yl)propan-2-ylcarbamate TTA 08100 was obtained as a beige solid (2.00 g, 64% yield). A Sample of TTA 08100 (55 mg) was dissolved in CH$_2$Cl$_2$ (1 mL) and Et$_2$O (30 mL) and a solution of HCl (0.1 M, 2 mL) in Et$_2$O was added at 0° C. Evaporation of the volatiles led to tert-butyl(±)-threo-1-hydroxy-3-oxo-1-(pyridin-4-yl)-3-(pyrrolidin-1-yl)propan-2-ylcarbamate hydrochloride Compound 218 (50 mg, 52% yield) as a white solid.

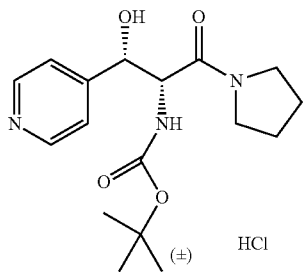

Compound 218

MW: 371.86; Yield: 52.0%; White Solid; Mp (° C.): 141.2.

R$_f$:0.30 (EtOAc:MeOH=90:10, free base).

$^1$H-NMR (CD$_3$OD, *): 1.33 (s, 9H, 3×CH$_3$) 1.91-2.00 (m, 4H, 2×CH$_2$), 3.44-3.49 (m, 2H, CH$_2$), 3.60-3.64 (m, 2H, CH$_2$—N), 4.78 (s, 1H, N—CH), 5.38 (s, 1H, O—CH), 8.16 (s, 2H, ArH), 8.83 (s, 2H, ArH).

$^{13}$C-NMR (CD$_3$OD, *): 25.0, 27.1, 28.5 (3×C), 47.5, 48.0, 58.3, 72.8, 81.0, 126.7 (2×C), 142.0 (2×C), 157.3, 164.6, 169.5.

MS-ESI m/z (% rel. Int.): 336.1 ([MH]$^+$, 20), 219.1 (100).

HPLC: Method A, detection UV 254 nm, Compound 218 RT=3.8 min, peak area 98.0%.

Preparation of (±)-erythro-2-amino-3-hydroxy-3-(pyridin-4-yl)-1-(pyrrolidin-1-yl)propan-1-one dihydrochloride Compound 219 tert-Butyl(±)-threo-1-hydroxy-3-oxo-1-(pyridin-4-yl)-3-(pyrrolidin-1-yl)propan-2-ylcarbamate VIB 01080

To a solution of (±)-threo-2-amino-3-hydroxy-3-(pyridin-4-yl)-1-(pyrrolidin-1-yl)propan-1-one dihydrochloride Compound 22 (3.25 g, 10.54 mmol) in CH$_2$Cl$_2$ (250 mL) in a 500 mL round bottom flask equipped with a magnetic stirrer and under nitrogen atmosphere was added via syringe at 0° C. triethylamine (4.69 mL, 33.73 mmol). A solution of di-tert-butyldicarbonate (2.76 g, 12.65 mmol) in CH$_2$Cl$_2$ (75 mL) was added at 0° C. dropwise via a dropping funnel. The reaction mixture was abandoned at 0° C. for 2 h then at RT overnight. A solution of brine (130 mL) was added and the solution was extracted with CH$_2$Cl$_2$ (3×75 mL), dried over MgSO$_4$, filtered and evaporated. The crude product was purified by column chromatography (SiO$_2$, EtOAc:MeOH=90:10). After evaporation to dryness of the combined fractions, tert-butyl(±)-threo-1-hydroxy-3-oxo-1-(pyridin-4-yl)-3-(pyrrolidin-1-yl)propan-2-ylcarbamate VIB 01080 (2.79 g, 79% yield) was obtained as a yellow solid.

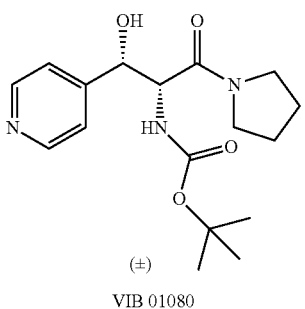 [SMILES: CC(C)(C)OC(=O)N[C@@H](C(=O)N1CCCC1)[C@@H](O)c1ccncc1]

(±)
VIB 01080

MW: 335.4; Yield: 79%; Yellow Solid; Mp (° C.): 160.5 R$_f$:0.31 (EtOAc:MeOH=90:10).
$^1$H-NMR (CDCl$_3$, *): 1.26 (s, 9H, 3×CH$_3$), 1.71-2.00 (m, 4H, 2×CH$_2$), 3.25-3.60 (m, 4H, 2×CH$_2$N), 4.61 (dd, 1H, J=9.8 Hz, J=2.6 Hz, N—CH), 4.96 (s, 1H, OH), 5.08 (d, 1H, J=2.6 Hz, NH), 5.47 (d, 1H, J=9.8 Hz, O—CH), 7.35 (d, 2H, J=5.7 Hz, ArH), 8.58 (d, 2H, J=5.4 Hz, ArH).
$^{13}$C-NMR (CDCl$_3$, *): 24.0 (2×C), 25.9 (2×C), 28.1 (3×C), 46.1, 46.7, 56.1, 60.4, 72.8, 80.2, 121.4 (2×C), 148.7, 149.5 (2×C), 155.6, 169.4.
MS-ESI m/z (% rel. Int.): 336.1 ([MH]$^+$, 45), 280 (18), 219 (100); 148 (38).

tert-Butyl(±)-1,3-dioxo-3-(pyridin-4-yl)-1-(pyrrolidin-1-yl)propan-2-ylcarbamate TTA 08120

To a solution of tert-butyl(±)-threo-1-hydroxy-3-oxo-1-(pyridin-4-yl)-3-(pyrrolidin-1-yl)propan-2-ylcarbamate VIB 01080 (3.92 g, 11.70 mmol) in CH$_2$Cl$_2$ (320 mL) in a 500 mL round bottom flask equipped with a magnetic stirrer and under nitrogen atmosphere was added slowly Dess-Martin periodinane (4.96 g, 11.70 mmol) at RT. The reaction mixture was stirred at RT for 0.5 h and CH$_2$Cl$_2$ washed with a mixture of saturated sodium bicarbonate (100 mL), 1 M sodium thiosulfate (50 mL), brine (50 mL) and dried over MgSO$_4$, filtered and evaporated. Diethyl ether (250 mL) was added and the precipitate was filtered off. After evaporation of the filtrate, the crude product was purified by column chromatography (SiO$_2$, CH$_2$Cl$_2$:EtOAc=4:6). After evaporation to dryness of the combined fractions tert-butyl(±)-1,3-dioxo-3-(pyridin-4-yl)-1-(pyrrolidin-1-yl)propan-2-ylcarbamate TTA 08120 (3.0 g, 77% yield) was obtained as a white solid.

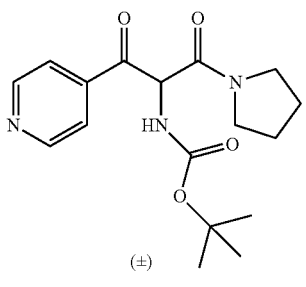

(±)
TTA 08120

MW: 333.38; Yield: 77%; White Solid; Mp (° C.): 125.4 R$_f$:0.25 (CH$_2$Cl$_2$:EtOAc=4:6).
$^1$H-NMR (CDCl$_3$, *): 1.36 (s, 9H, 3×CH$_3$), 1.86-2.00 (m, 4H, 2×CH$_2$), 3.47-3.71 (m, 4H, 2×CH$_2$N), 5.62 (d, 1H, J=7.4 Hz, N—CH), 6.07 (d, 1H, J=7.4 Hz, NH), 7.80 (dd, 2H, J=4.6 Hz, J=1.3 Hz, ArH), 8.80 (dd, 2H, J=4.5 Hz, J=1.5 Hz, ArH).
$^{13}$C-NMR (CDCl$_3$, *): 24.0, 26.0, 28.1 (3×C), 46.8, 47.0, 61.0, 80.9, 121.5 (2×C), 141.4, 150.8 (2×C), 155.1, 163.8, 194.3.
MS-ESI m/z (% rel. Int.): 334.1 ([MH]$^+$, 10), 173.1 (30), 129.1 (100).

tert-Butyl(±)-erythro-3-hydroxy-1-oxo-3-(pyridin-4-yl)-1-(pyrrolidin-1-yl)propan-2-ylcarbamate TTA 08124P To a solution of tert-butyl(±)-1,3-dioxo-3-(pyridin-4-yl)-1-(pyrrolidin-1-yl)propan-2-ylcarbamate TTA 08120 (2.28 g, 6.80 mmol) in MeOH (50 mL) in a 250 mL round bottom flask equipped with a magnetic stirrer and under nitrogen atmosphere was added slowly sodium borohydride (285 mg, 7.50 mmol) at RT. The reaction mixture was stirred at RT for 0.5 h and was cooled at 4° C. A solution of 2 M NaOH (10 mL) was added and MeOH was evaporated at 30° C. EtOAc (300 mL) was added and the organic phase was washed with brine (20 mL), dried over MgSO$_4$, filtered and evaporated to give a crude compound (ratio erythro:threo=80:20 estimated by $^1$H NMR 300 MHz) TTA 08124 (2.1 g, 92% yield). The crude product was recrystallized in EtOAc and after filtration and drying tert-butyl(±)-erythro-3-hydroxy-1-oxo-3-(pyridin-4-yl)-1-(pyrrolidin-1-yl)propan-2-ylcarbamate TTA 08124P (1.30 g, ratio erythro:threo=96:4 estimated by $^1$H NMR 300 MHz analysis, 57% yield) was obtained as a white solid.

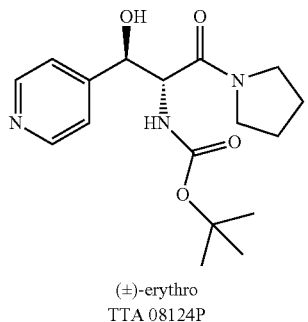 [SMILES: CC(C)(C)OC(=O)N[C@@H](C(=O)N1CCCC1)[C@H](O)c1ccncc1]

(±)-erythro
TTA 08124P

MW: 335.40; Yield: 57%; White Solid; Mp (° C.): 170.3 R$_f$:0.45 (EtOAc:MeOH=85:15).
$^1$H-NMR (CDCl$_3$, *): 1.43 (s, 9H, 3×CH$_3$), 1.64-1.83 (m, 4H, 2×CH$_2$), 2.88-2.96 (m, 1H, CH$_2$N), 3.23-3.29 (m, 1H, CH$_2$N), 3.34-3.43 (m, 1H, CH$_2$N), 3.56-3.63 (m, 1H, CH$_2$N), 4.66 (dd, 1H, J=8.9 Hz, J=3.7 Hz, N—CH), 4.91 (dd, 1H, J=8.4 Hz, J=3.4 Hz, O—CH), 5.42 (d, 1H, J=8.8 Hz, OH), 5.75 (d, 1H, J=8.8 Hz, NH), 7.30 (d, 2H, J=5.9 Hz, ArH), 8.57 (d, 2H, J=5.8 Hz, ArH). Ratio erythro:threo=96:4.
$^{13}$C-NMR (CDCl$_3$, *): 24.0, 25.7, 28.1 (3×C), 45.7, 46.8, 55.2, 74.5, 80.5, 120.9 (2×C), 149.6, 149.8 (2×C), 155.4, 168.8.
MS-ESI m/z (% rel. Int.): 336.1 ([MH]$^+$, 10), 280.1 (20), 110.0 (100).

(±)-erythro-2-Amino-3-hydroxy-3-(pyridin-4-yl)-1-(pyrrolidin-1-yl)propan-1-one dihydrochloride Compound 219

To a solution of tert-butyl(±)-erythro-3-hydroxy-1-oxo-3-(pyridin-4-yl)-1-(pyrrolidin-1-yl)propan-2-ylcarbamate TTA 08124P (1.15 g, 3.40 mmol) in MeOH (30 mL) in a 250 mL round bottom flask equipped with a magnetic stirrer was added HCl 37% (3 mL, 35 mmol) at RT. The reaction mixture was stirred at RT for 0.4 h at 45° C. and MeOH was evaporated at 45° C. to give after drying, a white solid TTA 08136 (ratio erythro:threo=96:4 estimated by ¹H NMR 300 MHz analysis). Amberlite IRA-400 (Cl⁻) (10 g) was washed successively with water (2×10 mL), 0.5 N NaOH (3×20 mL), water (2×10 mL) and MeOH (3×10 mL). A solution of TTA 08136 in MeOH (30 mL) was stirred with washed Amberlite IRA-400 for 5 min at RT. After filtration, the MeOH was evaporated and the free base form was purified by column chromatography (SiO₂, CHCl₃:EtOH 95°=86:14) to give TTA 08136A (445 mg, 55% yield) as a beige solid (no threo isomer detected by ¹H NMR 300 MHz and HPLC). TTA 08136A (193 mg) was stirred at RT in ethyl acetate (5 mL) with a solution of 0.1 N HCl in isopropanol (17 mL). Solvents were evaporated at 33° C., MeOH (0.5 mL) was added and the salt was precipitated by addition of EtOAc (20 mL) to give nearly quantitatively after filtration and drying (±)-erythro-2-amino-3-hydroxy-3-(pyridin-4-yl)-1-(pyrrolidin-1-yl)propan-1-one dihydrochloride Compound 219 as a white solid (no threo isomer detected by ¹H NMR 300 MHz and HPLC).

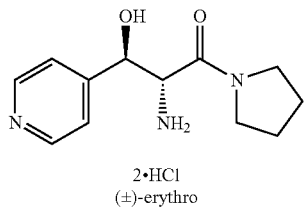

Compound 219

2•HCl
(±)-erythro

MW: 308.20; Yield: 55%; White Solid; Mp (° C.): 154.1.
R_f:0.18 (CHCl₃:EtOH 95°=86:14, free base).
¹H-NMR (CD₃OD, *): 1.94-2.04 (m, 4H, 2×CH₂), 3.45-3.56 (m, 2H, CH₂N), 3.66-3.78 (m, 2H, CH₂N), 4.71 (d, 1H, J=5.2 Hz N—CH), 5.50 (d, 1H, J=5.1 Hz, O—CH), 8.12 (d, 2H, J=5.6 Hz, ArH), 8.92 (d, 2H, J=5.4 Hz, ArH).
¹³C-NMR (CD₃OD, *): 25.0, 27.0, 47.8, 58.4, 70.0, 127.2 (2×C), 143.1 (2×C), 159.8, 164.8.
MS-ESI m/z (% rel. Int.): 236.1 ([MH]⁺, 10), 219.1 (55), 110.0 (100).

Preparation of (−)-(2R,3R)-2-amino-3-hydroxy-3-(pyridin-4-yl)-1-(pyrrolidin-1-yl)propan-1-one dihydrochloride Compound 220 and (+)-(2S,3S)-2-amino-3-hydroxy-3-(pyridin-4-yl)-1-(pyrrolidin-1-yl)propan-1-one dihydrochloride Compound 221

Analytical Chiral Separation:
20 μL of a 1 mg/mL solution of Compound 219 were injected on Chiralpak AD: flow-rate=1 mL/min, temperature=25° C., mobile phase: hexane:ethanol=8:2, detection UV at 220 nm and by polarimeter, Rt (−)=16.26 min, Rt (+)=19.02 min, k(−)=4.38, k(+)=5.30, α=1.21 and resolution Rs=1.90.
Semi-Preparative Separation was Performed on Chiralpak AS (250×10 mm):
A 40 mg/mL solution of (±)-erythro-2-amino-3-hydroxy-3-(pyridin-4-yl)-1-(pyrrolidin-1-yl)propan-1-one Compound 219 racemate was prepared and 100 μL of this solution were injected every 4 min on Chiralpak AS, flow-rate=5 mL/min, mobile phase hexane:ethanol=1:1, UV detection at 254 nm. 56 successive injections were done. The two main fractions were identified on UV and collected in two different flasks. The solvent was removed in vacuo at 30° C. The resulting solid was dissolved in 50 mL of CH₂Cl₂ and then filtered on a 0.45 μm millipore membrane. After evaporation of CH₂Cl₂, the solid was dissolved in 50 mL of methanol and then filtered. The salt was regenerated according to the procedure reported for Compound 203 and Compound 204.

The enantiomeric purity of the compounds was checked by analytical injection on Chiralpak AD of the regenerated salts:

(−)-(2R,3R)-2-amino-3-hydroxy-3-(pyridin-4-yl)-1-(pyrrolidin-1-yl)propan-1-one dihydrochloride Compound 220

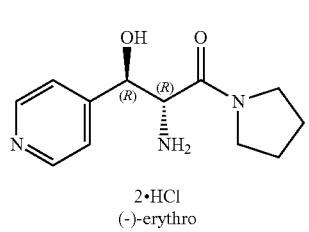

Compound 220

2•HCl
(−)-erythro

MW: 308.20; 133 mg obtained; White Solid; Mp (° C.): too hygroscopic.
R_f:0.18 (CHCl₃:EtOH 95°=86:14, free base).
Enantiomeric excess=99.1% measured by HPLC at 220 nm (Chiralpak AD)
$\alpha^{25}_D$=−6.4 (MeOH, c=1)
¹H-NMR (CD₃OD, δ): 1.94-2.03 (m, 4H, 2×CH₂), 3.45-3.55 (m, 2H, CH₂—N), 3.63-3.76 (m, 2H, CH₂—N), 4.68 (d, 1H, J=5.1 Hz, N—CH), 5.48 (d, 1H, J=5.5 Hz, O—CH), 8.08 (d, 2H, J=6.4 Hz, ArH), 8.90 (d, 2H, J=6.6 Hz, ArH).
¹³C-NMR (CD₃OD, δ): 23.4, 25.4, 46.2, 56.7, 68.4, 125.7 (2×C), 141.3 (2×C), 158.5, 163.2.

(+)-(2S,3S)-2-amino-3-hydroxy-3-(pyridin-4-yl)-1-(pyrrolidin-1-yl)propan-1-one dihydrochloride Compound 221

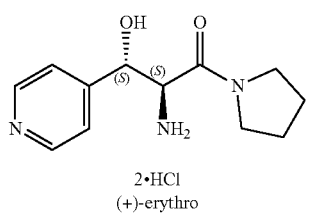

Compound 221

2•HCl
(+)-erythro

MW: 308.20; 140 mg obtained; White Solid; Mp (° C.): too hygroscopic.
R_f:0.18 (CHCl₃:EtOH 95°=86:14, free base).
Enantiomeric excess=99.1% measured by HPLC at 220 nm (Chiralpak AD)
$\alpha^{25}_D$=+6.3 (MeOH, c=1).
¹H-NMR (CD₃OD, δ): 1.94-2.02 (m, 4H, 2×CH₂), 3.44-3.52 (m, 2H, CH₂—N), 3.64-3.74 (m, 2H, CH₂—N), 4.68 (d, 1H, J=5.2 Hz, N—CH), 5.48 (d, 1H, J=4.3 Hz, O—CH), 8.09 (d, 2H, J=6.4 Hz, ArH), 8.90 (d, 2H, J=6.1 Hz, ArH).
¹³C-NMR (CD₃OD, δ): 23.4, 25.4, 46.2, 56.8, 68.4, 125.7 (2×C), 141.3 (2×C), 158.5, 163.2.

Preparation of (±)-threo-3-hydroxy-2-(isopropy-lamino)-3-(pyridin-4-yl)-1-(pyrrolidin-1-yl)propan-1-one dihydrochloride Compound 223

To a stirred solution of (±)-threo-2-amino-3-hydroxy-3-(pyridin-4-yl)-1-(pyrrolidin-1-yl)propan-1-one dihydrochloride Compound 22 (0.20 g, 0.65 mmol) in 3 mL of MeOH were added triethylamine (180 μl, 1.30 mmol) and acetone (75 μL, 1.00 mmol). The mixture was stirred overnight at RT under nitrogen and then was added AcOH (200 μL, 3.2 mmol) and NaBH$_3$CN (85 mg, 1.3 mmol). After 5 h at 20° C., MeOH was evaporated and the residue was partitioned between CH$_2$Cl$_2$ and 1 N aqueous sodium carbonate. The organic layer was evaporated and the obtained residue was purified by column chromatography (SiO$_2$, EtOAc:MeOH=9:1). HCl treatment in MeOH gave (±)-threo-3-hydroxy-2-(isopropy-lamino)-3-(pyridin-4-yl)-1-(pyrrolidin-1-yl)propan-1-one dihydrochloride Compound 223 (56 mg, 25% yield) as a white solid.

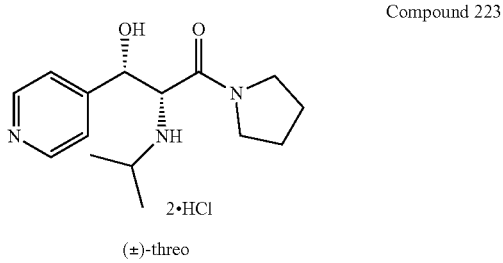 [SMILES: CC(C)N[C@@H](C(=O)N1CCCC1)[C@@H](O)c1ccncc1]

Compound 223
(±)-threo

MW: 350.28; Yield: 25%; White Solid; Mp (° C.): 189.8.

R$_f$:0.20 (EtOAc:MeOH=9:1, free base).

$^1$H-NMR (CD$_3$OD, δ): 1.32 (d, 3H, J=6.5 Hz, CH$_3$), 1.40 (d, 3H, J=6.5 Hz, CH$_3$), 1.55-1.84 (m, 4H, 2×CH$_2$), 2.66-2.74 (m, 1H, CH), 3.27-3.54 (m, 4H, CH$_2$—N), 4.60 (d, 1H, J=7.9 Hz, N—CH), 5.38 (d, 1H, J=7.8 Hz, O—CH), 8.24 (d, 2H, J=6.3 Hz, ArH), 8.98 (d, 2H, J=6.3 Hz, ArH).

$^{13}$C-NMR (CD$_3$OD, δ): 18.7, 20.1, 24.7, 26.7, 47.7, 48.5, 52.2, 62.4, 72.5, 127.0 (2×C), 143.2 (2×C), 161.1, 164.1.

MS-ESI m/z (% rel. Int.): 278.1 ([MH]$^+$, 25), 179.1 (100).

HPLC: Method A, detection UV 254 nm, Compound 223 RT=1.30 min, peak area 99.0%.

Preparation of (±)-2-amino-3-(hydroxyimino)-3-(pyridin-4-yl)-1-(pyrrolidin-1-yl)propan-1-one dihydrochloride Compound 224

(±)-2-tert-Butyloxycarbonylamino-3-(hydroxyimino)-3-(pyridin-4-yl)-1-(pyrrolidin-1-yl)propan-1-one TTA 08160

To a stirred solution of tert-butyl(±)-1,3-dioxo-3-(pyridin-4-yl)-1-(pyrrolidin-1-yl)propan-2-ylcarbamate TTA 08120 (0.20 g, 0.60 mmol) in 10 mL of dioxane were added Et$_3$N (125 μl, 0.90 mmol) and hydroxylamine hydrochloride (65 mg, 0.90 mmol). The mixture was stirred 2 h at 110° C. in a sealed tube then dioxane was evaporated. The obtained residue was purified by column chromatography (SiO$_2$, CH$_2$Cl$_2$:MeOH=9:1 to 97:3) to give (±)-2-tert-butyloxycarbony-lamino-3-(hydroxyimino)-3-(pyridin-4-yl)-1-(pyrrolidin-1-yl)propan-1-one TTA 08160 (100 mg, 48% yield) as an oil.

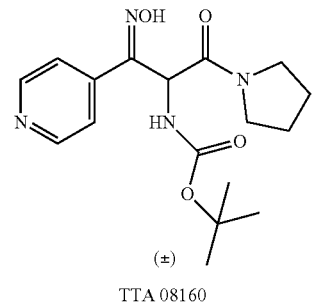

TTA 08160

MW: 348.40; Yield: 48%; Oil.

R$_f$:0.30 (CH$_2$Cl$_2$:MeOH=97:3).

$^1$H-NMR (CDCl$_3$, δ): 1.39 (s, 9H, 3×CH$_3$), 1.81-1.98 (m, 4H, 2×CH$_2$), 3.37-3.62 (m, 4H, 2×CH$_2$—N), 5.44 (d, 1H, J=8.1 Hz, N—CH), 5.97 (d, 1H, J=8.1 Hz, NH), 7.37 (d, 2H, J=5.6 Hz, ArH), 8.65 (d, 2H, J=6.0 Hz, ArH).

$^{13}$C-NMR (CDCl$_3$, δ): 24.0, 26.0, 28.2 (3×C), 46.5, 46.7, 55.8, 80.3, 123.1 (2×C), 139.7, 149.4 (2×C), 155.1, 166.4.

MS-ESI m/z (% rel. Int.): 349.2 ([MH]$^+$, 85), 293.2 (100).

HPLC: Method A, detection UV 254 nm, TTA 08160 RT=3.90 min, peak area 97.0%.

(±)-2-Amino-3-(hydroxyimino)-3-(pyridin-4-yl)-1-(pyrrolidin-1-yl)propan-1-one dihydrochloride Compound 224

(±)-2-tert-Butyloxycarbonylamino-3-(hydroxyimino)-3-(pyridin-4-yl)-1-(pyrrolidin-1-yl)propan-1-one TTA 08160 (100 mg, 0.29 mmol) was dissolved in MeOH (2 mL) and a solution of 1 M HCl in MeOH (1 mL, 3.00 mmol) was added and the mixture was heated for 10 min at 45° C. MeOH was evaporated and the residue was dried to give crude (±)-2-amino-3-(hydroxyimino)-3-(pyridin-4-yl)-1-(pyrrolidin-1-yl)propan-1-one TTA 08164. Amberlite IRA-400 (Cl$^-$) (1 mL, 1.4 mmol) was washed successively with water (2×10 mL), NaOH 0.5 N (3×20 mL), water (2×10 mL) and MeOH (3×10 mL). A solution of TTA 08164 in MeOH (30 mL) was stirred with washed Amberlite IRA-400 for 5 min at RT. After filtration, the MeOH was evaporated and the free base form was purified by column chromatography (SiO$_2$, CH$_2$Cl$_2$:MeOH=9:1). HCl Treatment in MeOH gave (±)-2-amino-3-(hydroxyimino)-3-(pyridin-4-yl)-1-(pyrrolidin-1-yl)propan-1-one dihydrochloride Compound 224 (29 mg, 31% yield) as a beige solid.

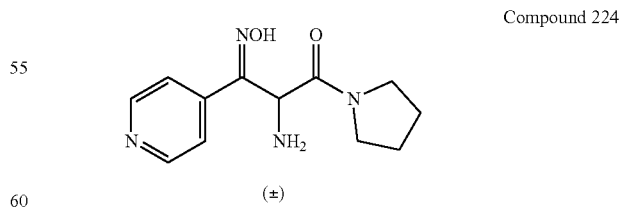

Compound 224

MW: 321.20; Yield: 31%; Beige Solid; Mp (° C.): 225.2

R$_f$:0.30 (EtOAc:MeOH=9:1, free base).

$^1$H-NMR (CD$_3$OD, δ): 1.85-2.04 (m, 4H, 2×CH$_2$), 3.23-3.73 (m, 4H, CH$_2$—N), 5.58 (d, 1H, J=4.4 Hz, CH), 8.23 (d, 2H, J=5.0 Hz, ArH), 9.03 (d, 2H, J=5.0 Hz, ArH).

$^{13}$C-NMR (CD$_3$OD, δ): 24.9, 26.9, 47.9, 48.0, 55.6, 128.7 (2×C), 143.8 (2×C), 145.5, 148.8, 163.8.

MS-ESI m/z (% rel. Int.): 249.2 ([MH]$^+$, 10), 115.0 (100).

HPLC: Method A, detection UV 254 nm, Compound 224 RT=0.60 min, peak area 99.0%.

Preparation of (±)-threo-2-(4-iodobenzylamino)-3-hydroxy-3-(pyridin-4-yl)-1-(pyrrolidin-1-yl)propan-1-one hydrochloride Compound 225

To a stirred solution of (±)-threo-2-amino-3-hydroxy-3-(pyridin-4-yl)-1-(pyrrolidin-1-yl)propan-1-one dihydrochloride Compound 22 (500 mg, 1.62 mmol) in 7.5 mL of MeOH at RT under nitrogen was added dropwise triethylamine (495 μL, 3.56 mmol) and 4-iodobenzaldehyde (413 mg, 1.73 mmol). The mixture was stirred for 5 h at RT under nitrogen. Acetic acid (463 μL, 8.1 mmol) and NaBH$_3$CN (356 mg, 5.67 mmol) were added. The mixture was stirred for another 15 h at RT. The mixture was partitioned between EtOAc (750 mL) and an 10% aqueous solution of potassium carbonate. The organic layer was washed with brine (2×20 mL), dried over MgSO$_4$ and filtered. After evaporation, the crude product was purified by column chromatography (SiO$_2$, EtOAc: MeOH=85:15) to give (±)-threo-2-(4-iodobenzylamino)-3-hydroxy-3-(pyridin-4-yl)-1-(pyrrolidin-1-yl)propan-1-one VIB 01096 as a yellow solid (380 mg, 52% yield). To a solution of (±)-threo-2-(4-iodobenzylamino)-3-hydroxy-3-(pyridin-4-yl)-1-(pyrrolidin-1-yl)propan-1-one VIB 01096 (380 mg, 8.43 mmol) in methanol (10 mL) was added a solution of 0.5 M aqueous hydrochloric acid (7 mL). After stirring the mixture at RT for 0.5 h the reaction mixture was concentrated and the crude product was coevaporated twice with EtOAc. After trituration with EtOAc, filtration and drying, (±)-threo-2-(4-iodobenzylamino)-3-hydroxy-3-(pyridin-4-yl)-1-(pyrrolidin-1-yl)propan-1-one hydrochloride Compound 225 (373 mg, 44% yield) was obtained as a pale yellow solid.

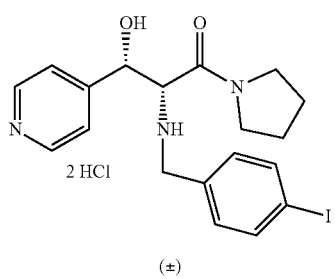

Compound 225

MW: 524.37; Yield 44%; Pale Yellow Solid; Mp (° C.): 194.7

$^1$H-NMR (CD$_3$OD, δ): 1.42-1.80 (m, 4H, 2×CH$_2$), 2.32-2.50 (m, 1H, CH$_2$), 2.96-3.12 (m, 1H, CH$_2$), 3.12-3.25 (m, 2H, CH$_2$), 4.27 (q, 2H, J=13.3 Hz, CH$_2$), 4.42 (d, 1H, J=7.8 Hz, HC—N), 5.31 (d, 2H, J=7.7 Hz, HC—O), 7.29 (d, 2H, J=8.1 Hz, ArH), 7.80 (dd, 2H, J=2.9 Hz, J=8.1 Hz, ArH), 8.15 (d, 2H, J=5.5 Hz, ArH), 8.91 (d, 2H, J=5.5 Hz, ArH).

$^{13}$C-NMR (CD$_3$OD, δ): 24.7, 26.5, 47.5, 48.4, 51.1, 63.7, 72.3, 96.9, 126.9 (2×C), 131.0, 133.6 (2×C), 139.5 (2×C), 143.2 (2×C), 161.1, 163.8.

MS-ESI m/z (% rel. Int.): 451.9 ([MH]$^+$, 100), 363.8 (45), 342.9 (70), 216.9 (75), 148.0 (30).

HPLC: Method A, detection UV 254 nm, Compound 225 RT=3.83 min, peak area 98.7%.

Preparation of (±)-threo-2-(2-iodobenzylamino)-3-hydroxy-3-(pyridin-4-yl)-1-(pyrrolidin-1-yl)-propan-1-one dihydrochloride Compound 226

To a stirred solution of (±)-threo-2-amino-3-hydroxy-3-pyridin-4-yl-1-pyrrolidin-1-yl-propan-1-one Compound 22 (500 mg, 1.62 mmol) in 10 ml methanol was added successively Et$_3$N (496 μL, 3.57 mmol) and 2-iodo-benzaldehyde (414 mg, 1.78 mmol) in 1 ml methanol. The mixture was stirred 6 h at RT under nitrogen and acetic acid (464 μL, 8.11 mmol) and sodium cyanoborohydride (356 mg, 5.57 mmol) were added. The mixture was stirred overnight at 20° C. and evaporated to give a residue which was partitioned between CH$_2$Cl$_2$ and 1 N aqueous potassium hydroxyde. The organic layer was washed with brine and dried over MgSO$_4$, filtered and evaporated. The crude product was purified by column chromatography (SiO$_2$, EtOAc:MeOH=9:1). After evaporation and drying a white solid (±)-threo-2-(2-iodobenzylamino)-3-hydroxy-3-(pyridin-4-yl)-1-(pyrrolidin-1-yl)-propan-1-one was obtained (419.6 mg, 57% yield). The product was dissolved in methanol (10 mL). The solution was stirred at room temperature and a solution of HCl (1 M, 7.4 mL) was added via syringe at RT for 10 min. The mixture was concentrated and triturated with EtOAc. After filtration and drying, (±)-threo-2-(2-iodobenzylamino)-3-hydroxy-3-(pyridin-4-yl)-1-(pyrrolidin-1-yl)-propan-1-one dihydrochloride Compound 226 was obtained (195 mg, 25% yield) as a white solid.

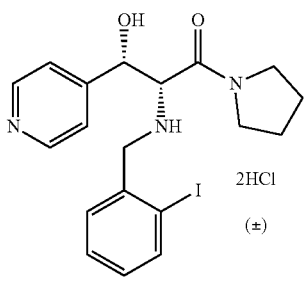

Compound 226

MW: 524.22; Yield: 25%; White Solid; Mp (° C.): 148.0

R$_f$:0.50 (MeOH:EtOAc=20:80, free base).

$^1$H-NMR (CD$_3$OD, δ): 1.33-1.80 (m, 4H, 2×CH$_2$), 2.12-2.25 (m, 1H, CH$_2$), 2.75-2.88 (m, 1H, CH$_2$), 3.14-3.25 (m, 1H, CH$_2$), 3.25-3.31 (m, 1H, CH$_2$), 4.14 (d, 1H, J=8.4 Hz, NH—CH), 4.37-4.52 (m, 2H, NH—CH$_2$) 5.10 (d, 1H, J=8.3. Hz, CH—O), 7.18 (t, 1H, J=7.6 Hz, ArH), 7.49 (d, 1H, J=7.5 Hz, ArH), 7.61 (d, 1H, J=7.7 Hz, ArH), 7.68 (d, 2H, J=5.2 Hz, ArH), 7.97 (d, J=7.9 Hz, 1H, ArH), 8.66 (d, J=4.9 Hz, 2H, ArH).

$^{13}$C-NMR (CD$_3$OD, δ): 24.7, 26.5, 47.6, 47.8, 55.3, 64.3, 72.7, 101.8, 124.4 (2×C), 130.3, 132.0, 132.5, 135.1, 141.7 (2×C), 148.2, 154.0, 164.2.

MS-ESI m/z (% rel. Int.): 451.9 ([MH]$^+$, 100), 352.9 (55), 342.9 (30).

HPLC: Method A, detection UV 254 nm, Compound 226 RT=3.72 min, peak area 98.95%.

Preparation of (±)-threo-2-(3-iodobenzylamino)-3-hydroxy-3-(pyridin-4-yl)-1-(pyrrolidin-1-yl)-propan-1-one dihydrochloride Compound 227

To a stirred solution of (±)-threo-2-amino-3-hydroxy-3-pyridin-4-yl-1-pyrrolidin-1-yl-propan-1-one Compound 22

(500 mg, 1.62 mmol) in 10 ml methanol was added successively Et₃N (496 µL, 3.55 mmol) and 3-iodo-benzaldehyde (414 mg, 1.78 mmol) in 1 ml methanol. The mixture was stirred 6 h at RT under nitrogen and acetic acid (464 µL, 8.11 mmol) and sodium cyanoborohydride (356 mg, 5.57 mmol) were added. The mixture was stirred overnight at 20° C. then evaporated and the residue was partitioned between CH₂Cl₂ and 1 N aqueous potassium hydroxyde. The organic layer was washed with brine and dried. The organic layer was evaporated. The crude product was purified by column chromatography (SiO₂, CH₂Cl₂:MeOH=95:5). After evaporation and drying a white solid (±)-threo-2-(3-iodobenzylamino)-3-hydroxy-3-(pyridin-4-yl)-1-(pyrrolidin-1-yl)-propan-1-one (437 mg, 60% yield). This product was dissolved in methanol (10 mL). The solution was stirred at RT and a solution of HCl (1 M, 7.7 mL) was added at room temperature for 10 min. The mixture was concentrated and triturated with diethyl ether. After filtration and drying, (±)-threo-2-(3-iodobenzylamino)-3-hydroxy-3-(pyridin-4-yl)-1-(pyrrolidin-1-yl)-propan-1-one dihydrochloride Compound 227 was obtained (205 mg, 26% yield) as a white solid.

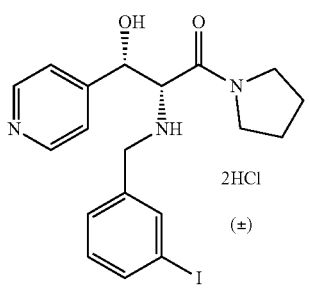

Compound 227

MW: 524.22; Yield: 26%; White Solid; Mp (° C.): 142.8
R_f: 0.30 (MeOH:CH₂Cl₂=5:95, free base).
¹H-NMR (CD₃OD, δ): 1.25-1.80 (m, 4H, 2×CH₂), 2.03-2.12 (m, 1H, CH₂), 2.80-2.92 (m, 1H, CH₂), 3.11-3.25 (m, 2H, CH₂), 4.06-4.30 (m, 3H, CH—N & N—CH₂), 5.04 (d, 1H, J=8.8 Hz, CH—OH), 7.23 (t, 1H, J=7.8 Hz, ArH), 7.51 (d, 1H, J=7.5 Hz, ArH), 7.67 (d, 2H, J=5.8 Hz, ArH), 7.80 (d, 1H, J=5.2 Hz, ArH), 7.87 (s, 1H, ArH), 8.66 (d, J=5.2 Hz, 2H, ArH).
¹³C-NMR (CD₃OD, δ): 24.7, 26.5, 47.3, 47.7, 50.5, 64.3, 72.8, 95.3, 124.5 (2×C), 130.9, 132.0, 133.9, 140.1, 140.5, 148.3, 153.7, 164.2.
MS-ESI m/z (% rel. Int.): 451.9 ([MH]⁺, 100), 352.9 (40), 342.9 (50).
HPLC: Method A, detection UV 254 nm, Compound 227 RT=3.80 min, peak area 98.7%.

Preparation of (+)-(2S,3R)-2-(3-iodobenzylamino)-3-hydroxy-3-(pyridin-4-yl)-1-(pyrrolidin-1-yl)-propan-1-one dihydrochloride Compound 228

To a stirred solution of (+)-(2S,3R)-2-amino-3-hydroxy-3-(pyridin-4-yl)-1-(pyrrolidin-1-yl)propan-1-one dihydrochloride Compound 204 (204 mg, 0.67 mmol) in MeOH (6 mL) was added Et₃N (202 µL, 1.46 mmol) and, via syringe, a solution of 3-iodobenzaldehyde (169 mg, 0.73 mmol) in methanol (1 mL). The mixture was stirred 5 h at RT under nitrogen. CH₃COOH (190 µL, 3.30 mmol) and sodium cyanoborohydride (146 mg, 2.32 mmol) were added and the reaction mixture was stirred overnight at RT. MeOH was evaporated and the residue was partitioned between CH₂Cl₂ and a solution of 1 N aqueous potassium carbonate. The organic layer was washed with brine, dried over MgSO₄, filtered and evaporated. The crude product was purified by column chromatography (SiO₂, CH₂Cl₂:MeOH=95:5). After evaporation and drying (2S,3R)-2-(3-iodobenzylamino)-3-hydroxy-3-(pyridin-4-yl)-1-(pyrrolidin-1-yl)-propan-1-one (246 mg) was obtained as a white solid. The product was dissolved in methanol (5 mL) and a solution of HCl in MeOH (1 M, 2.5 mL) was added via syringe and the solution was stirred at RT for 0.6 h. The mixture was concentrated and the resulting solid triturated with Et₂O. After filtration and drying (+)-(2S,3R)-2-(3-iodobenzylamino)-3-hydroxy-3-(pyridin-4-yl)-1-(pyrrolidin-1-yl)-propan-1-one dihydrochloride Compound 228 (280 mg, 80% yield) was obtained as a white solid.

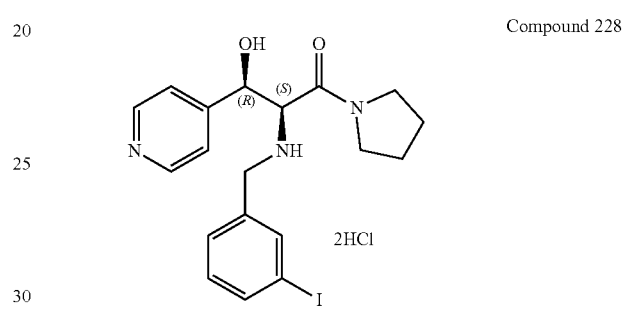

Compound 228

MW: 524.22; Yield: 80%; White Solid; Mp (° C.): 107.4
α²²_D=±101.9 (MeOH, c=1.02).
R_f: 0.30 (MeOH:CH₂Cl₂=5:95, free base).
¹H-NMR (CD₃OD, *): 1.52-1.82 (m, 4H, 2×CH₂), 2.38-2.45 (m, 1H, CH₂), 3.01-3.09 (m, 1H, CH₂), 3.18-3.32 (m, 2H, CH₂), 4.20-4.29 (dd, 2H, J=28.1 Hz, J=13.4 Hz, NH—CH₂), 4.40 (d, 1H, J=7.9 Hz, N—CH), 5.30 (d, J=7.9 Hz, 1H, CH—O), 7.25 (t, 1H, J=5.4 Hz, ArH), 7.54 (d, 1H, J=7.1 Hz, ArH), 7.81 (d, 1H, J=7.2 Hz, ArH), 7.89 (d, 1H, J=1.3 Hz, ArH), 8.13 (d, J=5.5 Hz, 2H, ArH), 8.90 (d, J=5.3 Hz, 2H, ArH).
MS-ESI m/z (% rel. Int.): 452.1 ([MH]⁺, 100), 353.0 (65), 343.1 (80).
HPLC: Method A, detection UV 254 nm, Compound 228 RT=3.87 min, peak area 97.0%.

Preparation of (2R,3S)-2-(3-iodobenzylamino)-3-hydroxy-3-(pyridin-4-yl)-1-(pyrrolidin-1-yl)-propan-1-one dihydrochloride Compound 229

Similar to Compound 228 with (−)-(2R,3S)-2-amino-3-hydroxy-3-(pyridin-4-yl)-1-(pyrrolidin-1-yl)propan-1-one dihydrochloride Compound 203 (77 mg, 0.25 mmol) in 2.3 ml of MeOH, Et₃N (76 µL, 0.79 mmol), 3-iodobenzaldehyde (64 mg, 0.275 mmol), CH₃COOH (78.6 µL, 1.37 mmol) and NaBH₃CN (60.5 mg, 0.96 mmol).

(2R,3S)-2-(3-iodobenzylamino)-3-hydroxy-3-(pyridin-4-yl)-1-(pyrrolidin-1-yl)-propan-1-one dihydrochloride Compound 229 (70 mg, 53.5% yield) was obtained as a pale yellow solid.

Compound 229

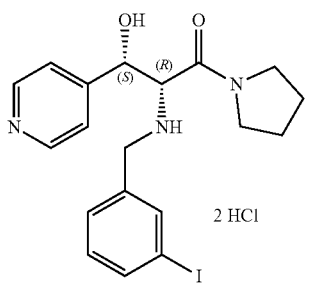

2 HCl

MW: 524.22; Yield: 53.5%; Pale Yellow Solid; Mp (° C.): 179.7
R_f: 0.30 (MeOH:CH₂Cl₂=5:95, free base).
¹H-NMR (CD₃OD, *): idem to Compound 228.
MS-ESI m/z (% rel. Int.): 452.1 ([MH]⁺, 100), 353.0 (70), 343.1 (60).
HPLC: Method A, detection UV 254 nm, Compound 228 RT=3.78 min, peak area 99.0%.

Preparation of (±)-threo-2-amino-3-hydroxy-1-morpholino-3-(thiophen-3-yl)propan-1-one hydrochloride Compound 230 trans-(4,5-Dihydro-5-(thiophen-3-yl)oxazol-4-yl)(morpholino)methanone SLA 09052A SLA 09052A was prepared in accordance with method D using thiophene-3-carbaldehyde (0.768 mL, 5.35 mmol), KOH (0.273 mg, 4.86 mmol) in methanol (5 mL) and 2-isocyano-1-morpholinoethanone SLA 07118 (0.75 g, 4.86 mmol). The solution was stirred for 2 h at 0° C. After work-up the residue was purified by column chromatography (florisil, EtOAc). After evaporation and drying, trans-(4,5-dihydro-5-(thiophen-3-yl)oxazol-4-yl)(morpholino)methanone SLA 09052A (0.327 g, 25% yield) was obtained as a yellow oil.

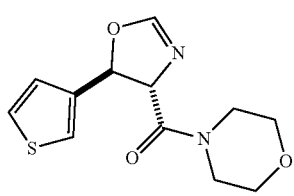

(±)-trans

SLA 09052A

MW: 266.32; Yield: 25%; Yellow Oil.
¹H-NMR (CDCl₃, *): 3.40-4.00 (m, 8H, 4×CH₂), 4.67 (dd, 1H, J=7.3 Hz, J=2.2 Hz, CH—N), 6.29 (d, 1H, J=7.3 Hz, CH—O), 6.97 (d, 1H, J=2.2 Hz, CH=N), 7.01 (dd, 1H, J=5.0 Hz, J=1.3 Hz, CH=C), 7.28-7.40 (m, 2H, CH=C).

(±)-threo-2-Amino-3-hydroxy-1-morpholino-3-(thiophen-3-yl)propan-1-one hydrochloride Compound 230

To a solution of trans-(4,5-dihydro-5-(thiophen-3-yl)oxazol-4-yl)(morpholino)methanone SLA 09052A (0.327 g, 1.12 mmol) in MeOH (5 mL) was added HCl 37% (2 mL). After heating (50° C.) the mixture for 24 h the reaction mixture was concentrated and the crude product was coevaporated twice with EtOAc. After trituration with EtOAc, filtration and drying (±)-threo-2-amino-3-hydroxy-1-morpholino-3-(thiophen-3-yl)propan-1-one hydrochloride Compound 230 (276 mg, 77% yield) was obtained as a pale yellow solid.

Compound 230

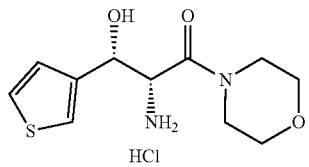

HCl (±)

MW: 292.78; Yield: 77%; Pale Yellow Solid; Mp (° C.): 209.1
¹H-NMR (CD₃OD, δ): 2.77-2.92 (m, 2H, CH₂), 3.20-3.60 (m, 6H, 3×CH₂), 4.49 (d, 1H, J=8.7 Hz, CH⁻N), 4.95 (d, 1H, J=8.8 Hz, CH⁻O), 7.18 (d, 1H, J=4.5 Hz, CH=C), 7.44 (d, 1H, J=1.7 Hz CH=C), 7.44 (dd, 1H, J=4.5 Hz, J=1.7 Hz CH=C).

Preparation of (±)-threo-2-amino-3-hydroxy-1-(piperidin-1-yl)-3-(thiophen-3-yl)propan-1-one hydrochloride Compound 231 trans-(4,5-Dihydro-5-(thiophen-3-yl)oxazol-4-yl)(piperidin-1-yl)methanone SLA 09052B SLA 09052B was prepared in accordance with method D using thiophene-3-carbaldehyde (0.778 mL, 5.43 mmol), KOH (0.273 mg, 4.94 mmol) in methanol (5 mL) and 2-isocyano-1-(piperidin-1-yl)ethanone SLA 07116B (0.75 g, 4.94 mmol). The solution was stirred for 2 h at 0° C. After work-up (without any further purification) and drying trans-(4,5-dihydro-5-(thiophen-3-yl)oxazol-4-yl)(piperidin-1-yl)methanone SLA 09052B was obtained as a yellow oil (1.29 g, 99% yield).

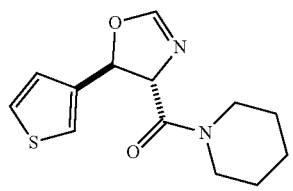

(±)-trans

SLA 09052B

MW: 264.34; Yield: 99%; Yellow Oil.
¹H-NMR (CDCl₃, δ): 1.47-1.75 (m, 6H, 3×CH₂), 3.42-3.82 (m, 4H, 2×CH₂), 4.72 (dd, 1H, J=7.2 Hz, J=2.2 Hz, CH—N), 6.28 (d, 1H, J=7.2 Hz, CH—O), 6.96 (d, 1H, J=2.2 Hz, CH=N), 7.01 (dd, 1H, J=5.0 Hz, J=1.2 Hz, CH=C), 7.30-7.35 (m, 2H, CH=C).
¹³C-NMR (CDCl₃, δ): 24.5, 25.5, 26.5, 43.7, 46.8, 73.4, 78.0, 122.6, 125.1, 127.2, 140.5, 155.0, 166.3.

(±)-threo-2-Amino-3-hydroxy-1-(piperidin-1-yl)-3-(thiophen-3-yl)propan-1-one hydrochloride Compound 231

To a solution of trans-(4,5-dihydro-5-(thiophen-3-yl)oxazol-4-yl)(piperidin-1-yl)methanone SLA 09052B (1.29 g, 4.88 mmol) in methanol (5 mL) was added hydrochloric acid 37% (5 mL). After heating (50° C.) the mixture for 24 h the reaction mixture was concentrated and the crude product was coevaporated twice with EtOAc. After trituration with EtOAc, filtration and drying (±)-threo-2-amino-3-hydroxy-1-morpholino-3-(thiophen-3-yl)propan-1-one hydrochloride Compound 231 was obtained as a pale yellow solid (1.07 g, 75% yield).

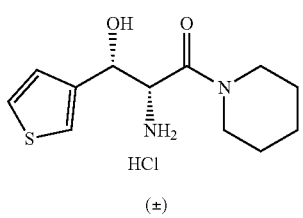

Compound 231

(±)

MW: 290.81; Yield: 75%; Pale Yellow Solid; Mp (° C.): 210.6

¹H-NMR (CD₃OD, δ): 0.82-0.97 (m, 1H, 0.5×CH₂), 1.30-1.70 (m, 5H, 2.5×CH₂), 2.75-2.91 (m, 1H, CH₂), 3.12-3.55 (m, 3H, 1.5×CH₂), 4.51 (d, 1H, J=8.4 Hz, CH⁻N), 4.94 (d, 1H, J=8.5 Hz, CH⁻O), 7.16 (d, 1H, J=4.9 Hz, CH=C), 7.44 (d, 1H, J=2.5, Hz CH=C), 7.44 (dd, 1H, J=4.5 Hz, J=3.2 Hz CH=C).

Preparation of (±)-threo-2-amino-3-hydroxy-1-morpholino-3-(pyridin-3-yl)propan-1-one dihydrochloride Compound 232 trans-(4,5-Dihydro-5-(pyridin-3-yl)oxazol-4-yl)(morpholino)methanone SLA 09050A

SLA 09050A was prepared in accordance with method D using pyridine-3-carbaldehyde (0.65 mL, 4.86 mmol), KOH (0.273 mg, 4.86 mmol) in methanol (10 mL) and 2-isocyano-1-morpholinoethanone SLA 07118 (0.75 g, 4.86 mmol). The solution was stirred for 20 h at 0° C. After work-up (without any further purification), evaporation and drying trans-(4,5-dihydro-5-(pyridin-3-yl)oxazol-4-yl)(morpholino)methanone SLA 09050A was obtained as a yellow solid (0.92 g, 72.5% yield).

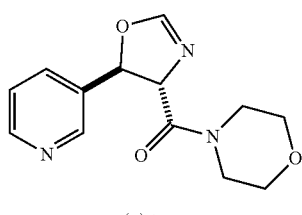

(±)-trans

SLA 09050A

MW: 261.28; Yield: 72.5%; Yellow Solid.

¹H-NMR (CDCl₃, δ): 3.42-4.00 (m, 8H, 4×CH₂), 4.63 (dd, 1H, J=7.7 Hz, J=2.3 Hz, CH—N), 6.29 (d, 1H, J=7.7 Hz, CH—O), 7.02 (d, 1H, J=2.2 Hz, CH=N), 7.33 (m, 1H, ArH), 7.60-7.66 (m, 1H, ArH), 8.57-8.62 (m, 2H, ArH).

¹³C-NMR (CDCl₃, δ): 43.0, 46.3, 66.7, 66.8, 74.6, 79.2, 123.5, 133.4, 135.1, 147.5, 150.0, 155.0, 166.3.

MS-ESI m/z (% rel. Int.): 262.1 ([MH]⁺, 55), 108.0 (100).

(±)-threo-2-Amino-3-hydroxy-1-morpholino-3-(pyridin-3-yl)propan-1-one dihydrochloride Compound 232

To a solution of trans-(4,5-dihydro-5-(pyridin-3-yl)oxazol-4-yl)(morpholino)methanone SLA 09050A (0.911 g, 3.48 mmol) in methanol (10 mL) was added hydrochloric acid 37% (5 mL). After heating (50° C.) the mixture for 2.25 h the reaction mixture was concentrated and the crude product was coevaporated twice with EtOAc and the crude product was dissolved in a 1 N solution of K₂CO₃ which was extracted with a mixture CH₂Cl₂:iPrOH=9:1 (6×100 mL). The combined organic layer was dried over MgSO₄, filtered and evaporated to led to a crude product which was purified by column chromatography (SiO₂, EtOAC:MeOH=70:30). After evaporation the product was dissolved in a solution of HCl in MeOH (0.5M, 29 mL) and stirred at RT for 1.5 h. The product was co-evaporated twice with EtOAc. After trituration with EtOAc, filtration and drying, (±)-threo-2-amino-3-hydroxy-1-morpholino-3-(pyridin-3-yl)propan-1-one dihydrochloride Compound 232 (270 mg, 24% yield) was obtained as a yellow solid.

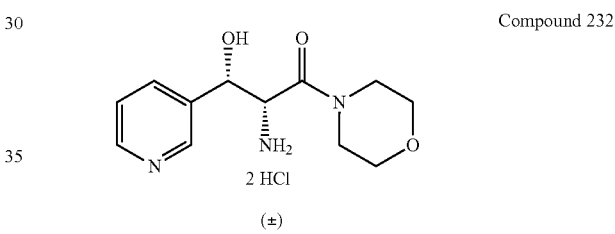

Compound 232

2 HCl (±)

MW: 324.2; Yield: 24%; Yellow Solid.

¹H-NMR (CD₃OD, δ): 3.20-3.78 (m, 8H, 4×CH₂), 4.87 (d, 1H, J=5.5 Hz, CH⁻N), 5.40 (d, 1H, J=5.4 Hz, CH⁻O), 8.20 (m, 1H, ArH), 8.77 (d, 1H, J=8.3 Hz, ArH), 8.93 (d, 1H, J=5.5 Hz, ArH), 9.03 (s, 1H, ArH).

Preparation of (±)-threo-2-amino-3-hydroxy-1-piperidin-3-(pyridin-3-yl)propan-1-one dihydrochloride Compound 233 trans-(4,5-Dihydro-5-(pyridin-3-yl)oxazol-4-yl)(piperidin)methanone SLA 09050B

SLA 09050B was prepared in accordance with method D using pyridine-3-carbaldehyde (0.512 mL, 5.42 mmol), KOH (0.277 mg, 4.93 mmol) in methanol (10 mL) and 2-isocyano-1-piperidinethanone SLA 07116B (0.75 g, 4.93 mmol). The solution was stirred for 20 h at 0° C. After work-up (without any further purification), evaporation and drying, trans-(4,5-dihydro-5-(pyridin-3-yl)oxazol-4-yl)(piperidin)methanone SLA 09050B (0.917 g, 72% yield) was obtained as a yellow solid.

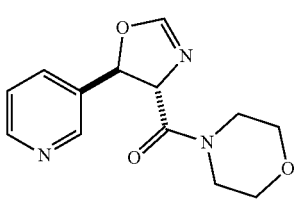

(±) trans
SLA 09050B

MW: 259.30; Yield: 72%; Yellow Solid.

$^1$H-NMR (CDCl$_3$, δ): 1.59-1.73 (m, 6H, 3×CH$_2$), 3.44-3.83 (m, 4H, 2×CH$_2$), 4.68 (dd, 1H, J=7.6 Hz, J=2.3 Hz, CH—N), 6.30 (d, 1H, J=7.6 Hz, CH—O), 7.02 (d, 1H, J=2.2 Hz, CH=N), 7.32 (m, 1H, ArH), 7.60-7.66 (m, 1H, ArH), 8.57-8.62 (m, 2H, ArH).

$^{13}$C-NMR (CDCl$_3$, δ): 24.4, 25.5, 26.4, 43.8, 46.9, 74.6, 79.5, 123.6, 133.5, 135.4, 147.5, 149.9, 154.8, 165.9.

(±)-threo-2-Amino-3-hydroxy-1-piperidin-3-(pyridin-3-yl)propan-1-one dihydrochloride Compound 233

To a solution of trans-(4,5-dihydro-5-(pyridin-3-yl)oxazol-4-yl)(piperidin)methanone SLA 09050B (0.917 g, 3.54 mmol) in methanol (10 mL) was added hydrochloric acid 37% (5 mL). After heating at 50° C. the mixture for 2.25 h the reaction mixture was concentrated and the crude product was coevaporated twice with EtOAc. After trituration with EtOAc, filtration and drying, the crude product was dissolved in a 1 N solution of K$_2$CO$_3$ and the product was extracted CH$_2$Cl$_2$:iPrOH=9:1 (6×100 mL). The crude product was purified by column chromatography (EtOAc:MeOH=7:3) (±)-threo-2-amino-3-hydroxy-1-piperidin-3-(pyridin-3-yl)propan-1-one was obtained pale yellow solid (223.5 mg). The product was dissolved in a solution of HCl in MeOH (0.5 M, 18 mL) and stirred at RT for 1.5 h. After trituration with EtOAc, filtration and drying, (±)-threo-2-amino-3-hydroxy-1-piperidin-3-(pyridin-3-yl)propan-1-one dihydrochloride Compound 233 (208 mg, 18% yield) was obtained as a yellow solid.

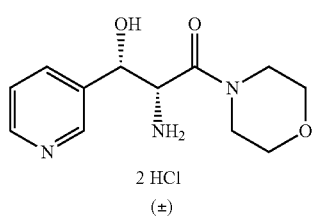

Compound 233
2 HCl
(±)

MW: 322.2; Yield: 18%; Yellow Solid.

$^1$H-NMR (CD$_3$OD, *): 1.15-1.80 (m, 6H, 4×CH$_2$), 3.10-3.80 (m, 4H, 2×CH$_2$), 4.88 (d, 1H, J=5.6 Hz, CH-N), 5.33 (d, 1H, J=5.6 Hz, CH-O), 8.19 (t, 1H, J=7.1 Hz, ArH), 8.74 (d, 1H, J=7.9 Hz, ArH), 8.93 (d, 1H, J=5.6 Hz, ArH), 9.01 (s, 1H, ArH).

Preparation of (2R,3S)-2-(R)-2-hydroxy-1-phenylethylamino)-3-hydroxy-3-(pyridin-4-yl)-1-(pyrrolidin-1-yl)propan-1-one dihydrochloride Compound 234

(R)-5-Phenylmorpholin-2-one EBE 06134

To a solution of phenylbromoacetate (18.58 g, 86 mmol) in CH$_3$CN under nitrogen was added a solution of (R)-phenylglycinol (10.17 g, 74 mmol) and di-isopropylethylamine (34 mL, 195 mmol) in CH$_3$CN. The volatiles were removed under reduced pressure keeping the bath temperature below 25° C. to obtain an oil that was treated with EtOAc (120 mL) and stirred for 15 min. The resulting white precipitate was removed by filtration. The filtrate was concentrated under reduced pressure and the desired product was isolated using column chromatography (SiO$_2$) with a step gradient of 10% to 50% [v/v] EtOAc in cyclohexane to give after evaporation (R)-5-phenylmorpholin-2-one EBE 06134 (3.17 g, 24% yield) as a white solid.

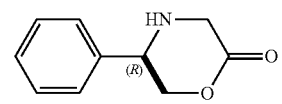

EBE 06134

MW: 177.2; Yield: 24%; White Solid; Mp (° C.): 50.3

R$_f$:0.30 (EtOAc:cyclohexane=50:50).

$^1$H-NMR (CDCl$_3$, δ): 1.99 (s, 1H, NH), 3.89 (q, 2H, J=17.8 Hz, N—CH$_2$), 4.18 (dd, 1H, J=3.7 Hz, J=10.3 Hz, O—CH), 4.29 (t, 1H, J=10.5 Hz, N—CH), 4.40 (dd, 1H, J=3.7 Hz, J=10.5 Hz, O—CH), 7.30-7.45 (m, 5H, ArH).

$^{13}$C-NMR (CDCl$_3$, δ): 46.8, 54.8, 72.8, 125.3 (2×C), 127.0, 127.3 (2×C), 135.9, 166.0.

[α]$^{22}_D$=+ 30.3° (c=1.00, MeOH).

(1S,3R,5R,8aR)-Tetrahydro-5-phenyl-1,3-di(pyridin-4-yl)oxazolo[4,3-c][1,4]oxazin-8(3H)-one EBE 06136

A solution of (R)-5-phenylmorpholinon-2-one EBE 06134 (3.0 g, 16.9 mmol) and pyridine-4-carboxaldehyde (5.43 g, 50.7 mmol) in toluene (75 mL) was refluxed in a soxhlet extractor filled with molecular sieves 4A (25 g) for 16 hours. All the volatiles were evaporated and the desired product was purified by column chromatography (SiO$_2$) using a gradient of 80% to 100% [v/v] EtOAc in cyclohexane to give after evaporation (1S,3R,5R,8aR)-tetrahydro-5-phenyl-1,3-di(pyridin-4-yl)oxazolo[4,3-c][1,4]oxazin-8(311)-one EBE 06136 (1.7 g, 46% yield) as a pale yellow solid.

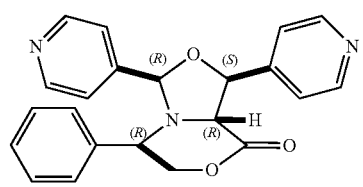

EBE 06136

MW: 373.4; Yield: 46%; Pale Yellow Solid; Mp (° C.): 155.6

R$_f$:0.20 (EtOAc).

$^1$H-NMR (CDCl$_3$, δ): 4.10-4.17 (m, 1H, N—CH), 4.25 (dd, 1H, J=3.3 Hz, N—CH), 4.36-4.54 (m, 2H, O—CH), 5.38 (d, 1H, O—CH, J=8.2 Hz), 5.53 (s, 1H, N—CH), 7.20-7.35 (m, 8H, ArH), 7.40-7.50 (m, 1H, ArH), 8.51 (dd, 2H, J=1.4 Hz, J=4.5 Hz), 8.57 (dd, 2H, J=1.4 Hz, J=4.5 Hz, ArH).

((2R,4S,5R)-3-((R)-2-Hydroxy-1-phenylethyl)-2,5-di(pyridin-4-yl)oxazolidin-4-yl)(pyrrolidin-1-yl)methanone EBE 06138

To a solution of (1S,3R,5R,8aR)-tetrahydro-5-phenyl-1,3-di(pyridin-4-yl)oxazolo[4,3-c][1,4]oxazin-8(3H)-one EBE 06136 (1.7 g, 4.55 mmol) in CH$_2$Cl$_2$ was added pyrrolidine (1.90 mL, 22.8 mmol) and the solution was stirred under nitrogen at 25° C. for 16 h. All the volatiles were evaporated and the resulting product was isolated using column chromatography (SiO$_2$) with a gradient of 0-20% [v/v] MeOH in EtOAc to give after evaporation ((2R,4S,5R)-3-((R)-2-hydroxy-1-phenylethyl)-2,5-di(pyridin-4-yl)oxazolidin-4-yl)(pyrrolidin-1-yl)methanone EBE 06138 (0.665 g, 33% yield) as a white solid.

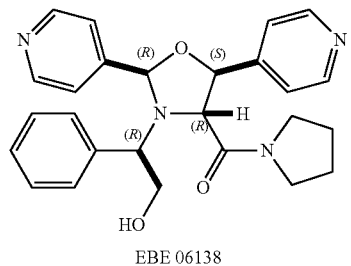

EBE 06138

MW: 444.5; Yield: 33%; White Solid; Mp (° C.): 63.6.

R$_f$:0.25 (MeOH:EtOAc=20:80).

$^1$H-NMR (CDCl$_3$, δ): 1.70-1.90 (m, 4H, 2×CH$_2$), 2.25 (bs, 1H, OH), 2.75-2.85 (m, 1H, CH—N), 2.95-3.05 (m, 1H, N—CH), 3.50-3.60 (m, 2H, N—CH$_2$), 3.80-4.15 (m, 4H, 2×CH+CH$_2$—O), 5.10 (d, 1H, J=4.7 Hz, CH), 6.32 (s, 1H, CH), 7.18-7.32 (m, 7H, ArH), 7.45 (d, 2H, J=5.9 Hz, ArH), 8.54 (d, 2H, J=6.0 Hz, ArH), 8.64 (d, 2H, J=6.0 Hz).

$^{13}$C-NMR (CDCl$_3$, δ): 23.9, 26.0, 46.3, 46.6, 60.3, 63.8, 65.2, 94.1, 121.1 (2×C), 123.0 (2×C), 128.0, 128.3 (2×C), 128.5 (2×C), 137.8, 147.8. MS-ESI m/z (% rel. Int.): 445.1 ([MH]$^+$, 20).

HPLC: Method A, detection at 254 nm, EBE 06138 RT=3.50 min, peak area 99%.

[α]$^{22}_D$=−16.0° (c=1.00, CHCl$_3$).

(2R,3S)-2-((R)-2-Hydroxy-1-phenylethylamino)-3-hydroxy-3-(pyridin-4-yl)-1-(pyrrolidin-1-yl)propan-1-one dihydrochloride Compound 234

To a solution of ((2R,4S,5R)-3-((R)-2-hydroxy-1-phenylethyl)-2,5-di(pyridin-4-yl)oxazolidin-4-yl)(pyrrolidin-1-yl)methanone EBE 06138 (600 mg, 1.34 mmol) in MeOH (6 mL) was added a solution of 1 N HCl (6 mL) and the reaction mixture was stirred at 60° C. for 2 h, evaporated to dryness to give a white solid (745 mg). This crude product was dissolved in CH$_2$Cl$_2$ (10 mL) and Na$_2$CO$_3$ (sat. sol.). The organic layer was separated was separated and the aqueous layer was washed with CH$_2$Cl$_2$ (5×2 mL). The combined organic layer were dried over Na$_2$SO$_4$, filtered over cotton mixed with silica gel (600 mg), evaporated and loaded on a silica gel column of 25 g. The desired product was eluted using a gradient of MeOH 0% to 20% in EtOAc to give after evaporation (2R,3S)-2-((R)-2-hydroxy-1-phenylethylamino)-3-hydroxy-3-(pyridin-4-yl)-1-(pyrrolidin-1-yl)propan-1-one (320 mg, 67% yield) as a white solid.

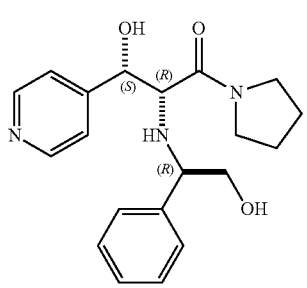

Compound 234

MW=355.43; Yield: 67%; White Solid; Mp (° C.)=76.4

R$_f$:0.3 (MeOH:EtOAc=20:80).

$^1$H NMR (CDCl$_3$, δ): 1.18-1.30 (m, 2H, CH$_2$), 1.30-1.48 (m, 2H, CH$_2$), 1.80-1.90 (m, 1H, CH$_2$), 2.23-2.33 (m, 1H, N—CH$_2$), 2.85-2.95 (m, 2H, N—CH$_2$), 3.00-3.12 (m, 2H, N—CH+N—CH), 3.72-3.85 (m, 3H, O—CH$_2$+NH), 4.58 (d, 1H, J=8.4 Hz, O—CH), 7.18-7.35 (m, 7H, ArH), 8.51 (d, 2H, J=6.0 Hz, ArH).

[α]$^{22}_D$=−68.8° (c=1.00, CHCl$_3$).

To a solution of (2R,3S)-2-((R)-2-hydroxy-1-phenylethylamino)-3-hydroxy-3-(pyridin-4-yl)-1-(pyrrolidin-1-yl)propan-1-one in MeOH (100 mg), in MeOH (1 mL) was added a solution HCl (1 N, 1.1 mL) at 0° C. and the solution was stirred for 10 min to give after evaporation (2R,3S)-2-((R)-2-hydroxy-1-phenylethylamino)-3-hydroxy-3-(pyridin-4-yl)-1-(pyrrolidin-1-yl)propan-1-one dihydrochloride Compound 234 (120 mg, 99% yield) as a white solid.

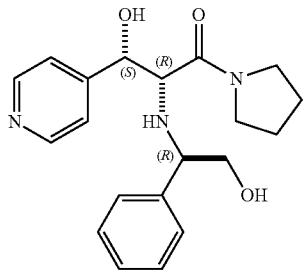

Compound 234

2 HCl

MW: 430.4; Global Yield: 66%; White Solid; Mp (° C.): 38.6.

$^1$H-NMR (CD$_3$OD, δ): 1.38-1.58 (m, 4H, CH$_2$), 2.12-2.22 (m, 1H, N—CH$_2$), 2.80-2.90 (m, 1H, N—CH$_2$), 3.00-3.10 (m, 2H, N—CH$_2$), 3.91 (dd, 1H, J=4.3 Hz, J=11.3 Hz, CH$_2$—O), 4.02-4.12 (m, 1H, CH$_2$—O), 4.55-4.65 (m, 2H, N—CH), 5.27 (d, 1H, J=8.9 Hz, 7.35-7.45 (m, 3H, ArH), 7.45-7.58 (m, 2H, ArH).

$^{13}$C-NMR (CD$_3$OD, δ): 24.5, 26.3, 47.2, 48.0, 63.5, 64.4, 67.3, 72.6, 126.7, 130.2, 131.5, 132.3, 143.3, 160.7, 163.8.

Preparation of N-((±)-threo-1-hydroxy-3-oxo-1-(pyridin-4-yl)-3-(pyrrolidin-1-yl)propan-2-yl)acetamide hydrochloride Compound 235

To a suspension of (±)-threo-2-amino-3-hydroxy-3-(pyridin-4-yl)-1-(pyrrolidin-1-yl)propan-1-one dihydrochloride Compound 22 (300 mg, 0.89 mmol) in CH$_2$Cl$_2$ (6 mL) was added Et$_3$N (370 μL, 2.67 mmol) and the mixture was stirred for 10 min, cooled at 4° C. and a solution of acetic anhydride (65 mL, 0.89 mmol) in CH$_2$Cl$_2$ was added dropwise for 10 min. The reaction mixture was brought to room temperature, stirred for 16 h and washed with water (3×4 mL), NaOH (0.5 N) (3×4 mL) evaporated to give an oily residue that was purified using column chromatography (SiO$_2$) with a gradient of 0% to 20% MeOH in EtOAc. The product in MeOH at 4° C. was treated with a solution of 1 N HCl (4 mL) and all the volatiles were evaporated. Product was precipitated using a mixture of methanol in EtOAc to obtain after evaporation N-((±)-threo-1-hydroxy-3-oxo-1-(pyridin-4-yl)-3-(pyrrolidin-1-yl)propan-2-yl)acetamide hydrochloride Compound 235 (209 mg, 52% yield).

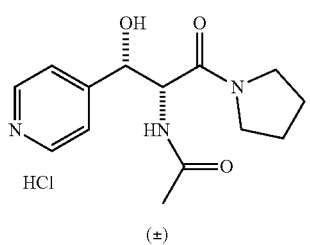

Compound 235

MW: 313.78; Yield: 52%; White Solid; Mp (° C.): 181.3

R$_f$: 0.20 (MeOH:EtOAc=20:80, free base).

$^1$H-NMR (CD$_3$OD, δ): 1.82-2.05 (m, 7H, 2×CH$_2$ & CH$_3$), 3.35-3.45 (m, 2H, CH$_2$), 3.50-3.65 (m, 2H, CH$_2$), 5.10 (d, 1H, J=3.8 Hz, N—CH), 5.39 (d, 1H, J=3.9 Hz, O—CH), 8.16 (d, 2H, J=6.2 Hz, ArH), 8.81 (d, 2H, J=6.7 Hz, ArH).

$^{13}$C-NMR (CD$_3$OD, δ): 22.1, 25.0, 27.0, 47.5, 48.2, 57.0, 72.0, 126.6 (2×C), 142.0 (2C), 142.0 (2×C), 164.4, 169.0, 173.0.

Preparation of (R)-2-amino-3-(pyridin-4-yl)-1-(pyrrolidin-1-yl)propan-1-one dihydrochloride Compound 236 tert-Butyl(R)-1-oxo-3-(pyridin-4-yl)-1-(pyrrolidin-1-yl)propan-2-ylcarbamate EBE 06172.

N-Boc-(S)-3-(pyridin-4-yl)alanine (0.500 g, 1.88 mmol) was dissolved in CH$_2$Cl$_2$ (15 mL) and DIEA (361 μL, 2.07 mmol) was added. The mixture was cooled to 0° C. and isobutyl chloroformate (270 μL, 2.07 mmol) was added. The mixture was stirred for 10 min and pyrrolidine (267 mg, 3.76 mmol) in CH$_2$Cl$_2$ (5 mL) was added. This mixture was stirred for 15 min at 4° C., 12 h at 25° C., washed successively with NaH$_2$PO$_4$, saturated sodium hydrogen carbonate, water and brine. The organic layer was dried over magnesium sulfate and evaporated to dryness. The residue obtained was purify by column chromatography (SiO$_2$) using a gradient of MeOH 0-10% [v/v] in EtOAc to give tert-butyl(R)-1-oxo-3-(pyridin-4-yl)-1-(pyrrolidin-1-yl)propan-2-ylcarbamate EBE 06172 (146 mg, 24% yield) as a white solid.

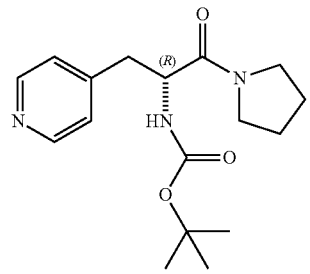

EBE 06172

MW: 319.4; Yield: 24%; White Solid; Mp (° C.): 52.5.

R$_f$: 0.30 (MeOH:EtOAc=20:80).

$^1$H-NMR (CDCl$_3$, δ): 1.40 (s, 9H, (CH$_3$)$_3$), 1.65-1.90 (m, 4H, CH$_2$), 2.80-2.90 (m, 1H, CH), 2.90-3.00 (m, 2H, CH$_2$), 3.28-3.38 (m, 1H, N—CH), 3.40-3.50 (m, 2H, N—CH$_2$), 4.60-4.70 (m, 1H, N—CH), 5.38-5.48 (m, 1H, NH), 7.16 (d, 2H, J=4.5 Hz, ArH), 8.50 (d, 2H, J=4.5 Hz, ArH).

MS-ESI m/z (% rel. Int.): 320.2 ([MH]$^+$, 20).

HPLC: Method A, detection at 254 nm, EBE 06172 RT=3.82 min, peak area 85%.

(R)-2-Amino-3-(pyridin-4-yl)-1-(pyrrolidin-1-yl)propan-1-one dihydrochloride Compound 236

To a solution of TFA (2 mL) in CH$_2$Cl$_2$ (8 mL) was added (R)-1-oxo-3-(pyridin-4-yl)-1-(pyrrolidin-1-yl)propan-2-ylcarbamate EBE 06172 (146 mg, 0.654 mmol) and the mixture was stirred for 2 h at 25° C. The volatiles were evaporated and the product was treated with a suspension on amberlite-400 (OH$^-$ form, 2 g) in MeOH. The suspension was filtered and washed with MeOH (3×5 mL). The combined methanol fractions were evaporated under reduced pressure and the desired product was isolated using column chromatography (SiO$_2$) with a mixture of EtOAc:MeOH:NH$_4$OH=70:30:4 to give an oily residue that was treated with a solution of 0.1 N HCl in iPrOH for 10 min. Evaporation of the volatile afforded (R)-2-amino-3-(pyridin-4-yl)-1-(pyrrolidin-1-yl)propan-1-one dihydrochloride Compound 236 (78 mg, 47% yield) as a pale yellow solid.

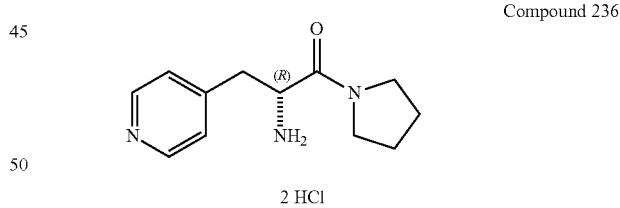

Compound 236

MW: 255.75; Yield: 47%; Pale Yellow Solid; Mp (° C.): 127.5

R$_f$: 0.30 (EtOAc:MeOH:NH$_4$OH=70:30:4, free base).

$^1$H-NMR (CD$_3$OD, δ): 1.80-2.05 (m, 4H, CH$_2$), 3.28-3.80 (m, 6H, CH$_2$, N—CH$_2$), 3.70 (t, 1H, J=6.7 Hz, CH—N), 8.10 (d, 2H, J=5.9 Hz, ArH), 8.88 (d, 2H, J=5.6 Hz, ArH).

$^{13}$C-NMR (CD$_3$OD, δ): 23.4, 25.4, 35.6, 46.1, 46.5, 51.1, 128.5 (2×C), 146.3 (2×C), 156.1, 165.0.

Preparation of tert-butyl 5-((±)-threo-1-hydroxy-3-oxo-1-(pyridin-4-yl)-3-(pyrrolidin-1-yl)propan-2-ylcarbamoyl)pentylcarbamate Compound 237

To a solution of N-Boc-aminohexanoic acid (342 mg, 1.48 mmol) in THF (10 mL) was added N-methylmorpholine (163

μL, 1.48 mmol). The solution was stirred for 5 min, cooled at −15° C. and treated dropwise with isobutyl chloroformate (211 μL, 1.48 mmol). This solution was added via a stainless steal cannula to a solution of (±)-threo-2-amino-3-hydroxy-3-(pyridin-4-yl)-1-(pyrrolidin-1-yl)propan-1-one dihydrochloride Compound 22 (500 mg, 1.48 mmol) and N-methylmorpholine (489 mg, 1.47 mmol) in THF (10 mL) at −15° C. The reaction mixture was kept for 0.5 h at −15° C. followed by 2 h at 25° C. with continuous stirring. After evaporation of the solvent, the residue was partitioned between EtOAc and H$_2$O, washed with NaH$_2$PO$_4$, saturated aqueous NaHCO$_3$, dried over sodium sulfate and purified by column chromatography (SiO$_2$) with a gradient of 0% to 10% [v/v] MeOH in EtOAc to give tert-butyl 5-((±)-threo-1-hydroxy-3-oxo-1-(pyridin-4-yl)-3-(pyrrolidin-1-yl)propan-2-ylcarbamoyl)pentylcarbamate Compound 237 (455 mg, 69% yield) as a white solid.

Compound 237

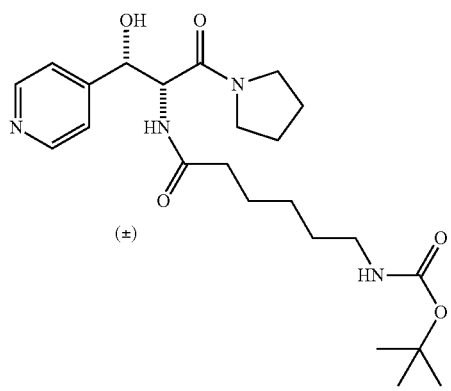

MW: 448.6; Yield: 69%; White Solid.
R$_f$:0.20 (EtOAc:MeOH=90:10).
$^1$H-NMR (CD$_3$OD, δ): 1.05-1.15 (m, 2H, CH$_2$), 1.35-1.55 (m, 13H, 2×CH$_2$+C(CH$_3$)$_3$), 1.75-1.95 (m, 4H, 2×CH$_2$), 2.00-2.20 (m, 2H, O═CCH$_2$), 3.05 (q, 2H, J=6.7 Hz, N—CH$_2$), 3.20-3.35 (m, 1H, N—CH), 3.38-3.50 (m, 2H, N—CH$_2$), 3.65-3.75 (m, 1H, N—CH), 4.72 (bs, 1H, NH), 4.98 (dd, 1H, J=8.8 Hz, J=3.6 Hz), 5.08 (d, 1H, J=3.3 Hz, OCH), 5.23 (bs, 1H, OH), 6.50 (d, 1H, J=8.7 Hz, NH), 7.35 (d, 2H, J=6.0 Hz, ArH), 8.58 (d, 2H, J=4.6 Hz, J=1.4 Hz, ArH).
MS-ESI m/z (% rel. Int.): 449.2 ([MH]$^+$, 30), 349.2 (100).
HPLC: Method A, detection at 254 nm, Compound 237 RT=4.03 min, peak area 99.9%.

Preparation of 6-amino-N-((±)-threo-1-hydroxy-3-oxo-1-(pyridin-4-yl)-3-(pyrrolidin-1-yl)propan-2-yl)hexanamide Compound 238

To a solution of tert-butyl 5-((±)-threo-1-hydroxy-3-oxo-1-(pyridin-4-yl)-3-(pyrrolidin-1-yl)propan-2-ylcarbamoyl)pentylcarbamate Compound 237 (81 mg, 0.181 mmol) in CH$_2$Cl$_2$ (8 mL) was added TFA (2 mL) at 0° C. and stirred for 2 h at 0° C. All the volatiles were evaporated to give a residue that was treated with a suspension of Amberlite-400 (OH$^-$) in MeOH. After filtration, the filtrate was evaporated and the product was isolated by column chromatography (SiO$_2$) with CH$_2$Cl$_2$:MeOH:NH$_4$OH=10:5:0.4 to afford 6-amino-N-((±)-threo-1-hydroxy-3-oxo-1-(pyridin-4-yl)-3-(pyrrolidin-1-yl)propan-2-yl)hexanamide Compound 238 (40 mg, 64% yield) as a white solid.

Compound 238

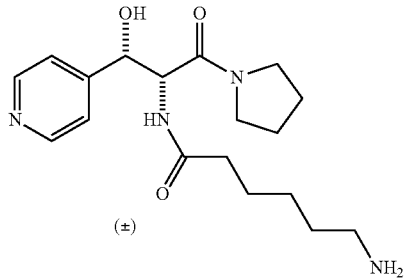

MW: 448.6; Yield: 64%; White Solid; Mp (° C.): 134.4
R$_f$:0.30 (CH$_2$Cl$_2$:MeOH:NH$_4$OH=10:5:0.4).
$^1$H NMR (CDCl$_3$, δ): 1.12-1.30 (m, 2H, CH$_2$), 1.30-1.50 (m, 2H, CH$_2$), 1.50-1.65 (m, 2H, CH$_2$), 1.65-1.95 (m, 4H, CH$_2$), 2.10-2.30 (m, 2H, CH$_2$), 2.55-2.70 (t, 2H, J=6.9 Hz, CH$_2$), 3.10-3.20 (m, 2H, CH$_2$), 3.28-3.50 (m, 2H, CH$_2$), 3.60-3.70 (m, 1H, CH), 4.95 (dd, 1H, J=5.1 Hz, J=8.4 Hz, O—CH), 5.02 (d, 1H, J=5.0 Hz, OH), 7.11 Hz (d, J=8.48 Hz, 1H, ArH), 7.35 (dd, 2H, J=4.4 Hz, J=1.5 Hz, ArH), 8.55 (dd, J=1.5 Hz, J=4.6 Hz, 2H, ArH).
$^{13}$C NMR (CDCl$_3$, δ): 24.0, 25.1, 25.8, 25.9, 32.5, 35.8, 41.7, 46.0, 46.9, 55.6, 72.6, 121.3 (2×C), 149.2, 149.5 (2×C), 168.9, 173.7.

Preparation of (±)-erythro-2-amino-3-hydroxy-3-(pyridin-4-yl)-1-(pyrrolidin-1-yl)butan-1-one dihydrochloride Compound 239

(±)-cis-(5-Methyl-5-pyridin-4-yl-4,5-dihydro-oxazol-4-yl)-pyrrolidin-1-yl-methanone EBE 06180

To a stirred solution of KOH (223 mg, 39.7 mmol) in MeOH was added 4-acetylpyridine (478 mg, 39.7 mmol) and 2-isocyano-1-(pyrrolidin-1-yl)ethanone BLE 04098 (500 mg, 3.2 mmol). The reaction mixture was stirred for 3 h at 0° C. and then concentrated. The residue was partitioned between EtOAc and H$_2$O. The organic layer was washed with brine, dried over MgSO$_4$, filtered and evaporated to give a yellow oil that was purified by column chromatography (SiO$_2$) with 20% [v/v] MeOH in EtOAc to give cis- and trans-(±)-(5-methyl-5-pyridin-4-yl-4,5-dihydro-oxazol-4-yl)-pyrrolidin-1-yl-methanone. The mixture was further purified by column chromatography (SiO$_2$) using a gradient of 2% to 5% [v/v] MeOH [v/v] in CH$_2$Cl$_2$ to obtain the pure cis-(±)-(5-methyl-5-pyridin-4-yl-4,5-dihydro-oxazol-4-yl)-pyrrolidin-1-yl-methanone EBE 06180 (122 mg, 51% yield) as white solid.

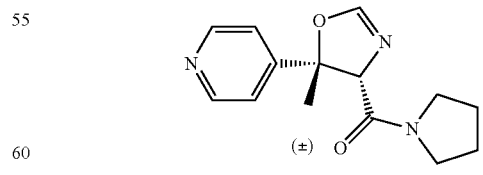

EBE 06180

MW: 259.3; Yield: 51%; White Solid; Mp (° C.): 140.9
R$_f$:0.30 (EtOAc:MeOH=80:20).
$^1$H-NMR (CDCl$_3$, δ): 1.45-1.75 (m, 4H, 2×CH$_2$), 1.81 (s, 3H, CH$_3$), 2.75-2.90 (m, 1H, N—CH$_2$), 3.10-3.22 (m, 1H, N—CH$_2$), 3.30-3.40 (t, 2H, J=6.7 Hz, N—CH$_2$), 4.83 (d, 1H, J=1.7 Hz, NCH), 7.22 (d, 1H, J=1.4 Hz, N=CH), 7.27 (d, 2H, J=6.0 Hz, Ar), 8.57 (d, 2H, J=6.1 Hz, ArH).

$^{13}$C-NMR (CDCl$_3$, δ): 23.6, 26.0, 27.9, 46.0, 46.5, 77.8, 87.2, 120.2, 148.9, 149.6 (2×C), 155.6 (2×C), 165.4.

(±)-erythro-2-Amino-3-hydroxy-3-(pyridin-4-yl)-1-(pyrrolidin-1-yl)butan-1-one dihydrochloride Compound 239

To a solution cis-(±)-(5-methyl-5-pyridin-4-yl-4,5-dihydro-oxazol-4-yl)-pyrrolidin-1-yl-methanone EBE 06180 (50 mg, 0.19 mmol) in MeOH (1 mL) was added a solution of 1 N HCl (1 mL) and the reaction mixture was heated at 60° C. for 2 h. All the volatiles were evaporated to give (±)-erythro-2-amino-3-hydroxy-3-(pyridin-4-yl)-1-(pyrrolidin-1-yl)butan-1-one dihydrochloride Compound 239 (54 mg, 87% yield) as a white solid.

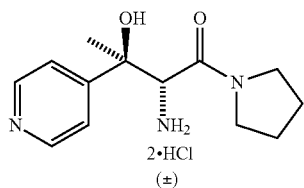

Compound 239

MW: 322.23; Yield: 87%; White Solid; Mp (° C.): 140.9
R$_f$:0.1 (EtOAc:MeOH=80:20, free base).
$^1$H-NMR (CDCl$_3$, δ): 1.85-2.05 (m, 7H, CH$_3$+2×CH$_2$), 3.35-3.65 (m, 4H, 2×N—CH$_2$), 4.61 (s, 1H, O—CH), 8.23 (d, 2H, J=4.5 Hz, ArH), 8.89 (d, 2H, J=4.3 Hz, ArH).

Preparation of (S)-2-amino-3-(pyridin-4-yl)-1-(pyrrolidin-1-yl)propan-1-one dihydrochloride Compound 240 tert-Butyl(S)-1-oxo-3-(pyridin-4-yl)-1-(pyrrolidin-1-yl)propan-2-ylcarbamate EBE 06190

To a solution of N-Boc-(2S)-3-(pyridin-4-yl)alanine (500 mg, 1.9 mmol) in THF (12 mL) was added N-methylmorpholine (200 μL, 1.9 mmol) and the solution was stirred for 5 min, cooled at −15° C. and treated dropwise with isobutyl chloroformate (249 μL, 1.9 mmol). The mixture was stirred for 10 min and pyrrolidine (1.08 g, 15.2 mmol) was added and allowed to warm to 25° C. with stirring for 3 h. The solvent were removed under reduced pressure and the residue was partitioned between EtOAc and NaH$_2$PO$_4$ pH=7.2. The aqueous layer was discarded and the organic layer was washed with aqueous saturated NaHCO$_3$, dried over Na$_2$SO$_4$, filtered and evaporated. The resulting solid was purified by column chromatography (SiO$_2$) with a gradient of 0% to 10% [v/v] MeOH in EtOAc to give tert-butyl(S)-1-oxo-3-(pyridin-4-yl)-1-(pyrrolidin-1-yl)propan-2-ylcarbamate EBE 06190 (167 mg, 28% yield) as a white solid.

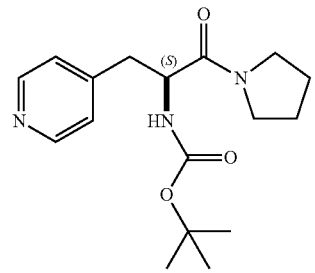

EBE 06190

MW: 319.4; Yield: 28%; White Solid; Mp (° C.): 130.0
R$_f$:0.30 (EtOAc:MeOH=90:10).
$^1$H-NMR (CDCl$_3$, δ): 1.40 (s, 9H, C(CH$_3$)$_3$), 1.65-1.90 (m, 4H, CH$_2$), 2.80-2.95 (m, 1H, CH), 2.95-3.05 (m, 2H, CH$_2$), 3.30-3.45 (m, 1H, NCH), 3.45-3.55 (m, 2H, N—CH$_2$), 4.60-4.75 (m, 1H, N—CH), 5.42 (d, 1H, J=8.8 Hz, NH), 7.16 (dd, 2H, J=4.5 Hz, J=1.5 Hz, ArH), 8.51 (dd, 2H, J=1.5 Hz, J=4.5 Hz, ArH).
$^{13}$C-NMR (CDCl$_3$, δ): 24.1, 25.8, 28.3 (3×C), 39.1, 45.8, 46.5, 52.6, 79.9, 124.8 (2×C), 145.7, 149.8 (2×C), 155.0, 169.2.

(S)-2-Amino-3-(pyridin-4-yl)-1-(pyrrolidin-1-yl)propan-1-one dihydrochloride Compound 240

To a solution of tert-butyl(S)-1-oxo-3-(pyridin-4-yl)-1-(pyrrolidin-1-yl)propan-2-ylcarbamate EBE 06190 (100 mg, 0.313 mmol) in CH$_2$Cl$_2$ (3 mL) at 4° C. was added TFA (479 μL, 6.26 mmol) and MeOH (0.3 mL) and the reaction was stirred for 2 h. All the volatiles were evaporated to give a product that was treated with a suspension of amberlite-400 (OH$^−$ form, 5 g) in MeOH. The suspension was filtered and washed with MeOH (5×5 mL). The combined methanol fractions were evaporated under reduced pressure and the desired product was isolated by column chromatography (SiO$_2$) with a gradient of 0% to 30% [v/v] MeOH in EtOAc to give (5)-2-amino-3-(pyridin-4-yl)-1-(pyrrolidin-1-yl)propan-1-one. The product was dissolved in MeOH, cooled at 5° C. and a solution of HCl (0.1 N) (9 mL) was added dropwise. All the volatiles were evaporated to give (5)-2-amino-3-(pyridin-4-yl)-1-(pyrrolidin-1-yl)propan-1-one dihydrochloride Compound 240 (91 mg, 99% yield) as a white solid.

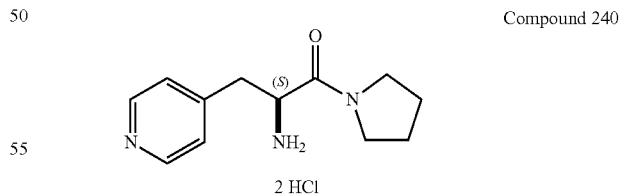

Compound 240

MW: 292.21; Yield: 99%; White Solid; Mp (° C.): 195.9
R$_f$:0.10 (EtOAc:MeOH=90:10, free base).
$^1$H-NMR (CD$_3$OD, δ): 1.80-2.05 (m, 4H, CH$_2$), 3.30-3.40 (m, 5H, N—CH$_2$+N—CH), 3.60-3.75 (m, 1H, CH), 4.72 (t, 1H, J=7.3 Hz, CH), 8.08 (d, 2H, J=5.4 Hz, ArH), 8.87 (d, 2H, J=5.3 Hz, ArH).
$^{13}$C-NMR (CD$_3$OD, δ): 25.0, 26.9, 37.2, 47.6, 48.0, 57.2, 130.0 (2×C), 143.1 (2×C), 157.3, 166.6.
MS-ESI m/z (% rel. Int.): 220.1 ([MH]$^+$, 10), 203.1 (50).

Preparation of (±)-threo-2-amino-3-(6-(trifluoromethyl)pyridin-3-yl)-3-hydroxy-1-(pyrrolidin-1-yl)propan-1-one dihydrochloride Compound 241

(±)-trans-(5-(6-(Trifluoromethyl)pyridin-3-yl)-4,5-dihydrooxazol-4-yl)(pyrrolidin-1-yl)methanone EBE 06196

To a solution of KOH (184 mg, 3.28 mmol) in MeOH (10 mL) at 4° C. was added 6-(trifluoromethyl)pyridine-3-carbaldehyde (575 mg, 3.28 mmol) and 2-isocyano-1-(pyrrolidin-1-yl)ethanone BLE 04098 (500 mg, 3.28 mmol). The mixture was stirred for 2 h at 4° C. and allowed to warm to 25° C.

All the volatiles were evaporated and the resulting product was partitioned between brine and EtOAc. The organic layer was separated, dried over Na₂SO₄, filtered to give after evaporation of the solvent (±)-trans-(5-(6-(trifluoromethyl)pyridin-3-yl)-4,5-dihydrooxazol-4-yl)(pyrrolidin-1-yl)methanone EBE 06196 (801 mg, 78% yield) as a pale brown solid.

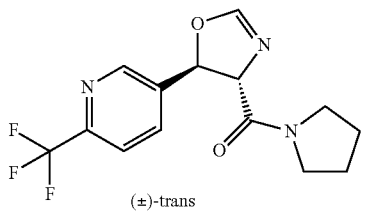

EBE 06196

MW: 310.13; Yield: 78%; Pale brown solid.

$^1$H-NMR (CDCl$_3$, δ): 1.75-2.10 (m, 4H, 2×CH$_2$), 3.40-3.60 (m, 3H, 2×N—CH$_2$), 3.90-4.00 (m, 1H, N—CH), 4.57 (dd, 1H, J=8.0 Hz, J=2.2 Hz, N—CH), 6.31 (d, 1H, J=8.0 Hz, O—CH), 7.06 (d, 1H, J=2.2 Hz, N=CH), 7.71 (d, 1H, J=8.1 Hz, ArH), 7.84 (dd, 1H, J=1.8 Hz, J=8.1 Hz, ArH), 8.70 (d, 1H, J=1.5 Hz, ArH).

(±)-threo-2-Amino-3-(6-(trifluoromethyl)pyridin-3-yl)-3-hydroxy-1-(pyrrolidin-1-yl)propan-1-one dihydrochloride Compound 241

To a solution of (±)-trans-(5-(6-(trifluoromethyl)pyridin-3-yl)-4,5-dihydrooxazol-4-yl)(pyrrolidin-1-yl)methanone EBE 06196 (400 mg, 1.28 mmol) in MeOH (2 mL) was added HCl (37%) (10 mL) and the mixture was heated at 60° C. for 2 h with continuous stirring. After evaporation the resulting white solid was treated with a suspension of amberlite-400 (OH⁻ form) in MeOH. The suspension was filtered and washed with MeOH (5×5 mL). The combined methanol fraction were evaporated under reduced pressure and the desired product was isolated by column chromatography (SiO$_2$) with a gradient of 0% to 8% [v/v] MeOH in EtOAc to obtain (±)-threo-2-amino-3-(6-(trifluoromethyl)pyridin-3-yl)-3-hydroxy-1-(pyrrolidin-1-yl)propan-1-one (287 mg). To a solution (±)-threo-2-amino-3-(6-(trifluoromethyl)pyridin-3-yl)-3-hydroxy-1-(pyrrolidin-1-yl)propan-1-one (209 mg, 0.69 mmol) in MeOH (2 mL) at 4° C. and treated HCl 37% (10 mL). All the volatiles were evaporated to give (±)-threo-2-amino-3-(6-(trifluoromethyl)pyridin-3-yl)-3-hydroxy-1-(pyrrolidin-1-yl)propan-1-one dihydrochloride Compound 241 as a white solid (269 mg, 74% yield).

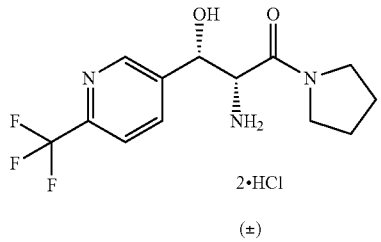

Compound 241

MW: 376.2; Yield: 74%; White Solid; Mp (° C.): 190.0.

R$_f$:0.3 (EtOAc:MeOH=92:8, free base).

$^1$H-NMR (CD$_3$OD, δ): 1.40-1.70 (m, 2H, CH$_2$), 1.70-1.90 (m, 2H, CH$_2$), 2.35-2.50 (m, 1H, N—CH), 3.15-3.35 (m, 1H, N—CH$_2$), 3.35-3.45 (m, 2H, N—CH$_2$), 4.32 (d, 1H, J=8.3 Hz, N—CH), 5.11 (d, 1H, J=8.2 Hz, O—CH), 7.88 (d, 1H, J=8.3 Hz, ArH), 8.16 (d, 1H, J=8.0 Hz, ArH), 8.73 (s, 1H, ArH).

$^{13}$C-NMR (CD$_3$OD, δ): 24.8, 26.6, 47.4, 47.9, 58.7, 71.3, 121.7, 122.9 (d, 1C, J=273.2 Hz, CF$_3$), 137.9, 140.3, 149.0, 149.7, 165.8.

Preparation of (±)-threo-2-amino-3-hydroxy-1-(thiazolidin-3-yl)-3-(pyridin-4-yl)propan-1-one dihydrochloride Compound 242

(±)-threo-2-Amino-3-hydroxy-3-(pyridin-4-yl)propanoic acid dihydrochloride EBE 10038B To a stirred solution of KOH (2.57 g, 35.4 mmol) in MeOH (35 mL) at 0° C. was added 4-pyridinecarboxaldehyde (3.80 g, 35.4 mmol) and tert-butylisocyano acetate (5 g, 35.4 mmol). The solution was stirred for 3 h at 0° C. and concentrated to obtain intermediate trans-4,5-dihydro-5-(pyridin-4-yl)oxazole-4-carboxylate as a pale yellow solid EBE 10038A.

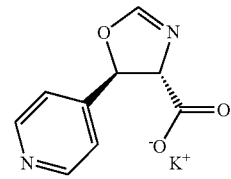

EBE 10038A $^1$H NMR (CD$_3$OD, δ): 4.29 (dd, 1H, J=1.7 Hz, J=7.6 Hz, N—CH), 5.67 (d, 1H, J=7.6 Hz, O—CH), 7.29 (d, 1H, J=1.9 Hz, N=CH), 7.46 (d, 2H, J=4.7 Hz, ArH), 8.55 (dd, 2H, J=1.7 Hz, J=4.4 Hz, ArH).

The solid EBE 10038A was dissolved in MeOH (100 mL), stirred 5 min at 0° C. and treated with HCl (12 N) (10.5 mL). The reaction was heated at 60° C. for 2 h, cooled down to 4° C. to form a precipitate that was filtered. The filtrate was evaporated and dried to obtain (±)-threo-2-amino-3-hydroxy-3-(pyridin-4-yl)propanoic acid dihydrochloride EBE 10038B with 20% of (±)-erythro isomer (9 g, 99% crude yield) as a pale beige solid.

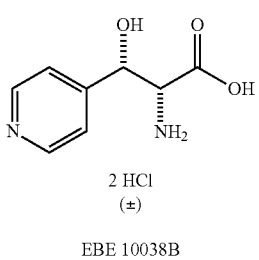 [SMILES: N[C@@H](C(=O)O)[C@@H](O)c1ccncc1]

EBE 10038B

MW: 255.10; Yield: 99%; Pale Beige Solid.

$^1$H-NMR (CD$_3$OD, δ): 3.94 (d, 1H, J=3.9 Hz, N—CH), 4.61 (t, 1H, J=3.0 Hz, O—CH), 8.31 (d, 2H, ArH), 8.95 (m, 2H, ArH). Only the formula and the $^1$H-NMR description of major threo isomer is shown.

MS-ESI m/z (% rel. Int.): 183.1 ([MH]$^+$, 5).

(±)-threo-N-Boc-2-amino-3-(pyridin-4-yl)-3-hydroxy-propionic acid EBE 10040

A solution of di-tert-butyldicarbonate (9.28 g, 42.5 mmol) in dioxane (40 mL) was added to a pre-mixed ice cold solution of (±)-threo-2-amino-3-hydroxy-3-(pyridin-4-yl)propanoic acid dihydrochloride EBE 10038B (9.01 g, 35.4 mmol) in a solution of 1 N NaOH (145 mL). The biphasic mixture was stirred at 5° C. for 30 min and allowed to warm to room temperature for 3.5 h, concentrated, cooled in an ice bath, acidified to pH 4-5 and extracted with n-butanol. The combined extracts were dried over Na$_2$SO$_4$ and filtered to give (±)-threo-N-Boc-2-amino-3-(pyridin-4-yl)-3-hydroxy-propionic acid EBE 10040 (3.34 g, 33% yield) as a pale yellow solid.

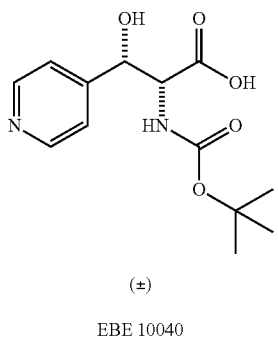 [SMILES: CC(C)(C)OC(=O)N[C@@H](C(=O)O)[C@@H](O)c1ccncc1]

EBE 10040

MW: 282.2; Yield: 33%; Pale Yellow Solid.

$^1$H-NMR (DMSO-d$_6$, δ): 1.24 (s, 9H, C(CH$_3$)$_3$), 4.32 (d, 1H, J=9.4 Hz, N—CH), 5.13 (s, 1H, O—CH), 6.35 (d, 1H, J=9.4 Hz, NH), 7.37 (d, 2H, J=3.8 Hz, ArH), 8.48 (d, 2H, J=3.6 Hz), 20H not seen.

$^{13}$C-NMR (DMSO-d$_6$, δ): 27.9 (3×C), 59.0, 71.3, 78.2, 121.4, 122.8, 148.9, 150.3, 151.0, 155.2, 171.6.

MS-ESI m/z (% rel. Int.): 283.2 ([MH]$^+$, 10).

HPLC: Method A, detection at 254 nm, EBE 10040 RT=3.17 min, peak area 95.9%.

tert-butyl(±)-threo-1-hydroxy-3-oxo-1-(pyridin-4-yl)-3-(thiazolidin-3-yl)propan-2-ylcarbamate EBE 10042

To a solution of (±)-threo-N-Boc-2-amino-3-(pyridin-4-yl)-3-hydroxy-propionic acid EBE 10040 (500 mg, 1.77 mmol) in CH$_2$Cl$_2$ (10 mL) at 0° C. was added triethylamine (253 μL, 3.54 mmol), hydroxybenzotriazole (239 mg, 1.77 mmol), 1-(3-dimethylaminopropyl)-3-ethylcarbo-diimide hydrochloride (EDCI) (340 mg, 1.77 mmol) and thiazolidine (140 μL, 1.77 mmol). The reaction mixture was stirred for 2 h at 0° C., allowed to warm to room temperature, stirred for 16 h and diluted in CH$_2$Cl$_2$ (90 mL). The mixture was washed with brine (3×10 mL), 1 N NaOH (3×10 mL), dried over Na$_2$SO$_4$, filtered to give a crude oil that was purified using column chromatography (SiO$_2$) with a gradient of 3% to 4% MeOH in CH$_2$Cl$_2$. After evaporation tert-butyl(±)-threo-1-hydroxy-3-oxo-1-(pyridin-4-yl)-3-(thiazolidin-3-yl)propan-2-ylcarbamate EBE 10042 (200 mg, 32% yield) was obtained as a yellow oil.

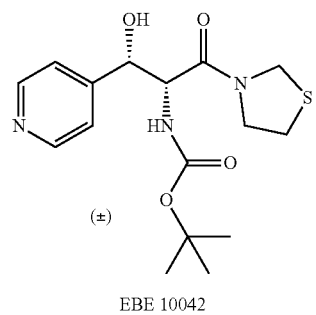 [SMILES: CC(C)(C)OC(=O)N[C@@H](C(=O)N1CCSC1)[C@@H](O)c1ccncc1]

EBE 10042

MW: 353.4; Yield: 32%; Yellow Oil.

R$_f$:0.2 (CH$_2$Cl$_2$:MeOH=97:3).

$^1$H-NMR (CDCl$_3$, δ): 1.29 (s, 9H, (CH$_3$)$_3$), 2.90-3.05 (m, 2H, S—CH$_2$), 3.60-3.95 (m, 2H, N—CH$_2$), 4.40-4.72 (m, 3H, N—CH+S—CH$_2$—N), 5.10-5.15 (m, 1H, OCH), 5.68 (m, 1H, NH), 7.34 (d, 2H, J=6.0 Hz, ArH), 8.53 (d, 2H, J=6.0 Hz, ArH), OH not seen.

$^{13}$C-NMR (CDCl$_3$, δ), minor rotamer in parenthesis: 28.1 (29.2) [3×C], 31.1, (48.5) 48.7, 49.0 (49.1), (56.4) 56.7, 72.3, 80.5, 121.4 [2×C], 148.7, 149.4 [2×C], 155.5, (169.0) 169.2.

MS-ESI m/z (% rel. Int.): 354.2 ([MH]$^+$, 20).

HPLC: Method A, detection at 254 nm, EBE 10042 RT=3.87 min, peak area 98.1%.

(±)-threo-2-Amino-3-hydroxy-1-(thiazolidin-3-yl)-3-(pyridin-4-yl)propan-1-one dihydrochloride Compound 242

To a solution of tert-butyl(±)-threo-1-hydroxy-3-oxo-1-(pyridin-4-yl)-3-(thiazolidin-3-yl)propan-2-ylcarbamate EBE 10042 (150 mg, 424 mg) in MeOH (10 mL) at 4° C. was added a solution of 1 N HCl in MeOH (12 mL). The reaction mixture was allowed to warm at room temperature and stirred for 1 h. All the volatiles were evaporated to give an oily residue that was dissolved in MeOH and treated with EtOAc to form a precipitate. The volatiles were evaporated to give (±)-threo-2-amino-3-hydroxy-1-(thiazolidin-3-yl)-3-(pyridin-4-yl)propan-1-one dihydrochloride Compound 242 (135 mg, 98% yield) as a pale yellow solid.

Compound 242

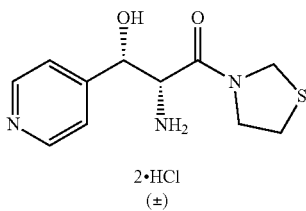

MW: 326.24; Yield: 98%; Pale Yellow solid; Mp (° C.): 210.6

$^1$H-NMR (CDCl$_3$, δ): 2.90-3.15 (m, 2H, S—CH$_2$), 3.55-3.90 (m, 1H, N—CH), 4.00-4.15 (m, 1H, N—CH), 4.18-4.53 (m, 1H, N—CH), 4.62-4.78 (m, 2H, N—CH$_2$—S), 5.38-5.49 (m, 1H, O—CH), 8.25 (d, 2H, J=5.7 Hz, 2H, ArH), 8.94 (d, 2H, J=5.7 Hz, ArH).

$^{13}$C-NMR (CDCl$_3$, δ), minor rotamer in parenthesis: (29.9) 31.8, 34.8, (51.1) 52.1, (57.8) 58.2, 71.0 (71.3), 126.8 [2×C], 143.2 [2×C], 161.4, (164.8) 165.2.

MS-ESI m/z (% rel. Int.): 254.2 ([MH]$^+$, 15).

Preparation of (±)-threo-2-amino-3-hydroxy-1-(indolin-1-yl)-3-(pyridin-4-yl)propan-1-one dihydrochloride Compound 243

To a solution of potassium trans-4,5-dihydro-5-(pyridin-4-yl)oxazole-4-carboxylate EBE 10038A (500 mg, 2.60 mmol) in CH$_2$Cl$_2$ (13 mL) were added HOBT (352 mg, 2.60 mmol), EDCI (499 mg, 2.60 mmol) and indoline (292 mL, 2.60 mmol). The reaction mixture was stirred 2 h at 0° C., allowed to warm to RT and stirred for 16 h. The reaction mixture was diluted in CH$_2$Cl$_2$ (100 mL), wash with brine (3×25 mL), NaOH 1N (3×25 mL), dried over MgSO$_4$, filtered to give after evaporation trans-(4,5-dihydro-5-(pyridin-4-yl)oxazol-4-yl)(1H-indol-1-yl)methanone SLA 09182 (533 mg, 70% yield) as a pale brown oil. To a solution of SLA 09182 (533 mg, 2.6 mmol) in MeOH (12 mL) was added a solution of HCl 37% (880 μL). The reaction was stirred for 3 h at 50° C. and concentrated under reduced pressure. The resulting product was dissolved in MeOH and treated with amberlite (OH$^-$ form), filtered to give after evaporation a residue that was purified using silica gel chromatography with a gradient of MeOH 0%-10% in CH$_2$Cl$_2$ to yield (±)-threo-2-amino-3-hydroxy-1-(indolin-1-yl)-3-(pyridin-4-yl)propan-1-one. The hydrochloride salt was formed by treatment with a solution of 1M HCl in MeOH (3.2 mL) to give after evaporation (±)-threo-2-amino-3-hydroxy-1-(indolin-1-yl)-3-(pyridin-4-yl)propan-1-one dihydrochloride Compound 243 (149 mg, 16% yield) as a white solid.

Compound 243

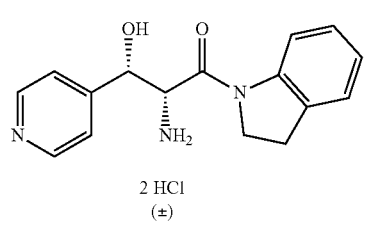

MW: 356.25; Yield: 16%; White Solid; Mp (° C.): 202.5
R$_f$:0.30 (CH$_2$Cl$_2$: MeOH=90:10, free base)

$^1$H-NMR (CD$_3$OD, δ): 3.65-3.80 (m, 1H, N—CH$_2$), 4.15-4.28 (m, 1H, CH$_2$), 3.65-3.80 (m, 1H, CH$_2$), 4.15-4.30 (m, 1H, N—CH$_2$), 4.64 (d, 1H, J=5.4 Hz, N—CH), 5.45 (d, 1H, J=5.3 Hz, O—CH), 6.70 (t, 1H, J=7.4 Hz, ArH), 7.12 (dd, 2H, J=7.7 Hz, ArH), 8.07 (d, 1H, J=7.9 Hz, ArH), 8.15 (d, 2H, J=6.2 Hz, ArH), 8.79 (d, 2H, J=6.2 Hz, ArH).

$^{13}$C-NMR (CD$_3$OD, δ): 28.9, 30.8, 58.4, 71.1, 118.5, 126.1, 126.4, 126.5 (2×C), 128.4, 133.6, 142.9, 143.6 (2×C), 161.0, 164.7.

MS-ESI m/z (% rel. Int.): 284.2 ([MH]$^+$, 10).

Preparation of (±)-threo-2-amino-3-(3,5-dichloropyridin-4-yl)-3-hydroxy-1-(2H-pyrrol-1(5H)-yl)propan-1-one dihydrochloride Compound 245 trans-(5-(3,5-Dichloropyridin-4-yl)-4,5-dihydrooxazol-4-yl)(2H-pyrrol-1(5H)-yl)methanone SLA 09022.

To a stirred and cooled (0° C.) solution of KOH (0.315 g, 5.62 mmol) in methanol (70 mL) was added a mixture of 3,5-dichloropyridine-4-carbaldehyde (0.989 mg, 5.62 mmol) and 2-isocyano-1-(2H-pyrrol-1(5H)-yl)ethanone SLA 07178 (0.696 g, 5.11 mmol). The solution was stirred 2 h with continued cooling and then concentrated. The residue was partitioned between EtOAc (50 mL) and water (50 mL). The organic layer was combined with additional EtOAc extracts (3×50 mL), washed with brine (70 mL) and dried with MgSO$_4$, filtered and evaporated to obtain a crude product which was purified by column chromatography (florisil, EtOAc:cyclohexane=80:20) to obtain after evaporation trans-(5-(3,5-dichloropyridin-4-yl)-4,5-dihydrooxazol-4-yl)(2H-pyrrol-1(5H)-yl)methanone SLA 09022 (1.267 g, 80% yield) as a pale yellow solid.

SLA 09022

MW: 312.15; Yield: 80%; Pale Yellow Solid.
R$_f$:0.15 (EtOAc: cyclohexane=80:20).

$^1$H-NMR (CDCl$_3$, δ): 4.30-4.32 (m, 3H, 1.5×CH$_2$), 4.77-4.83 (m, 1H, 0.5×CH$_2$), 4.86 (dd, 1H, J=2.2 Hz, J=8.8 Hz, CH—N), 5.84-5.88 (m, 2H, CH=CH), 6.86 (d, 1H, J=8.7 Hz, CH—O), 6.96 (d, 1H, J=2.2 Hz, O—CH=N), 8.52 (s, 2H, ArH).

$^{13}$C-NMR (CDCl$_3$, δ): 52.1, 52.6, 59.2, 75.1, 123.9, 124.4, 131.5, 139.5, 147.6, 148.3, 151.0, 153.9, 164.3.

(±)-threo-2-Amino-3-(3,5-dichloropyridin-4-yl)-3-hydroxy-1-(2H-pyrrol-1(5H)-yl)propan-1-one dihydrochloride Compound 245

To a stirred solution of trans-(5-(3,5-dichloropyridin-4-yl)-4,5-dihydrooxazol-4-yl)(2H-pyrrol-1(5H)-yl)methanone SLA 09022 (1.26 g, 4.04 mmol) in methanol (20 mL) was added HCl 37% (1.5 mL). The reaction mixture was stirred for 3 h at RT, concentrated and the resulting yellow oil was co evaporated twice with EtOAc and triturated with EtOAc to obtain after filtration and drying under vacuum (±)-threo-2-amino-3-(3,5-dichloropyridin-4-yl)-3-hydroxy-1-(2H-pyrrol-1(5H)-yl)propan-1-one dihydrochloride (1.13 g, 75% yield) as a pale yellow solid.

Compound 245

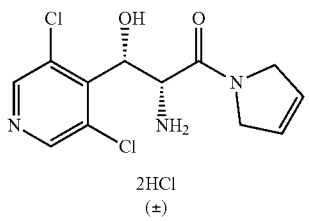

MW: 375.16; Yield: 75%; Pale yellow solid; Mp (° C.): 176.5
$R_f$: 0.15 (CH$_2$Cl$_2$: MeOH=90:10, free base).
$^1$H-NMR (CD$_3$OD, δ): 3.30-3.32 (m, 1H, 0.5×CH$_2$), 3.90-3.97 (m, 1H, 0.5×CH$_2$), 4.25-4.37 (m, 2H, CH$_2$), 4.76 (d, 1H, J=10.3 Hz, N—CH), 5.60-5.65 (m, 1H, =CH), 5.70 (d, 1H, J=10.3 Hz, O—CH) 5.78-5.82 (m, 1H, =CH), 8.57 (s, 2H, ArH).
$^{13}$C-NMR (CD$_3$OD, δ): 56.6, 56.7, 57.3, 72.4, 128.0, 128.9, 136.3 (2C), 145.8, 152.5 (2C), 168.1.

Preparation of N-(1-oxo-3-(pyridin-4-yl)-1-(pyrrolidin-1-yl)prop-2-en-2-yl)formamide hydrochloride (cis: trans isomers mixture) Compound 246

To a stirred solution of triphenylphosphine (200 mg, 0.76 mmol) in 5 mL of CH$_3$CN were added at 20° C. diethylazodicarbonate (120 µl, 0.76 mmol), Et$_3$N (55 µl, 0.38 mmol) and N-((±)-threo-1-hydroxy-3-oxo-1-(pyridin-4-yl)-3-(pyrrolidin-1-yl)propan-2-yl)formamide hydrochloride Compound 216 (115 mg, 0.38 mmol). The mixture was stirred 2 h at 70° C. then solvent was evaporated. The obtained residue was purified by column chromatography (SiO$_2$, EtOAc: MeOH=9:1) to give N-(1-oxo-3-(pyridin-4-yl)-1-(pyrrolidin-1-yl)prop-2-en-2-yl)formamide TTA 08074A (80 mg, 43% yield). HCl treatment in EtOAc with HCl 0.4 N in diethyl ether (1 mL, 0.4 mmol) gave after evaporation and drying N-(1-oxo-3-(pyridin-4-yl)-1-(pyrrolidin-1-yl)prop-2-en-2-yl)formamide hydrochloride (trans:cis isomers mixture) Compound 246 (60 mg, 28% yield) as a pale yellow pasty product.

Compound 246

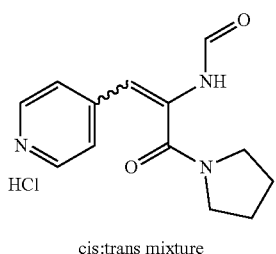

cis:trans mixture

MW: 281.74; Yield: 28%; Pale Yellow Pasty Product.
$R_f$:0.24 (EtOAc:MeOH=9:1).
$^1$H-NMR (CD$_3$OD, δ): 1.80-2.05 (bs, 4H, 2×CH$_2$), 3.25-3.45 (bs, 2H, CH$_2$—N), 3.55-3.70 (bs, 2H, CH$_2$—N), 6.87 (s, 1H, CH), 7.82 (d, 2H, J=5.0 Hz, ArH), 8.31 (s, 1H, HC=O), 8.65 (d, 2H, J=5.0 Hz, ArH).
$^{13}$C-NMR (CD$_3$OD, δ): 25.1, 26.5, 47.1, 48.9, 109.0, 125.6 (2×C), 127.7, 142.2 (2×C), 142.6, 154.9, 161.6.
MS-ESI m/z (% rel. Int.): 246.1 ([MH]$^+$, 5), 175.1 (100).
HPLC: Method A, detection UV 254 nm, Compound 246 RT=1.90 min, peak area 95.0%.

Preparation of (2S,3R)- & (2R,3S)-2-amino-1-((R)-3-hydroxypyrrolidin-1-yl)-3-hydroxy-3-(pyridin-4-yl)propan-1-one dihydrochlorides Compound 247

1-((R)-3-hydroxypyrrolidin-1-yl)-2-isocyanoethanone VIB 01172

To stirred and cooled (0° C.) methyl isocyanoacetate (96% technical grade, 1.7 g, 17.21 mmol) was slowly added (R)-(+)-3-pyrrolidinol (1.5 g, 17.21 mmol) and MeOH (5 mL). The mixture was stirred for 3 h at RT and concentrated. Brine was added (30 mL) and the mixture was extracted with EtOAc (3×50 mL), dried over MgSO$_4$, filtered and evaporated to obtained crude 1-((R)-3-hydroxypyrrolidin-1-yl)-2-isocyanoethanone VIB 01172 (1.3 g, 49% yield) as a yellow solid.

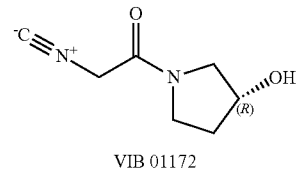

VIB 01172

MW: 154.17; Yield: 49%; Yellow Solid; Mp (° C.)=55.9
$^1$H-NMR (CDCl$_3$, δ): 1.95-2.20 (m, 2H, CH$_2$), 2.60-2.82 (m, 1H, OH), 3.30-3.68 (m, 4H, 2×CH$_2$), 4.20-4.36 (m, 2H, CH$_2$), 4.49-4.65 (m, 1H, CH—O).
MS-ESI m/z (% rel. Int.): 155.1 ([MH]$^+$, 90).

trans-((R)-3-hydroxypyrrolidin-1-yl)((4S,5R)- & (4R,5S)-4,5-dihydro-5-(pyridin-4-yl)oxazol-4-yl) methanones VIB 01174

To a stirred and cooled (0° C.) solution of KOH (0.40 g, 7.13 mmol) in MeOH (8 mL) were added successively pyridine-4-carbaldehyde (0.84 g, 7.84 mmol) and 1-((R)-3-hydroxypyrrolidin-1-yl)-2-isocyanoethanone VIB 01172 (1.10 g, 7.13 mmol). The mixture was stirred at 0° C. to RT for 24 h. After evaporation of MeOH, the mixture was partitioned between EtOAc (50 mL) and H$_2$O (10 mL). The aqueous layer was further extracted with EtOAc (2×50 mL). The EtOAc fractions were combined, washed twice with brine (2×10 mL), dried over MgSO$_4$, filtered and evaporated. After evaporation and drying trans-((R)-3-hydroxypyrrolidin-1-yl)((4S,5R)- & (4R,5S)-4,5-dihydro-5-(pyridin-4-yl)oxazol-4-yl)methanones VIB 01174 (490 mg, diastereoisomeric mixture in ratio 1:1, 26% yield) were obtained as a crude pale yellow solid.

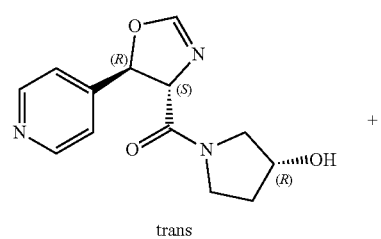

trans

-continued

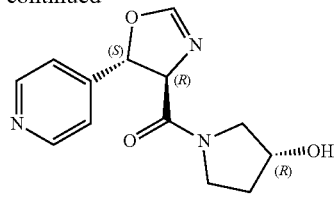

trans
VIB 01174

MW: 261.28; Yield: 26%; Pale Yellow Solid.
¹H NMR (CDCl₃, δ): 1.88-2.22 (m, 2H, CH₂), 3.50-3.80 (m, 3H, 1.5×CH₂), 3.95-4.20 (m, 1H, 0.5×CH₂), 4.40-4.65 (m, 2H, CH—N & CH—O), 4.74 (s, 1H, OH), 6.18-6.22 (m, 1H, CH—O), 7.00-7.12 (m, 1H, HC=N), 7.20-7.30 (m, 2H, ArH), 8.52-8.68 (m, 2H, ArH).
MS-ESI m/z (% rel. Int.): 262.2 ([MH]⁺, 45), 235.2 (75), 148 (100).

(2S,3R)- & (2R,3S)-2-Amino-1-((R)-3-hydroxypyrrolidin-1-yl)-3-hydroxy-3-(pyridin-4-yl)propan-1-one dihydrochlorides Compound 247

To a solution of trans-((R)-3-hydroxypyrrolidin-1-yl)((4S, 5R)- & (4R,5S)-4,5-dihydro-5-(pyridin-4-yl)oxazol-4-yl) methanones VIB 01174 (0.49 g, 1.87 mmol) in methanol (6.5 mL) was added hydrochloric acid 37% (575 µL). After heating (50° C.) the mixture for 2 h the reaction mixture was concentrated and the crude product was coevaporated twice with EtOAc. After trituration with EtOAc, filtration and drying (2S,3R)- & (2R,3S)-2-amino-1-((R)-3-hydroxypyrrolidin-1-yl)-3-hydroxy-3-(pyridin-4-yl)propan-1-one dihydrochlorides (420 mg, diastereoisomeric mixture in ratio 1:1, 69% yield) were obtained as a pale pink solid.

Compound 247

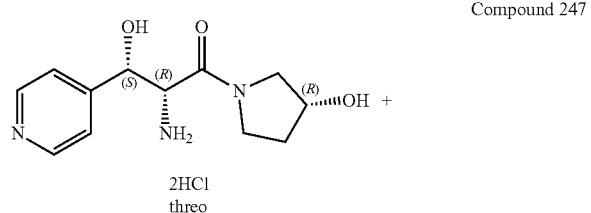

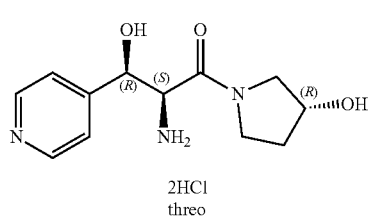

MW: 324.2; Yield: 69%; Pale Pink Solid; Mp (° C.): 177.0
¹H-NMR (CD₃OD, δ): 1.88-2.22 (m, 2H, CH₂), 2.70-3.80 (m, 4H, 2×CH₂), 4.20-4.65 (m, 2H, CH—O & CH—N), 5.20-5.45 (m, 1H, CH—O), 8.10-8.25 (m, 2H, ArH), 8.80-9.00 (m, 2H, ArH), 2×OH & NH₂ not seen.
MS-ESI m/z (% rel. Int.): 252.2 ([MH]⁺, 37), 235.1 (63), 148.0 (100).

Preparation of (−)-threo-2-amino-1-((S)-3-fluoropyrrolidin-1-yl)-3-hydroxy-3-(pyridin-4-yl)propan-1-one dihydrochloride Compound 248 and (+)-threo-2-amino-1-((S)-3-fluoropyrrolidin-1-yl)-3-hydroxy-3-(pyridin-4-yl)propan-1-one dihydrochloride Compound 249

Extraction of the Free Base:

(2S,3R)- & (2R,3S)-2-amino-1-((S)-3-fluoropyrrolidin-1-yl)-3-hydroxy-3-(pyridin-4-yl)propan-1-one dihydrochlorides Compound 214 (300 mg, 0.92 mmol) were dissolved in 10 mL of a Na₂CO₃ (10%) solution and the aqueous mixture was then saturated with NaCl. The aqueous phase was extracted by 5×15 mL of a mixture CH₂Cl₂:2-PrOH (9:1). The organic phase was dried over MgSO₄ and evaporated to afford 163 mg (70%) of the corresponding free base of Compound 214.

Analytical Chiral Separation:

20 µL of a 1 mg/mL solution of Compound 214 were injected on Chiralpak AD: flow-rate=1 mL/min, temperature=25° C., mobile phase hexane:ethanol=7:3, detection on UV 220 nm and on polarimeter, first eluted diastereoisomer Compound 248 Rt1(−)=20.94 min, second eluted diastereoisomer Rt2(+)=24.77 min, k1(−)=5.93, k2(+)=7.20, α=1.21 and resolution Rs=1.21. The integration of the UV signal gives 42% for the first diastereoisomer compound 248 and 58% for the second Compound 249 (the UV response is different for the two diastereoisomers).

Semi-Preparative Chiral Separation:

170 mg of the free base of Compound 214 were dissolved in 6 mL of ethanol, and 30 µL of this solution were injected every 9 min on Chiralpak AD-H, flow-rate=2 mL/min, mobile phase hexane:ethanol=7:3, detection on UV 220 nm. 195 successive injections were done. The two main fractions were identified on UV and collected in two different flasks. The solvent was removed in vacuo at 30° C. The resulting solid was dissolved in 50 mL of CH₂Cl₂ and then filtered on a 0.45 µm millipore membrane. After evaporation of CH₂Cl₂, the solid was dissolved in 50 mL of methanol and then filtered. For the free base of the first diastereoisomer, a new series of injections was needed to remove two UV-visible impurities collected in the same flask: in the same chromatographic conditions, 30 injections of 100 µL of a 25 mg/mL solution were made every 20 min. The salts Compound 248 and Compound 249 were regenerated according to the same procedure reported for Compound 203 and Compound 204.

The regenerated salts Compound 248 and Compound 249 were injected in analytical conditions, the diastereoisomeric excesses for Compound 248 and Compound 249 were determined to be higher than 96%.

(−)-threo-2-Amino-1-((S)-3-fluoropyrrolidin-1-yl)-3-hydroxy-3-(pyridin-4-yl)propan-1-one dihydrochloride Compound 248

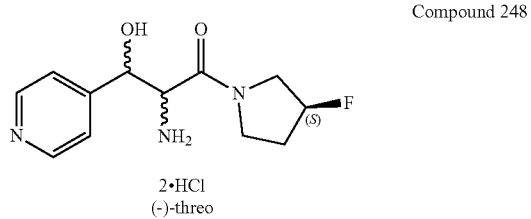

Compound 248

MW: 326.19; 70 mg obtained; Pale Yellow Solid; Mp (° C.): too hygroscopic. Diastereoisomeric excess>96% measured by HPLC at 220 nm (Chiralpak AD).

$\alpha^{25}_D = -2.0$ (methanol, c=1).

$^1$H-NMR (CD$_3$OD, δ): 1.85-2.38 (m, 2H, CH$_2$), 2.72-4.05 (m, 4H, 2×CH$_2$), 4.49-4.62 (m, 1H, CH⁻N), 5.10-5.48 (m, 2H, CH—O & CH—F), 8.11-8.25 (m, 2H, ArH), 8.82-8.98 (m, 2H, ArH).

(+)-threo-2-Amino-1-((S)-3-fluoropyrrolidin-1-yl)-3-hydroxy-3-(pyridin-4-yl)propan-1-one dihydrochloride Compound 249

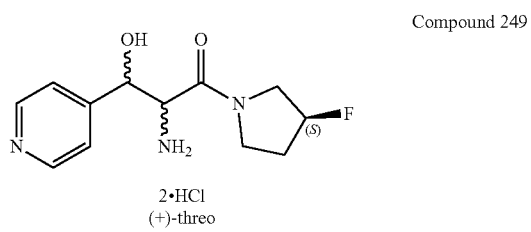

Compound 249

MW: 326.19; 85 mg obtained; Pale Yellow Solid; Mp (° C.): too hygroscopic. Diastereoisomeric excess>96% measured by HPLC at 220 nm (Chiralpak AD).

$\alpha^{25}_D = +31.7$ (methanol, c=1).

$^1$H-NMR (CD$_3$OD, δ): 1.82-2.38 (m, 2H, CH$_2$), 2.90-4.00 (m, 4H, 2×CH$_2$), 4.35-4.60 (m, 1H, CH⁻N), 5.00-5.48 (m, 2H, CH—O & CH—F), 8.11-8.25 (m, 2H, ArH), 8.82-9.00 (m, 2H, ArH).

Preparation of (±)-threo-2-Amino-N-ethyl-3-hydroxy-N-methyl-3-pyridin-4-yl-propanamide dihydrochloride Compound 250 trans-N-ethyl-4,5-dihydro-N-methyl-5-(pyridin-4-yl)oxazole-4-carboxamide SLA 09190

To a solution of potassium trans-4,5-dihydro-5-(pyridin-4-yl)oxazole-4-carboxylate EBE 10038A (501 mg, 2.60 mmol) in CH$_2$Cl$_2$ (12 mL) were added HOBT (352 mg, 2.60 mmol), EDCI (500 mg, 2.60 mmol) and N-methylethanamine (223 mL, 2.60 mmol). The reaction mixture was stirred 2 h at 0° C., allowed to warm to room temperature and stirred for 16 h. The reaction mixture was diluted in CH$_2$Cl$_2$ (100 mL), washed with brine (2×25 mL), 1 N NaOH (2×25 mL), dried over MgSO$_4$, filtered to give after evaporation trans-N-ethyl-4,5-dihydro-N-methyl-5-(pyridin-4-yl)oxazole-4-carboxamide SLA 09190 (144 mg, 24% yield) as a pale brown oil.

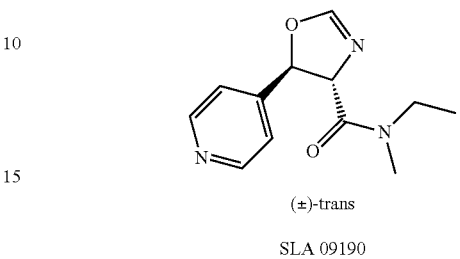

(±)-trans

SLA 09190

MW: 233.27; Yield: 24%; Pale Brown Oil.

$^1$H NMR (CDCl$_3$, δ): 1.15-1.30 (m, 3H, CH$_3$), 3.22 (s, 3H, CH$_3$—N), 3.40-3.80 (m, 2H, N—CH$_2$), 4.59 (dd, 1H, J=2.2 Hz, J=7.8 Hz, N—CH), 6.24 (d, J=7.7 Hz, OCH), 7.02 (d, 1H, J=1.0 Hz, N=CH), 7.23 (d, 2H, J=4.8 Hz, ArH), 8.61 (d, 2H, J=4.6 Hz, ArH).

MS-ESI m/z (% rel. Int.): 234.2 ([MH]$^+$, 30).

(±)-threo-2-Amino-N-ethyl-3-hydroxy-N-methyl-3-pyridin-4-yl-propanamide dihydrochloride Compound 250

To a solution of N-ethyl-4,5-dihydro-N-methyl-5-(pyridin-4-yl)oxazole-4-carboxamide SLA 09190 (144 mg, 0.6 mmol) in MeOH (5 mL) was added a solution of HCl 37% (240 μL). The reaction was stirred for 3 h at 50° C. and concentrated under reduced pressure. The resulting product was dissolved in MeOH and treated with amberlite (OH⁻ form), filtered to give after evaporation a residue that was purified by column chromatography (SiO$_2$, with a gradient of MeOH 10% in CH$_2$Cl$_2$) to yield to 2-amino-N-ethyl-3-hydroxy-N-methyl-3-pyridin-4-yl-propionamide. The hydrochloride salt was formed by treatment of this free base with a solution of HCl 1 M in MeOH (1 mL) to give after evaporation 2-amino-N-ethyl-3-hydroxy-N-methyl-3-pyridin-4-yl-propanamide dihydrochloride Compound 250 as a pale yellow solid (80 mg, 44% yield).

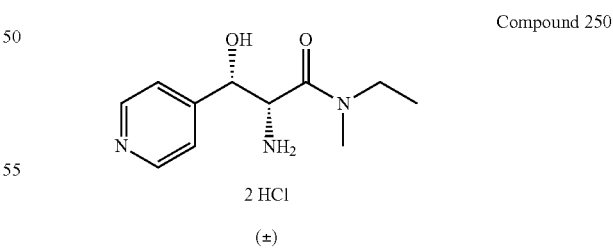

Compound 250

MW: 296.19; Yield: 44%; Pale Yellow Solid; Mp (° C.): 114.7

R$_f$: 0.30 (CH$_2$Cl$_2$:MeOH=90:10, freebase).

$^1$H-NMR (CD$_3$OD, δ): 0.96-1.10 (m, 3H, CH$_3$), 2.81 (s, 1.8H major rotamer, 0.6×CH$_3$), 2.88 (s, 1.2H minor rotamer, 0.4CH$_3$), 3.18-3.55 (m, 2H, CH$_2$), 4.66 (d, 0.4H minor rotamer, J=6.6 Hz, 0.4×N—CH), 4.69 (d, 0.6H major rotamer, J=6.3 Hz, 0.6×N—CH), 5.24 (d, 0.4H minor rotamer, J=6.9

Hz, 0.4×O—CH), 5.27 (d, 0.6H major rotamer, J=6.3 Hz, 0.6×O—CH), 8.08 (t, 2H, J=6.5 Hz, ArH), 8.86 (d, 2H, J=5.0 Hz, ArH).

$^{13}$C-NMR (CD$_3$OD, δ): 12.0, (13.6), (33.4), 35.3, 44.5, (45.6), 56.1, (56.2), 71.6, (72.1), 126.2 (2×C), 144.5, 144.6, 159.6, 166.5. ( ) Minor rotamer in parenthesis.

Preparation of (2R,3S)-2-(3,4-dichlorobenzylamino)-3-hydroxy-3-(pyridin-4-yl)-1-(pyrrolidin-1-yl)propan-1-one dihydrochloride Compound 251

To a solution of (−)-(2R,3S)-2-amino-3-hydroxy-3-(pyridin-4-yl)-1-(pyrrolidin-1-yl)propan-1-one dihydrochloride Compound 203 (175 mg, 0.57 mmol) and Et$_3$N (175 μL, 1.25 mmol) in MeOH (5 mL) in a 50 mL round bottom flask equipped with a magnetic stirrer and under nitrogen atmosphere was added slowly at RT 3,4-dichlorobenzaldehyde (112 mg, 0.63 mmol). The reaction mixture was stirred at RT for 20 h. Then AcOH (65 μL, 1.15 mmol) and NaBH$_3$CN (50 mg, 0.74 mmol) were added. The reaction mixture was stirred at RT for another 15 h. MeOH was evaporated and EtOAc (100 mL) was added. The organic phase was washed with a mixture of saturated sodium carbonate (5 mL) and brine (20 mL), then with brine (10 mL) and dried over MgSO$_4$, filtered and evaporated. The crude product was purified by column chromatography (SiO$_2$, eluent EtOAc:MeOH=95:5) to give an oil (−)-(2R,3S)-2-amino-3-hydroxy-3-(pyridin-4-yl)-1-(pyrrolidin-1-yl)propan-1-one (182 mg, 81% yield). This free base (182 mg, 0.46 mmol) was dissolved in MeOH (2 mL) at 4° C. and a solution of HCl 0.1 N in isopropanol (10.2 mL, 1.01 mmol) was added. After evaporation at 30° C., a mixture of EtOAc:MeOH=95:5 was added to yield, after evaporation and drying, to (2R,3S)-2-(3,4-dichlorobenzylamino)-3-hydroxy-3-(pyridin-4-yl)-1-(pyrrolidin-1-yl)propan-1-one dihydrochloride Compound 251 as a white solid (208 mg, 78% yield).

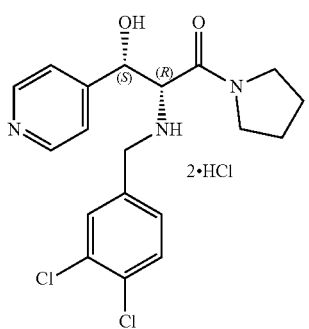

Compound 251

MW: 467.22; Yield: 78%; White Solid; Mp (° C.): 195.1 R$_f$:0.22 (EtOAc:MeOH=95:5, free base).

$^1$H-NMR (CD$_3$OD, δ): 1.55-1.77 (m, 4H, 2×CH$_2$), 2.46-2.53 (m, 1H, 0.5×N—CH$_2$), 3.20-3.30 (m, 3H, 1.5×N—CH$_2$), 4.25 (d, 1H, J=13.3 Hz, 0.5×N—CH$_2$), 4.38 (d, 1H, J=13.3 Hz, 0.5×N—CH$_2$), 4.52 (d, 1H, J=7.7 Hz, N—CH), 5.33 (d, 1H, J=7.7 Hz, O—CH), 7.48 (dd, 1H, J=8.3 Hz, J=1.7 Hz, ArH), 7.62 (dd, 1H, J=8.3 Hz, J=1.2 Hz, ArH), 7.74 (s, 1H, ArH), 8.15 (d, 2H, J=5.6 Hz, ArH), 8.91 (d, 2H, J=5.6 Hz, ArH).

$^{13}$C-NMR (CD$_3$OD, δ): 24.7, 26.6, 47.6, 48.2, 50.4, 64.0, 72.2, 126.8 (2×C), 131.7, 132.2, 132.3, 133.8, 133.9, 135.1, 143.5 (2×C), 160.6, 163.8.

MS-ESI m/z (% rel. Int.): 394.1/396.1/398.1 ([MH]$^+$, 60/45/10), 219.2 (100).

HPLC: Method A, detection UV 254 nm, Compound 251 RT=3.83 min, peak area 99.5%.

Preparation of (2S,3R)-2-(3,4-dichlorobenzylamino)-3-hydroxy-3-(pyridin-4-yl)-1-(pyrrolidin-1-yl)propan-1-one dihydrochloride Compound 252

Same experimental as for Compound 251 preparation starting from (+)-(2S,3R)-2-amino-3-hydroxy-3-(pyridin-4-yl)-1-(pyrrolidin-1-yl)propan-1-one dihydrochloride Compound 204 (175 mg, 0.57 mmol). After purification by column chromatography (2S,3R)-2-(3,4-dichlorobenzylamino)-3-hydroxy-3-(pyridin-4-yl)-1-(pyrrolidin-1-yl)propan-1-one was obtained (187 mg, 83% yield). This free base (187 mg, 0.47 mmol) was dissolved in MeOH (2 mL) at 4° C. and a solution of HCl 0.1 N in isopropanol (10.4 mL, 1.04 mmol) was added. After evaporation at 30° C., a mixture of EtOAc:MeOH=95:5 was added to yield, after evaporation and drying, to Compound 252 as a white solid (212 mg, 80% yield).

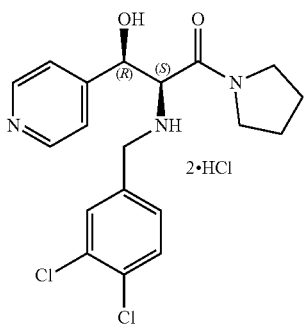

Compound 252

MW: 467.22; Yield: 80%; White Solid; Mp (° C.): 187.5 R$_f$:0.22 (EtOAc:MeOH=95:5, free base).

$^1$H-NMR (CDCl$_3$, δ): 1.55-1.77 (m, 4H, 2×CH$_2$), 2.46-2.53 (m, 1H, 0.5×N—CH$_2$), 3.20-3.30 (m, 3H, 1.5×N—CH$_2$), 4.25 (dd, 1H, J=13.3 Hz, 0.5×N—CH$_2$), 4.40 (d, 1H, J=13.3 Hz, 0.5×N—CH$_2$), 4.52 (d, 1H, J=7.7 Hz, N—CH), 5.33 (d, 1H, J=7.4 Hz, O—CH), 7.48 (d, 1H, J=8.3 Hz, ArH), 7.62 (dd, 1H, J=8.3 Hz, J=0.8 Hz, ArH), 7.74 (s, 1H, ArH), 8.15 (d, 2H, J=5.7 Hz, ArH) 8.91 (d, 2H, J=5.7 Hz, ArH).

$^{13}$C-NMR (CD$_3$OD, *): 24.7, 26.6, 47.6, 48.2, 50.4, 64.0, 72.3, 126.8 (2×C), 131.7, 132.2, 132.3, 133.8, 133.9, 135.1, 143.5 (2×C), 160.6, 163.8.

MS-ESI m/z (% rel. Int.): 394.1/396.1/398.1 ([MH]$^+$, 60/45/10), 219.2 (100).

HPLC: Method A, detection UV 254 nm, Compound 252 RT=3.83 min, peak area 99.5%.

Preparation of (E)-3-(pyridin-4-yl)-1-(pyrrolidin-1-yl)prop-2-en-1-one hydrochloride Compound 253

To a solution of 3-(4-pyridinyl)acrylic acid (1.01 g, 6.77 mmol) in CHCl$_3$ (20 mL) in a 100 mL round bottom flask equipped with a magnetic stirrer and under nitrogen atmosphere was added 1-hydroxybenzotriazole (1.11 g, 8.21 mmol). The reaction mixture was stirred at RT for 10 min. Then 1-(3-dimethylaminopropyl)-3-ethylcarbodiimide (1.56 g, 8.15 mmol) was added. The reaction mixture was stirred at 4° C. for 10 min. Then pyrrolidine (1.11 mL, 18.3 mmol) was added slowly and the reaction mixture was stirred for 15 h at +4° C. to RT. Dichloromethane (200 mL) was added and organic phase was washed with brine (100 mL), a solution of NaOH 0.5 N (100 mL) and brine (50 mL). The organic phase was dried over MgSO$_4$, filtered, and evaporated to obtain (E)-3-(pyridin-4-yl)-1-(pyrrolidin-1-yl)prop-2-en-1-one (1.30 g, 94% yield). This free base (1.3 g, 6.40 mmol) was dissolved in MeOH (10 mL) at 4° C. and a solution of HCl 0.1 N in isopropanol (79 mL, 7.9 mmol) was added. After evaporation at 30° C. and drying, (E)-3-(pyridin-4-yl)-1-(pyrrolidin-1-yl)prop-2-en-1-one hydrochloride Compound 253 was obtained as a beige solid (1.40 g, 87% yield).

Compound 253

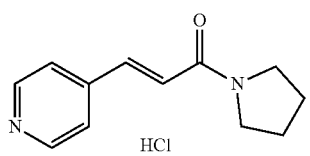

MW: 238.71; Yield: 87%; Beige Solid; Mp (° C.): 229.4

R$_f$:0.35 (EtOAc:MeOH=95:5, free base).

$^1$H-NMR (CD$_3$OD, δ): 1.92-2.10 (m, 4H, 2×CH$_2$), 3.56 (t, 2H, J=6.7 Hz, N—CH$_2$), 3.80 (t, 2H, J=6.7 Hz, N—CH$_2$), 7.59 (d, 1H, J=15.6 Hz, CH=C), 7.68 (d, 1H, J=15.6 Hz, CH=C), 8.35 (d, 2H, J=5.7 Hz, ArH) 8.86 (d, 2H, J=5.6 Hz, ArH).

$^{13}$C-NMR (CD$_3$OD, δ): 25.2, 27.0, 47.6, 48.2, 126.7 (2×C), 131.9, 136.5, 143.1 (2×C), 154.5, 164.6.

MS-ESI m/z (% rel. Int.): 203.2 ([MH]$^+$, 100).

HPLC: Method A, detection UV 254 nm, Compound 253 RT=3.18 min, peak area 99.5%.

Preparation of (±)-threo-2-amino-3-hydroxy-3-(1-methyl-1H-imidazol-2-yl)-1-(pyrrolidin-1-yl)propan-1-one dihydrochloride Compound 254 trans-(4,5-Dihydro-5-(1-methyl-1H-imidazol-2-yl) oxazol-4-yl)(pyrrolidin-1-yl)methanone LPO 01190B To a stirred and cooled (0° C.) solution of potassium hydroxide (0.33 g, 5.0 mmol) in MeOH (6 mL) were added a mixture of 1-methyl-2-imidazole carboxaldehyde (0.56 g, 5.0 mmol) and 2-isocyano-1-(pyrrolidin-1-yl)ethanone BLE 04098 (0.70 g, 5.0 mmol). The solution was stirred 3 h at 4° C. and then concentrated. The residue was partitioned between EtOAc (100 mL) and water (20 mL). The organic layer was washed with brine (10 mL) and dried over MgSO$_4$, filtered and evaporated. Concentration afforded a crude product which was purified by column chromatography (florisil, EtOAc:MeOH=95:5 to 90:10) to yield, after evaporation and drying, to trans-(4,5-dihydro-5-(1-methyl-1H-imidazol-2-yl)oxazol-4-yl)(pyrrolidin-1-yl)methanone LPO 01190B (0.32 g, 25% yield) as a brown oil.

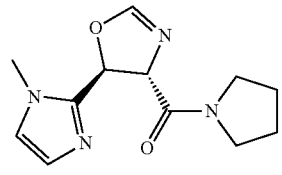

(±)-trans

LPO 01190B

MW: 248.28; Yield: 25%; Brown Oil.

R$_f$:0.30 (EtOAc:MeOH=9:1, free base).

$^1$H-NMR (CDCl$_3$, δ): 1.94-2.12 (m, 4H, 2×CH$_2$), 3.50 (t, 2H, J=6.5 Hz, N—CH$_2$), 3.69-4.13 (m, 5H, N—CH$_2$,N—CH$_3$), 5.68 (dd, 1H, J=7.7 Hz, J=2.3 Hz, CH—N), 6.19 (d, 1H, J=7.7 Hz, CH—O), 6.82 (d, 1H, J=2.2 Hz, CH=N), 6.94 (d, 1H, J=1.1 Hz, ArH), 7.00 (d, 1H, J=1.1 Hz, ArH).

$^{13}$C-NMR (CDCl$_3$, δ): 24.2, 26.0, 32.9, 46.4, 46.7, 71.2, 72.7, 123.0, 127.9, 143.7, 153.7, 166.6.

MS-ESI m/z (% rel. Int.): 267.3 ([MH+18]$^+$, 10), 196.2 (100).

HPLC: Method A, detection UV 254 nm, LPO 01190B RT=3.92 min, peak area 99.5%.

(±)-threo-2-Amino-3-hydroxy-3-(1-methyl-1H-imidazol-2-yl)-1-(pyrrolidin-1-yl)propan-1-one dihydrochloride Compound 254

A solution of trans-(4,5-dihydro-5-(1-methyl-1H-imidazol-2-yl)oxazol-4-yl)(pyrrolidin-1-yl)methanone LPO 01190B (320 mg, 1.29 mmol) and HCl 37% (0.4 mL, 13 mmol) in MeOH (6 mL) was stirred at 50° C. for 3 h in a 50 mL round bottom flask. The solvent was evaporated and the product was precipitated by a mixture of MeOH:EtOAc:Et$_2$O=3:12:5 (20 mL). Solvents were evaporated at 30° C. to give, after evaporation and drying, (±)-threo-2-amino-3-hydroxy-3-(1-methyl-1H-imidazol-2-yl)-1-(pyrrolidin-1-yl) propan-1-one dihydrochloride Compound 254 as a pale yellow solid (305 mg, 76% yield).

Compound 254

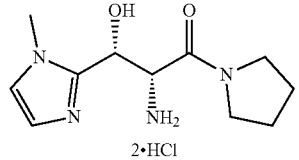

(±)-threo

MW: 311.21; Yield: 76%; Pale Yellow Solid; Mp (° C.): 183.4

R$_f$:0.30 (CH$_2$Cl$_2$:MeOH=95:5, free base).

$^1$H-NMR (CD$_3$OD, δ): 1.75-1.99 (m, 4H, 2×CH$_2$), 2.80-2.88 (m, 1H, 0.5×N—CH$_2$), 3.30-3.70 (m, 3H, 1.5×N—CH$_2$), 3.95 (s, 3H, N—CH$_3$), 4.62 (d, 1H, J=8.3 Hz, N—CH), 5.51 (d, 1H, J=8.3 Hz, O—CH), 7.66 (s, 2H, ArH).

$^{13}$C-NMR (CD$_3$OD, δ): 24.9, 26.9, 36.0, 47.9 (2×C), 56.2, 65.1, 121.1, 126.5, 145.1, 164.4.

MS-ESI m/z (% rel. Int.): 239.3 ([MH]$^+$, 10), 134.1 (100).

HPLC: Method A, detection UV 254 nm, RT=0.8 min, peak area 99.5%.

Preparation of (2S,3R)- & (2R,3S)-2-amino-1-[(S)-3-fluoropyrrolidin-1-yl)-3-hydroxy-3-(pyridin-3-yl)propan-1-one dihydrochlorides Compound 255 trans-((S)-3-fluoropyrrolidin-1-yl)((4S,5R)- & (4R,5S)-4,5-dihydro-5-(pyridin-4-yl)oxazol-4-yl)methanones SLA 11014

To a stirred and cooled 0° C. solution of KOH (0.216 mg, 4.22 mmol) in methanol (5 mL) was added 1-((S)-3-fluoropyrrolidin-1-yl)-2-isocyanoethanone VIB 01166 (0.600 g, 4.22 mmol) and pyridine-3-carbaldehyde (0.40 mL, 3.84 mmol). The solution was stirred for 20 h at 0° C. After evaporation under reduced pressure, the residue obtained was partitioned between EtOAc and H₂O. The product was extracted with EtOAc (4×50 mL) and washed with brine (25 mL), dried over MgSO₄, filtered and evaporated to yield to a product that was purified using chromatography (florisil, EtOAc:MeOH=95:5), trans-((S)-3-fluoropyrrolidin-1-yl)((4S,5R)- & (4R,5S)-4,5-dihydro-5-(pyridin-4-yl)oxazol-4-yl)methanones SLA 11014 were obtained as a yellow solid (0.464 g, diastereoisomeric mixture in ratio about 1:1, 46% yield).

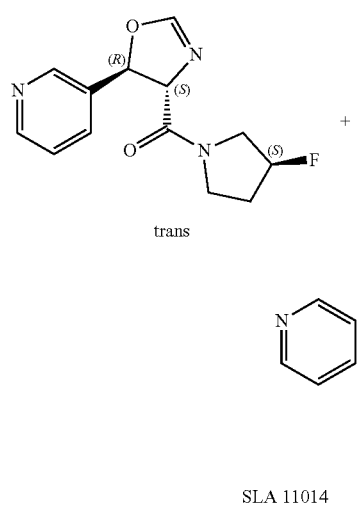

SLA 11014

MW: 263.27; Yield: 46%; Yellow Solid; Mp (° C.)=171.7 R$_f$:0.25 (EtOAc:MeOH=95:5).

¹H-NMR (CDCl₃, δ): 1.85-2.45 (m, 2H, CH₂), 3.50-4.10 (m, 3H, CH₂ & N—CH), 4.25-4.65 (m, 2H, N—CH₂), 5.15-5.25 (m, 0.5H, 0.5×CHF), 5.35-5.45 (m, 0.5H, 0.5×CHF), 6.21 (d, 1H, J=7.6 Hz, O—CH), 7.04 (d, 1H, J=2.1 Hz, N=CH), 7.30-7.38 (m, 1H, ArH), 7.60-7.68 (m, 1H, ArH), 8.55-8.65 (m, 2H, ArH).

MS-ESI m/z (% rel. Int.): 264.1 ([MH]⁺, 18).

(2S,3R)- & (2R,3S)-2-Amino-1-(5)-3-fluoropyrrolidin-1-yl)-3-hydroxy-3-(pyridin-3-yl)propan-1-one dihydrochlorides Compound 255

To a solution of trans-((5)-3-fluoropyrrolidin-1-yl)((4S,5R)- & (4R,5S)-4,5-dihydro-5-(pyridin-4-yl)oxazol-4-yl) methanones SLA 11014 (0.450 g, 1.71 mmol) in methanol (40 mL) was added HCl 37% (5 mL). After heating at 50° C. for 3 h, the mixture was concentrated and the crude product was co-evaporated twice with EtOAc. Trituration with EtOAc and filtration yielded, after drying, to (2S,3R)- & (2R,3S)-2-amino-1-((5)-3-fluoropyrrolidin-1-yl)-3-hydroxy-3-(pyridin-3-yl)propan-1-one dihydrochlorides Compound 255 (540 mg, diastereoisomeric mixture in ratio about 1:1, 97% yield) as a yellow solid.

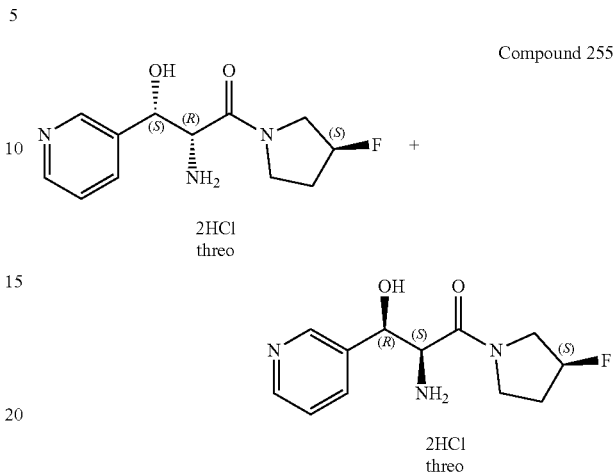

Compound 255

MW: 326.19; Yield: 97%; Yellow Solid; Mp (° C.): 168.9

¹H-NMR (CD₃OD, δ): 1.85-2.40 (m, 2H, CH₂), 3.45-4.20 (m, 4H, 2×CH₂), 4.40-4.75 (m, 1H, N—CH), 5.30-5.60 (m, 2H, O—CH & CHF), 8.15-8.25 (m, 1H, ArH), 8.70-8.80 (m, 1H, ArH), 8.90-9.10 (m, 2H, ArH).

MS-ESI m/z (% rel. Int.): 254.1 ([MH]⁺, 81.38), 236.2 (25).

((S)-3-fluoropyrrolidin-1-yl)((4S,5R)— & (4R,5,S)-4,5-dihydro-5-(thiophen-3-yl)oxazol-4-yl)methanones SLA 11016

To a stirred and cooled 0° C. solution of KOH (0.216 mg, 3.85 mmol) in methanol (8 mL) was added 1-((5)-3-fluoropyrrolidin-1-yl)-2-isocyanoethanone VIB 01166 (0.600 g, 4.22 mmol) and thiophene-3-carbaldehyde (0.37 mL, 3.85 mmol). The solution was stirred for 20 h at 0° C. After evaporation under reduced pressure, the residue obtained was partitioned between EtOAc and H₂O. The product was extracted with EtOAc (4×50 mL) and washed brine (25 mL), dried over MgSO₄, filtered and evaporated to yield to a product that was purified using chromatography (florisil, gradient EtOAc:MeOH=95:5 to 85:15). ((S)-3-fluoropyrrolidin-1-yl)((4S, 5R)- and (4R,5S)-4,5-dihydro-5-(thiophen-3-yl)oxazol-4-yl) methanones SLA 11016 were obtained as a yellow solid (0.411 g, diastereoisomeric mixture in ratio about 1:1, 32% yield).

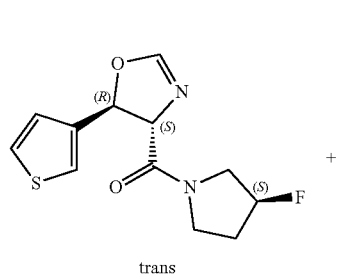

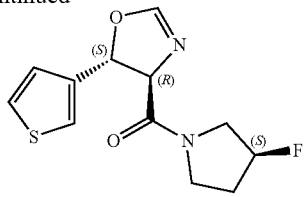

trans

SLA 11016

MW: 268.31; Yield: 32%; Yellow Solid; Mp (° C.)=132.9 $R_f$:0.35 (EtOAc:MeOH=80:20).
$^1$H-NMR (CDCl$_3$, δ): 1.80-2.45 (m, 2H, CH$_2$), 3.50-4.10 (m, 3H, CH—N & CH$_2$), 4.20-4.70 (m, 2H, CH$_2$), 5.15-5.45 (m, 1H, CHF), 6.18-6.25 (m, 1H, O—CH), 6.99 (d, 1H, J=2.2 Hz, N=CH), 7.00-7.15 (m, 1H, ArH), 7.28-7.35 (m, 1H, ArH), 7.32-7.40 (m, 1H, ArH).
MS-ESI m/z (% rel. Int.): 269.0 ([MH]$^+$, 10).

(2S,3R)- & (2R,3S)-2-Amino-1-((S)-3-fluoropyrrolidin-1-yl)-3-hydroxy-3-(thiophen-3-yl)propan-1-one dihydrochlorides Compound 256

To a solution of ((S)-3-fluoropyrrolidin-1-yl)((4S,5R)- & (4R,5S)-4,5-dihydro-5-(thiophen-3-yl)oxazol-4-yl)methanones SLA 11016 (0.400 g, 1.49 mmol) in methanol (50 mL) was added hydrochloric acid 37% (4 mL). After heating at 50° C. for 3 h, the mixture was concentrated and the crude product was co-evaporated twice with EtOAc. Trituration with EtOAc and filtration and drying afforded (2S,3R)- & (2R,3S)-2-amino-1-((S)-3-fluoropyrrolidin-1-yl)-3-hydroxy-3-(thiophen-3-yl)propan-1-one dihydrochlorides Compound 256 (451 mg, diastereoisomeric mixture about 1:1, 91% yield) as a yellow solid.

Compound 256

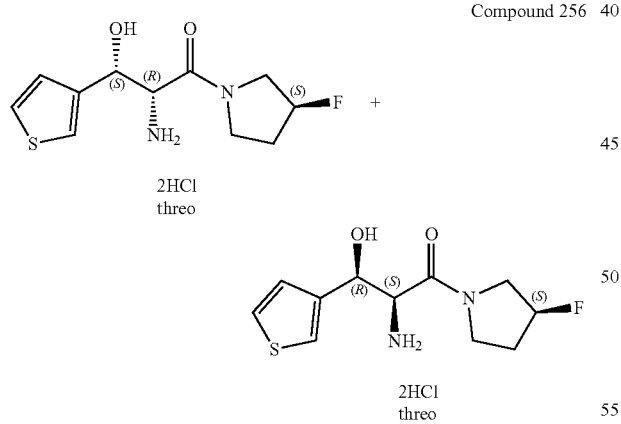

MW: 331.23; Yield: 91%; Yellow Solid; Mp (° C.): 221.6
$^1$H-NMR (CD$_3$OD, δ): 1.25-2.05 (m, 2H, CH$_2$), 2.10-2.50 (m, 1H, 0.5×CH$_2$), 3.20-3.65 (m, 3H, 1.5×CH$_2$), 3.90-4.10 (m, 1H, CH—N), 4.70-5.10 (m, 2H, O—CH & CHF), 6.92-6.99 (m, 1H, ArH), 7.21-7.32 (m, 2H, ArH).
MS-ESI m/z (% rel. Int.): 259.1 ([MH]$^+$, 25).

What is claimed is:

1. A method for treating chronic pain in a mammal, comprising administering to said mammal at least one compound of the formula:

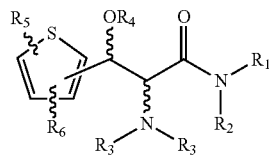

or a pharmaceutically acceptable salt thereof, wherein:

$R_1$ is H or alkyl of 1 to 6 carbons;

$R_2$ is selected from the group consisting of H, and alkyl of 1 to 6 carbons; or the $R_1$ and $R_2$ groups together with the nitrogen atom to which they are shown attached form a saturated or unsaturated 4, 5, 6 or 7 membered ring that optionally additionally includes one or two heteroatoms independently selected from the group consisting of N, O and S, said 4, 5, 6 or 7 membered ring optionally being substituted with one or two COOH, CH$_2$OH, OH, B(OH)$_2$, halogen groups, cyano groups or with one or two alkyl groups having 1 to 6 carbons;

$R_3$ is H, CO—$R_7$ or CO—O—$R_7$ where $R_7$ is H, alkyl of 1 to 20 carbons, cycloalkyl of 3 to 6 carbons, aryl or heteroaryl, aryl-alkyl, aryl(hydroxy)alkyl, heteroaryl-alkyl or heteroalkyl(hydroxy)alkyl where the alkyl moiety has 1 to 4 carbons, said aryl or heteroaryl groups being optionally substituted with 1 to 3 groups independently selected from the group consisting of halogen, alkyl of 1 to 6 carbons, alkoxy of 1 to 6 carbons and thioxy of 1 to 3 carbons;

$R_4$ is H, alkyl of 1 to 6 carbons, or CO—$R_8$ where $R_8$ is alkyl of 1 to 6 carbons;

$R_5$ and $R_6$ are independently selected from the group consisting of H, halogen, alkyl of 1 to 6 carbons, alkoxy of 1 to 6 carbons and thioxy of 1 to 3 carbons; or $R_5$ and $R_6$ together with the atoms to which they are attached jointly form a carbocyclic or a heterocyclic ring, the carbocyclic ring having 5 or 6 atoms in the ring, the heterocyclic ring having 5 or 6 atoms in the ring and 1 to 3 heteroatoms independently selected from N, O and S;

said carbocyclic or heterocyclic ring jointly formed by $R_5$ and $R_6$ being optionally substituted with 1 to 6 $R_9$ groups where $R_9$ is independently selected from halogen, alkyl of 1 to 6 carbons, alkoxy of 1 to 6 carbons, and the wavy lines represent bonds of the alpha or beta configuration with the proviso that the formula excludes the compound of the formula below:

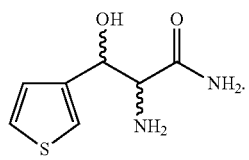 [SMILES: NC(=O)C(N)C(O)c1ccsc1]

2. A method for treating chronic pain in a mammal, comprising administering to said mammal at least one compound of the formula:

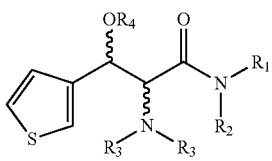

or a pharmaceutically acceptable salt of said compound, wherein:

$R_1$ and $R_2$ groups together with the nitrogen atom to which they are shown attached form a saturated 5 or 6 membered ring, said ring optionally being substituted with one or two COOH, $CH_2OH$, OH, $B(OH)_2$, halogen groups, cyano groups or with one or two alkyl groups having 1 to 6 carbons;

$R_3$ is H or alkyl of 1 to 20 carbons; and $R_4$ is H or alkyl of 1 to 6 carbons.

3. A method for treating chronic pain in a mammal, comprising administering to said mammal a compound of the formula:

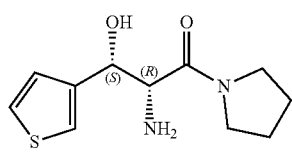

HCl
DL-threo or any other pharmaceutically acceptable salt of

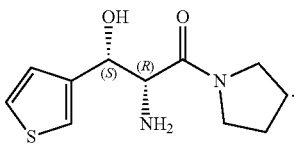

DL-threo

4. A method for treating chronic pain in a mammal, comprising administering to said mammal a compound of the formula:

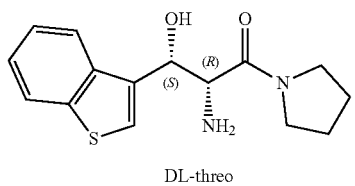

DL-threo or a pharmaceutically acceptable salt thereof.

5. A compound of the formula:

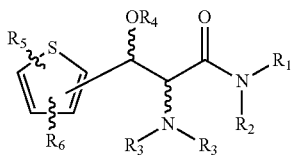

or a pharmaceutically acceptable salt thereof, wherein:

$R_1$ is H or alkyl of 1 to 6 carbons;

$R_2$ is selected from the group consisting of H, and alkyl of 1 to 6 carbons; or the $R_1$ and $R_2$ groups together with the nitrogen atom to which they are shown attached form a saturated or unsaturated 4, 5, 6 or 7 membered ring that optionally additionally includes one or two heteroatoms independently selected from the group consisting of N, O and S, said 4, 5, 6 or 7 membered ring optionally being substituted with one or two COOH, $CH_2OH$, OH, $B(OH)_2$, halogen groups, cyano groups or with one or two alkyl groups having 1 to 6 carbons;

$R_3$ is H, CO—$R_7$ or CO—O—$R_7$ where $R_7$ is H, alkyl of 1 to 20 carbons, cycloalkyl of 3 to 6 carbons, aryl or heteroaryl, aryl-alkyl, aryl(hydroxy)alkyl, heteroaryl-alkyl or heteroalkyl(hydroxy)alkyl where the alkyl moiety has 1 to 4 carbons, said aryl or heteroaryl groups being optionally substituted with 1 to 3 groups independently selected from the group consisting of halogen, alkyl of 1 to 6 carbons, alkoxy of 1 to 6 carbons and thioxy of 1 to 3 carbons;

$R_4$ is H, alkyl of 1 to 6 carbons, or CO—$R_8$ where $R_8$ is alkyl of 1 to 6 carbons;

$R_5$ and $R_6$ are independently selected from the group consisting of H, halogen, alkyl of 1 to 6 carbons, alkoxy of 1 to 6 carbons and thioxy of 1 to 3 carbons; or $R_5$ and $R_6$ together with the atoms to which they are attached jointly form a carbocyclic or a heterocyclic ring, the carbocyclic ring having 5 or 6 atoms in the ring, the heterocyclic ring having 5 or 6 atoms in the ring and 1 to 3 heteroatoms independently selected from N, O and S;

said carbocyclic or heterocyclic ring jointly formed by $R_5$ and $R_6$ being optionally substituted with 1 to 6 $R_9$ groups where $R_9$ is independently selected from halogen, alkyl of 1 to 6 carbons, alkoxy of 1 to 6 carbons, and the wavy lines represent bonds of the alpha or beta configuration with the proviso that the formula excludes the compound of the formula below:

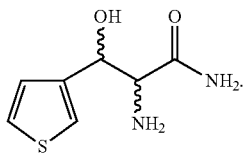 [SMILES: NC(=O)C(N)C(O)c1ccsc1]

6. A compound of the formula:

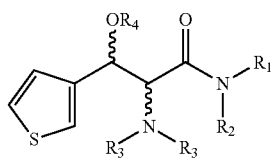

or a pharmaceutically acceptable salt thereof, wherein:
   $R_1$ and $R_2$ groups together with the nitrogen atom to which they are shown attached form a saturated 5 or 6 membered ring, said ring optionally being substituted with one or two COOH, $CH_2OH$, OH, $B(OH)_2$, halogen groups, cyano groups or with one or two alkyl groups having 1 to 6 carbons;
   $R_3$ is H or alkyl of 1 to 20 carbons; and
   $R_4$ is H or alkyl of 1 to 6 carbons.

7. The compound of claim 6, or a pharmaceutically acceptable salt thereof, wherein the compound has the formula:

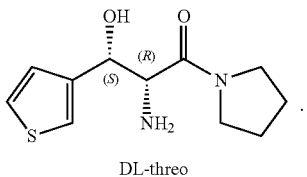

DL-threo

8. The compound of claim 6, or a pharmaceutically acceptable salt thereof, wherein the compound has the formula:

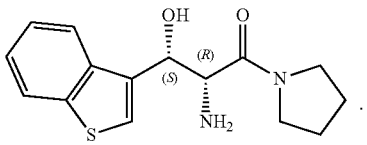

DL-threo

9. A pharmaceutical composition comprising at least one compound of claim 5, or a pharmaceutically acceptable salt thereof, and at least one pharmaceutically acceptable excipient.

10. A pharmaceutical composition comprising at least one compound of claim 6, or a pharmaceutically acceptable salt thereof, and at least one pharmaceutically acceptable excipient.

* * * * *